United States Patent
He

(10) Patent No.: US 9,861,636 B2
(45) Date of Patent: Jan. 9, 2018

(54) POLYFLUORINATED COMPOUNDS ACTING AS BRUTON TYROSINE KINASE INHIBITORS

(71) Applicant: Wei He, Audubon, PA (US)

(72) Inventor: Wei He, Audubon, PA (US)

(73) Assignee: ZHEJIANG DTRM BIOPHARMA CO. LTD., Shanghai (CN)

( * ) Notice: Subject to any disclaimer, the term of this patent is extended or adjusted under 35 U.S.C. 154(b) by 0 days.

(21) Appl. No.: 15/356,014

(22) Filed: Nov. 18, 2016

(65) Prior Publication Data

US 2017/0065594 A1 Mar. 9, 2017

Related U.S. Application Data

(63) Continuation of application No. 15/075,033, filed on Mar. 18, 2016, now Pat. No. 9,532,990, which is a (Continued)

(30) Foreign Application Priority Data

Apr. 29, 2014 (CN) .......................... 2014 1 0175783

(51) Int. Cl.
  *A61K 31/519* (2006.01)
  *C07D 487/04* (2006.01)
  (Continued)

(52) U.S. Cl.
  CPC .......... *A61K 31/519* (2013.01); *C07C 303/38* (2013.01); *C07C 311/08* (2013.01);
  (Continued)

(58) Field of Classification Search
  CPC .............................. A61K 31/519; C07D 487/04
  (Continued)

(56) References Cited

U.S. PATENT DOCUMENTS

| 8,673,925 B1 | 3/2014 | Goldstein |
| 8,940,744 B2 | 1/2015 | Owens et al. |
| 2012/0108612 A1 | 5/2012 | Honigberg et al. |

FOREIGN PATENT DOCUMENTS

| WO | 2008039218 A2 | 4/2008 |
| WO | 2008/058944 | 5/2008 |

(Continued)

OTHER PUBLICATIONS

Vargas et al, "Inhibitors of BTK and ITK: State of the New Drugs for Cancer, Autoimmunity and Inflammatory Diseases," Scandinavian Journal of Immunology (2013), pp. 130-139.*

(Continued)

*Primary Examiner* — Kathrien Cruz
*Assistant Examiner* — Janet L Coppins
(74) *Attorney, Agent, or Firm* — Steptoe & Johnson LLP; Z. Ying Li; Dong Chen

(57) ABSTRACT

Described herein is a novel series of multi-fluoro-substituted pyrazolopyrimidine compounds or salts thereof. These compounds are Bruton's tyrosine kinase (BTK) inhibitors. These compounds may possess better BTK inhibition selectivity and pharmacokinetic properties. Disclosed herein are the synthesis methods of these compounds. Disclosed herein are novel synthesis methods of the multi-fluoro-substituted benzophenone and substituted phenoxy benzene. Also disclosed are pharmaceutical compositions comprising the BTK inhibitors described herein. The present invention also relates to pharmaceutical formulations comprising the compounds described herein as active ingredients. The present invention also includes the therapeutic methods by administering the BTK inhibitors and their formulations to treat and inhibit autoimmune disease, hypersensitivity disease, inflammatory diseases and cancer.

30 Claims, 2 Drawing Sheets

Related U.S. Application Data continuation-in-part of application No. PCT/CN2015/000290, filed on Apr. 27, 2015.

(51) Int. Cl.

| | | |
|---|---|---|
| *C07C 303/38* | (2006.01) | |
| *C07C 311/08* | (2006.01) | |
| *C07D 519/00* | (2006.01) | |
| *C07F 5/04* | (2006.01) | |
| *C07F 5/02* | (2006.01) | |

(52) U.S. Cl.
CPC ......... *C07D 487/04* (2013.01); *C07D 519/00* (2013.01); *C07F 5/025* (2013.01); *C07F 5/04* (2013.01)

(58) Field of Classification Search
USPC ...................................................... 514/262.1
See application file for complete search history.

(56) References Cited

FOREIGN PATENT DOCUMENTS

| WO | 2010009342 A2 | 1/2010 |
|---|---|---|
| WO | 2011/046964 | 4/2011 |
| WO | 2012/158764 | 11/2012 |
| WO | 2013010136 A2 | 1/2013 |
| WO | 2013/191965 | 12/2013 |
| WO | 2014/022569 | 2/2014 |
| WO | 2014/143807 | 9/2014 |
| WO | 2014/166820 | 10/2014 |
| WO | 2014/168975 | 10/2014 |

OTHER PUBLICATIONS

Shi et al, "Purine derivatives as potent Bruton's tyrosine kinase (BTK) inhibitors for autoimmune diseases," Bioorganic & Medicinal Chemistry Letters (2014), pp. 2206-2211.*

Levy et al., "Dications of Fluorenylidenes. The Effect of Substituent Eectronegativity and Position on the Antiaromaticity of Substituted Tetrabenzo[5.5]fulvalene Dications", J. Org. Chem. (2003) 68(10):3990-3998.

Marostica, Eleonora, et al., "Population pharmacokinetic model of ibrutinib, a Bruton tyrosine kinase inhibitor, in patients with B cell malignancies," Cancer Chemother Pharmacol (2015) 75:111-121.

Roschewski, Mark, et al., "Diffuse large B-cell lymphoma—treatment approached in the molecular era," Nature Reviews Clinical Oncology (advanced online publication Nov. 12, 2013):1-12.

Shi et al., "Purine derivatives as potent Bruton's tyrosine kinase (BKT) inhibitors for autoimmune diseases," Bioorganic & Medicinal Chemistry Letters (2014) 24(9):2206-2211.

Vargas et al., "Inhibitors of BTK and ITK: State of the New Drugs for Cancer, Autoimmunity and Inflammatory Diseases", Scandinavian Journal of Immunology (2013) 78:130-139.

* cited by examiner

POLYFLUORINATED COMPOUNDS ACTING AS BRUTON TYROSINE KINASE INHIBITORS

CROSS-REFERENCE TO RELATED APPLICATIONS

This application is a continuation of U.S. patent application Ser. No. 15/075,033, filed Mar. 18, 2016, which is a continuation-in-part of International Patent Application No. PCT/CN2015/000290, filed Apr. 27, 2015, which claims the benefit of Chinese Patent Application No. 201410175783.7, filed Apr. 29, 2014, the contents of all of which are incorporated herein by reference in their entireties.

BACKGROUND OF THE INVENTION

Bruton tyrosine kinase (BTK) is a member of the Tec family of protein tyrosine kinases. BTK has domains with pleckstrin homology (PH), Tec homology (TH), Src homology 3 (SH3), Src homology 2 (SH2), and tyrosine kinase or Src homology 1 (TK or SH1) (Akinleye et al., "Ibrutinib and novel BTK inhibitors in clinical development," Journal of Hematology & Oncology, 2013, 6:59). In the normal development of B lymphocytes, the correct expression of BTK gene in different regions plays a key role in the function of B cells and various signal transduction pathways.

BTK functions downstream of multiple receptors, include B-cell Receptor (BCR), receptors for growth factors and chemokines, and innate immune receptors. BTK initiates a diverse range of cellular processes, such as cell proliferation, survival, differentiation, motility, adhesion, angiogenesis, cytokine production, and antigen presentation, and plays an important role in hematological malignancies and immune disorders (Kurosaki, "Molecular mechanisms in B cell antigen receptor signaling," Curr OP Imm, 1997, 9(3):309-18). In a mouse model for chronic lymphocytic leukemia (CLL), BTK expression levels were shown to set the threshold for malignant transformation; BTK overexpression accelerated leukemia and increased mortality (Kil et al., "Bruton's tyrosine kinase mediated signaling enhances leukemogenesis in a mouse model for chronic lymphocytic leukemia," Am J Blood Res 2013, 3(1):71-83).

Ibrutinib (also known commercially as IMBRUVICA®) was the first BTK inhibitor approved by the United States Food and Drug Administration for treating mantle cell lymphoma (MCL), chronic lymphocytic leukemia (CLL), and Waldenström's macroglobulinemia (WM). In general, however, the selectivity of known BTK inhibitors is not ideal—they inhibit not only BTK, but also various other kinases (such as ETK, EGF, BLK, FGR, HCK, YES, BRK and JAK3, etc.). Known BTK inhibitors also produce a variety of derivatives. These characteristics of known BTK inhibitors lead to a decrease in therapeutic efficacy and an increase in side effects. The pharmacokinetics of known BTK inhibitors also needs to be improved. Indeed, significant variations in bioavailability of ibrutinib have been observed clinically among patients (Marostica et al., "Population pharmacokinetic model of ibrutinib, a Bruton tyrosine kinase inhibitor, in patients with B cell malignancies," Cancer Chemother Pharmacol, 2015, 75:111-121).

SUMMARY OF THE INVENTION

A novel series of multi-fluoro-substituted pyrazolopyrimidine compounds and the synthesis methods, as well as pharmaceutical compositions comprising the compounds described herein as an active ingredient and the methods of inhibiting BTK activities, are described. The compounds of interest include multi-fluoro-substituted compounds and the corresponding borate, multi-fluoro-substituted phenoxybenzene and the corresponding borate, and the synthesis methods. The polyfluorinated compounds contain at least two fluorine atoms.

One aspect of the invention described herein relates to a compound represented by Formula (I), or an enantiomer, diastereomer or pharmaceutically acceptable salt thereof:

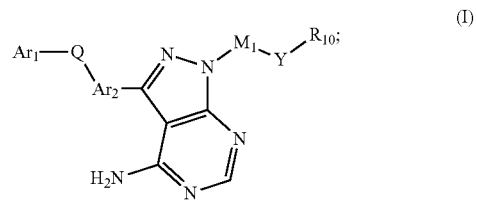

wherein $Ar_1$ and $Ar_2$ are represented by Formulae (III) and (IV), respectively:

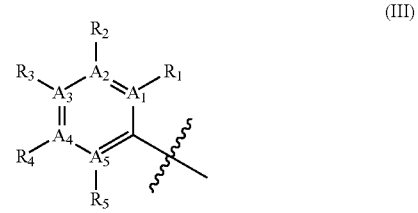

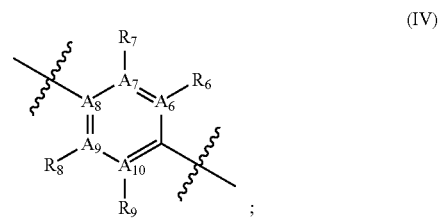

or are pyrimidine, or quinolone, wherein:

each of $A_1$, $A_2$, $A_3$, $A_4$, $A_5$, $A_6$, $A_7$, $A_8$, $A_9$ and $A_{10}$, independently, is C, each of $R_1$, $R_2$, $R_3$, $R_4$, $R_5$, $R_6$, $R_7$, $R_8$, and $R_9$, independently, is selected from H, $NO_2$, $CF_3$, Cl, or F wherein at least two of $R_1$, $R_2$, $R_3$, $R_4$, $R_5$, $R_6$, $R_7$, $R_8$, and $R_9$ are F, Q is O, S, $NR_a$, and —C(=O)—, wherein $R_a$ is acyl, alkyl, alkenyl or alkynyl;

$M_1$ is unsubstituted or substituted piperidinyl or pyrrolidinyl,

Y is C(=O), and $R_{10}$ is unsubstituted or substituted $C_2$-$C_6$ alkenyl or $C_2$-$C_6$ alkynyl, or an enantiomer, diastereomer, prodrug or pharmaceutically acceptable salt thereof.

In the compound, each H can be optionally substituted with deuterium.

In some embodiments, $Ar_1$ is represented by the following formula:

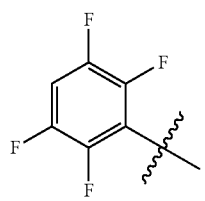

In some embodiments, Ar$_2$ is represented by a formula selected from the group consisting of

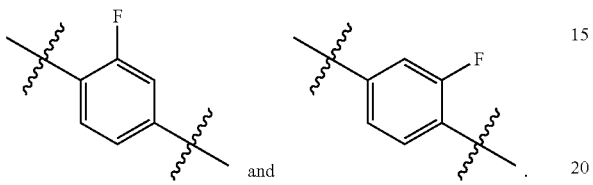

In some embodiments, the compound is represented by Formula (IX), or an enantiomer, diastereomer or pharmaceutically acceptable salt thereof:

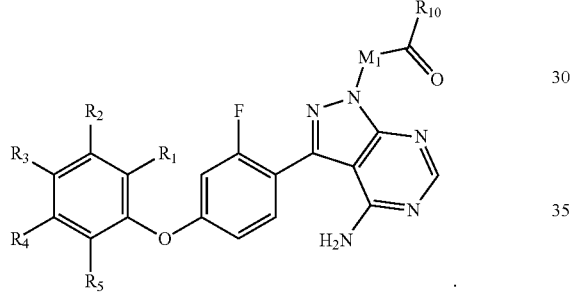

(IX)

In some embodiments, R$_1$, R$_2$, R$_4$ and R$_5$ are F, and R$_3$ is H. In some embodiments, R$_2$ is F, and R$_1$, R$_3$, R$_4$ and R$_5$ are H.

In some embodiments, M$_1$ is piperidinyl, and R$_{10}$ is vinyl, optionally substituted with deuterium. In some embodiments, M$_1$ is pyrrolidinyl, and R$_{10}$ is vinyl, optionally substituted with deuterium.

In some embodiments, R$_{10}$ is unsubstituted vinyl. In some embodiments, R$_{10}$ is deuterium-substituted vinyl.

In some embodiments, the compound is selected from the group consisting of:

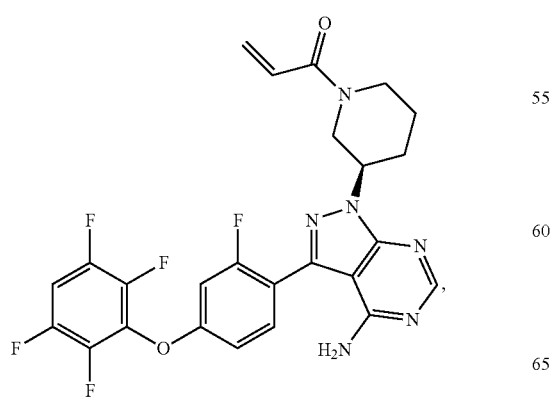

-continued

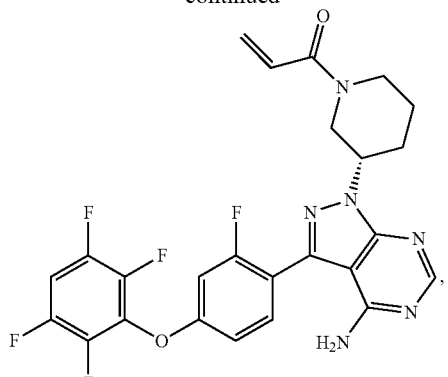

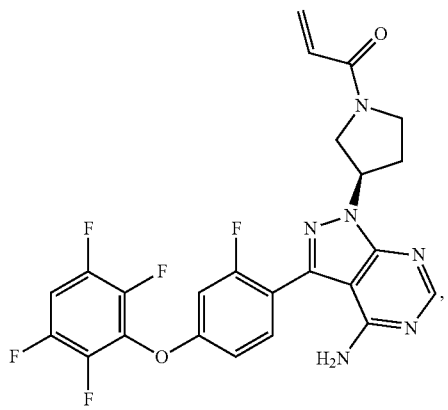

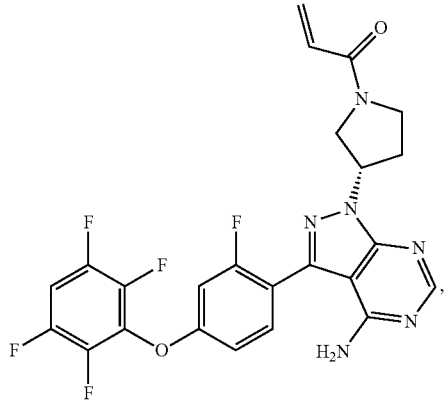

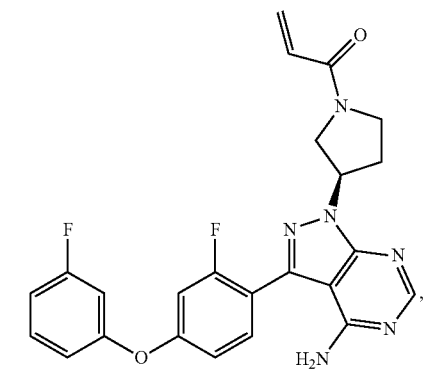

-continued

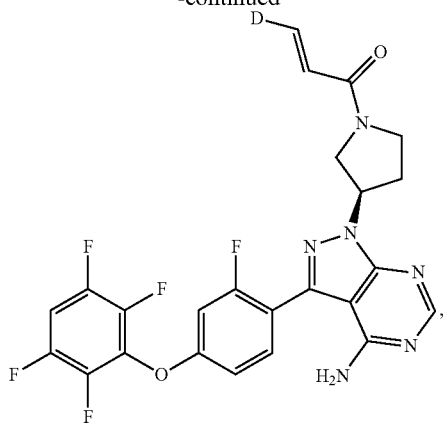

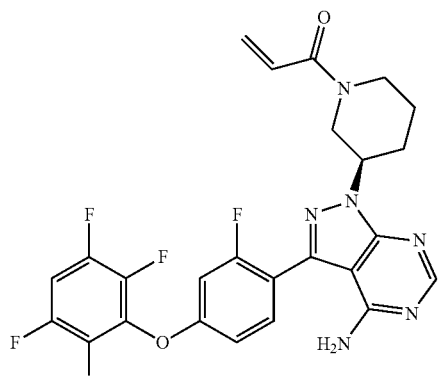

or an enantiomer, diastereomer, or pharmaceutically acceptable salt thereof.

In some embodiments, the compound is represented by the following formula:

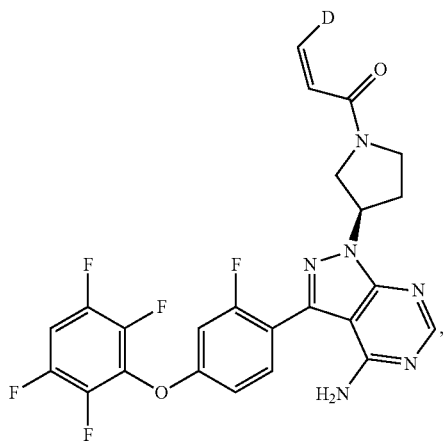

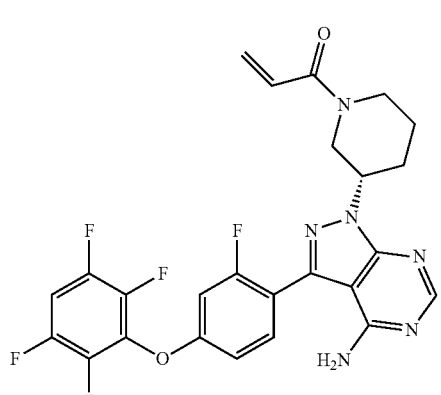

or an enantiomer, diastereomer, or pharmaceutically acceptable salt thereof.

In some embodiments, the compound is represented by the following formula:

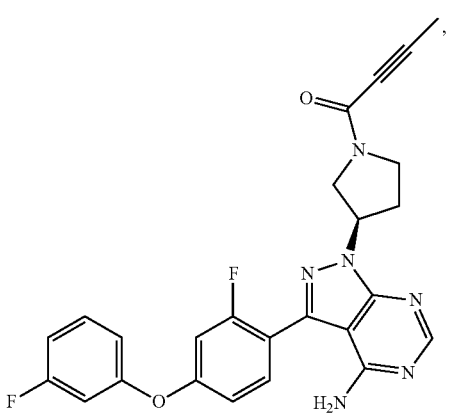

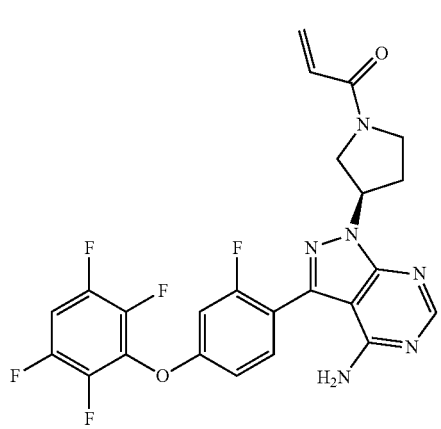 [SMILES: C=CC(=O)N1CC[C@@H](n2nc(-c3ccc(Oc4c(F)c(F)cc(F)c4F)cc3F)c3c(N)ncnc32)C1]

and enantiomers, diastereomers, and pharmaceutically acceptable salts thereof.

In some embodiments, the compound is represented by the following formula:

or an enantiomer, diastereomer, pharmaceutically acceptable salt thereof.

In some embodiments, the compound is represented by the following formula:

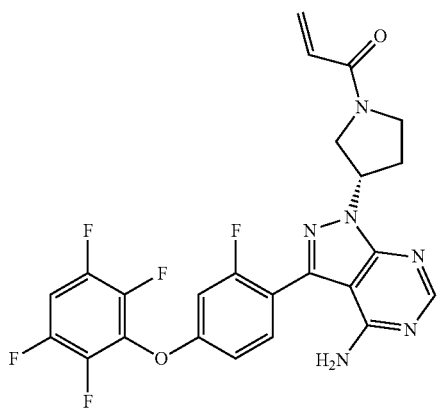 [SMILES: C=CC(=O)N1CC[C@H](n2nc(-c3ccc(Oc4c(F)c(F)cc(F)c4F)cc3F)c3c(N)ncnc32)C1]

or an enantiomer, diastereomer, or pharmaceutically acceptable salt thereof.

In some embodiments, the compound is represented by the following formula:

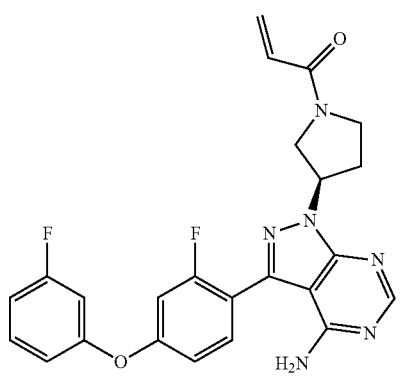 [SMILES: C=CC(=O)N1CC[C@@H](n2nc(-c3ccc(Oc4cccc(F)c4)cc3F)c3c(N)ncnc32)C1]

or an enantiomer, diastereomer, or pharmaceutically acceptable salt thereof.

In some embodiments, the compound is represented by the following formula:

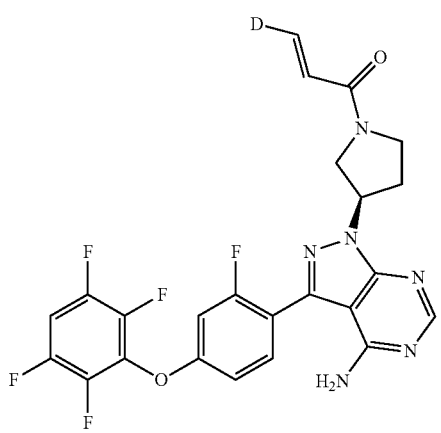 [SMILES: [2H]/C=C/C(=O)N1CC[C@@H](n2nc(-c3ccc(Oc4c(F)c(F)cc(F)c4F)cc3F)c3c(N)ncnc32)C1]

or an enantiomer, diastereomer, pharmaceutically acceptable salt thereof.

In some embodiments, the compound is represented by the following formula:

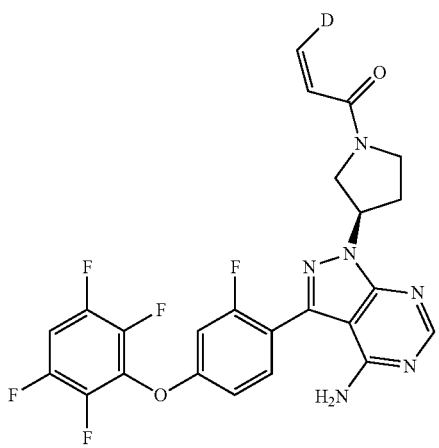 [SMILES: [2H]/C=C\C(=O)N1CC[C@@H](n2nc(-c3ccc(Oc4c(F)c(F)cc(F)c4F)cc3F)c3c(N)ncnc32)C1]

or an enantiomer, diastereomer, pharmaceutically acceptable salt thereof.

In some embodiments, the compound is represented by the following formula:

or an enantiomer, diastereomer, pharmaceutically acceptable salt thereof.

In some embodiments, the compound, enantiomer, diastereomer, or pharmaceutically acceptable salt inhibits Bruton's tyrosine kinase (BTK) with an $IC_{50}$ of 0.5 μM or less.

In some embodiments, the compound, enantiomer, diastereomer, or pharmaceutically acceptable salt inhibits BTK with an $IC_{50}$ of 0.05 μM or less.

Preferred BTK inhibitory compounds of the present invention include, but not limited to, Compound 11, 12, 13, 15, 16, 17, 18, 20, 21, 23, 33, 45, 47, 61, 72, 73, 74, 75, 87, 91, 94, 95, 98, 99, 100, 106, 116, 120, 121, and 123 (all compounds with $IC_{50}$ of less 10 nM) described herein.

Another aspect of the invention described herein relates to a pharmaceutical composition comprising the compound, enantiomer, diastereomer, or pharmaceutically acceptable salt described herein, and a carrier.

Another aspect of the invention described herein relates to a method for inhibiting BTK activity, comprising administering to a subject in need thereof a therapeutically effective amount of the compound, enantiomer, diastereomer, or pharmaceutically acceptable salt described herein.

A further aspect of the invention described herein relates to a method for treating an immune disorder, such as an autoimmune disease, inflammation, and hypersensitivity, comprising administering to a subject in need thereof a therapeutically effective amount of the compound, enantiomer, diastereomer, or pharmaceutically acceptable salt described herein.

A further aspect of the invention described herein relates to a method for treating a cancer, such as a hematological malignancy (e.g., a B-cell malignancy), comprising administering to a subject in need thereof a therapeutically effective amount of the compound, enantiomer, diastereomer, or pharmaceutically acceptable salt described herein.

These and other features, together with the organization and manner of operation thereof, will become apparent from the following detailed description and claims.

DETAILED DESCRIPTION OF THE INVENTION

Figure 1:
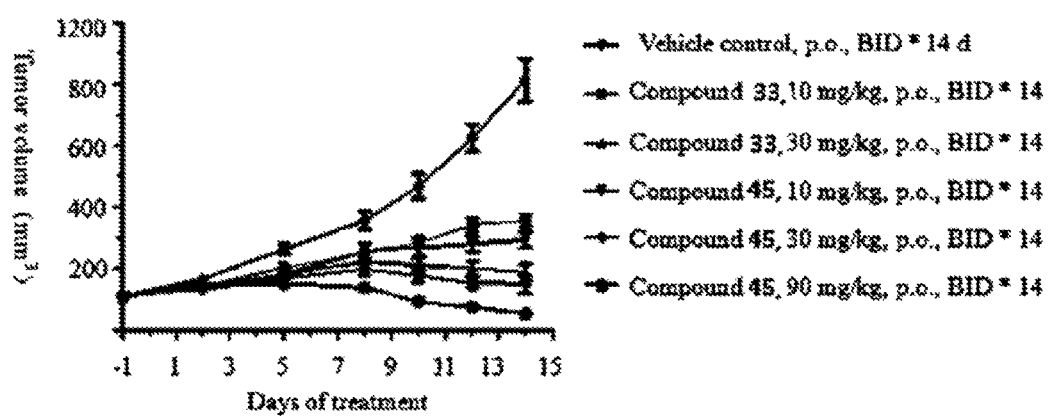
FIG. 1 is a graph showing the antitumor effect of multiple doses of Compounds 33 and 45 on tumor volume in a TMD-8 lymphoma xenograft SCID mouse model. "p.o., BID*14": by mouth twice a day, for 14 days.

Reference will now be made in detail to some specific embodiments of the invention contemplated by the inventors for carrying out the invention. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

The invention relates to the therapeutic methods to treat or inhibit an autoimmune disease, a hypersensitivity disease, an inflammatory disease, and cancer, including administering to a patient in need thereof a therapeutically effective amount of a compound that has a structure of Formula (I) or (II), or an enantiomer, diastereomer, or a pharmaceutically acceptable salt thereof.

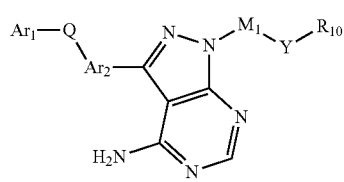

(I)

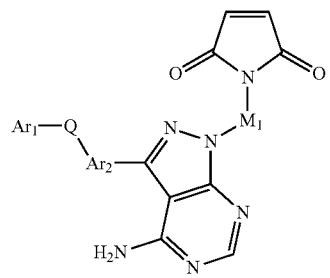

(II)

wherein:
Ar$_1$ and Ar$_2$ are independently selected from (III) and (IV):

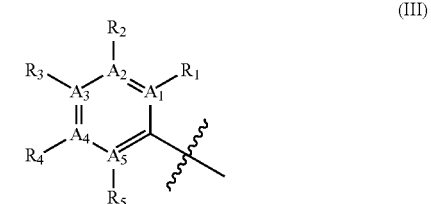

(III)

(IV)

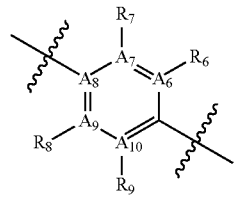

wherein:
each of A$_1$, A$_2$, A$_3$, A$_4$, A$_5$, A$_6$, A$_7$, A$_8$, A$_9$ and A$_{10}$, independently, is selected from C and N;
each of R$_1$, R$_2$, R$_3$, R$_4$, R$_5$, R$_6$, R$_7$, R$_8$, and R$_9$, independently, is selected from among hydrogen, deuterium, amino, halogen, hydroxy, carbonyl, nitro, cyano, amide, alkyl sulfonamide, C$_2$-C$_6$ alkenyl, C$_2$-C$_6$ alkynyl, trifluoromethyl, trifluoromethoxy, C$_1$-C$_6$ alkyl, C$_1$-C$_6$ alkoxyl, and C$_3$-C$_{10}$ cycloalkyl; wherein each of R$_1$-R$_9$ substituents is optionally substituted with one or more substituents independently selected from the group consisting of deuterium, halogen, amino, hydroxy, carbonyl, nitro, cyano, C$_1$-C$_6$ alkyl, and C$_1$-C$_6$ alkoxyl;
each of R$_6$, R$_7$, R$_8$, and R$_9$ with NH$_2$ can form a 6-8-membered cycloalkyl ring or heterocyclic ring;
Ar$_1$ is independently selected from benzoaryl and benzoheteroaryl, wherein said hydrogen is independently replaced with deuterium, halogen, amino, hydroxy, carbonyl, nitro, cyano, C$_1$-C$_6$ alkyl, or C$_1$-C$_6$ alkoxyl;
Q is O, S or C(=O);
M$_1$ is a saturated or unsaturated C$_1$-C$_8$ alkyl, aryl, alkylaryl, arylalkyl, heteroaryl, heteroaryl alkyl, alkyl heteroaryl, cycloalkyl, cycloalkyl alkyl, alkyl cycloalkyl, heterocycloalkyl, heterocycloalkyl alkyl, or alkyl heterocycloalkyl; wherein each of said alkyl, aryl, heteroaryl, cycloalkyl and heterocycloalkyl is optionally substituted with alkyl, cycloalkyl, alkoxyl, epoxyalkyl, amino, cyano, amide or halogen;
Y is C(=O), NR$_{11}$C(=O) or S(=O)$_2$;
each of R$_{10}$ and R$_{11}$, independently, is selected from among amino, azacycloalkyl, aryl, heteroaryl, heterocycloalkyl, epoxyalkyl, trifluoromethyl, trifluoromethoxy, trifluoroacetyl, amide, acyl, guanidyl, $C_2$-$C_6$ alkenyl, $C_2$-$C_6$ alkynyl, $C_1$-$C_6$ alkyl, $C_3$-$C_{10}$ cycloalkyl, $C_1$-$C_6$ alkoxyl, and $C_1$-$C_6$ oxoalkyl; wherein each pf said amino, amide, acyl, $C_2$-$C_6$ alkenyl, alkyl, alkoxyl and cycloalkyl is optionally substituted with one or more substituents independently selected from the group consisting of deuterium, halogen, amino, hydroxy, hydroxy alkyl, carbonyl, ester, amide, nitro, cyano, trifluoroacetyl, trifluoromethyl, trifluoromethoxy, $C_1$-$C_6$ alkyl, $C_1$-$C_6$ alkoxyl, $C_1$-$C_6$ oxoalkyl, and $C_3$-$C_{10}$ cycloalkyl.

The hydrogen atom connected with carbon or nitrogen in the described aryl or hetero-ring can be replaced with alkyl, cycloalkyl, alkoxyl, epoxyalkyl, amino, cyano, amide or halogen.

$Ar_1$ is preferably selected from below formula:

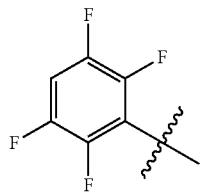 [SMILES: *c1c(F)c(F)cc(F)c1F]

Q is preferably O to form Formula (X) and (XI):

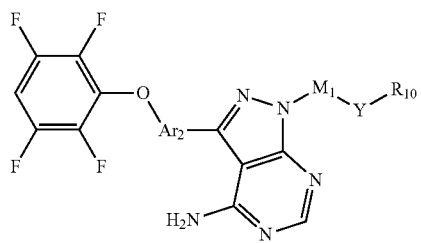
(X)

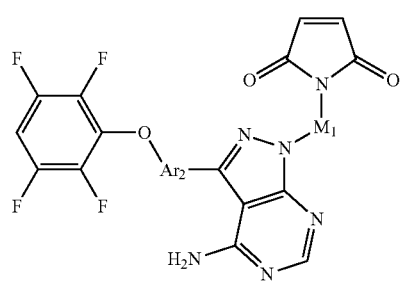
(XI)

wherein: $Ar_2$, $M_1$, Y and $R_{10}$ are defined as aforementioned.

Wherein: $Ar_2$ is phenyl or heteroaryl, preferably phenyl, and more preferably

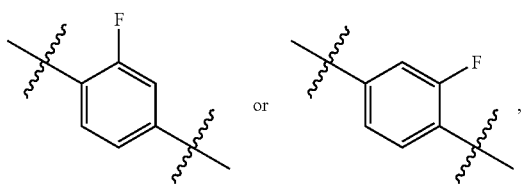 [SMILES: *c1ccc(*)c(F)c1 ; *c1ccc(*)c(F)c1]

more preferably

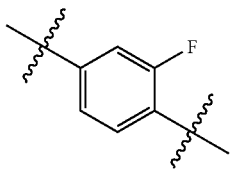 [SMILES: *c1ccc(*)c(F)c1]

therefore Formula (XII) and (XIII) are formed:

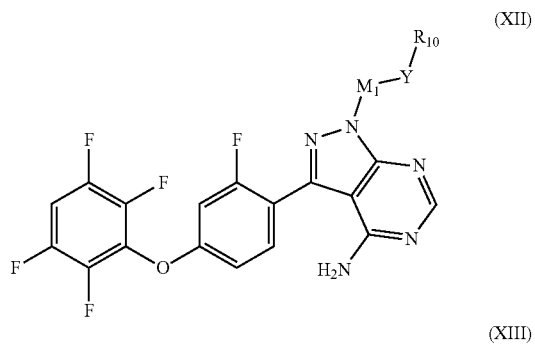
(XII)

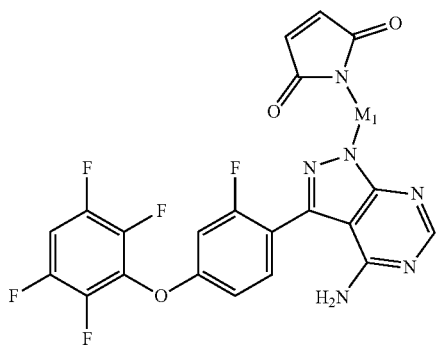
(XIII)

wherein:

$M_1$ is selected from saturated or unsaturated $C_1$-$C_8$ alkyl, cycloalkyl, cycloalkyl alkyl, alkyl cycloalkyl, heterocycloalkyl, heterocycloalkyl alkyl, and alkyl heterocycloalkyl; wherein each of said alkyl, aryl, heteroaryl, cycloalkyl and heterocycloalkyl is optionally substituted with alkyl, cycloalkyl, alkoxyl, amino, cyano, amide or halogen;

$M_1$ is preferably piperidinyl or pyrrolidinyl;

Y is C(=O), $NR_{11}$C(=O) or S(=O)$_2$, preferably C(=O) or $NR_{11}$C(=O), more preferably C(=O);

$R_{10}$ is independently selected from among amino, azacycloalkyl, aryl, heteroaryl, heterocycloalkyl, epoxyalkyl, trifluoromethyl, trifluoromethoxy, trifluoroacetyl, amide, acyl, guanidyl, $C_2$-$C_6$ alkenyl, $C_2$-$C_6$ alkynyl, $C_1$-$C_6$ alkyl, $C_3$-$C_{10}$ cycloalkyl, $C_1$-$C_6$ alkoxyl, and $C_1$-$C_6$ oxoalkyl; wherein said amino, amide, acyl, $C_2$-$C_6$ alkenyl, alkyl, alkoxyl and cycloalkyl are each optionally substituted with one or more substituents independently selected from the group consisting of deuterium, halogen, amino, hydroxy, hydroxy alkyl, carbonyl, ester, amide, nitro, cyano, trifluoroacetyl, trifluoromethyl, trifluoromethoxy, $C_1$-$C_6$ alkyl, $C_1$-$C_6$ alkoxyl, $C_1$-$C_6$ oxoalkyl, and $C_3$-$C_{10}$ cycloalkyl.

$R_{10}$ is the most preferably vinyl.

Unless specified otherwise, as used herein, the terms "alkyl," "alkenyl," and "alkynyl" refer to straight or branched alkyl groups containing 1 to 6 carbon atoms, and straight or branched "alkenyl" or "alkynyl" groups containing 2 to 6 carbon atoms, for example, methyl, ethyl, propyl, butyl, pentyl, hexyl, vinyl, propenyl, butenyl, pentenyl, hexenyl and isomers thereof.

The term "hydroxyl" refers to a group with a —OH.

The term "halo" or "halogen" refers to fluoro, chloro, bromo or iodo.

The term "cycloalkyl" refers to a monocyclic or polycyclic radical that contains only carbon and hydrogen. Each ring has 3 to 10 carbon atoms containing one or more double or triple bonds. Examples of cycloalkyl group include, but are not limited to, cyclopropyl, cyclobutyl, cyclopentyl, cyclohexyl and cycloheptyl. The term "cycloalkyl" also refers to spiral ring system, in which the cycloalkyl rings share one carbon atom.

The term "heterocycloalkyl" refers to a non-aromatic saturated 5- to 6-member ring that contains one or more heteroatoms each selected from N, O and S (including oxide thereof). The heterocycloalkyl group includes unsaturated ring or fused ring with phenyl, but not includes aza-bridged cyclic hydrocarbon group. Examples of heterocycloalkyl group includes, but are not limited to, aziridinyl, azetidinyl, pyrrolidinyl, piperidinyl, homopiperidinyl, morpholinyl, thiomorpholinyl, piperazinyl, tetrahydrofuranyl, tetrahydrothienyl, dihydrooxazolyl, tetrahydropyranyl, tetrahydrothiopyranyl, indolinyl, tetrahydroquinolyl, tetrahydroisoquinolin and benzoxazinyl, preferably dihydrooxazolyl and tetrahydrofuranyl.

The term "azacycloalkyl," belonging to "heterocycloalkyl," refers to a non-aromatic saturated 3- to 8-member ring that contains at least one nitrogen atom and one or more heteroatoms each selected from N, O and S (including oxide thereof), but not includes aza-bridged cyclic hydrocarbon group. Examples of azacycloalkyl group includes but are not limited to, aziridinyl, azetidinyl, pyrrolidinyl, piperidinyl, homopiperidinyl, morpholinyl, thiomorpholinyl, and piperazinyl.

The term "aryl" refers to an aromatic carbocyclic group, including phenyl, naphthyl and indenyl, preferably with 6 to 10 carbon atoms.

The term "heteroaryl" refers to a 5- or 6-membered aromatic heterocyclic group having one or more heteroatoms selected from the group consisting of a nitrogen atom, an oxygen atoms, and a sulfur atom. The term "heteroaryl" encompasses an aromatic heterocyclic group fused with benzyl group. Examples of heteroaryl group include, but are not limited to, pyridyl, pyrazinyl, pyrimidinyl, pyridazinyl, pyrrolyl, pyrazolyl, imidazolyl, oxazolyl, thiazolyl, thienyl, furyl, oxadiazolyl, thiadiazolyl, quinolinyl, isoquinolinyl, benzthiazolyl, benzoxazolyl, indolyl, indazolyl, quinoxalinyl, quinazolinyl, preferably pyridazinyl, pyridyl, pyrazinyl, pyrazolyl, thiazolyl, pyrazolyl and thio oxazolyl.

The term "bridged ring group means" refers to "bridged cyclic hydrocarbon group" and "aza-bridged cyclic hydrocarbon group."

The term "bridged cyclic hydrocarbon group" is a saturated or unsaturated, bridged bicyclic or polycyclic hydrocarbon group that contains two or three cycloalkyl rings with 3-10 carbon atoms. Unbridged cycloalkyl are not included. Particularly preferred are bridged bicyclic or polycyclic hydrocarbon group containing 4-16 carbon atoms. Examples of bridged cyclic hydrocarbon group include, but are not limited to, bicyclo[2.1.1]hexyl, bicyclo[2.2.1]heptyl, bicyclo[2.2.2]octyl, bicyclo[4.3.1]decyl, bicyclo[3.3.1]nonyl, bornyl, norbornene group, norbornyl, norbornenyl, 6,6-dimethyl-bicyclo[3.1.1]heptyl, tricyclo butyl and adamantyl, preferably adamantyl or bicyclo [2.2.1] heptyl.

The term "nitro" refers to a group with a —NO$_2$.

The term "amine" refers to unsubstituted or substituted —NH$_2$ containing one, two or three groups, for example, alkyl, alkenyl, alkynyl, aryl, etc.

The term "cyano" refers to a group with a —CN.

The term "alkoxy" refers to an alkyl group covalently linked to an oxygen atom, which is attached to another molecular moiety. Examples of cycloalkyl group include, but are not limited to, methoxyl, ethoxyl, propoxyl, isopropoxyl, n-butoxyl and tert-butoxyl.

The term "acyl" refers to —C(=O)-alkyl, —C(=O)-alkenyl, —C(=O)-alkynyl, —C(=O)-cycloalkyl, —C(=O)-heterocycloalkyl, —C(=O)-aryl, —C(=O)-heteroaryl, carbamoyl, —C(=O)—C(=O)-alkyl, —C(=O)—C(=O)—NH-alkyl. The terms "alkyl," "cycloalkyl," "heterocycloalkyl," "aryl," and "heteroaryl" herein have the same meaning as stated above.

The term "carboxyl" refers to a group with a —CO$_2$H or a salt thereof.

The term "trifloromethyl" refers to a group with a —CF$_3$.

The term "trifluoromethoxy" refers to a group with a —OCF$_3$.

The term "trifluoroacetyl" refers to a group with a CF$_3$C(=O)—.

The term "alkyl sulfonamide" refers to a group with —NR'S(=O)$_2$R. R can be alkyl, R' can be hydrogen or C$_1$-C$_6$ alkyl and the term "alkyl" has the same meaning as defined herein.

The term "amide" refers to a group with —C(=O)NHR or —NHC(=O)R. R can be alkyl, and the term "alkyl" has the same meaning as defined herein.

The term "ester" refers to a group with —C(=O)OR. R can be alkyl, and the term "alkyl" has the same meaning as defined herein.

When two or more terms are used in combination, for example, "alkylaryl" or "arylakyl," each term herein has the same meaning as defined above.

The term "pharmaceutically acceptable salt" refers to salts formed with acid or base, including, but not limited to, (a) acid addition salts: inorganic acid (e.g., hydrochloric acid, hydrobromic acid, sulfuric acid, phosphoric acid, nitric acid and other organic acids), and organic acid (e.g., acetic acid, oxalic acid, tartaric acid, succinic acid, malic acid, and ascorbic acid); (b) base addition salts, the formation of metal cations, such as zinc, calcium, sodium, and potassium.

The present invention encompasses prodrugs of the compounds described herein. The term "prodrug" refers to a biologically inactive compound that can be metabolized in the body to produce a drug. For example, a prodrug of a BTK inhibitor can be a prodrug at the amino group, for example, an amide, carbamate, or a polyethylene glycol.

The term "therapeutically effective amount" refers to an amount of a drug that is effective in treating the targeted disease as determined by healthcare professionals.

Nitrogen atom can form three bonds with other atoms. Any atom other than hydrogen has to be drawn. Hydrogen may or may not be clearly drawn as a typical practice by chemists. For example, R—N means R—NH$_2$, R—NC(=O)—W means R—NH(C=O)—W.

Synthesis Scheme

The examples and embodiments that exemplify the present invention are disclosed herein. The particular embodiment of the present invention is selected from the group of disclosed embodiments and their pharmaceutically acceptable salts thereof and their individual enantiomers, diastereomers or salts thereof.

The invention of synthesis methods have been actively explored. A variety of preparation methods were excluded (see Schemes 1-3), and then novel methods for the synthesis of pyrazolopyrimidine compounds were successfully designed (see Schemes 4-11 and the specific reaction instances).

Unless otherwise specified, in the following reaction schemes and discussion, $A_1$, $A_2$, $A_3$, $A_4$, $A_5$, $A_6$, $A_7$, $A_8$, $A_9$, $R_1$, $R_2$, $R_3$, $R_4$, $R_5$, $R_6$, $R_7$, $R_8$, $R_9$, $R_{10}$ have the same meaning as defined above.

Scheme 1

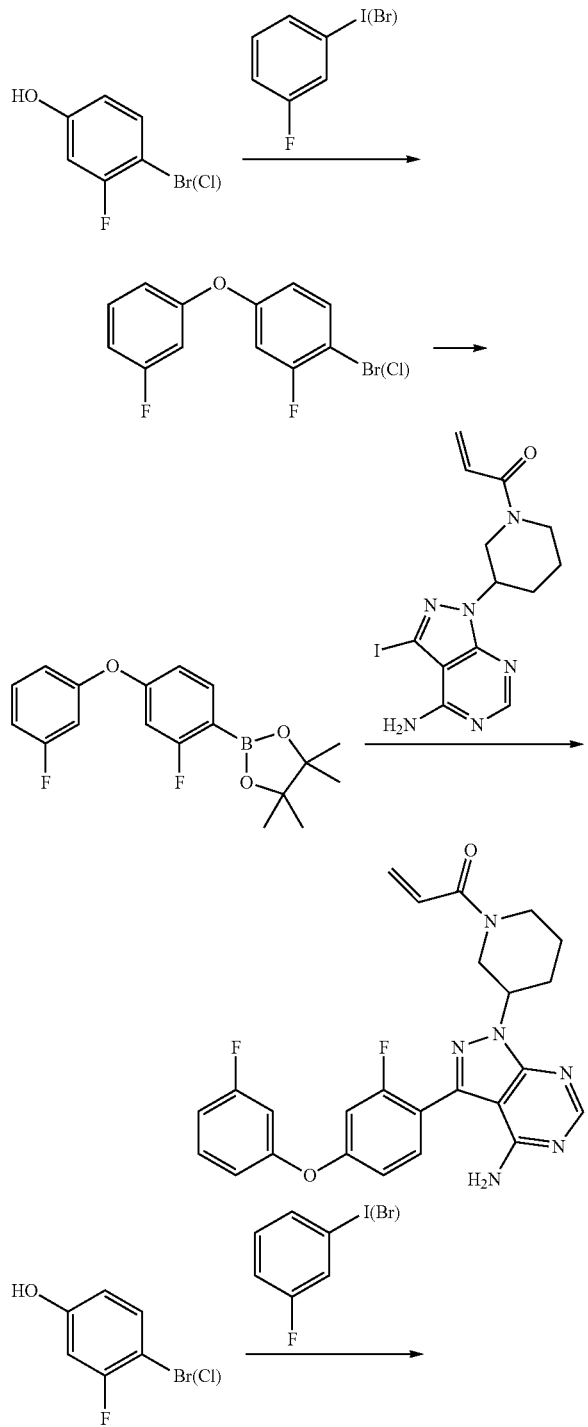

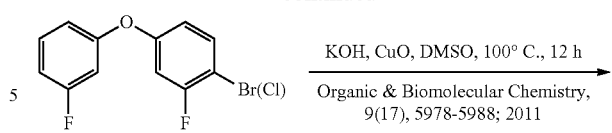

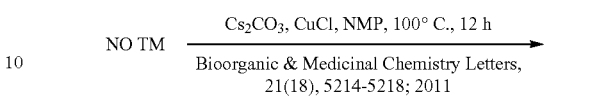

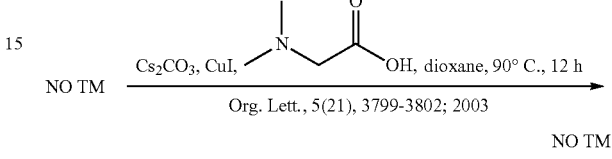

Scheme 1 was designed basing on the literature reported method: 3-fluoro-4-bromo-phenol (or 3-fluoro-4-chloro-phenol) and 3-iodo-fluorobenzene (or 3-fluoro-bromophenyl) under basic conditions was catalyzed by a copper reagent to form 1-bromo-2-fluoro-4-(3-fluorophenoxy)benzene (or 1-chloro-2-fluoro-4-(3-fluorophenoxy)benzene), and then treated with bis(pinacolato)borate with a suitable catalyst (e.g., [1,1'-bis(diphenylphosphino)ferrocene]dichloropalladium) to provide the corresponding boronate ester. The resulting boronate ester with a substituted 3-iodo-1H-pyrazolo[3,4-d]pyrimidin-4-amine in a suitable catalyst (e.g., Pd-118) afforded the desired compound by Suzuki reaction. For the first step, synthesis of 1-bromo-2-fluoro-4-(3-fluorophenoxy)benzene (or 1-chloro-2-fluoro-4-(3-fluorophenoxy)benzene), different the reaction conditions were tried according to the literature methods, including different bases (e.g., such as potassium carbonate, cesium carbonate), different copper catalysts (e.g., copper oxide, cuprous chloride, cuprous iodide) as well as different solvents (e.g., DMSO, N-methylpyrrolidone, 1,4-dioxane). No desired compound was not obtained with these methods.

Scheme 2

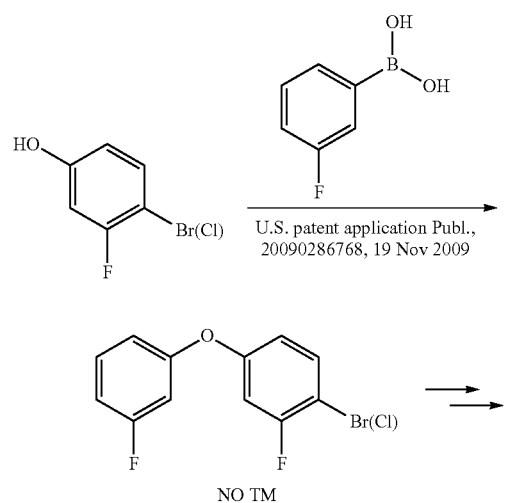

-continued

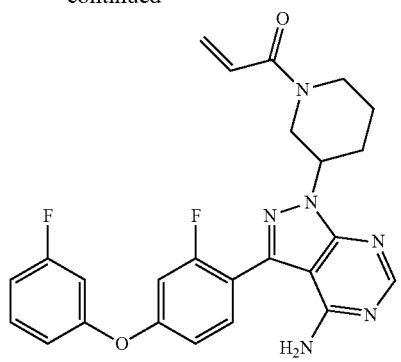

Scheme 2 was designed basing on the literature reported method: 3-fluoro-4-bromo-phenol (or 3-fluoro-4-chlorophenol) and 1-bromo-3-fluorophenyl boronic acid gave 2-fluoro-4-(3-fluorophenoxy)benzene (or 1-chloro-2-fluoro-4-(3-fluorophenoxy)benzene), which then was converted to the corresponding boronate ester and then generated the target compound. For the first step, synthesis of 1-bromo-2-fluoro-4-(3-fluorophenoxy)benzene (or 1-chloro-2-fluoro-4-(3-fluorophenoxy)benzene), different the reaction conditions were tried according to the literature methods, including different bases (e.g., triethylamine), different catalysts (e.g., copper acetate) and different solvents (e.g., dichloromethane). No desired compound was not obtained with these methods.

Scheme 3

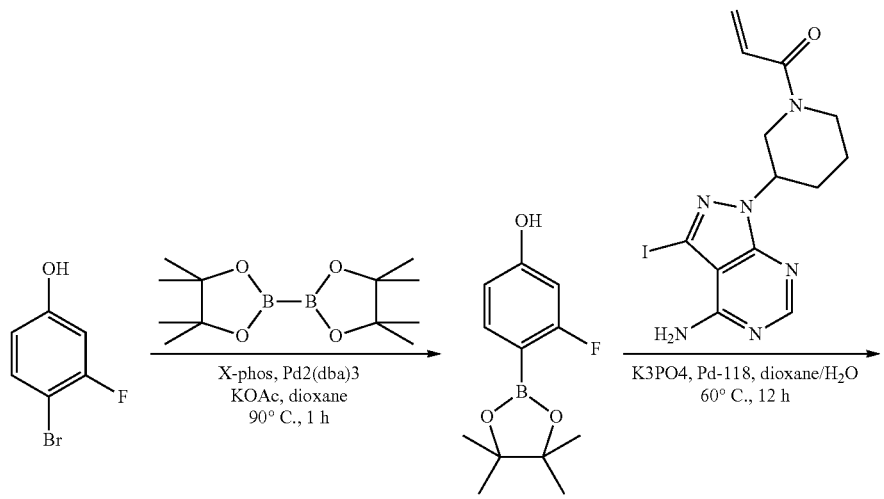

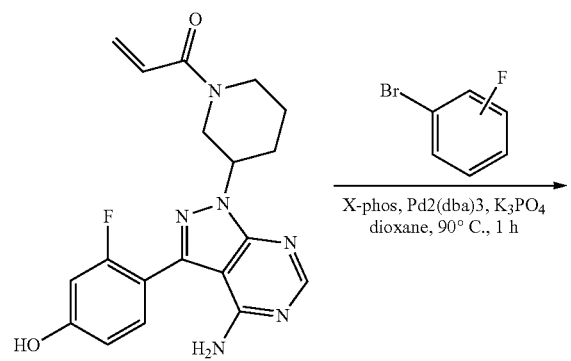

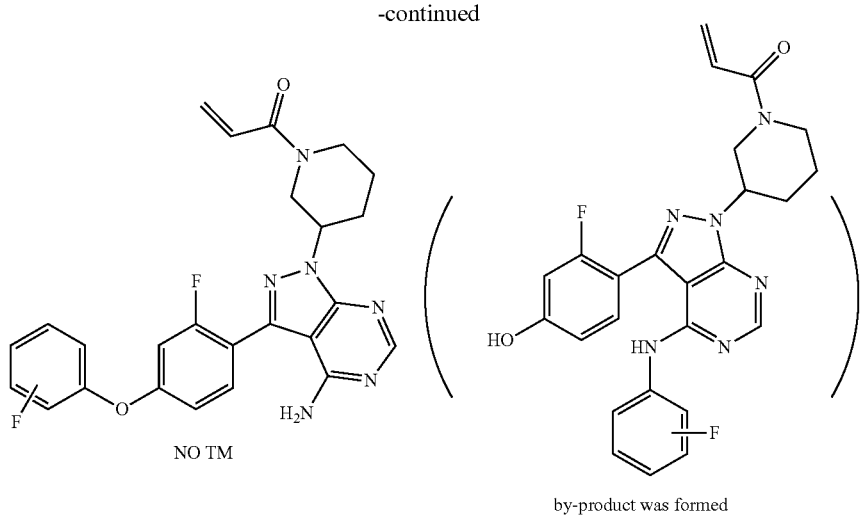

NO TM by-product was formed

Scheme 3 was designed basing on the literature reported method: 3-fluoro-4-bromo-phenol and bis(pinacolato)diboron with a suitable catalyst (e.g., $Pd_2(dba)_3$) and a suitable ligand (e.g., X-phos) gave the corresponding boronic acid ester. The resulting boronic acid ester and a substituted 3-iodo-1H-pyrazolo[3,4-d]pyrimidin-4-amine with a suitable catalyst (e.g., Pd-118) via Suzuki reaction formed the corresponding substituted 3-fluoro phenol, which was reacted with 3-fluoro-3-fluoro-bromobenzene (or 2-fluoro-bromobenzene) to generate the title compound under appropriate conditions. NMR, LCMS and biological activity data demonstrate that the resulting amino compound is alkylation product, rather than alkoxylation product.

Scheme 4

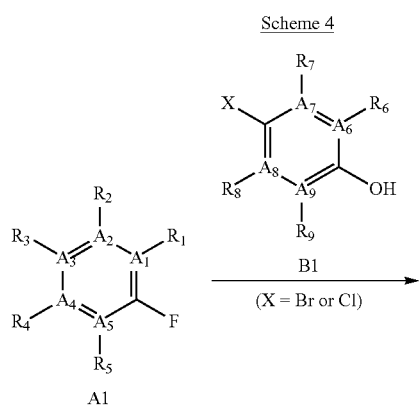

A1

B1
(X = Br or Cl)

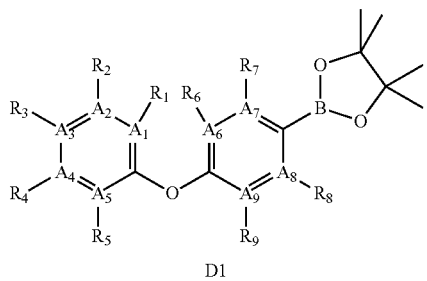

D1

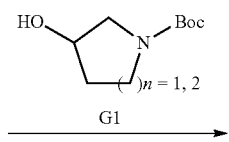

E1

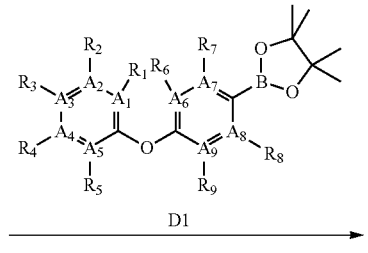

F1

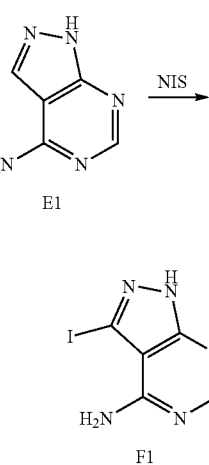

C1

H1

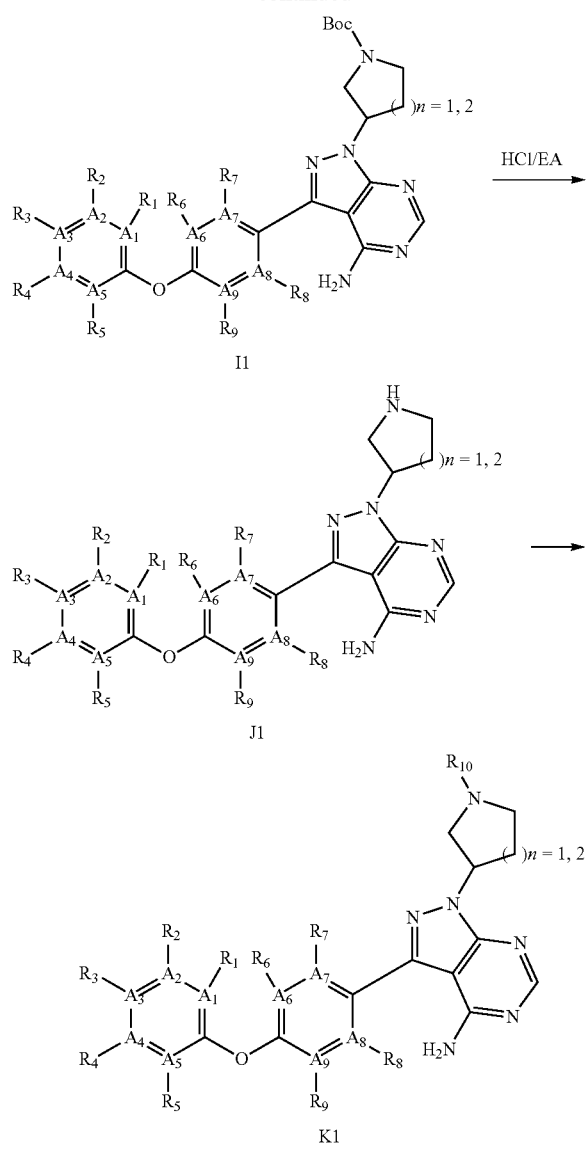
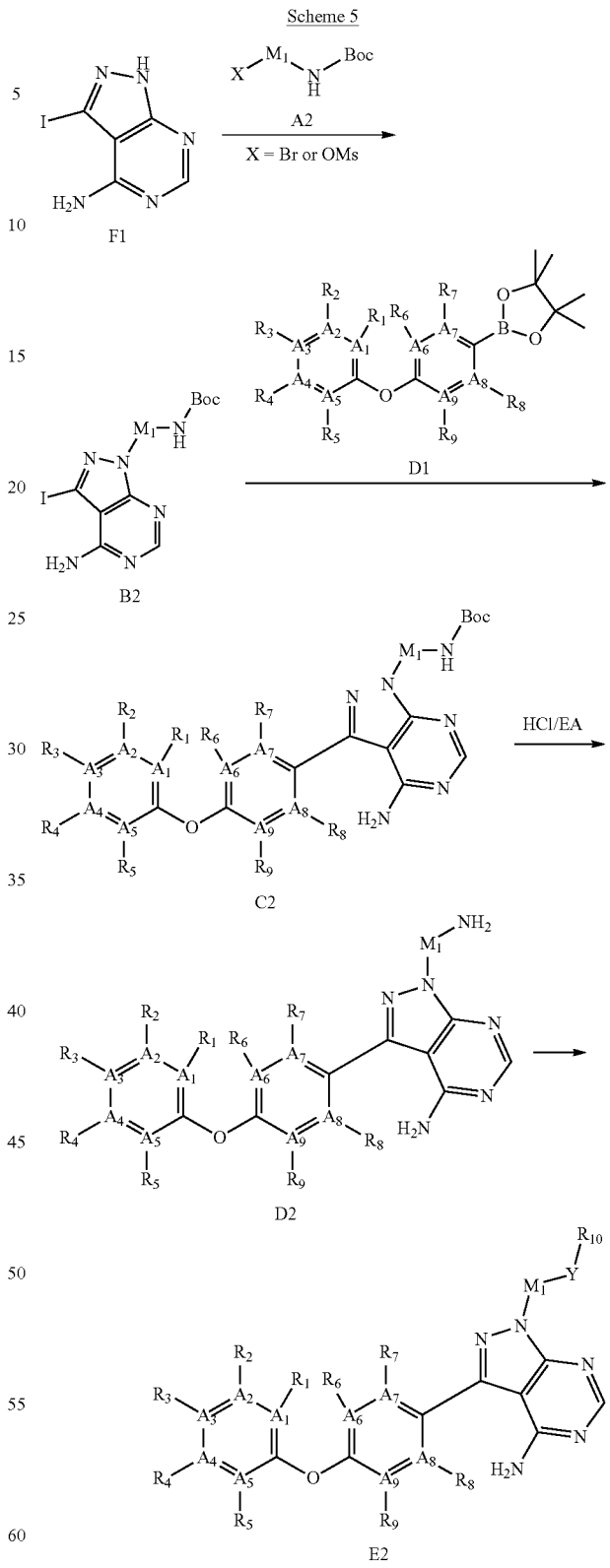

Fluoro-substituted starting material A1 was treated with substituted phenol B1 to generate intermediate C1 under basic condition (e.g., potassium carbonate) in a suitable solvent (e.g., DMF). Intermediate C1 then reacted with bis(pinacolato)diboron to give intermediate D1 with a suitable catalyst (e.g., [1,1'-bis(diphenylphosphino)ferrocene]dichloropalladium(II)) under basic condition (e.g., potassium acetate) in a suitable solvent (e.g., 1,4-dioxane). Iodination of 1H-pyrazolo[3,4-d]pyrimidin-4-amine with NIS formed intermediate F1, followed by Mitsunobu reaction or displacement reaction to furnish intermediate H1. Intermediate H1 was treated with compound D1 above obtained to give intermediate I1 with a suitable catalyst (e.g., Pd-118) under basic condition (e.g., potassium phosphate) in a suitable solvent (e.g., 1,4-dioxane). De-Boc protection of intermediate I1 gave amine J1 under acidic condition, which was reacted with an electrophilic reagent to form amide K1.

Intermediate F1 and Boc-protected bromo compound A2 (or mesylate) gave intermediate B2 under basic condition (e.g., potassium carbonate or cesium carbonate) in a suitable solvent (e.g., DMF). Intermediate B2 then reacted with heterocyclic borate D1 to give intermediate C2 via Suzuki coupling reaction with a suitable catalyst (e.g., Pd(PPh₃)₄) under basic condition (e.g., sodium carbonate) in a suitable solvent (e.g., 1,4-dioxane and H₂O). De-Boc protection of intermediate C2 gave amine D2 under acidic condition, which was reacted with an electrophilic reagent to form amide E2.

Scheme 6

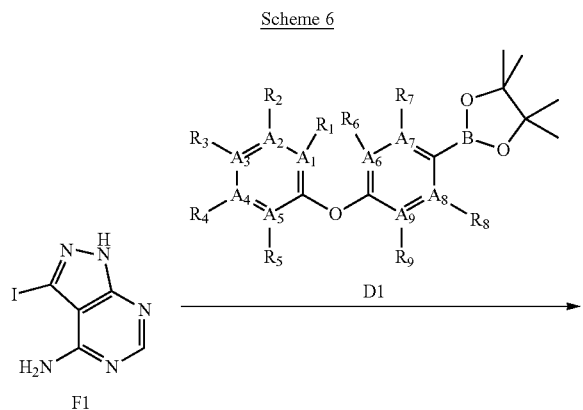

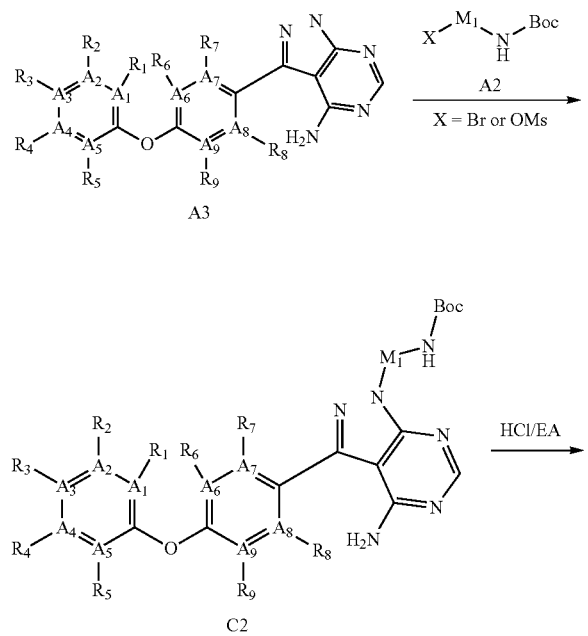

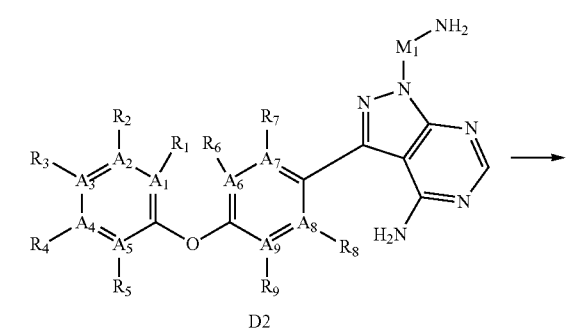

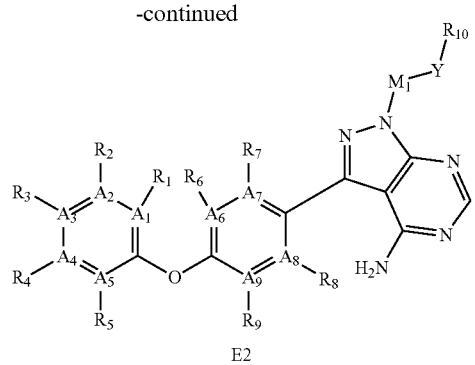

Intermediate F1 and heterocyclic borate D1 to give intermediate A3 via Suzuki coupling reaction with a suitable catalyst (e.g., Pd(PPh₃)₄) under basic condition (e.g., sodium carbonate) in a suitable solvent (e.g., 1,4-dioxane and H₂O). Intermediate A3 and Boc-protected bromo compound A2 (or mesylate) gave intermediate C2 under basic condition (e.g., potassium carbonate or cesium carbonate) in a suitable solvent (e.g., DMF). De-Boc protection of intermediate C2 gave amine D2 under acidic condition, which was reacted with an electrophilic reagent to form amide E2.

Scheme 7

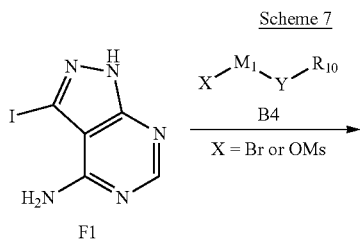

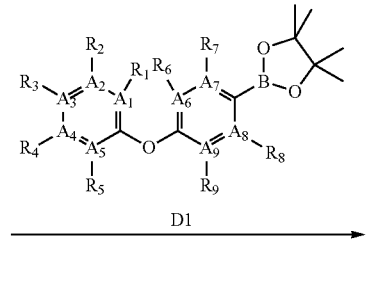

Intermediate F1 and Boc-protected bromo compound B4 (or mesylate) gave intermediate A4 under basic condition (e.g., potassium carbonate or cesium carbonate) in a suitable solvent (e.g., DMF). Intermediate A4 then reacted with heterocyclic borate D1 to give title compound E2 via Suzuki coupling reaction with a suitable catalyst (e.g., Pd(PPh$_3$)$_4$) under basic condition (e.g., sodium carbonate) in a suitable solvent (e.g., 1,4-dioxane and H$_2$O).

Starting material Grinard reagent A5 with bromo (or chloro) aryl aldehyde gave intermediate C5 in a suitable solvent (e.g., tetrahydrofuran), which was then oxidized to ketone D5 with suitable oxidation reagents (e.g., tetrapropylammonium perruthenate and N-methyl morpholine oxide) in a suitable solvent (e.g., dichloromethane). Intermediate D5 then reacted with bis(pinacolato)diboron to give intermediate E5 with a suitable catalyst (e.g., [1,1'-bis(diphenylphosphino)ferrocene]dichloropalladium(II)) under basic condition (e.g., potassium acetate) in a suitable solvent (e.g., 1,4-dioxane). Intermediate A4 then reacted with heterocyclic borate E5 to give title compound F5 via Suzuki coupling reaction with a suitable catalyst (e.g., Pd(PPh$_3$)$_4$) under basic condition (e.g., sodium carbonate) in a suitable solvent (e.g., 1,4-dioxane and H$_2$O).

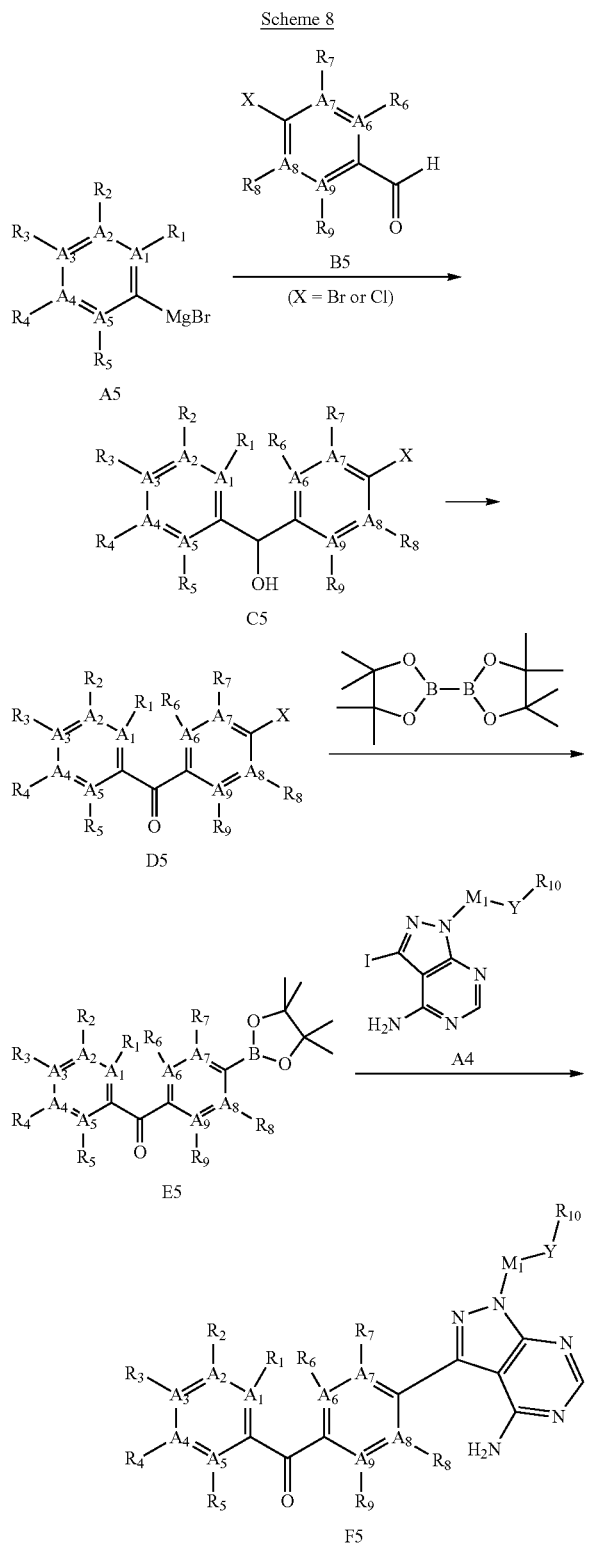

Scheme 8

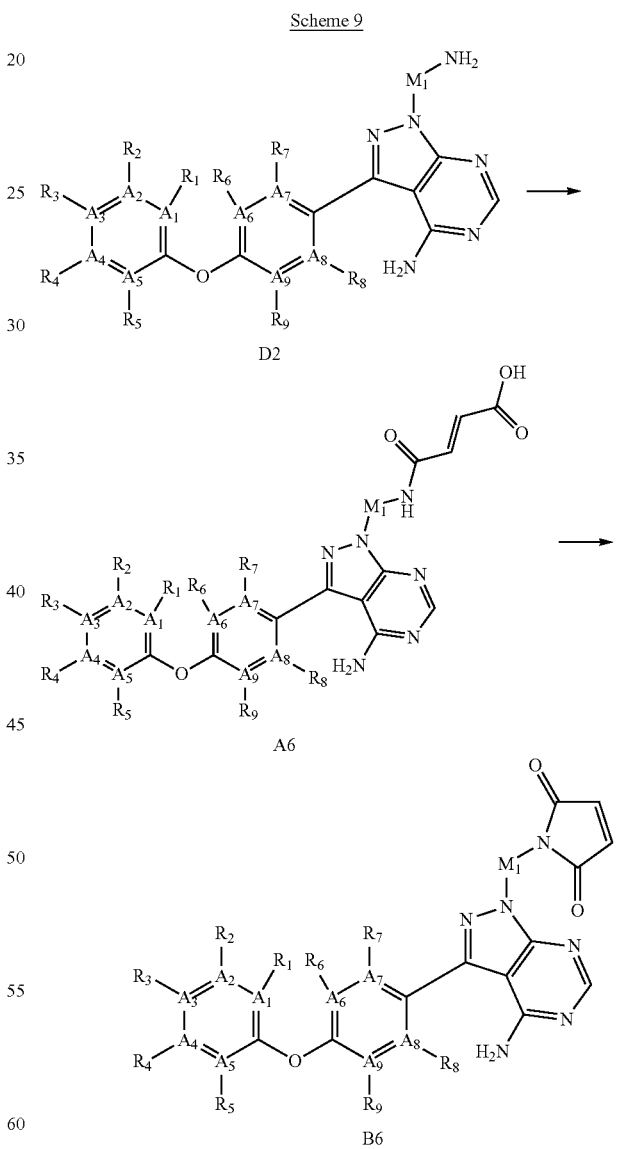

Scheme 9

Compound D2 was treated with maleic anhydride provided intermediate A6 under basic condition (e.g., sodium carbonate) in a suitable solvent (e.g., dichloromethane), which was then cyclized to form B6 at suitable temperature (e.g., 100° C.-110° C.) with polyphosphoric acid.

Scheme 10

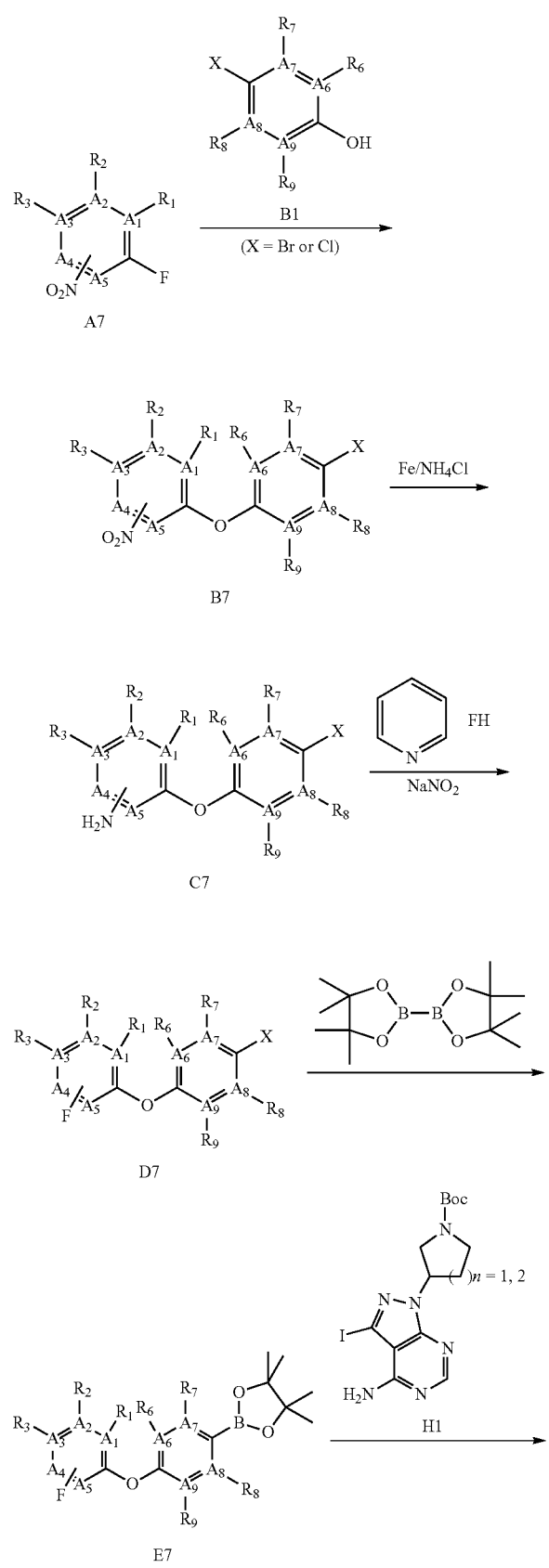

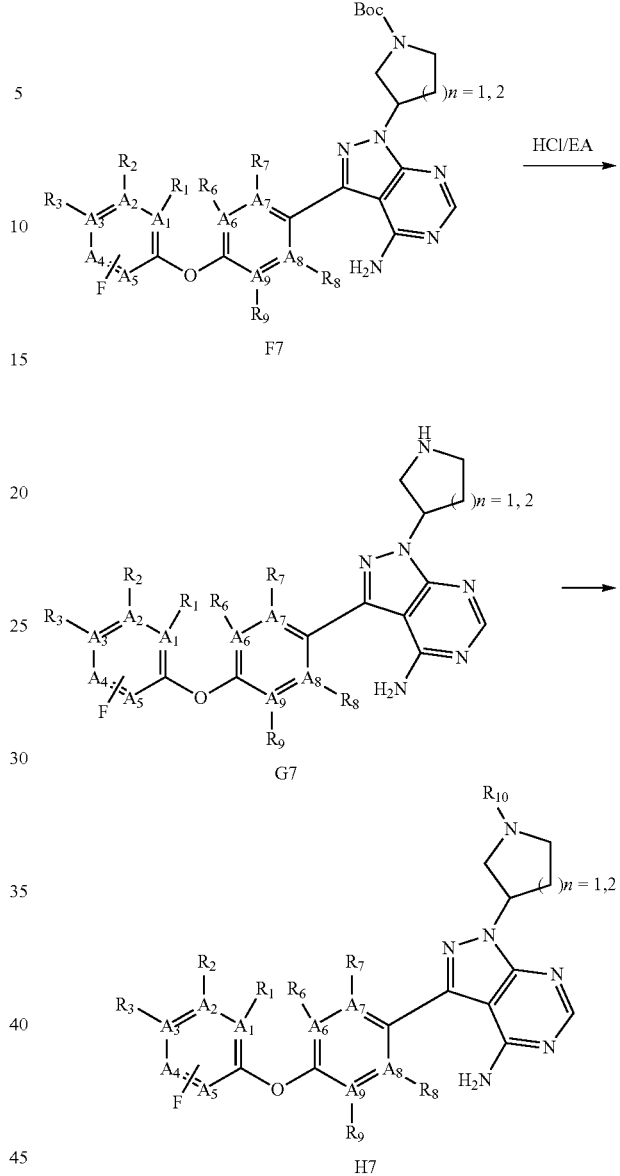

Starting material A7 reacted with substituted phenol B1 to generate intermediate B7 with a base (e.g., potassium carbonate) in a suitable solvent (e.g., DMF). The obtained nitro compound B7 was reduced to the amine C7 with appropriate reducing reagents (e.g., iron powder and ammonium chloride) in appropriate solvents (e.g., ethanol and water), followed by treatment with sodium nitrite and hydrogen fluoride pyridine to generate fluoro-substituted intermediate D7. Intermediate D7 then reacted with bis(pinacolato)diboron to give intermediate E7 with a suitable catalyst (e.g., [1,1'-bis(diphenylphosphino)ferrocene]dichloropalladium(II)) under basic condition (e.g., potassium acetate) in a suitable solvent (e.g., 1,4-dioxane). Intermediate H1 was treated with compound E7 above obtained to give intermediate F7 with a suitable catalyst (e.g., Pd-118) under basic condition (e.g., potassium phosphate) in a suitable solvent (e.g., 1,4-dioxane). De-Boc protection of intermediate F7 gave amine G7 under acidic condition, which was reacted with an electrophilic reagent to form amide H7.

Scheme 11

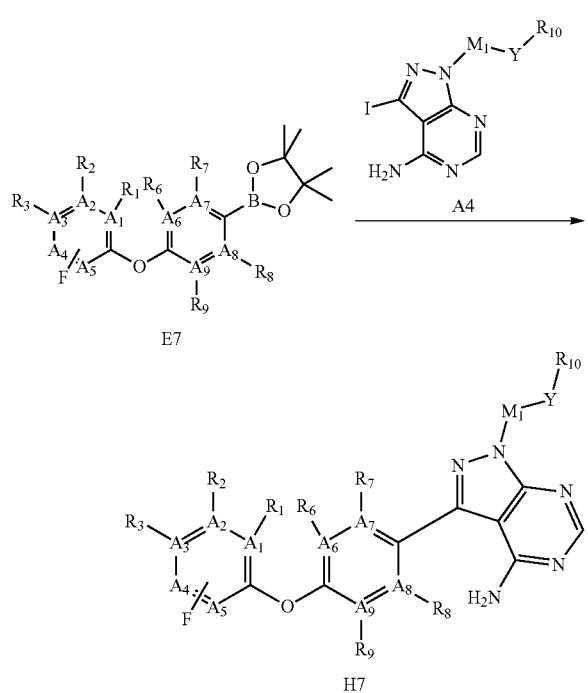

Intermediate A4 then reacted with heterocyclic borate E7 to give title compound A8 via Suzuki coupling reaction with a suitable catalyst (e.g., Pd(PPh$_3$)$_4$) under basic condition (e.g., sodium carbonate) in a suitable solvent (e.g., 1,4-dioxane and H$_2$O).

The table below shows assay data for representative compounds.

TABLE 1

Assay data for representative compounds

| Compound No. | BTK IC$_{50}$ (μM) | Compound No. | BTK IC$_{50}$ (μM) | Compound No. | BTK IC$_{50}$ (μM) |
|---|---|---|---|---|---|
| 1 | 0.066 | 2 | 0.005 | 3 | 0.010 |
| 4 | 0.002 | 5 | 0.002 | 6 | 0.138 |
| 7 | 0.73 | 8 | 0.002 | 9 | 0.083 |
| 10 | 1.970 | 11 | 0.0008 | 12 | 0.002 |
| 13 | 0.001 | 14 | 0.009 | 15 | 0.003 |
| 16 | 0.003 | 17 | 0.004 | 18 | 0.003 |
| 19 | 0.067 | 20 | 0.004 | 21 | 0.005 |
| 22 | 0.050 | 23 | 0.003 | 24 | 1.020 |
| 25 | 0.017 | 26 | 0.034 | 27 | 0.223 |
| 28 | 0.007 | 29 | 0.026 | 30 | 0.024 |
| 31 | 0.015 | 32 | 7.222 | 33 | 0.002 |
| 34 | 0.023 | 35 | 0.081 | 36 | 0.593 |
| 37 | 0.099 | 38 | 0.379 | 39 | 0.022 |
| 40 | 1.640 | 41 | 0.017 | 42 | 0.038 |
| 43 | 0.131 | 44 | 0.374 | 45 | 0.0005 |
| 46 | 0.021 | 47 | 0.006 | 48 | 0.964 |
| 49 | 0.509 | 50 | 0.087 | 51 | 0.527 |
| 52 | 0.060 | 53 | 1.653 | 54 | 1.617 |
| 55 | 1.740 | 56 | 0.365 | 57 | 0.692 |
| 58 | 0.148 | 59 | 0.174 | 60 | 0.576 |
| 61 | 0.0008 | 62 | 0.207 | 63 | 0.454 |
| 64 | 0.006 | 65 | 0.119 | 66 | 0.729 |
| 67 | 0.586 | 68 | 0.279 | 69 | 0.052 |
| 70 | 0.017 | 71 | 0.006 | 72 | 0.001 |
| 73 | 0.006 | 74 | 0.003 | 75 | 0.003 |
| 76 | 0.027 | 77 | 0.201 | 78 | 1.900 |
| 79 | 1.658 | 80 | 1.278 | 81 | 2.237 |
| 82 | 0.025 | 83 | 0.075 | 84 | 0.016 |
| 85 | 0.017 | 86 | 0.008 | 87 | 0.008 |
| 88 | 0.011 | 89 | 0.025 | 90 | 0.015 |
| 91 | 0.003 | 92 | 2.398 | 93 | 2.648 |
| 94 | 0.001 | 95 | 0.005 | 96 | 0.013 |
| 97 | 0.006 | 98 | 0.002 | 99 | 0.002 |
| 100 | 0.002 | 101 | 0.525 | 102 | 1.599 |
| 103 | 0.546 | 104 | 0.107 | 105 | 0.589 |
| 106 | 0.003 | 107 | 0.101 | 108 | 0.436 |
| 109 | 1.282 | 110 | 5.272 | 111 | 0.043 |
| 112 | 0.107 | 113 | 0.207 | 114 | 0.050 |
| 115 | 0.013 | 116 | 0.001 | 117 | 0.712 |
| 118 | 0.057 | 119 | 0.083 | | |

The invention provides a compound of Formula (I)-(XIII), enantiomers thereof, diastereomers thereof, or pharmaceutically acceptable salts thereof.

A compound of Formula (I)-(XIII) comprises one or more stable isotopes or radio isotopes, wherein the autoimmune disease includes, but not limited to, $^2$H, $^3$H, $^{13}$C, $^{14}$C, $^{15}$N, $^{18}$O and so on.

The present invention first introduces $^2$H, isotope of $^1$H, to BTK inhibitor.

$^1$H, which is at the end of the double bond of the vinyl group in the compound of Formula (I)-(XIII), might be replaced with $^2$H to reduce the drug inactivation caused by the oxidation/reduction of double bond.

The invention provides the synthetic methods of a compound of Formula (I)-(XIII), enantiomers thereof and diastereomers thereof.

Pharmacokinetic analysis of the Compounds can be performed as descried in Marostica et al., "Population pharmacokinetic model of ibrutinib, a Bruton tyrosine kinase inhibitor, in patients with B cell malignancies," Cancer Chemother Pharmacol, 2015, 75:111-121. The content of this publication is herein incorporated by reference in its entirety.

Toxicity and toxicokinetic (TK) studies of the compounds can be performed by well known methods. Applicant's TK studies showed that the BTK-inhibitory Compounds described herein had better safety profiles than ibrutinib in 28-day rat and dog studies. For example, Compound 45 demonstrated the following advantageous characteristics:

(i) higher no-observed-adverse-effect-level (NOAEL) than ibrutinib;

(ii) 5- to 14-fold higher exposure than ibrutinib at the same dose of 40 mg/kg in rats on day 1;

(iii) when administered to rats at 40 mg/kg, AUC (area under the curve) 13,700 h*ng/mL (male) and 17,300 h*ng/mL (female), as compared to 1,000 h*ng/mL (male) and 3300 h*ng/mL (female) for ibrutinib at 40 mg/kg (according to U.S. FDA NDA Application No. 205552Orig1s000_pharmacological review);

(iv) when administered to dogs at 15 mg/kg, AUC 3,550 (male) and 2,930 (female) h*ng/mL, as compared to AUC 1,780 (male) and 1,850 (female) h*ng/mL for ibrutinib at 24 mg/kg ((according to U.S. FDA NDA Application No. 205552Orig1s000_pharmacological review);

(v) no significant difference in drug exposure between Day 1 and Day 28, and (vi) no significant difference in drug exposure between male and female.

These characteristics show that Compound 45 has low toxicity, excellent pharmacokinetics, and superior bioavailability when compared to ibrutinib.

The BTK inhibitory compounds described herein, including those with Formula (I)-(XIII) can be provided as active ingredients in the pharmaceutical compositions of the invention for use in regulating the activity of BTK, and treating or preventing diseases associated with the activity of BTK, wherein inhibition of BTK is beneficial. These diseases, include, but are not limited to: (1) autoimmune diseases, such as chronic lymphocytic thyroiditis, hyperthyroidism, insulin-dependent diabetes mellitus, myasthenia gravis, chronic ulcerative colitis, ulcerative colitis, Crohn's disease, inflammatory bowel disease, pernicious anemia associated with chronic atrophic gastritis, Goodpasture's syndrome, pemphigus vulgaris, pemphigoid, primary biliary cirrhosis, multiple cerebrospinal sclerosis, acute idiopathic neuritis, systemic lupus erythematosus, rheumatoid arthritis, psoriasis, systemic vasculitis, scleroderma, pemphigus, mixed connective tissue disease, multiple sclerosis, autoimmune hemolytic anemia, and autoimmune thyroid disease; (2) hypersensitivity diseases, such as serum sickness, asthma, allergic rhinitis, and drug allergy; and (3) inflammatory diseases, such as keratitis, rhinitis, stomatitis, mumps, pharyngitis, tonsillitis, tracheitis, bronchitis, pneumonia, myocarditis, gastritis, gastroenteritis, cholecystitis, appendicitis. The therapies may also be used in treating rejection in transplantation.

The present compounds and compositions can also be used to treat a variety of cancer, including hematological malignanciesvarious such as B-cell malignancies, e.g., small lymphocytic lymphoma (SLL), prolymphocytic leukemia (PLL), acute lymphocytic leukemia (ALL), chronic lymphocytic leukemia (CLL), Richter's syndrome, diffuse large B-cell lymphoma (DLBCL), Waldenstrom Macroglobulinemia (WM), follicular lymphoma (FL), mantle cell lymphoma (MCL)), Hodgkin lymphoma, non-Hodgkin lymphoma, and T cell lymphomas.

Other diseases, which would benefit from inhibition of BTK activity, include but not limited to: brain tumors, bladder cancer, stomach cancer, ovarian cancer, pancreatic cancer, breast cancer, head and neck cancer, cervical cancer, endometrial cancer, colorectal cancer, kidney cancer, esophageal cancer, adenocarcinoma of the previous example, thyroid cancer, bone cancer, skin cancer, colon cancer, female reproductive tract tumors, lymphomas, multiple myeloma (MM), testicular cancer and so on.

The method herein includes administering to a patient in need thereof a therapeutically effective amount of a compound described herein. According to standard pharmaceutical practice, the BTK inhibitory compounds of the invention can be used alone in a pharmaceutical formulation or with one or more additional drugs in a pharmaceutical combination, wherein the pharmaceutical formulation comprising BTK inhibitors and the additional drugs may have the same or different administration route, and the same or different administration time. The additional drugs herein include (but are not limited to) other tyrosine kinase inhibitors (e.g., Axitinib, Dasatinib, Icotinib), topoisomerase inhibitors (e.g., topotecan), protein kinase C inhibitors (e.g., AEB-071), sphingosine-1-phosphate receptor agonist (e.g., fingolimod, KRP-203), anti-T cell immunoglobulin (e.g., AtGam), anti-IL-2 receptor antibody (e.g., daclizumab), amides (CTX), ifosfamide (IFO), adriamycin (ADM), daunorubicin (DNR), vincristine (VCR), vinblastine (VBL), etoposide (VP16), vermeer (Vumon), carboplatin (CBP) and methotrexate (MTX) cyclosporin A, tacrolimus, sirolimus, everolimus, azathioprine, brequinar, leflunomide, LEA-29Y, anti-CD3 antibody (e.g., 0KT3), aspirin, B7-CD28 blocking molecules (e.g., belatacept, abatacept), CD40-CD154 blocking molecules (anti-CD40 antibodies), acetaminophen, ibuprofen, naproxen, piroxicam, and antiinflammatory steroids (e.g., prednisolone or dexamethasone)

Carriers, excipients and other additives commonly used for pharmaceutical preparations may be used to prepare pharmaceutical compositions containing one or two or more compounds of formula (I)-(XIII) or pharmaceutically acceptable salts thereof as active ingredients.

The administration forms may be oral dosage forms, such as tablets, pills, capsules, granules, powders, emulsions, syrups, suspensions, liquid preparations, or non-oral dosage forms, such as intravenous injection or intramuscular injection, suppository, subcutaneous agent, transdermal agent, nasal agent, inhalation. Symptoms, age, weight, sex, and other relevant medical information of the individual patient should be considered in order to properly determine the dose of a compound. Generally speaking, in the case of oral administration, daily doses for adult patients of the compound is about 0.001 mg/kg to 100 mg/kg, a single dose or divided into 2 to 4 times daily. In the case of intravenous administration according to the patient symptoms, generally speaking, daily doses for adult patients are 0.0001 mg/kg to 10 mg/kg, once to more times daily. Further, in the case of using the inhalant administration, generally speaking, daily doses for adult patients is 0.0001 mg/kg to 1 mg/kg, once to more times daily.

In the present invention, solid compositions for oral administration may be tablets, powders, granules and the like. In such solid compositions, one or more active substance with at least one inert excipient (e.g., lactose, mannitol, glucose, hydroxypropylcellulose, microcrystalline cellulose, starch, poly vinyl pyrrolidone, magnesium aluminum silicate, etc.) were mixed. According to a conventional method, the composition may contain inert additives such as lubricants (e.g., magnesium stearate), disintegrating agents (e.g., sodium carboxymethyl starch) and dissolution aids. If necessary, tablets or pills may be coated with sugar coating or a gastric or enteric coating agent.

The liquid compositions for oral administration include pharmaceutically acceptable emulsions, solutions, suspensions, syrups, elixirs, and commonly used inert diluent (e.g., purified water, ethanol). In addition to the inert diluent, the composition may also contain additives such as solubilizing agents, wetting agents, suspending agents, and sweetener, flavoring agents, flavoring agents and preservatives.

Injections for parenteral administration include sterile aqueous or non-aqueous liquid preparations, suspensions, emulsions. Diluent aqueous solution can be used (for example) include distilled water for injection and physiological saline. Non-aqueous diluent solution can be used (e.g.) include propylene glycol, polyethylene glycol, vegetable oils (such as olive oil), alcohols (e.g., ethanol) and polysorbate 80. Such compositions may further contain isotonic agents, such as preservatives, wetting agents, emulsifying agents, dispersing agents, stabilizing agents, dissolving aids and the like additives. It may be employed by filtration through a bacteria retaining filter, adding bactericides or irradiation with light to a method of sterilizing the composition. In addition, these compositions may be made sterile solid compositions before use and then sterile water or a sterile solvent for injection prior to use dissolved or suspended.

Transmucosal agents such as inhalations and nasal agents and the like, can be solid, liquid, or semi-solid state of use, and can be in accordance with conventionally known methods used to prepare these transmucosal agent. For example, an excipient may be added as needed (e.g., lactose and starch), pH adjusting agent, a preservative IJ, surfactants, lubricants IJ, stabilizing and thickening agents and the like. You can use a suitable inhalation or insufflation device administered. For example, metered dose inhaler devices may be used a known device or sprayer, the compound alone or as a mixture after the powder formulation to be administered. In addition, after the compound may be combined with a pharmaceutically acceptable carrier, administered as a solution or suspension. The dry powder inhaler or the like may be used for a single dose or multiple doses, and can use a dry powder or a powder-containing capsule. Further, a pressurized aerosol spray can also be used in the form to be administered by the use of a suitable propellant (e.g., chlorofluoroalkane, hydrofluoroalkane, or a suitable gas such as carbon dioxide).

TABLE 2

BTK Representative Inhibitors

| Compound No. | Structure | Name | M + 1 |
| --- | --- | --- | --- |
| 1 | 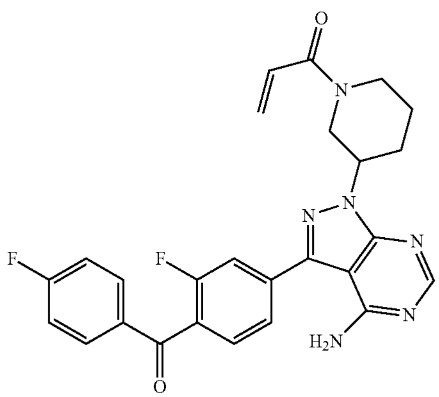 [SMILES: C=CC(=O)N1CCCC(n2nc(-c3ccc(C(=O)c4ccc(F)cc4)c(F)c3)c3c(N)ncnc32)C1] | 1-(3-(4-amino-3-(3-fluoro-4-(4-fluorobenzoyl)phenyl)-1H-pyrazolo[3,4-d]pyrimidin-1-yl)piperidin-1-yl)prop-2-en-1-one | 489 |
| 2 | 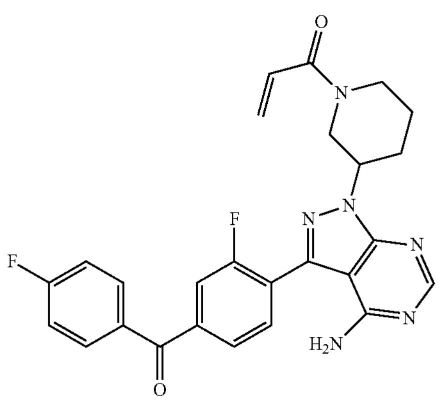 [SMILES: C=CC(=O)N1CCCC(n2nc(-c3ccc(C(=O)c4ccc(F)cc4)cc3F)c3c(N)ncnc32)C1] | 1-(3-(4-amino-3-(2-fluoro-4-(4-fluorobenzoyl)phenyl)-1H-pyrazolo[3,4-d]pyrimidin-1-yl)piperidin-1-yl)prop-2-en-1-one | 489 |
| 3 | 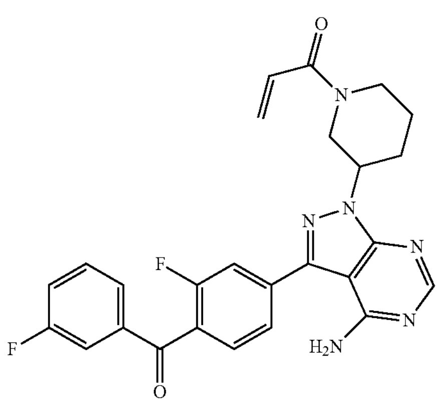 [SMILES: C=CC(=O)N1CCCC(n2nc(-c3ccc(C(=O)c4cccc(F)c4)c(F)c3)c3c(N)ncnc32)C1] | 1-(3-(4-amino-3-(3-fluoro-4-(3-fluorobenzoyl)phenyl)-1H-pyrazolo[3,4-d]pyrimidin-1-yl)piperidin-1-yl)prop-2-en-1-one | 489 |

TABLE 2-continued

BTK Representative Inhibitors

| Compound No. | Structure | Name | M + 1 |
|---|---|---|---|
| 4 | 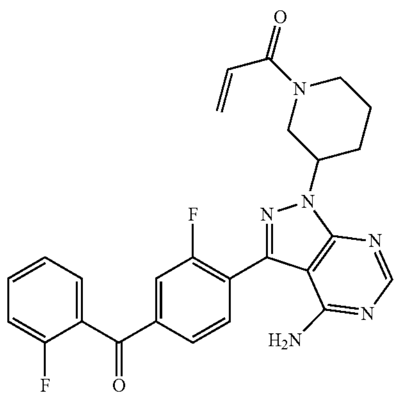 [SMILES: C=CC(=O)N1CCCC(n2nc(-c3ccc(C(=O)c4ccccc4F)cc3F)c3c(N)ncnc32)C1] | 1-(3-(4-amino-3-(2-fluoro-4-(2-fluorobenzoyl)phenyl)-1H-pyrazolo[3,4-d]pyrimidin-1-yl)piperidin-1-yl)prop-2-en-1-one | 489 |
| 5 | 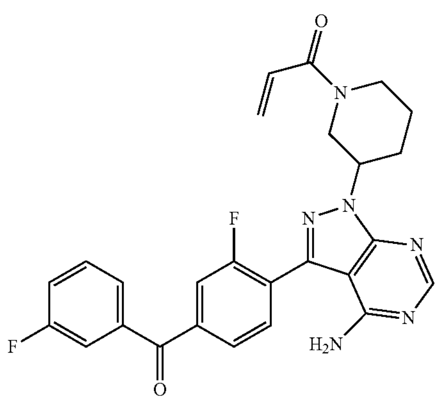 [SMILES: C=CC(=O)N1CCCC(n2nc(-c3ccc(C(=O)c4cccc(F)c4)cc3F)c3c(N)ncnc32)C1] | 1-(3-(4-amino-3-(2-fluoro-4-(3-fluorobenzoyl)phenyl)-1H-pyrazolo[3,4-d]pyrimidin-1-yl)piperidin-1-yl)prop-2-en-1-one | 489 |
| 6 | 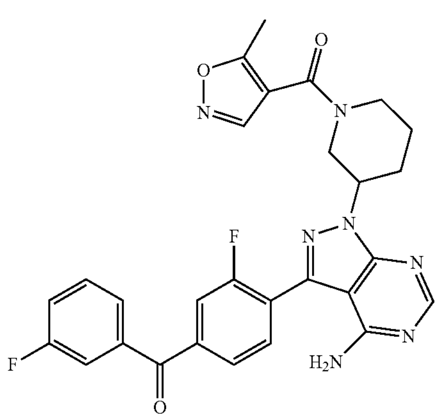 [SMILES: Cc1oncc1C(=O)N1CCCC(n2nc(-c3ccc(C(=O)c4cccc(F)c4)cc3F)c3c(N)ncnc32)C1] | (3-(4-amino-3-(2-fluoro-4-(3-fluorobenzoyl)phenyl)-1H-pyrazolo[3,4-d]pyrimidin-1-yl)piperidin-1-yl)(5-methylisoxazol-4-yl)methanone | 544 |

TABLE 2-continued

BTK Representative Inhibitors

| Compound No. | Structure | Name | M + 1 |
|---|---|---|---|
| 7 | 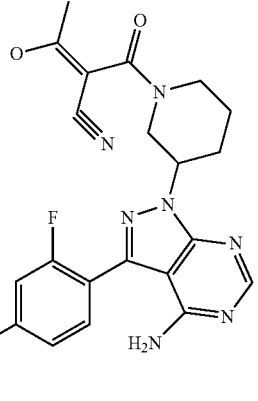 | (E)-2-(3-(4-amino-3-(2-fluoro-4-(3-fluorobenzoyl)phenyl)-1H-pyrazolo[3,4-d]pyrimidin-1-yl)piperidine-1-carbonyl)-3-hydroxybut-2-enenitrile | 544 |
| 8 | 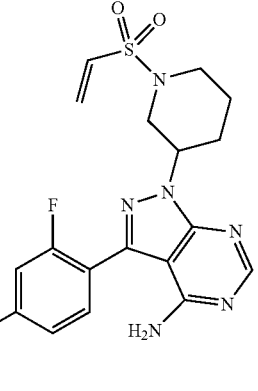 | (4-(4-amino-1-(1-(vinylsulfonyl)piperidin-3-yl)-1H-pyrazolo[3,4-d]pyrimidin-3-yl)-3-fluorophenyl)(3-fluorophenyl)methanone | 525 |
| 9 | 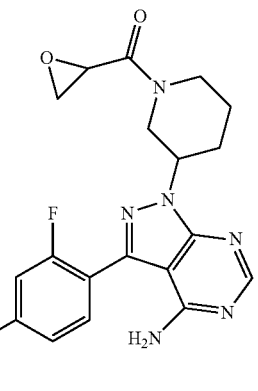 | (3-(4-amino-3-(2-fluoro-4-(3-fluorobenzoyl)phenyl)-1H-pyrazolo[3,4-d]pyrimidin-1-yl)piperidin-1-yl)(oxiran-2-yl)methanone | 505 |

TABLE 2-continued
BTK Representative Inhibitors
| Compound No. | Structure | Name | M + 1 |
|---|---|---|---|
| 10 | 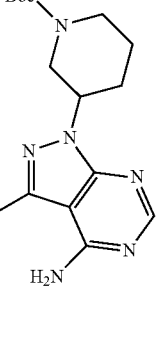 | tert-butyl 3-(4-amino-3-(2-fluoro-4-(2-nitrophenoxy)phenyl)-1H-pyrazolo[3,4-d]pyrimidin-1-yl)piperidine-1-carboxylate | 550 |
| 11 | 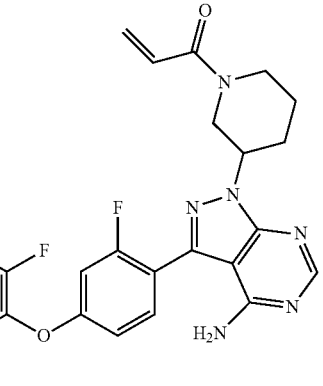 | 1-(3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one | 531 |
| 12 | 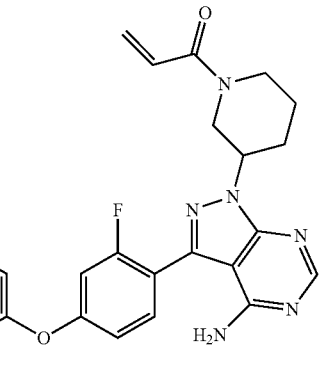 | 1-(3-(4-amino-3-(2-fluoro-4-(3-fluoro-2-nitrophenoxy)phenyl)-1H-pyrazolo[3,4-d]pyrimidin-1-yl)piperidin-1-yl)prop-2-en-1-one | 522 |

TABLE 2-continued

BTK Representative Inhibitors

| Compound No. | Structure | Name | M + 1 |
|---|---|---|---|
| 13 | 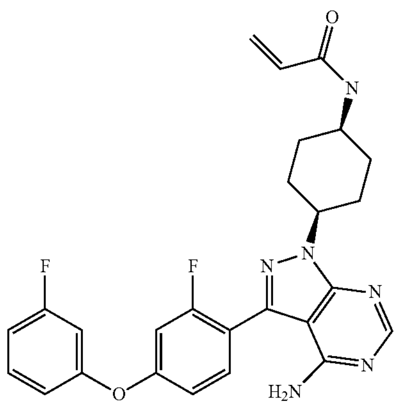 [SMILES: C=CC(=O)N[C@H]1CC[C@@H](n2nc(-c3ccc(Oc4cccc(F)c4)cc3F)c3c(N)ncnc32)CC1] | N-((1s,4s)-4-(4-amino-3-(2-fluoro-4-(3-fluorophenoxy)phenyl)-1H-pyrazolo[3,4-d]pyrimidin-1-yl)cyclohexyl)acrylamide | 491 |
| 14 | 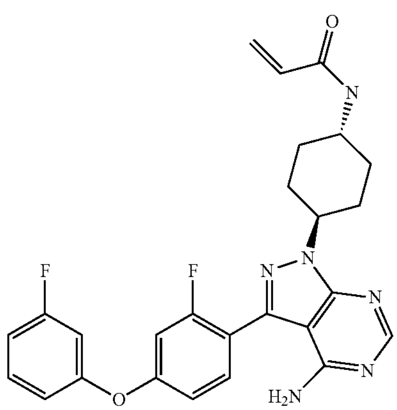 [SMILES: C=CC(=O)N[C@H]1CC[C@H](n2nc(-c3ccc(Oc4cccc(F)c4)cc3F)c3c(N)ncnc32)CC1] | N-((1r,4r)-4-(4-amino-3-(2-fluoro-4-(3-fluorophenoxy)phenyl)-1H-pyrazolo[3,4-d]pyrimidin-1-yl)cyclohexyl)acrylamide | 491 |
| 15 | 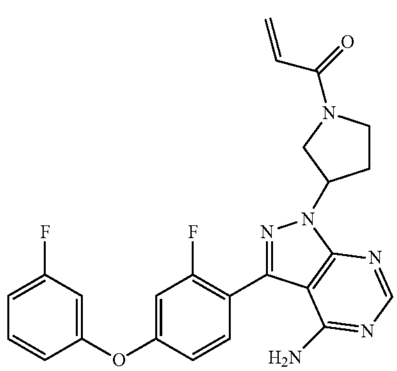 [SMILES: C=CC(=O)N1CCC(n2nc(-c3ccc(Oc4cccc(F)c4)cc3F)c3c(N)ncnc32)C1] | 1-(3-(4-amino-3-(2-fluoro-4-(3-fluorophenoxy)phenyl)-1H-pyrazolo[3,4-d]pyrimidin-1-yl)pyrrolidin-1-yl)prop-2-en-1-one | 463 |

TABLE 2-continued

BTK Representative Inhibitors

| Compound No. | Structure | Name | M + 1 |
|---|---|---|---|
| 16 | 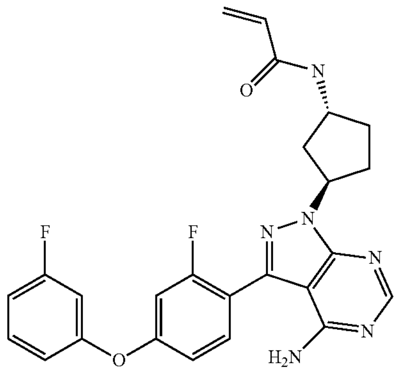 [SMILES: C=CC(=O)N[C@@H]1CC[C@@H](n2nc(-c3ccc(Oc4cccc(F)c4)cc3F)c3c(N)ncnc32)C1] | N-((1r,3r)-3-(4-amino-3-(2-fluoro-4-(3-fluorophenoxy)phenyl)-1H-pyrazolo[3,4-d]pyrimidin-1-yl)cyclopentyl)acrylamide | 476 |
| 17 | 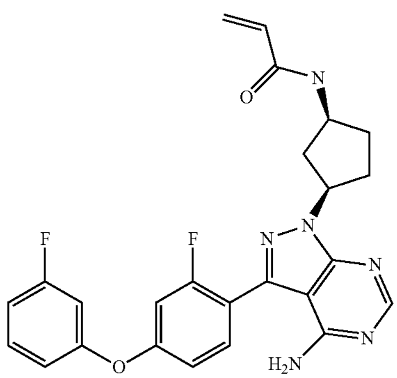 [SMILES: C=CC(=O)N[C@H]1CC[C@@H](n2nc(-c3ccc(Oc4cccc(F)c4)cc3F)c3c(N)ncnc32)C1] | N-((1s,3r)-3-(4-amino-3-(2-fluoro-4-(3-fluorophenoxy)phenyl)-1H-pyrazolo[3,4-d]pyrimidin-1-yl)cyclopentyl)acrylamide | 476 |
| 18 | 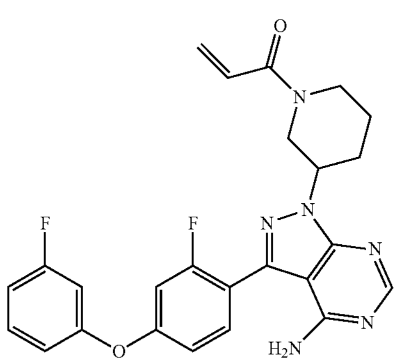 [SMILES: C=CC(=O)N1CCCC(n2nc(-c3ccc(Oc4cccc(F)c4)cc3F)c3c(N)ncnc32)C1] | 1-(3-(4-amino-3-(2-fluoro-4-(3-fluorophenoxy)phenyl)-1H-pyrazolo[3,4-d]pyrimidin-1-yl)piperidin-1-yl)prop-2-en-1-one | 476 |

TABLE 2-continued

BTK Representative Inhibitors

| Compound No. | Structure | Name | M + 1 |
|---|---|---|---|
| 19 | 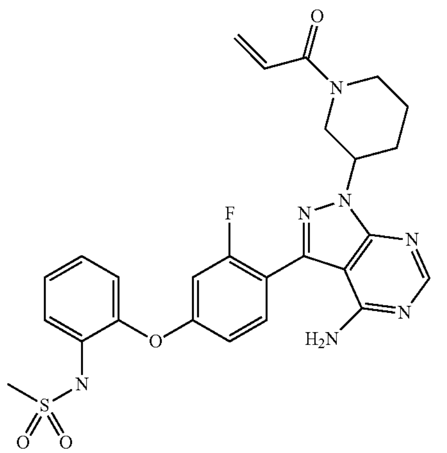 [SMILES: C=CC(=O)N1CCCC(n2nc(-c3ccc(Oc4ccccc4NS(C)(=O)=O)cc3F)c3c(N)ncnc32)C1] | N-(2-(4-(1-(1-acryloylpiperidin-3-yl)-4-amino-1H-pyrazolo[3,4-d]pyrimidin-3-yl)-3-fluorophenoxy)phenyl)methanesulfonamide | 552 |
| 20 | 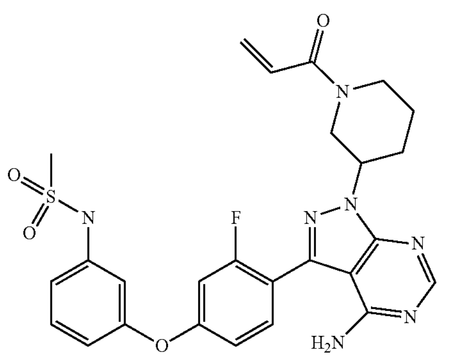 [SMILES: C=CC(=O)N1CCCC(n2nc(-c3ccc(Oc4cccc(NS(C)(=O)=O)c4)cc3F)c3c(N)ncnc32)C1] | N-(3-(4-(1-(1-acryloylpiperidin-3-yl)-4-amino-1H-pyrazolo[3,4-d]pyrimidin-3-yl)-3-fluorophenoxy)phenyl)methanesulfonamide | 552 |
| 21 | 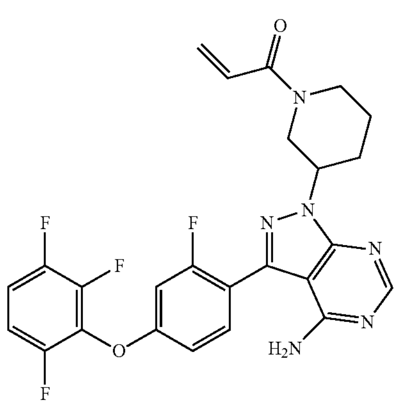 [SMILES: C=CC(=O)N1CCCC(n2nc(-c3ccc(Oc4c(F)ccc(F)c4F)cc3F)c3c(N)ncnc32)C1] | 1-(3-(4-amino-3-(2-fluoro-4-(2,3,6-trifluorophenoxy)phenyl)-1H-pyrazolo[3,4-d]pyrimidin-1-yl)piperidin-1-yl)prop-2-en-1-one | 513 |

TABLE 2-continued

BTK Representative Inhibitors

| Compound No. | Structure | Name | M + 1 |
|---|---|---|---|
| 22 | 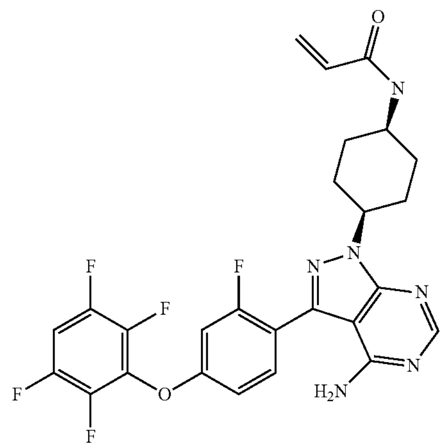 [SMILES: C=CC(=O)N[C@H]1CC[C@@H](n2nc(-c3ccc(Oc4c(F)c(F)cc(F)c4F)cc3F)c3c(N)ncnc32)CC1] | N-((1s,4s)-4-(4-amino-3-(2-fluoro-4-(2,3,5,6-tetrafluorophenoxy)phenyl)-1H-pyrazolo[3,4-d]pyrimidin-1-yl)cyclohexyl)acrylamide | 545 |
| 23 | 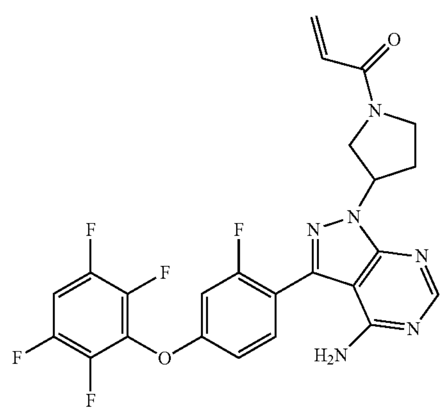 | 1-(3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one | 517 |
| 24 | 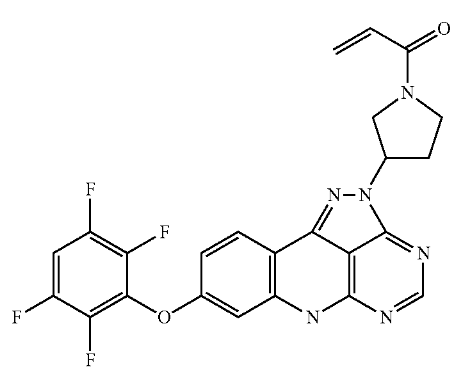 [SMILES: C=CC(=O)N1CCC(n2nc3c4c(ncnc42)Nc2cc(Oc4c(F)c(F)cc(F)c4F)ccc2-3)C1] | | 497 |

TABLE 2-continued

BTK Representative Inhibitors

| Compound No. | Structure | Name | M + 1 |
|---|---|---|---|
| 25 | 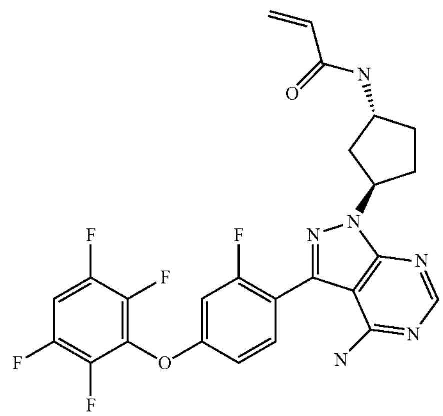 [SMILES: C=CC(=O)N[C@@H]1CC[C@@H](n2nc(-c3ccc(Oc4c(F)c(F)cc(F)c4F)cc3F)c3c(N)ncnc32)C1] | N-((1r,3r)-3-(4-amino-3-(2-fluoro-4-(2,3,5,6-tetrafluorophenoxy)phenyl)-1H-pyrazolo[3,4-d]pyrimidin-1-yl)cyclopentyl)acrylamide | 531 |
| 26 | 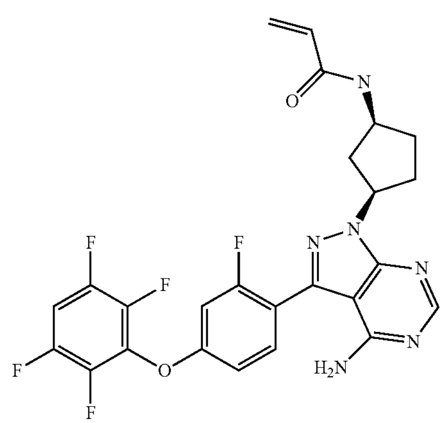 [SMILES: C=CC(=O)N[C@H]1CC[C@@H](n2nc(-c3ccc(Oc4c(F)c(F)cc(F)c4F)cc3F)c3c(N)ncnc32)C1] | N-((1s,3r)-3-(4-amino-3-(2-fluoro-4-(2,3,5,6-tetrafluorophenoxy)phenyl)-1H-pyrazolo[3,4-d]pyrimidin-1-yl)cyclopentyl)acrylamide | 531 |
| 27 | 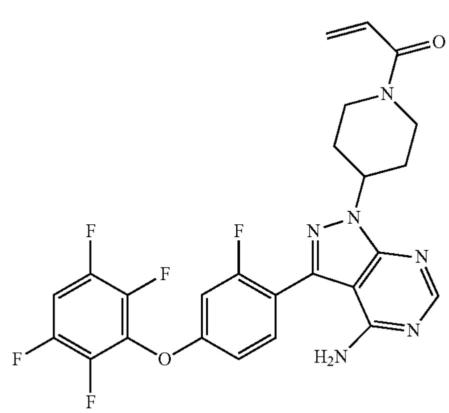 [SMILES: C=CC(=O)N1CCC(n2nc(-c3ccc(Oc4c(F)c(F)cc(F)c4F)cc3F)c3c(N)ncnc32)CC1] | 1-(4-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one | 531 |

TABLE 2-continued

BTK Representative Inhibitors

| Compound No. | Structure | Name | M + 1 |
|---|---|---|---|
| 28 | 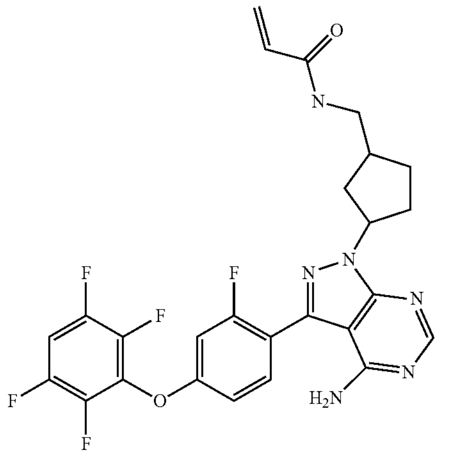 [SMILES: C=CC(=O)NCC1CCC(n2nc(-c3ccc(Oc4c(F)c(F)cc(F)c4F)cc3F)c3c(N)ncnc32)C1] | N-((3-(4-amino-3-(2-fluoro-4-(2,3,5,6-tetrafluorophenoxy)phenyl)-1H-pyrazolo[3,4-d]pyrimidin-1-yl)cyclopentyl)methyl)acrylamide | 544 |
| 29 | 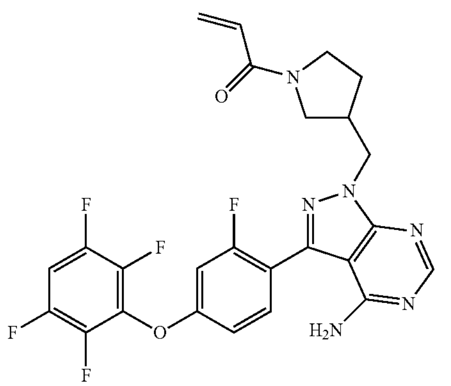 [SMILES: C=CC(=O)N1CCC(Cn2nc(-c3ccc(Oc4c(F)c(F)cc(F)c4F)cc3F)c3c(N)ncnc32)C1] | 1-(3-((4-amino-3-(2-fluoro-4-(2,3,5,6-tetrafluorophenoxy)phenyl)-1H-pyrazolo[3,4-d]pyrimidin-1-yl)methyl)pyrrolidin-1-yl)prop-2-en-1-one | 531 |
| 30 | 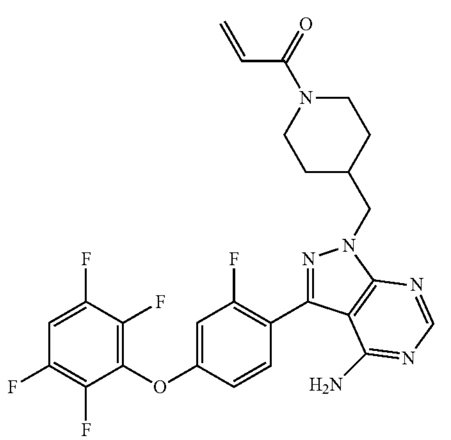 [SMILES: C=CC(=O)N1CCC(Cn2nc(-c3ccc(Oc4c(F)c(F)cc(F)c4F)cc3F)c3c(N)ncnc32)CC1] | 1-(4-((4-amino-3-(2-fluoro-4-(2,3,5,6-tetrafluorophenoxy)phenyl)-1H-pyrazolo[3,4-d]pyrimidin-1-yl)methyl)piperidin-1-yl)prop-2-en-1-one | 545 |

TABLE 2-continued

BTK Representative Inhibitors

| Compound No. | Structure | Name | M + 1 |
|---|---|---|---|
| 31 | 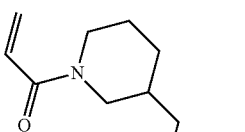 | 1-(3-((4-amino-3-(2-fluoro-4-(2,3,5,6-tetrafluorophenoxy)phenyl)-1H-pyrazolo[3,4-d]pyrimidin-1-yl)methyl)piperidin-1-yl)prop-2-en-1-one | 545 |
| 32 | 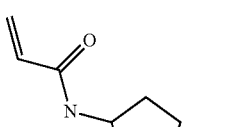 | N-(3-((4-amino-3-(2-fluoro-4-(2,3,5,6-tetrafluorophenoxy)phenyl)-1H-pyrazolo[3,4-d]pyrimidin-1-yl)methyl)cyclopentyl)acrylamide | 545 |
| 33 | 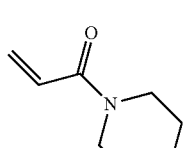 | 1-((R)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one | 531 |

TABLE 2-continued

BTK Representative Inhibitors

| Compound No. | Structure | Name | M + 1 |
|---|---|---|---|
| 34 | 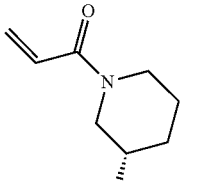 | 1-((S)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one | 531 |
| 35 | 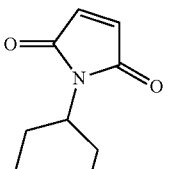 | 1-(4-(4-amino-3-(2-fluoro-4-(2,3,5,6-tetrafluorophenoxy)phenyl)-1H-pyrazolo[3,4-d]pyrimidin-1-yl)cyclohexyl)-1H-pyrrole-2,5-dione | 571 |
| 36 | 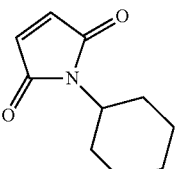 | 1-(3-(4-amino-3-(2-fluoro-4-(2,3,5,6-tetrafluorophenoxy)phenyl)-1H-pyrazolo[3,4-d]pyrimidin-1-yl)cyclohexyl)-1H-pyrrole-2,5-dione | 571 |

TABLE 2-continued

BTK Representative Inhibitors

| Compound No. | Structure | Name | M + 1 |
|---|---|---|---|
| 37 | 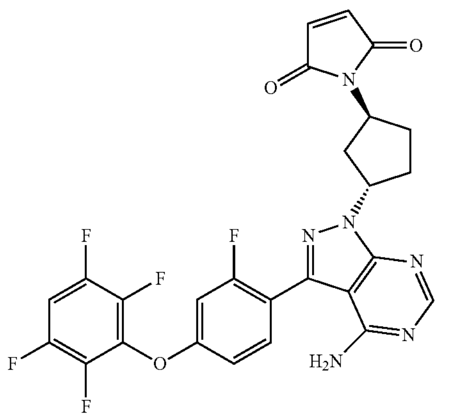 [SMILES: Nc1ncnc2c1c(-c1ccc(Oc3c(F)c(F)cc(F)c3F)cc1F)nn2[C@H]1CC[C@H](N2C(=O)C=CC2=O)C1] | 1-((1S,3S)-3-(4-amino-3-(2-fluoro-4-(2,3,5,6-tetrafluorophenoxy)phenyl)-1H-pyrazolo[3,4-d]pyrimidin-1-yl)cyclopentyl)-1H-pyrrole-2,5-dione | 557 |
| 38 | 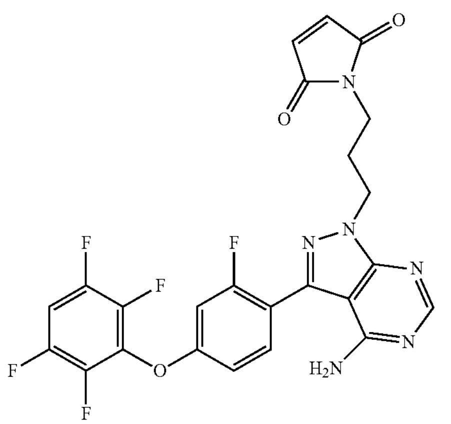 [SMILES: Nc1ncnc2c1c(-c1ccc(Oc3c(F)c(F)cc(F)c3F)cc1F)nn2CCCN1C(=O)C=CC1=O] | 1-(3-(4-amino-3-(2-fluoro-4-(2,3,5,6-tetrafluorophenoxy)phenyl)-1H-pyrazolo[3,4-d]pyrimidin-1-yl)propyl)-1H-pyrrole-2,5-dione | 531 |
| 9 | 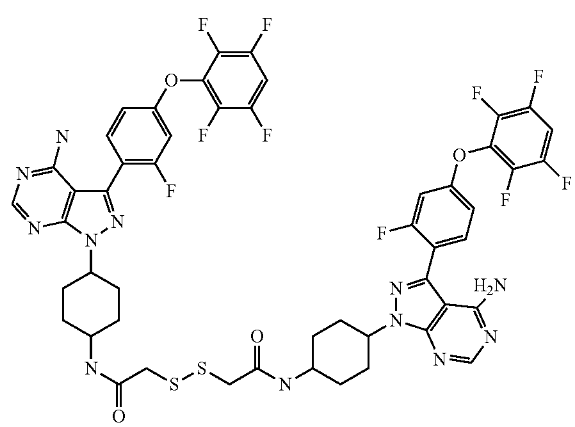 [SMILES: Nc1ncnc2c1c(-c1ccc(Oc3c(F)c(F)cc(F)c3F)cc1F)nn2C1CCC(NC(=O)CSSCC(=O)NC2CCC(n3nc(-c4ccc(Oc5c(F)c(F)cc(F)c5F)cc4F)c4c(N)ncnc43)CC2)CC1] | | 1127 |

/ TABLE 2-continued

BTK Representative Inhibitors

| Compound No. | Structure | Name | M + 1 |
|---|---|---|---|
| 40 | 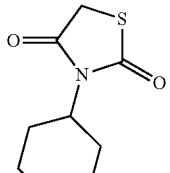 | 3-(4-(4-amino-3-(2-fluoro-4-(2,3,5,6-tetrafluorophenoxy)phenyl)-1H-pyrazolo[3,4-d]pyrimidin-1-yl)cyclohexyl)thiazolidine-2,4-dione | 591 |
| 41 | 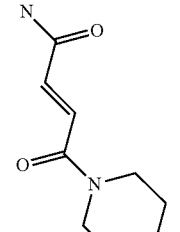 | (E)-4-(3-(4-amino-3-(2-fluoro-4-(2,3,5,6-tetrafluorophenoxy)phenyl)-1H-pyrazolo[3,4-d]pyrimidin-1-yl)piperidin-1-yl)-4-oxobut-2-enamide | 574 |
| 42 | 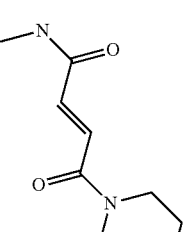 | (E)-4-(3-(4-amino-3-(2-fluoro-4-(2,3,5,6-tetrafluorophenoxy)phenyl)-1H-pyrazolo[3,4-d]pyrimidin-1-yl)piperidin-1-yl)-N-methyl-4-oxobut-2-enamide | 588 |

TABLE 2-continued

BTK Representative Inhibitors

| Compound No. | Structure | Name | M + 1 |
|---|---|---|---|
| 43 | 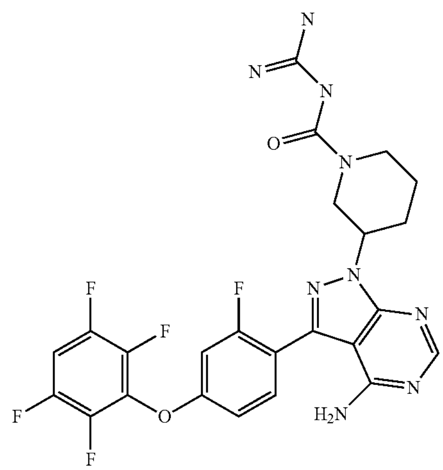 [SMILES: N=C(N)NC(=O)N1CCCC(n2nc(-c3ccc(Oc4c(F)c(F)cc(F)c4F)cc3F)c3c(N)ncnc32)C1] | N-[3-[4-amino-3-[2-fluoro-4-(2,3,5,6-trifluorophenoxy)phenyl]-1H-pyrazolo[3,4-d]pyrimidin-1-yl]piperidine-1-carbonyl]formamidine | 562 |
| 44 | 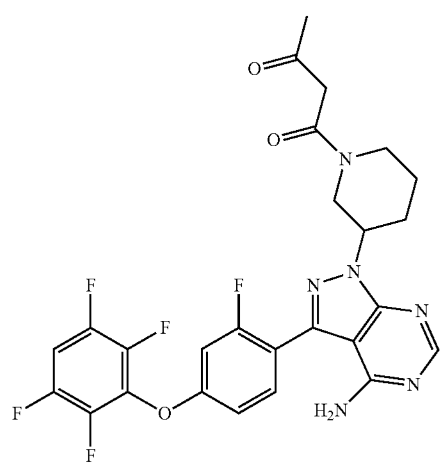 [SMILES: CC(=O)CC(=O)N1CCCC(n2nc(-c3ccc(Oc4c(F)c(F)cc(F)c4F)cc3F)c3c(N)ncnc32)C1] | 1-(3-(4-amino-3-(2-fluoro-4-(2,3,5,6-tetrafluorophenoxy)phenyl)-1H-pyrazolo[3,4-d]pyrimidin-1-yl)piperidin-1-yl)butane-1,3-dione | 561 |
| 45 | 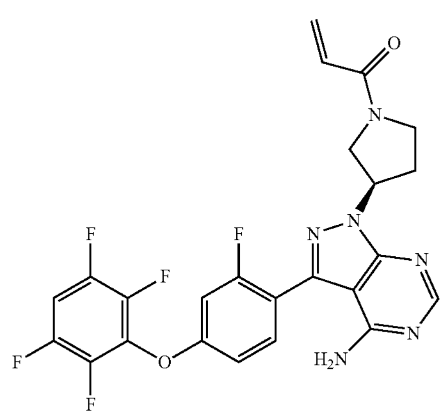 | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one | 517 |

TABLE 2-continued

BTK Representative Inhibitors

| Compound No. | Structure | Name | M + 1 |
|---|---|---|---|
| 46 | 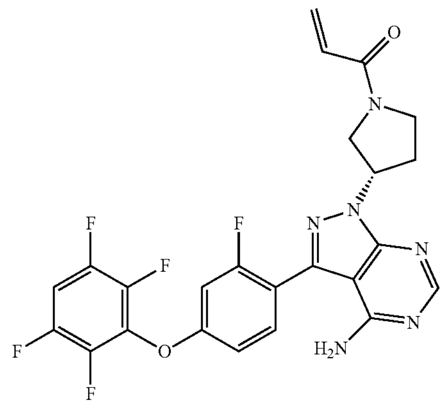 | 1-((S)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one | 517 |
| 47 | 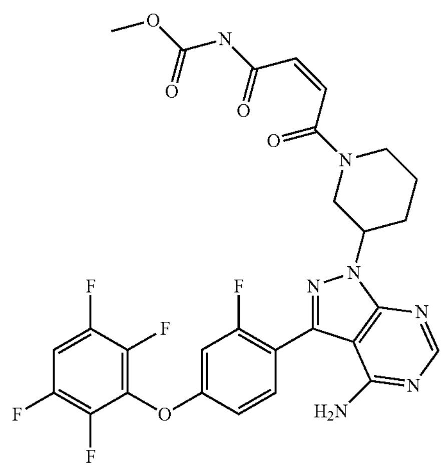 [SMILES: COC(=O)NC(=O)/C=C\C(=O)N1CCCC(n2nc(-c3ccc(Oc4c(F)c(F)cc(F)c4F)cc3F)c3c(N)ncnc32)C1] | (Z)-methyl 4-(3-(4-amino-3-(2-fluoro-4-(2,3,5,6-tetrafluorophenoxy)phenyl)-1H-pyrazolo[3,4-d]pyrimidin-1-yl)piperidin-1-yl)-4-oxobut-2-enoylcarbamate | 632 |
| 48 | 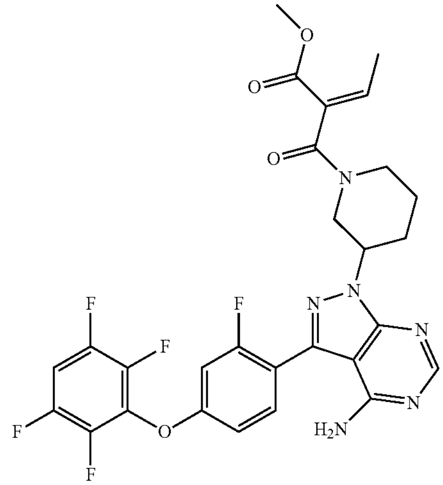 [SMILES: C/C=C(\C(=O)OC)C(=O)N1CCCC(n2nc(-c3ccc(Oc4c(F)c(F)cc(F)c4F)cc3F)c3c(N)ncnc32)C1] | (Z)-methyl 2-(3-(4-amino-3-(2-fluoro-4-(2,3,5,6-tetrafluorophenoxy)phenyl)-1H-pyrazolo[3,4-d]pyrimidin-1-yl)piperidine-1-carbonyl)but-2-enoate | 603 |

TABLE 2-continued

BTK Representative Inhibitors

| Compound No. | Structure | Name | M + 1 |
|---|---|---|---|
| 49 | 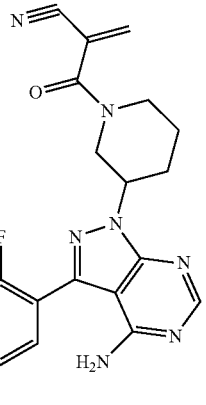 | 2-(3-(4-amino-3-(2-fluoro-4-(2,3,5,6-tetrafluorophenoxy)phenyl)-1H-pyrazolo[3,4-d]pyrimidin-1-yl)piperidine-1-carbonyl)acrylonitrile | 556 |
| 50 | 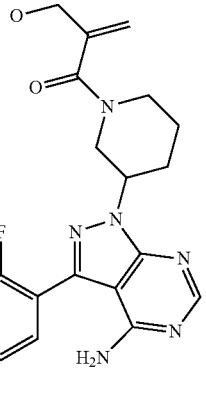 | 1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-(hydroxymethyl)prop-2-en-1-one | 561 |
| 51 | 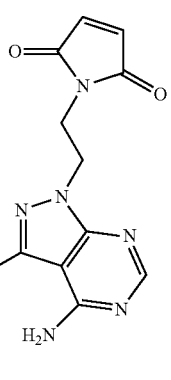 | 1-(2-(4-amino-3-(2-fluoro-4-(2,3,5,6-tetrafluorophenoxy)phenyl)-1H-pyrazolo[3,4-d]pyrimidin-1-yl)ethyl)-1H-pyrrole-2,5-dione | 517 |

TABLE 2-continued

BTK Representative Inhibitors

| Compound No. | Structure | Name | M + 1 |
|---|---|---|---|
| 52 | 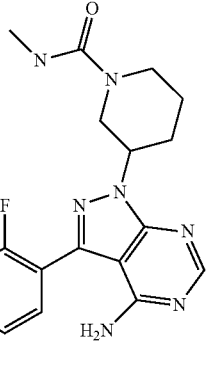 | 3-(4-amino-3-(2-fluoro-4-(2,3,5,6-tetrafluorophenoxy)phenyl)-1H-pyrazolo[3,4-d]pyrimidin-1-yl)-N-methylpiperidine-1-carboxamide | 534 |
| 53 | 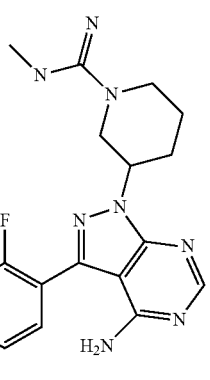 | 3-[4-amino-3-[2-fluoro-4-(2,3,5,6-fluorophenoxy)phenyl]-1H-pyrazolo[3,4-d]pyrimidine-1-yl]piperidine-1-carboxamidine | 533 |
| 54 | 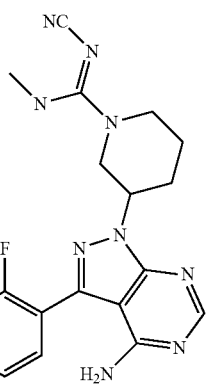 | 3-[4-amino-3-[2-fluoro-4-(2,3,5,6-fluorophenoxy)phenyl]-1H-pyrazolo[3,4-d]pyrimidine-1-yl]-N'-cyano-N-methyl-piperidine-1-carboxamidine | 558 |

TABLE 2-continued

BTK Representative Inhibitors

| Compound No. | Structure | Name | M + 1 |
|---|---|---|---|
| 55 | 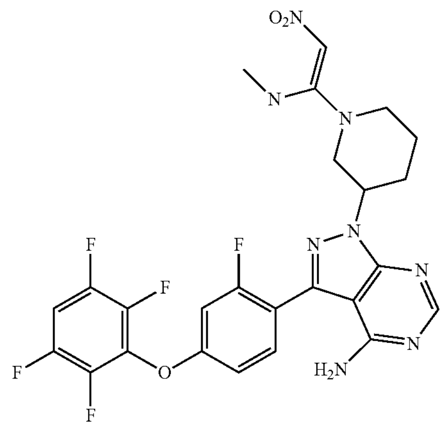 [SMILES: CN/C(=C\[N+](=O)[O-])N1CCCC(n2nc(-c3ccc(Oc4c(F)c(F)cc(F)c4F)cc3F)c3c(N)ncnc32)C1] | 1-[3-[4-amino-3-[2-fluoro-4-(2,3,5,6-three-fluorophenoxy)phenyl]-1H-pyrazolo[3,4-d]pyrimidin-1-yl]-1-piperidinyl]-1-(methylamino)-2-nitro ethylene | 578 |
| 56 | 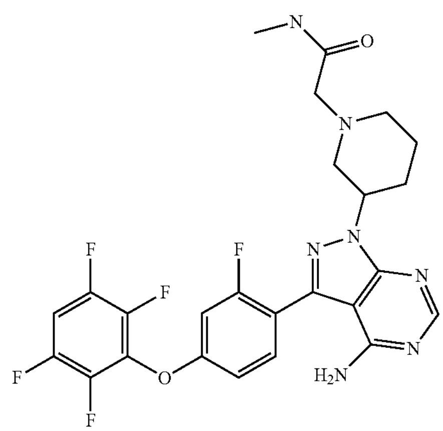 [SMILES: CNC(=O)CN1CCCC(n2nc(-c3ccc(Oc4c(F)c(F)cc(F)c4F)cc3F)c3c(N)ncnc32)C1] | 2-(3-(4-amino-3-(2-fluoro-4-(2,3,5,6-tetrafluorophenoxy)phenyl)-1H-pyrazolo[3,4-d]pyrimidin-1-yl)piperidin-1-yl)-N-methylacetamide | 548 |
| 57 | 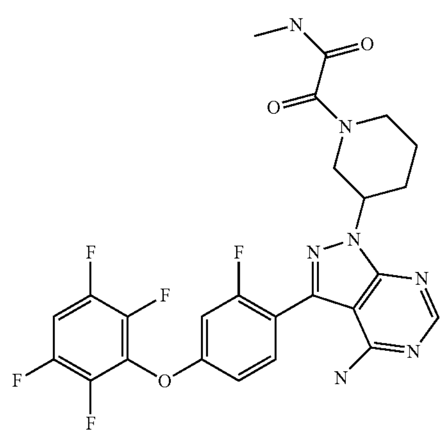 [SMILES: CNC(=O)C(=O)N1CCCC(n2nc(-c3ccc(Oc4c(F)c(F)cc(F)c4F)cc3F)c3c(N)ncnc32)C1] | 2-(3-(4-amino-3-(2-fluoro-4-(2,3,5,6-tetrafluorophenoxy)phenyl)-1H-pyrazolo[3,4-d]pyrimidin-1-yl)piperidin-1-yl)-N-methyl-2-oxoacetamide | 562 |

TABLE 2-continued

BTK Representative Inhibitors

| Compound No. | Structure | Name | M + 1 |
|---|---|---|---|
| 58 | 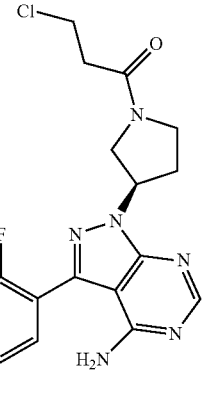 | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-3-chloropropan-1-one | 553 |
| 59 | 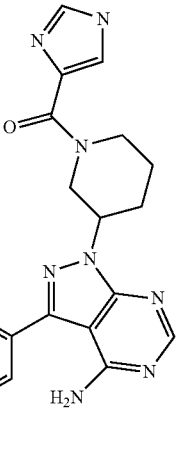 | (3-(4-amino-3-(2-fluoro-4-(2,3,5,6-tetrafluorophenoxy)phenyl)-1H-pyrazolo[3,4-d]pyrimidin-1-yl)piperidin-1-yl)(1H-imidazol-4-yl)methanone | 571 |
| 60 | 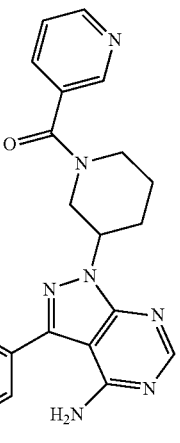 | (3-(4-amino-3-(2-fluoro-4-(2,3,5,6-tetrafluorophenoxy)phenyl)-1H-pyrazolo[3,4-d]pyrimidin-1-yl)piperidin-1-yl)(pyridin-3-yl)methanone | 582 |

TABLE 2-continued

BTK Representative Inhibitors

| Compound No. | Structure | Name | M + 1 |
|---|---|---|---|
| 61 | 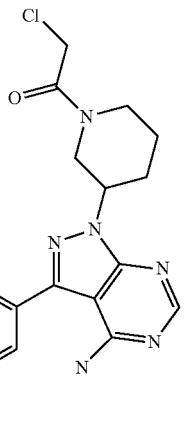 | 1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-chloroethanone | 553 |
| 62 | 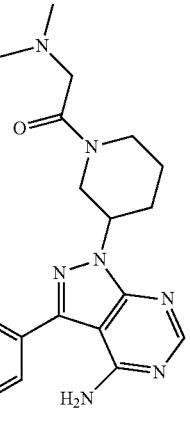 | 1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-(dimethylamino)ethanone | 562 |
| 63 | 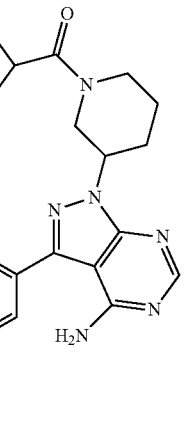 | 5-(3-(4-amino-3-(2-fluoro-4-(2,3,5,6-tetrafluorophenoxy)phenyl)-1H-pyrazolo[3,4-d]pyrimidin-1-yl)piperidine-1-carbonyl)thiazolidin-2-one | 606 |

TABLE 2-continued

BTK Representative Inhibitors

| Compound No. | Structure | Name | M + 1 |
|---|---|---|---|
| 64 | 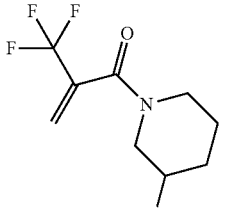 | 1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-(trifluoromethyl)prop-2-en-1-one | 599 |
| 65 | 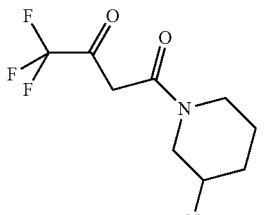 | 1-(3-(4-amino-3-(2-fluoro-4-(2,3,5,6-tetrafluorophenoxy)phenyl)-1H-pyrazolo[3,4-d]pyrimidin-1-yl)piperidin-1-yl)-4,4,4-trifluorobutane-1,3-dione | 615 |
| 66 | 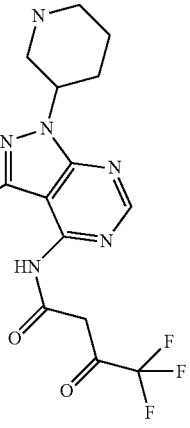 | 4,4,4-trifluoro-N-(3-(2-fluoro-4-(2,3,5,6-tetrafluorophenoxy)phenyl)-1-(piperidin-3-yl)-1H-pyrazolo[3,4-d]pyrimidin-4-yl)-3-oxobutanamide | 615 |

TABLE 2-continued

BTK Representative Inhibitors

| Compound No. | Structure | Name | M + 1 |
|---|---|---|---|
| 67 | 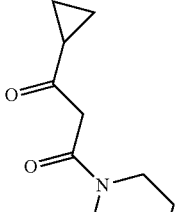 | 1-(3-(4-amino-3-(2-fluoro-4-(2,3,5,6-tetrafluorophenoxy)phenyl)-1H-pyrazolo[3,4-d]pyrimidin-1-yl)piperidin-1-yl)-3-cyclopropylpropane-1,3-dione | 587 |
| 68 | 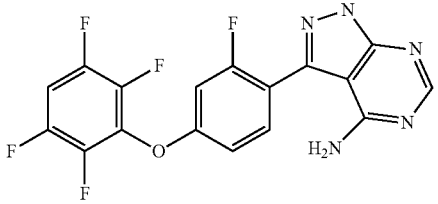 | ethyl 2-((3-(4-amino-3-(2-fluoro-4-(2,3,5,6-tetrafluorophenoxy)phenyl)-1H-pyrazolo[3,4-d]pyrimidin-1-yl)piperidin-1-yl)methyl)acrylate | 589 |
| 69 | 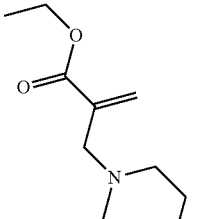 | 2-((3-(4-amino-3-(2-fluoro-4-(2,3,5,6-tetrafluorophenoxy)phenyl)-1H-pyrazolo[3,4-d]pyrimidin-1-yl)piperidin-1-yl)methyl)-N-methylacrylamide | 574 |

TABLE 2-continued
BTK Representative Inhibitors
| Compound No. | Structure | Name | M + 1 |
|---|---|---|---|
| 70 | 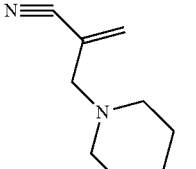 | 2-((3-(4-amino-3-(2-fluoro-4-(2,3,5,6-tetrafluorophenoxy)phenyl)-1H-pyrazolo[3,4-d]pyrimidin-1-yl)piperidin-1-yl)methyl)acrylonitrile | 542 |
| 71 | 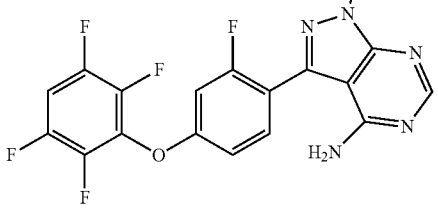 | 1-((R)-3-(4-amino-3-(2-fluoro-4-(4-fluorobenzoyl)phenyl)-1H-pyrazolo[3,4-d]pyrimidin-1-yl)pyrrolidin-1-yl)prop-2-en-1-one | 474 |
| 72 | 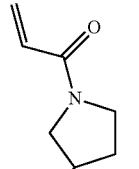 | 1-((R)-3-(4-amino-3-(2-fluoro-4-(2-fluorobenzoyl)phenyl)-1H-pyrazolo[3,4-d]pyrimidin-1-yl)pyrrolidin-1-yl)prop-2-en-1-one | 474 |

TABLE 2-continued

BTK Representative Inhibitors

| Compound No. | Structure | Name | M + 1 |
|---|---|---|---|
| 73 | 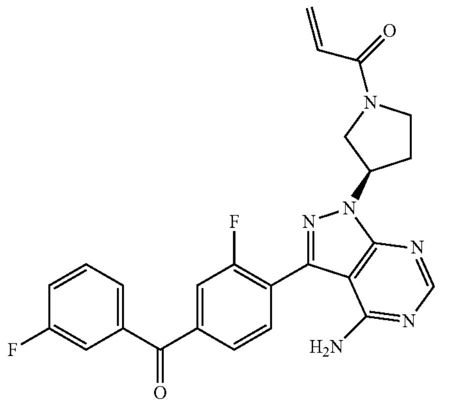 [SMILES: C=CC(=O)N1CC[C@@H](n2nc(-c3ccc(C(=O)c4cccc(F)c4)cc3F)c3c(N)ncnc32)C1] | 1-((R)-3-(4-amino-3-(2-fluoro-4-(3-fluorobenzoyl)phenyl)-1H-pyrazolo[3,4-d]pyrimidin-1-yl)pyrrolidin-1-yl)prop-2-en-1-one | 474 |
| 74 | 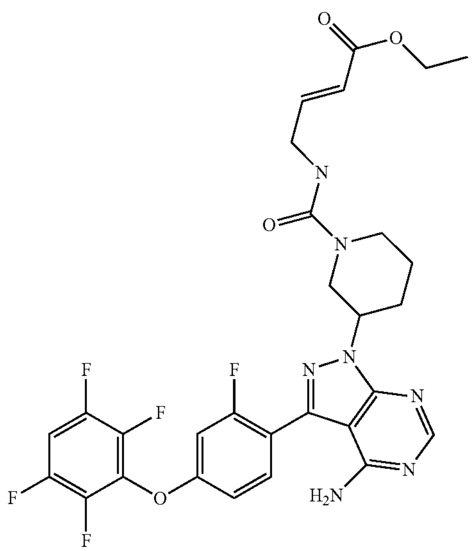 [SMILES: CCOC(=O)/C=C/CNC(=O)N1CCCC(n2nc(-c3ccc(Oc4c(F)c(F)cc(F)c4F)cc3F)c3c(N)ncnc32)C1] | (E)-ethyl 4-(3-(4-amino-3-(2-fluoro-4-(2,3,5,6-tetrafluorophenoxy)phenyl)-1H-pyrazolo[3,4-d]pyrimidin-1-yl)piperidine-1-carboxamido)but-2-enoate | 632 |
| 75 | 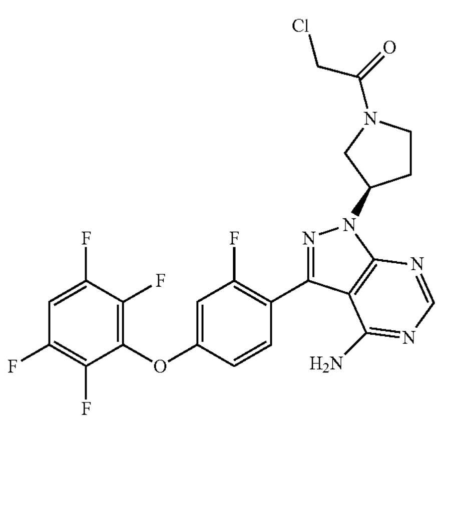 [SMILES: Nc1ncnc2c1c(-c1ccc(Oc3c(F)c(F)cc(F)c3F)cc1F)nn2[C@@H]1CCN(C(=O)CCl)C1] | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2-chloroethanone | 539 |

TABLE 2-continued

BTK Representative Inhibitors

| Compound No. | Structure | Name | M + 1 |
|---|---|---|---|
| 76 | 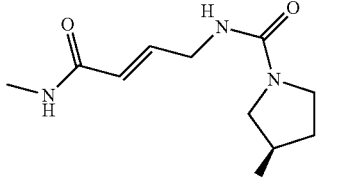 | (3R)-3-(4-amino-3-(2-fluoro-4-(2,3,5,6-tetrafluorophenoxy)phenyl)-1H-pyrazolo[3,4-d]pyrimidin-1-yl)-N-(4-(methylamino)-4-oxobut-2-enyl)pyrrolidine-1-carboxamide | 603 |
| 77 | 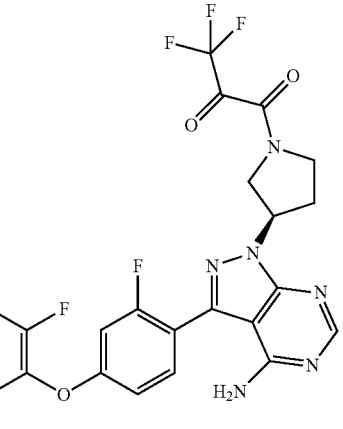 | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-3,3,3-trifluoropropane-1,2-dione | 587 |
| 78 | 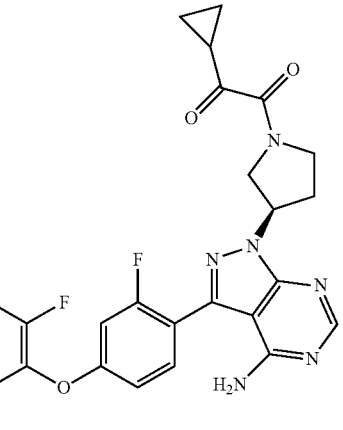 | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2-cyclopropylethane-1,2-dione | 559 |

TABLE 2-continued

BTK Representative Inhibitors

| Compound No. | Structure | Name | M + 1 |
|---|---|---|---|
| 79 | 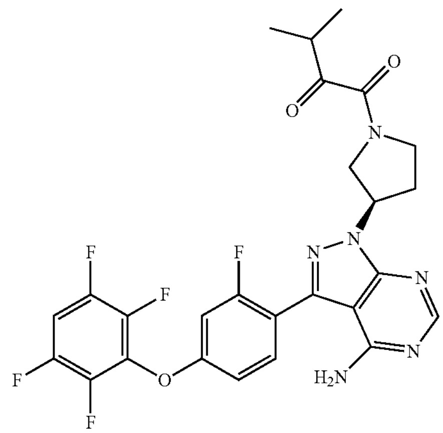 [SMILES: CC(C)C(=O)C(=O)N1CC[C@@H](n2nc(-c3ccc(Oc4c(F)c(F)cc(F)c4F)cc3F)c3c(N)ncnc32)C1] | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-3-methylbutane-1,2-dione | 561 |
| 80 | 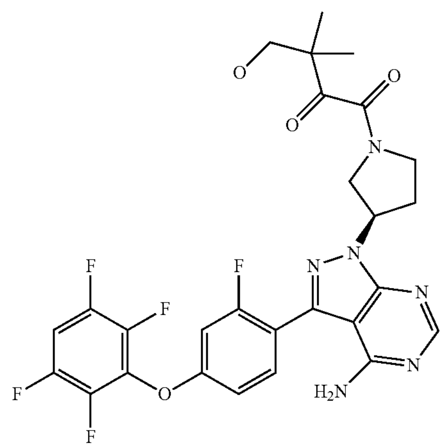 [SMILES: CC(C)(CO)C(=O)C(=O)N1CC[C@@H](n2nc(-c3ccc(Oc4c(F)c(F)cc(F)c4F)cc3F)c3c(N)ncnc32)C1] | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-4-hydroxy-3,3-dimethylbutane-1,2-dione | 591 |
| 81 | 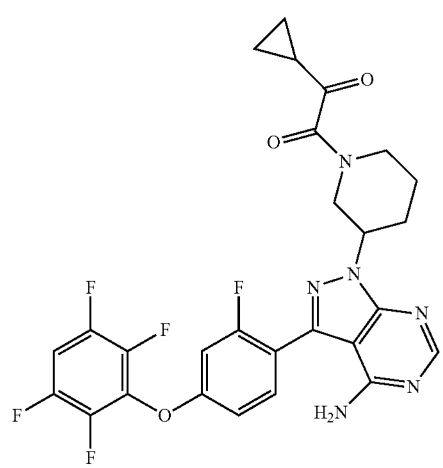 [SMILES: Nc1ncnc2c1c(-c1ccc(Oc3c(F)c(F)cc(F)c3F)cc1F)nn2C1CCCN(C(=O)C(=O)C2CC2)C1] | 1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-cyclopropylethane-1,2-dione | 573 |

TABLE 2-continued

BTK Representative Inhibitors

| Compound No. | Structure | Name | M + 1 |
|---|---|---|---|
| 82 | 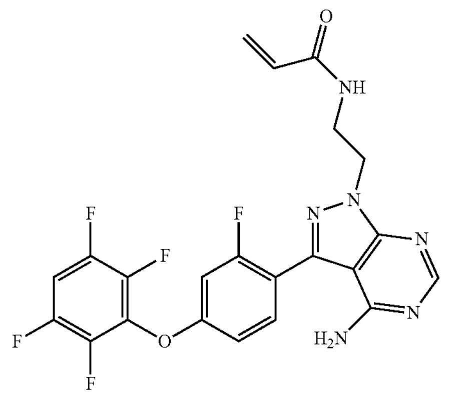 | N-(2-(4-amino-3-(2-fluoro-4-(2,3,5,6-tetrafluorophenoxy)phenyl)-1H-pyrazolo[3,4-d]pyrimidin-1-yl)ethyl)acrylamide | 491 |
| 83 | 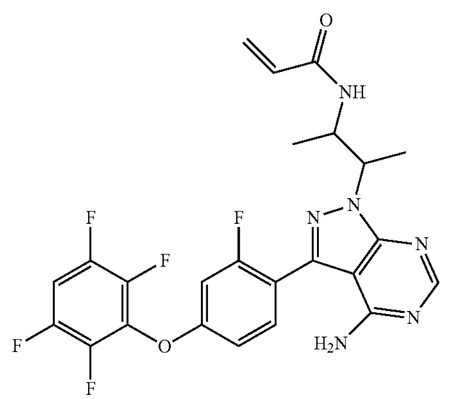 [SMILES: C=CC(=O)NC(C)C(C)n1nc(-c2ccc(Oc3c(F)c(F)cc(F)c3F)cc2F)c2c(N)ncnc21] | N-(3-(4-amino-3-(2-fluoro-4-(2,3,5,6-tetrafluorophenoxy)phenyl)-1H-pyrazolo[3,4-d]pyrimidin-1-yl)butan-2-yl)acrylamide | 519 |
| 84 | 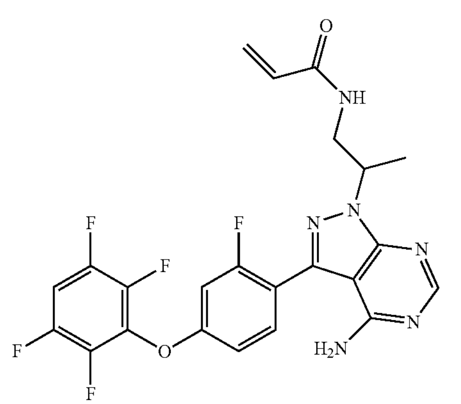 | N-(2-(4-amino-3-(2-fluoro-4-(2,3,5,6-tetrafluorophenoxy)phenyl)-1H-pyrazolo[3,4-d]pyrimidin-1-yl)propyl)acrylamide | 505 |

TABLE 2-continued

BTK Representative Inhibitors

| Compound No. | Structure | Name | M + 1 |
|---|---|---|---|
| 85 | 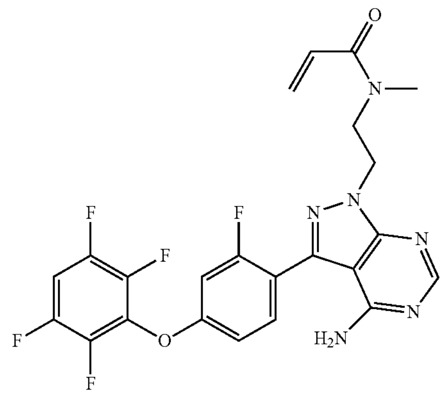 [SMILES: C=CC(=O)N(C)CCn1nc(-c2ccc(Oc3c(F)c(F)cc(F)c3F)cc2F)c2c(N)ncnc21] | N-(2-(4-amino-3-(2-fluoro-4-(2,3,5,6-tetrafluorophenoxy)phenyl)-1H-pyrazolo[3,4-d]pyrimidin-1-yl)ethyl)-N-methylacrylamide | 505 |
| 86 | 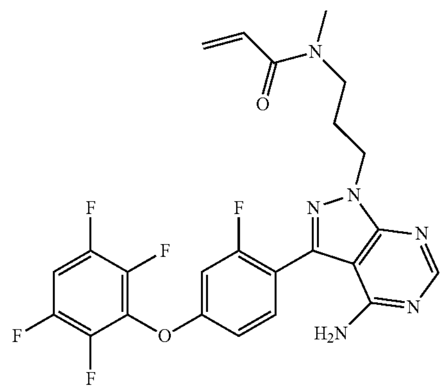 [SMILES: C=CC(=O)N(C)CCCn1nc(-c2ccc(Oc3c(F)c(F)cc(F)c3F)cc2F)c2c(N)ncnc21] | N-(3-(4-amino-3-(2-fluoro-4-(2,3,5,6-tetrafluorophenoxy)phenyl)-1H-pyrazolo[3,4-d]pyrimidin-1-yl)propyl)-N-methylacrylamide | 519 |
| 87 | 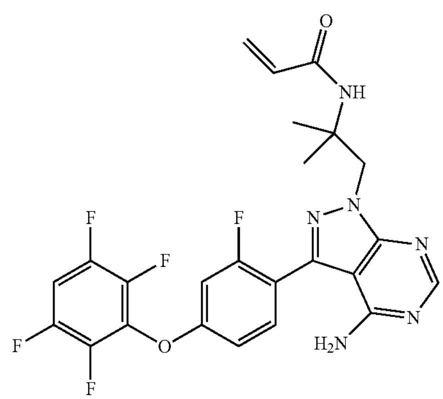 [SMILES: C=CC(=O)NC(C)(C)Cn1nc(-c2ccc(Oc3c(F)c(F)cc(F)c3F)cc2F)c2c(N)ncnc21] | N-(1-(4-amino-3-(2-fluoro-4-(2,3,5,6-tetrafluorophenoxy)phenyl)-1H-pyrazolo[3,4-d]pyrimidin-1-yl)-2-methylpropan-2-yl)acrylamide | 519 |
| 88 | 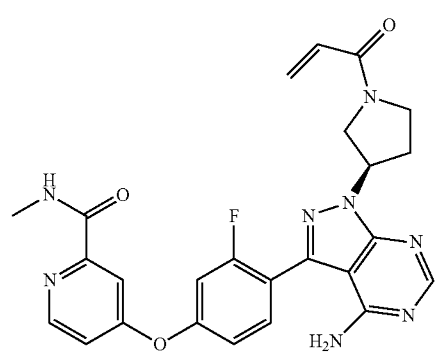 [SMILES: C=CC(=O)N1CC[C@@H](n2nc(-c3ccc(Oc4ccnc(C(=O)NC)c4)cc3F)c3c(N)ncnc32)C1] | 4-(4-(1-((R)-1-acryloylpyrrolidin-3-yl)-4-amino-1H-pyrazolo[3,4-d]pyrimidin-3-yl)-3-fluorophenoxy)-N-methylpicolinamide | 503 |

TABLE 2-continued

BTK Representative Inhibitors

| Compound No. | Structure | Name | M + 1 |
|---|---|---|---|
| 89 | 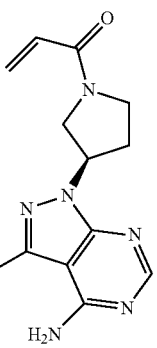 | 1-((R)-3-(4-amino-3-(4-(6,7-dimethoxyquinolin-4-yloxy)-2-fluorophenyl)-1H-pyrazolo[3,4-d]pyrimidin-1-yl)pyrrolidin-1-yl)prop-2-en-1-one | 556 |
| 90 | 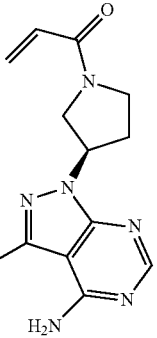 | 1-((R)-3-(4-amino-3-(2-fluoro-4-(quinolin-4-yloxy)phenyl)-1H-pyrazolo[3,4-d]pyrimidin-1-yl)pyrrolidin-1-yl)prop-2-en-1-one | 495 |
| 91 | 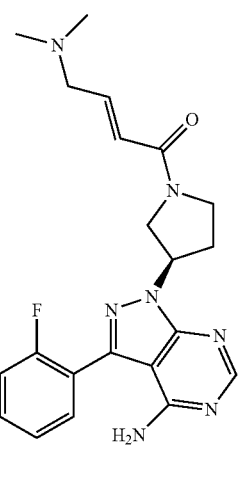 | (E)-1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-4-(dimethylamino)but-2-en-1-one | 574 |

TABLE 2-continued

BTK Representative Inhibitors

| Compound No. | Structure | Name | M + 1 |
|---|---|---|---|
| 92 | 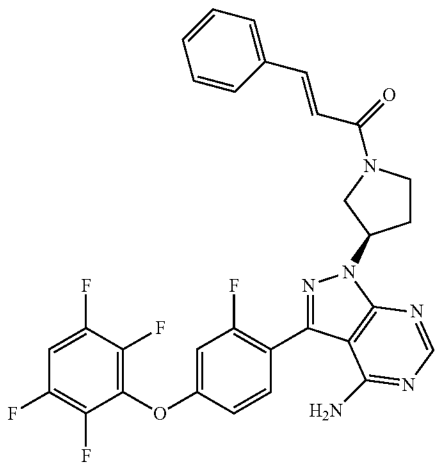 [SMILES: Nc1ncnc2c1c(-c1ccc(Oc3c(F)c(F)cc(F)c3F)cc1F)nn2[C@@H]1CCN(C(=O)/C=C/c2ccccc2)C1] | (E)-1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-3-phenylprop-2-en-1-one | 593 |
| 93 | 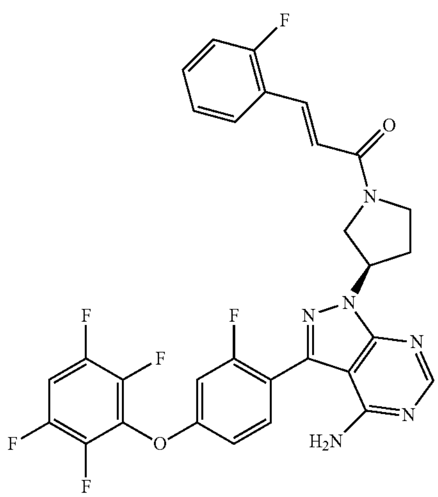 [SMILES: Nc1ncnc2c1c(-c1ccc(Oc3c(F)c(F)cc(F)c3F)cc1F)nn2[C@@H]1CCN(C(=O)/C=C/c2ccccc2F)C1] | (E)-1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-3-(2-fluorophenyl)prop-2-en-1-one | 611 |
| 94 | 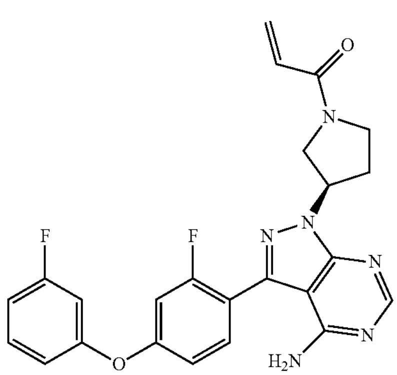 [SMILES: C=CC(=O)N1CC[C@@H](n2nc(-c3ccc(Oc4cccc(F)c4)cc3F)c3c(N)ncnc32)C1] | 1-((R)-3-(4-amino-3-(2-fluoro-4-(3-fluorophenoxy)phenyl)-1H-pyrazolo[3,4-d]pyrimidin-1-yl)pyrrolidin-1-yl)prop-2-en-1-one | 463 |

TABLE 2-continued

BTK Representative Inhibitors

| Compound No. | Structure | Name | M + 1 |
|---|---|---|---|
| 95 | 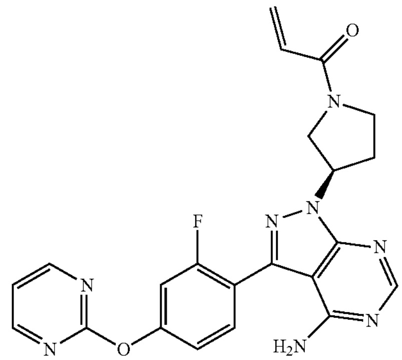 [SMILES: C=CC(=O)N1CC[C@@H](n2nc(-c3ccc(Oc4ncccn4)cc3F)c3c(N)ncnc32)C1] | 1-((R)-3-(4-amino-3-(2-fluoro-4-(pyrimidin-2-yloxy)phenyl)-1H-pyrazolo[3,4-d]pyrimidin-1-yl)pyrrolidin-1-yl)prop-2-en-1-one | 447 |
| 96 | 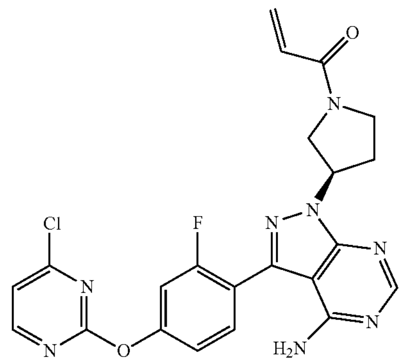 | 1-((R)-3-(4-amino-3-(4-(4-chloropyrimidin-2-yloxy)-2-fluorophenyl)-1H-pyrazolo[3,4-d]pyrimidin-1-yl)pyrrolidin-1-yl)prop-2-en-1-one | 481 |
| 97 | 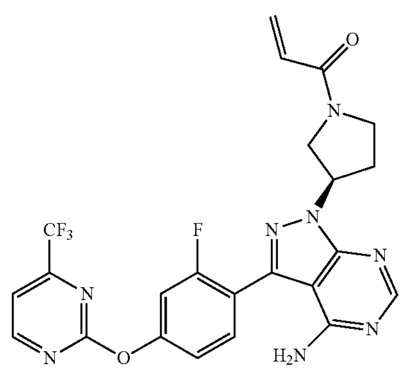 [SMILES: C=CC(=O)N1CC[C@@H](n2nc(-c3ccc(Oc4nccc(C(F)(F)F)n4)cc3F)c3c(N)ncnc32)C1] | 1-((R)-3-(4-amino-3-(2-fluoro-4-(4-(trifluoromethyl)pyrimidin-2-yloxy)phenyl)-1H-pyrazolo[3,4-d]pyrimidin-1-yl)pyrrolidin-1-yl)prop-2-en-1-one | 515 |
| 98 | 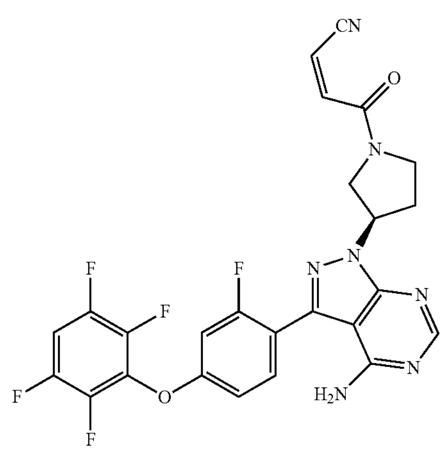 [SMILES: N#C/C=C\C(=O)N1CC[C@@H](n2nc(-c3ccc(Oc4c(F)c(F)cc(F)c4F)cc3F)c3c(N)ncnc32)C1] | (Z)-4-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-4-oxobut-2-enenitrile | 542 |

TABLE 2-continued

BTK Representative Inhibitors

| Compound No. | Structure | Name | M + 1 |
|---|---|---|---|
| 99-A | 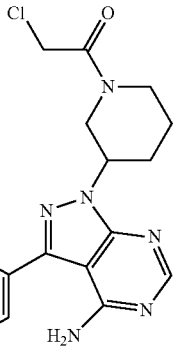 | 1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-chloroethanone | 553 |
| 99 | 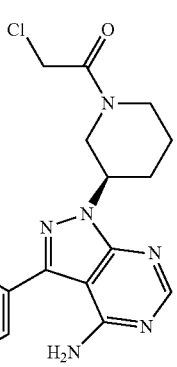 | 1-((R)-3-(4-amino-3-(2-fluoro-4-(2,3,5,6-tetrafluorophenoxy)phenyl)-1H-pyrazolo[3,4-d]pyrimidin-1-yl)piperidin-1-yl)-2-chloroethanone | 553 |
| 100 | 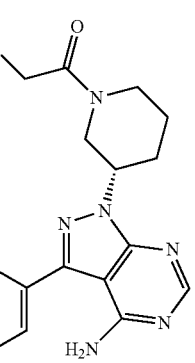 | 1-((S)-3-(4-amino-3-(2-fluoro-4-(2,3,5,6-tetrafluorophenoxy)phenyl)-1H-pyrazolo[3,4-d]pyrimidin-1-yl)piperidin-1-yl)-2-chloroethanone | 553 |

TABLE 2-continued

BTK Representative Inhibitors

| Compound No. | Structure | Name | M + 1 |
|---|---|---|---|
| 101-A | 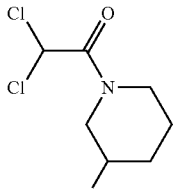 | 1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2,2-dichloroethanone | 587 |
| 101 | 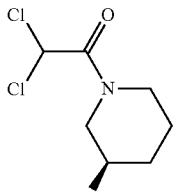 | 1-((R)-3-(4-amino-3-(2-fluoro-4-(2,3,5,6-tetrafluorophenoxy)phenyl)-1H-pyrazolo[3,4-d]pyrimidin-1-yl)piperidin-1-yl)-2,2-dichloroethanone | 587 |
| 102 | 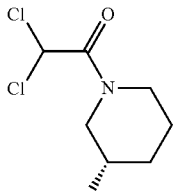 | 1-((S)-3-(4-amino-3-(2-fluoro-4-(2,3,5,6-tetrafluorophenoxy)phenyl)-1H-pyrazolo[3,4-d]pyrimidin-1-yl)piperidin-1-yl)-2,2-dichloroethanone | 587 |

TABLE 2-continued

BTK Representative Inhibitors

| Compound No. | Structure | Name | M + 1 |
|---|---|---|---|
| 103 | 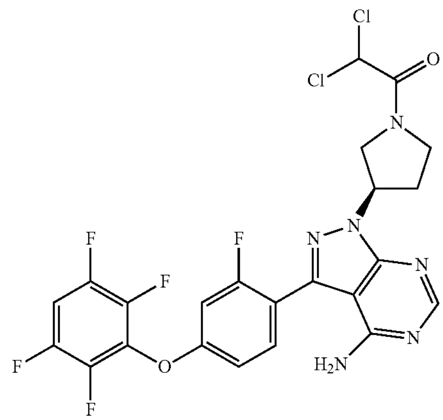 | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2,2-dichloroethanone | 573 |
| 104 | 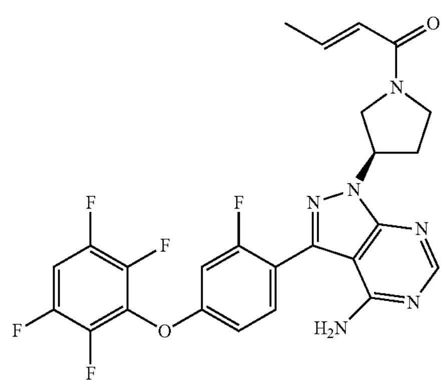 [SMILES: C/C=C/C(=O)N1CC[C@@H](n2nc(-c3ccc(Oc4c(F)c(F)cc(F)c4F)cc3F)c3c(N)ncnc32)C1] | (E)-1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)but-2-en-1-one | 531 |
| 105 | 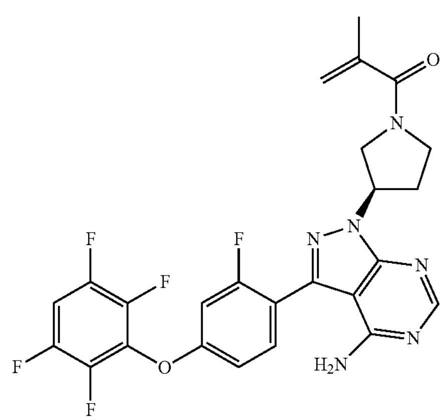 [SMILES: C=C(C)C(=O)N1CC[C@@H](n2nc(-c3ccc(Oc4c(F)c(F)cc(F)c4F)cc3F)c3c(N)ncnc32)C1] | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2-methylprop-2-en-1-one | 531 |

TABLE 2-continued

BTK Representative Inhibitors

| Compound No. | Structure | Name | M + 1 |
|---|---|---|---|
| 106 | 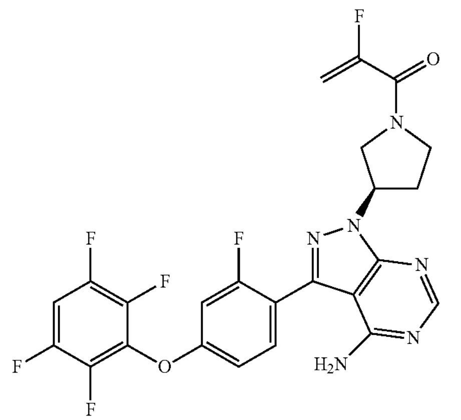 [SMILES: C=C(F)C(=O)N1CC[C@@H](n2nc(-c3ccc(Oc4c(F)c(F)cc(F)c4F)cc3F)c3c(N)ncnc32)C1] | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2-fluoroprop-2-en-1-one | 535 |
| 107-A | 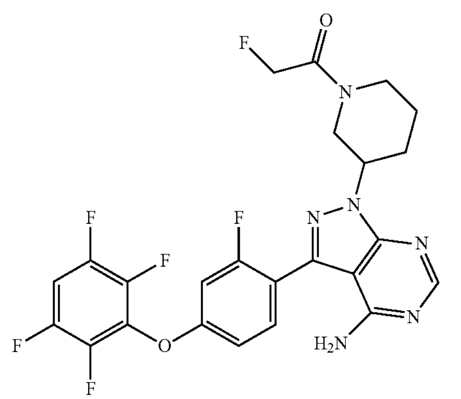 | 1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-fluoroethanone | 537 |
| 107 | 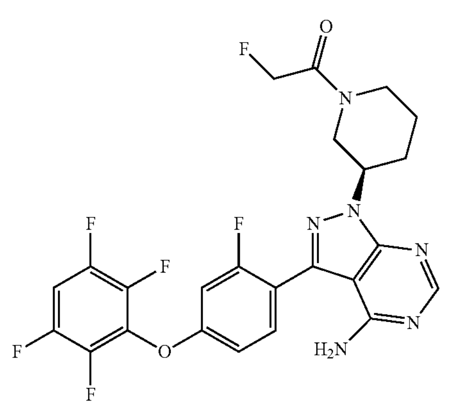 | 1-((R)-3-(4-amino-3-(2-fluoro-4-(2,3,5,6-tetrafluorophenoxy)phenyl)-1H-pyrazolo[3,4-d]pyrimidin-1-yl)piperidin-1-yl)-2-fluoroethanone | 537 |

TABLE 2-continued

BTK Representative Inhibitors

| Compound No. | Structure | Name | M + 1 |
|---|---|---|---|
| 108 | 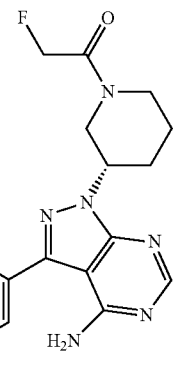 | 1-((S)-3-(4-amino-3-(2-fluoro-4-(2,3,5,6-tetrafluorophenoxy)phenyl)-1H-pyrazolo[3,4-d]pyrimidin-1-yl)piperidin-1-yl)-2-fluoroethanone | 537 |
| 109 | 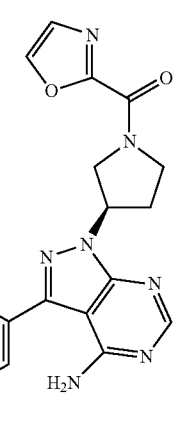 | ((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)(oxazol-2-yl)methanone | 558 |
| 110 | 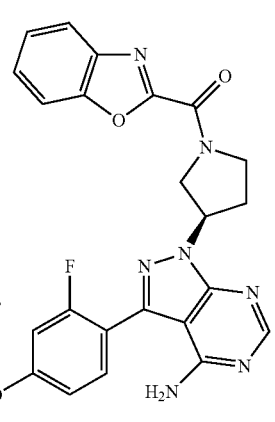 | ((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)(benzo[d]oxazol-2-yl)methanone | 608 |

TABLE 2-continued

BTK Representative Inhibitors

| Compound No. | Structure | Name | M + 1 |
|---|---|---|---|
| 111 | 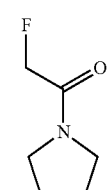 | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2-fluoroethanone | 523 |
| 112 | 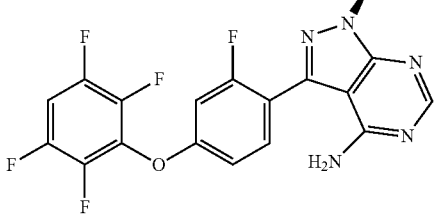 | 2-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2-oxoacetonitrile | 516 |
| 113 | 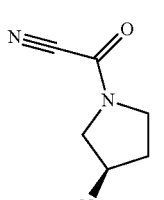 | 2-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)acetonitrile | 502 |

TABLE 2-continued

BTK Representative Inhibitors

| Compound No. | Structure | Name | M + 1 |
|---|---|---|---|
| 114 | 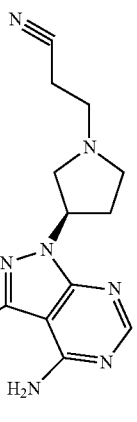 | 3-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)propanenitrile | 516 |
| 115 | 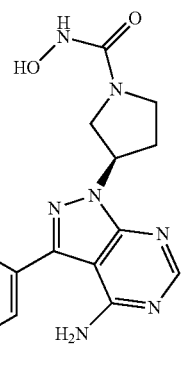 | (3R)-3-(4-amino-3-(2-fluoro-4-(2,3,5,6-tetrafluorophenoxy)phenyl)-1H-pyrazolo[3,4-d]pyrimidin-1-yl)-N-hydroxypyrrolidine-1-carboxamide | 522 |
| 116 | 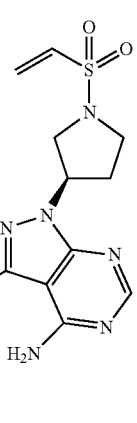 | 3-(2-fluoro-4-(2,3,5,6-tetrafluorophenoxy)phenyl)-1-((R)-1-(vinylsulfonyl)pyrrolidin-3-yl)-1H-pyrazolo[3,4-d]pyrimidin-4-amine | 553 |

TABLE 2-continued

BTK Representative Inhibitors

| Compound No. | Structure | Name | M + 1 |
|---|---|---|---|
| 117 | 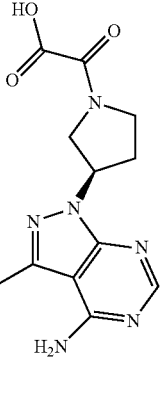 | 2-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2-oxoacetic acid | 535 |
| 118 | 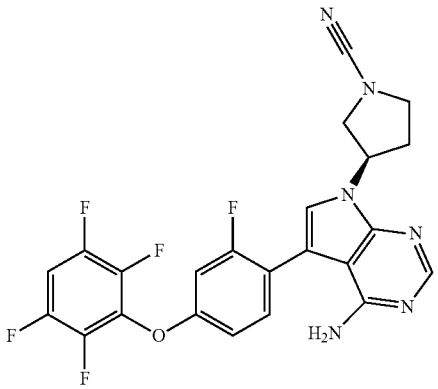 [SMILES: N#CN1CC[C@@H](n2cc(-c3ccc(Oc4c(F)c(F)cc(F)c4F)cc3F)c3c(N)ncnc32)C1] | (3R)-3-(4-amino-3-(2-fluoro-4-(2,3,5,6-tetrafluorophenoxy)phenyl)-1H-pyrrolo[2,3-d]pyrimidin-1-yl)pyrrolidine-1-carbonitrile | 488 |
| 119 | 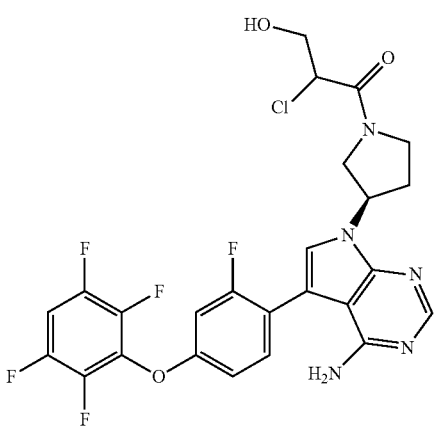 [SMILES: Nc1ncnc2c1c(-c1ccc(Oc3c(F)c(F)cc(F)c3F)cc1F)cn2[C@@H]1CCN(C(=O)C(Cl)CO)C1] | 1-((R)-3-(4-amino-3-(2-fluoro-4-(2,3,5,6-tetrafluorophenoxy)phenyl)-1H-pyrrolo[2,3-d]pyrimidin-1-yl)pyrrolidin-1-yl)-2-chloro-3-hydroxypropan-1-one | 569 |

TABLE 2-continued

BTK Representative Inhibitors

| Compound No. | Structure | Name | M + 1 |
|---|---|---|---|
| 120 | 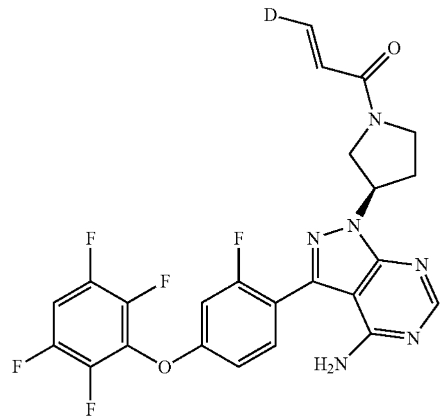 [SMILES: [2H]/C=C/C(=O)N1CC[C@@H](n2nc(-c3ccc(Oc4c(F)c(F)cc(F)c4F)cc3F)c3c(N)ncnc32)C1] | (E)-1-((R)-3-(4-amino-3-(2-fluoro-4-(2,3,5,6-tetrafluorophenoxy)phenyl)-1H-pyrrolo[2,3-d]pyrimidin-1-yl)pyrrolidin-1-yl)-3-deuterium-prop-2-en-1-one | 518 |
| 121 | 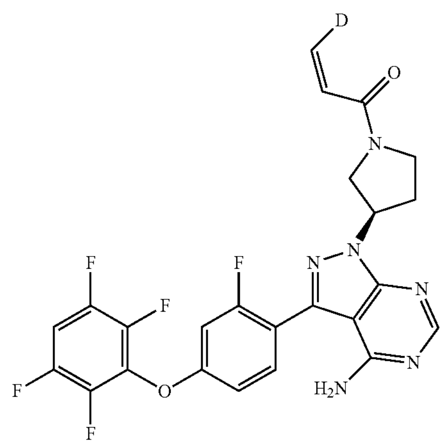 [SMILES: [2H]/C=C\C(=O)N1CC[C@@H](n2nc(-c3ccc(Oc4c(F)c(F)cc(F)c4F)cc3F)c3c(N)ncnc32)C1] | (Z)-1-((R)-3-(4-amino-3-(2-fluoro-4-(2,3,5,6-tetrafluorophenoxy)phenyl)-1H-pyrrolo[2,3-d]pyrimidin-1-yl)pyrrolidin-1-yl)-3-deuterium-prop-2-en-1-one | 518 |
| 122 | 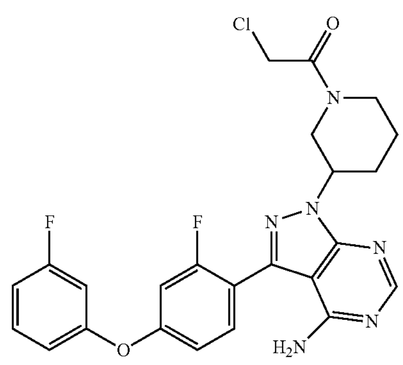 [SMILES: Nc1ncnc2c1c(-c1ccc(Oc3cccc(F)c3)cc1F)nn2C1CCCN(C(=O)CCl)C1] | 1-(3-(4-amino-3-(2-fluoro-4-(3-fluorophenoxy)phenyl)-1H-pyrazolo[3,4-d]pyrimidin-1-yl)piperidin-1-yl)-2-chloroethanone | 499 |

TABLE 2-continued

BTK Representative Inhibitors

| Compound No. | Structure | Name | M + 1 |
|---|---|---|---|
| 123 | 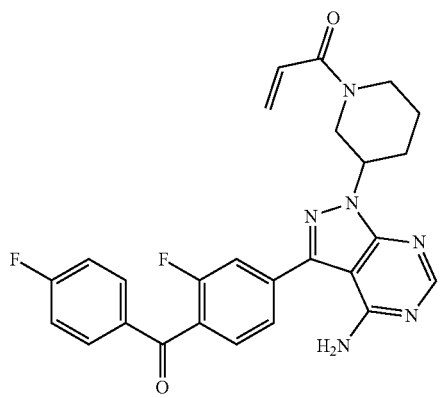 [SMILES: C=CC(=O)N1CCCC(n2nc(-c3ccc(C(=O)c4ccc(F)cc4)c(F)c3)c3c(N)ncnc32)C1] | 1-((R)-3-(4-amino-3-(2-fluoro-4-(3-fluorophenoxy)phenyl)-1H-pyrazolo[3,4-d]pyrimidin-1-yl)pyrrolidin-1-yl)but-2-yn-1-one | |

Note:
If there are differences between the structure and name, the structure will prevail.

Compound 1

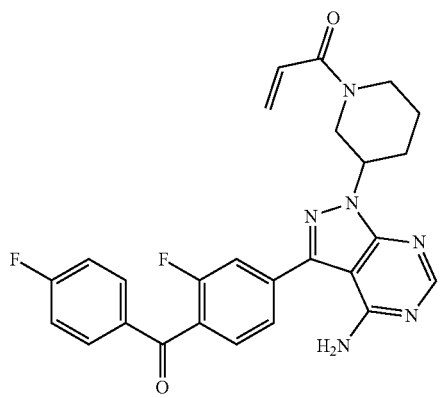 [SMILES: C=CC(=O)N1CCCC(n2nc(-c3ccc(C(=O)c4ccc(F)cc4)c(F)c3)c3c(N)ncnc32)C1]

1-(3-(4-amino-3-(3-fluoro-4-(4-fluorobenzoyl)phenyl)-1H-pyrazolo[3,4-d]pyrimidin-1-yl)piperidin-1-yl)prop-2-en-1-one Step A:

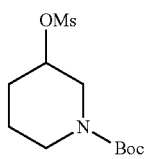

tert-butyl 3-(methylsulfonyloxy)piperidine-1-carboxylate

Procedure:

Triethylamine (15 g, 150 mmol, 3.0 eq.) and methanesulfonyl chloride (6.3 g, 55 mmol, 1.1 eq.) were sequentially added dropwise to a solution of tert-butyl 3-hydroxypiperidine-1-carboxylate (10.0 g, 50 mmol, 1.0 eq.) in dichloromethane (100 mL) at 0° C. The reaction was stirred at 20° C. for 1 hour, quenched with saturated NaHCO₃ (100 mL), and then extracted with methylene chloride (200 mL×3). The organic phase was dried over anhydrous sodium sulfate, and concentrated to give the title compound (13 g, yield: 95%).

Step B:

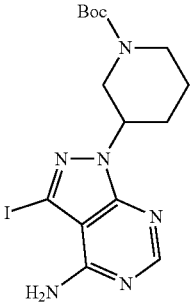 [SMILES: CC(C)(C)OC(=O)N1CCCC(n2nc(I)c3c(N)ncnc32)C1]

tert-butyl 3-(4-amino-3-iodo-1H-pyrazolo[3,4-d]pyrimidin-1-yl)piperidine-1-carboxylate Procedure:

Cesium carbonate (20.2 g, 62 mmol, 2.0 eq.) and tert-butyl 3-(methylsulfonyloxy)piperidine-1-carboxylate (13 g, 46.5 mmol, 1.5 eq.) were added to a solution of 3-iodo-1H-pyrazolo[3,4-d]-pyrimidin-4-amine (8.1 g, 31 mmol, 1.0 eq.) in DMF (50 mL) at 0° C. The reaction solution was stirred at 80° C. overnight. After cooling to room temperature, the mixture was filtered through celite. Filtrate was concentrated to give the crude product, which was purified by silica gel column chromatography (eluent:ethyl acetate) to give the title compound (5 g, yield: 25%).

Step C:

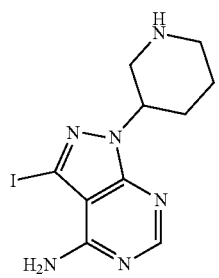 [SMILES: Nc1ncnc2c1c(I)nn2C1CCCNC1]

3-iodo-1-(piperidin-3-yl)-1H-pyrazolo[3,4-d]pyrimidin-4-amine

Procedure:

HCl/EA (20 mL, 4 mol/L) was added to a solution of tert-butyl 3-(4-amino-3-iodo-1H-pyrazolo[3,4-d]pyrimidin-1-yl)piperidine-1-carboxylate (5 g, 11.3 mmol) in dichloromethane (20 mL) at 0° C. The reaction was stirred for 1 hour at room temperature and concentrated to give the title compound hydrochloride (4 g, yield: 94%).

Step D:

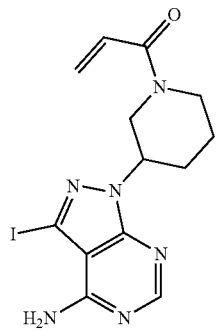 [SMILES: C=CC(=O)N1CCCC(n2nc(I)c3c(N)ncnc32)C1]

1-(3-(4-amino-3-iodo-1H-pyrazolo[3,4-d]pyrimidin-1-yl)piperidin-1-yl)prop-2-en-1-one Procedure:

Triethylamine (3.2 g, 31.5 mmol, 3.0 eq.) and acrylic chloride (950 mg, 10.5 mmol, 1.0 eq.) were subsequently added to a solution of 3-iodo-1-(piperidin-3-yl)-1H-pyrazolo[3,4-d]pyrimidin-4-amine hydrochloride (4 g, 10.5 mmol, 1.0 eq.) in dichloromethane (50 mL) at 0° C. The reaction mixture was stirred at 0° C. for 1 hour, and quenched with saturated sodium bicarbonate solution (30 mL). The aqueous phase was extracted with dichloromethane (50 mL×2). The combined organic phases were dried over anhydrous sodium sulfate, and then filtered. The filtrate was concentrated to give the crude product, which was purified by silica gel column chromatography (eluent:ethyl acetate) to give the title compound (3.7 g, yield: 90%).

Step E:

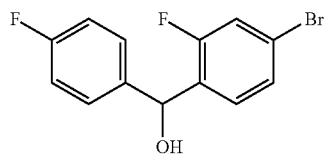 [SMILES: OC(c1ccc(F)cc1)c1ccc(Br)cc1F]

(4-bromo-2-fluorophenyl)(4-fluorophenyl)methanol

Procedure:

A solution of 4-fluorophenyl magnesium bromide in THF (1 M, 6.0 mL, 6.0 mmol, 1.2 eq.) was added dropwise to a solution of 4-bromo-2-fluorobenzaldehyde (1.0 g, 5.0 mmol, 1.0 eq.) in tetrahydrofuran (10 mL) at −78° C. The reaction mixture was stirred at room temperature for 2 hours, then cooled to 0° C. and quenched with saturated ammonium chloride solution. The mixture was extracted with ethyl acetate (10 mL×3). The combined organic phases were dried over anhydrous sodium sulfate, and then filtered. The filtrate was concentrated to give the crude product, which was purified by silica gel column chromatography (eluent:petroleum ether:ethyl acetate=1:0 to 1:1) to give the title compound (420 mg, yield: 30%).

Step F:

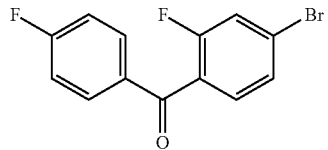 [SMILES: O=C(c1ccc(F)cc1)c1ccc(Br)cc1F]

(4-bromo-2-fluorophenyl)(4-fluorophenyl)methanone

Procedure:

Tetrapropylammonium perruthenate (80 mg, 0.22 mmol, 0.15 eq.), N-methyl morpholine oxide (346 mg, 2.96 mmol, 2.0 eq.) and 4 A molecular sieves (300 mg) were added to a solution of (4-bromo-2-fluorophenyl)(4-fluorophenyl)methanol (0.42 g, 1.48 mmol, 1.0 eq.) in dichloromethane (10 mL). The reaction mixture was stirred at room temperature for 2 hours, and then concentrated. The obtained crude product was purified by silica gel column chromatography (eluent:petroleum ether:ethyl acetate=1:0~1:1) to give the title compound (0.4 g, yield: 99%).

Step G:

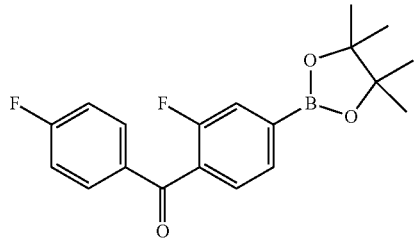 [SMILES: CC1(C)OB(c2ccc(C(=O)c3ccc(F)cc3)c(F)c2)OC1(C)C]

(2-fluoro-4-(4,4,5,5-tetramethyl-1,3,2-dioxaborolan-2-yl)phenyl)(4-fluorophenyl)methanone Procedure:

(4-bromo-2-fluorophenyl)(4-fluorophenyl)methanone (496 mg, 1.67 mmol, 1.0 eq.), bis(pinacolato)diboron (468 mg, 1.84 mmol, 1.1 eq.), potassium acetate (490 mg, 5.02 mmol, 3.0 eq.) and (1,1'-bis(diphenylphosphino)ferrocene)dichloropalladium (71 mg, 0.1 mmol, 0.058 eq.) were dissolved in 1,4-dioxane (3 mL), and then stirred at 80° C. under nitrogen for 4 hours. The reaction mixture was filtered through Celite. The filtrate was concentrated to give the crude product (574 mg, yield: 100%), which was used directly in the next step.

Step H:

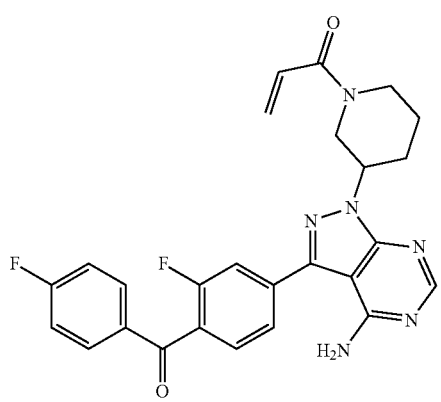 [SMILES: C=CC(=O)N1CCCC(n2nc(-c3ccc(C(=O)c4ccc(F)cc4)c(F)c3)c3c(N)ncnc32)C1]

1-(3-(4-amino-3-(3-fluoro-4-(4-fluorobenzoyl)phenyl)-1H-pyrazolo[3,4-d]pyrimidin-1-yl)piperidin-1-yl)prop-2-en-1-one Procedure:

(2-fluoro-4-(4,4,5,5-tetramethyl-1,3,2-dioxaborolan-2-yl)phenyl)(4-fluorophenyl)methanone (574 mg, 1.67 mmol, 1.0 eq.), 1-(3-(4-amino-3-iodo-1H-pyrazolo[3,4-d]pyrimidin-1-yl)piperidin-1-yl)prop-2-en-1-one (448 mg, 1.12 mmol, 1.0 eq.), sodium carbonate (356 mg, 3.36 mmol, 3.0 eq.) and Pd(PPh$_3$)$_4$ (127 mg, 0.11 mmol, 0.1 eq.) were dissolved in 1,4-dioxane/water (5 mL, 1/1, v/v). The reaction mixture was stirred at 85° C. for 30 minutes under nitrogen atmosphere with microwave irradiation. The reaction solution was diluted with water (10 mL), and then extracted with ethyl acetate (10 mL×3). The combined organic phases were dried over anhydrous sodium sulfate and filtered. The filtrate was concentrated to give the crude product, which was purified by thin layer chromatography (developer: ethyl acetate) to give the title compound (70 mg, yield: 12%).

LC/MS (Method: UFLC): RT=4.223 min; m/z=489.2 [M+H]$^+$; Total running time 7 min.

$^1$H NMR (400 MHz, DMSO-d$_6$) δ 8.30 (s, 1H), 8.00-7.97 (m, 2H), 7.73-7.55 (m, 3H), 7.46-7.41 (m, 2H), 6.91-6.70 (m, 1H), 6.16-6.05 (m, 1H), 5.73-5.58 (m, 1H), 4.80-4.73 (m, 1H), 4.56-4.54 (m, 0.5H), 4.22-4.06 (m, 1.5H), 3.81-3.75 (m, 0.5H), 3.30-3.12 (m, 1.5H), 2.35-2.15 (m, 2H), 1.97-1.94 (m, 1H), 1.66-1.60 (m, 1H).

Compound 2

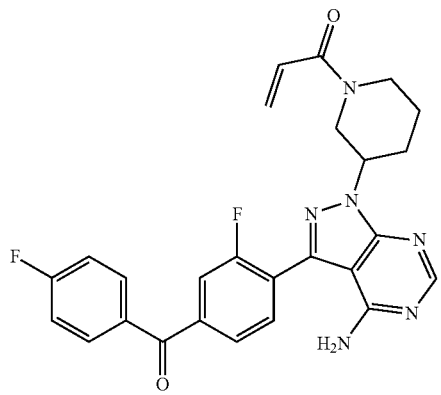 [SMILES: C=CC(=O)N1CCCC(n2nc(-c3ccc(C(=O)c4ccc(F)cc4)cc3F)c3c(N)ncnc32)C1]

1-(3-(4-amino-3-(2-fluoro-4-(4-fluorobenzoyl)phenyl)-1H-pyrazolo[3,4-d]pyrimidin-1-yl)piperidin-1-yl)prop-2-en-1-one Step A:

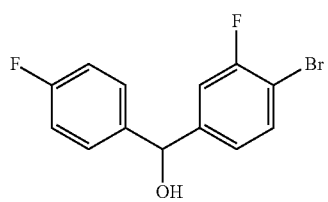 [SMILES: OC(c1ccc(F)cc1)c1ccc(Br)c(F)c1]

(4-bromo-3-fluorophenyl)(4-fluorophenyl)methanol

Procedure:

A solution of 4-fluorophenyl magnesium bromide in THF (1 M, 24.0 mL, 24.0 mmol, 1.2 eq.) was added dropwise to a solution of 4-bromo-3-fluorobenzaldehyde (4.06 g, 20.0 mmol, 1.0 eq.) in tetrahydrofuran (20 mL) at −78° C. The reaction mixture was stirred at room temperature for 2 hours, then cooled to 0° C. and quenched with saturated ammonium chloride solution. The mixture was extracted with ethyl acetate (10 mL×3). The combined organic phases were dried over anhydrous sodium sulfate, and then filtered. The filtrate was concentrated to give the crude product, which was purified by silica gel column chromatography (eluent:petroleum ether:ethyl acetate=1:0 to 1:1) to give the title compound (5.3 g, yield: 89%).

Step B:

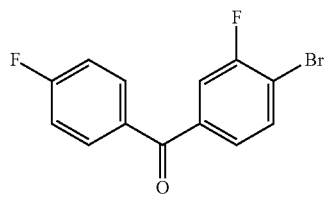 [SMILES: O=C(c1ccc(F)cc1)c1ccc(Br)c(F)c1]

(4-bromo-3-fluorophenyl)(4-fluorophenyl)methanone

Procedure:

Tetrapropylammonium perruthenate (580 mg, 1.66 mmol, 0.15 eq.), N-methyl morpholine oxide (2.6 g, 22.0 mmol, 2.0 eq.) and 4 A molecular sieves (1.0 g) were added to a solution of (4-bromo-3-fluorophenyl)(4-fluorophenyl) methanol (3.3 g, 11.0 mmol, 1.0 eq.) in dichloromethane (20 mL). The reaction mixture was stirred at room temperature for 2 hours, and then concentrated. The obtained crude product was purified by silica gel column chromatography (eluent:petroleum ether:ethyl acetate=1:0~1:1) to give the title compound (3.0 g, yield: 92%).

Step C:

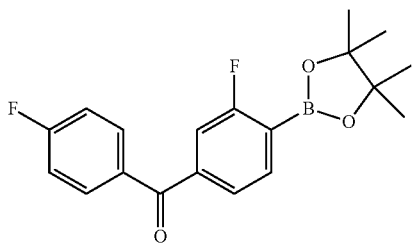 [SMILES: CC1(C)OB(c2ccc(C(=O)c3ccc(F)cc3)cc2F)OC1(C)C]

(3-fluoro-4-(4,4,5,5-tetramethyl-1,3,2-dioxaborolan-2-yl)phenyl)(4-fluorophenyl)methanone Procedure:

(4-bromo-3-fluorophenyl)(4-fluorophenyl)methanone (1.0 g, 3.5 mmol, 1.0 eq.), bis(pinacolato)diboron (980 mg, 3.9 mmol, 1.1 eq.), potassium acetate (1.2 g, 12.3 mmol, 3.5 eq.) and (1,1'-bis(diphenylphosphino)ferrocene)dichloropalladium (149 mg, 0.2 mmol, 0.058 eq.) were dissolved in 1,4-dioxane (10 mL), and then stirred at 80° C. under nitrogen for 4 hours. The reaction mixture was filtered through Celite. The filtrate was concentrated to give the crude product (1.2 g, yield: 100%), which was used directly in the next step.

Step D:

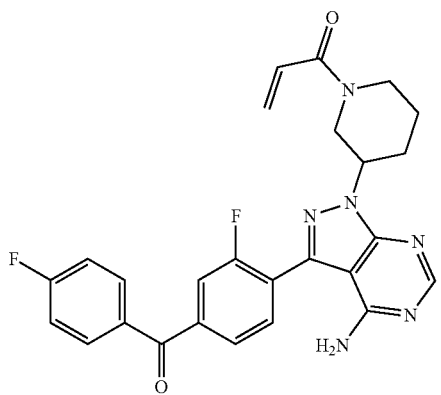 [SMILES: C=CC(=O)N1CCCC(n2nc(-c3ccc(C(=O)c4ccc(F)cc4)cc3F)c3c(N)ncnc32)C1]

1-(3-(4-amino-3-(2-fluoro-4-(4-fluorobenzoyl)phenyl)-1H-pyrazolo[3,4-d]pyrimidin-1-yl)piperidin-1-yl)prop-2-en-1-one Procedure:

(3-fluoro-4-(4,4,5,5-tetramethyl-1,3,2-dioxaborolan-2-yl) phenyl)(4-fluorophenyl)methanone (306 mg, 0.89 mmol, 1.0 eq.), 1-(3-(4-amino-3-iodo-1H-pyrazolo[3,4-d]pyrimidin-1-yl)piperidin-1-yl)prop-2-en-1-one (355 mg, 1.12 mmol, 1.0 eq.), sodium carbonate (283 mg, 2.67 mmol, 3.0 eq.) and Pd(PPh$_3$)$_4$ (100 mg, 0.09 mmol, 0.1 eq.) were dissolved in 1,4-dioxane/water (10 mL, 1/1, v/v). The reaction mixture was stirred at 85° C. for 30 minutes under nitrogen atmosphere with microwave irradiation. The reaction solution was diluted with water (10 mL), and then extracted with ethyl acetate (10 mL×3). The combined organic phases were dried over anhydrous sodium sulfate and filtered. The filtrate was concentrated to give the crude product, which was purified by HPLC (C18 reverse phase column, mobile phase: acetonitrile/water, gradient 10%-100% (volume ratio)) to give the title compound (42 mg, yield: 10%).

LC/MS (Method: UFLC): RT=0.740 min; m/z=488.9 [M+H]$^+$; Total running time2 min.

$^1$H NMR (400 MHz, DMSO-d$_6$) δ 8.25 (s, 1H), 7.97-7.93 (m, 2H), 7.75-7.63 (m, 3H), 7.45-7.41 (m, 2H), 6.88-6.71 (m, 1H), 6.14-6.02 (m, 1H), 5.74-5.56 (m, 1H), 4.73-4.54 (m, 1.5H), 4.19-4.04 (m, 1.5H), 3.71-3.65 (m, 0.5H), 3.23-3.15 (m, 1H), 3.02-2.97 (m, 0.5H), 2.31-2.07 (m, 2H), 1.97-1.90 (m, 1H), 1.60-1.52 (m, 1H).

Compound 3

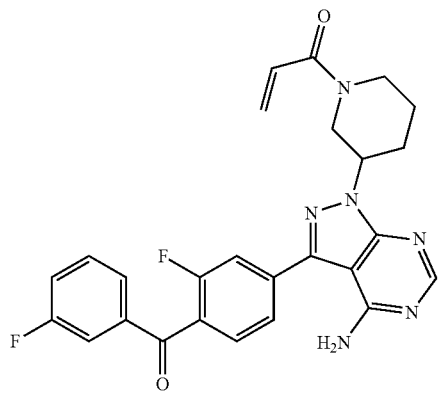 [SMILES: C=CC(=O)N1CCCC(n2nc(-c3ccc(C(=O)c4cccc(F)c4)c(F)c3)c3c(N)ncnc32)C1]

1-(3-(4-amino-3-(3-fluoro-4-(3-fluorobenzoyl)phenyl)-1H-pyrazolo[3,4-d]pyrimidin-1-yl)piperidin-1-yl)prop-2-en-1-one Step A:

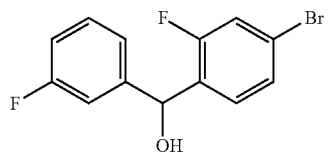 [SMILES: OC(c1cccc(F)c1)c1ccc(Br)cc1F]

(4-bromo-2-fluorophenyl)(3-fluorophenyl)methanol

Procedure:

A solution of 3-fluorophenyl magnesium bromide in THF (1 M, 6.0 mL, 6.0 mmol, 1.2 eq.) was added dropwise to a solution of 4-bromo-2-fluorobenzaldehyde (1.0 g, 5.0 mmol, 1.0 eq.) in tetrahydrofuran (10 mL) at −78° C. The reaction mixture was stirred at room temperature for 2 hours, then cooled to 0° C. and quenched with saturated ammonium chloride solution. The mixture was extracted with ethyl acetate (10 mL×3). The combined organic phases were dried over anhydrous sodium sulfate, and then filtered. The filtrate was concentrated to give the crude product, which was purified by silica gel column chromatography (eluent:petroleum ether:ethyl acetate=1:0 to 1:1) to give the title compound (420 mg, yield: 30%).

Step B:

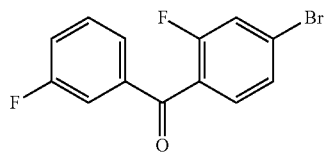 [SMILES: O=C(c1cccc(F)c1)c1ccc(Br)cc1F]

(4-bromo-2-fluorophenyl)(3-fluorophenyl)methanone

Procedure:

Tetrapropylammonium perruthenate (80 mg, 0.22 mmol, 0.15 eq.), N-methyl morpholine oxide (346 mg, 2.96 mmol, 2.0 eq.) and 4 A molecular sieves (300 mg) were added to a solution of (4-bromo-2-fluorophenyl)(3-fluorophenyl) methanol (0.42 g, 1.48 mmol, 1.0 eq.) in dichloromethane (10 mL). The reaction mixture was stirred at room temperature for 2 hours, and then concentrated. The obtained crude product was purified by silica gel column chromatography (eluent:petroleum ether:ethyl acetate=1:0~1:1) to give the title compound (0.4 g, yield: 99%).

Step C:

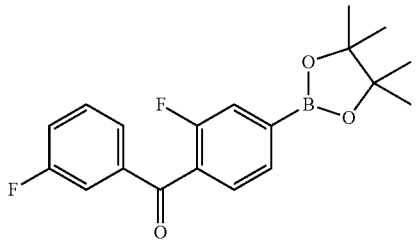 [SMILES: CC1(C)OB(c2ccc(C(=O)c3cccc(F)c3)c(F)c2)OC1(C)C]

(2-fluoro-4-(4,4,5,5-tetramethyl-1,3,2-dioxaborolan-2-yl)phenyl)(3-fluorophenyl)methanone Procedure:

(4-bromo-2-fluorophenyl)(3-fluorophenyl)methanone (200 mg, 0.67 mmol, 1.0 eq.), bis(pinacolato)diboron (188 mg, 0.73 mmol, 1.1 eq.), potassium acetate (200 mg, 2.01 mmol, 3.0 eq.) and (1,1'-bis(diphenylphosphino)ferrocene) dichloropalladium (28 mg, 0.039 mmol, 0.058 eq.) were dissolved in 1,4-dioxane (10 mL), and then stirred at 80° C. under nitrogen for 12 hours. The reaction mixture was filtered through celite. The filtrate was concentrated to give the crude product (240 mg, yield: 100%), which was used directly in the next step.

Step D:

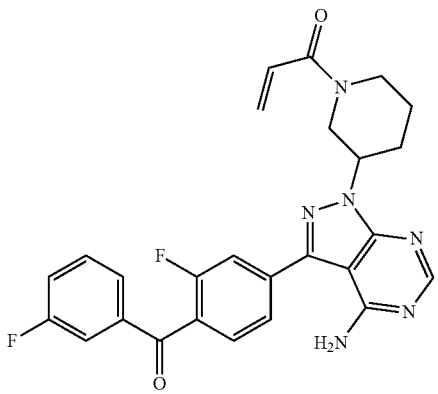 [SMILES: C=CC(=O)N1CCCC(n2nc(-c3ccc(C(=O)c4cccc(F)c4)c(F)c3)c3c(N)ncnc32)C1]

1-(3-(4-amino-3-(3-fluoro-4-(3-fluorobenzoyl)phenyl)-1H-pyrazolo[3,4-d]pyrimidin-1-yl)piperidin-1-yl)prop-2-en-1-one Procedure:

(2-fluoro-4-(4,4,5,5-tetramethyl-1,3,2-dioxaborolan-2-yl) phenyl)(3-fluorophenyl)methanone (192 mg, 0.48 mmol, 1.0 eq.), 1-(3-(4-amino-3-iodo-1H-pyrazolo[3,4-d]pyrimidin-1-yl)piperidin-1-yl)prop-2-en-1-one (300 mg, 0.87 mmol, 1.8 eq.), sodium carbonate (51 mg, 1.45 mmol, 3.0 eq.) and Pd(PPh$_3$)$_4$ (56 mg, 0.05 mmol, 0.1 eq.) were dissolved in 1,4-dioxane/water (10 mL, 1/1, v/v). The reaction mixture was stirred at 85° C. for 30 minutes under nitrogen atmosphere with microwave irradiation. The reaction solution was diluted with water (10 mL), and then extracted with ethyl acetate (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.5% HCl, gradient 10%-100% (volume ratio)) to give the title compound hydrochloride (10 mg, yield: 4%).

LC/MS (Method: UFLC): RT=2.969 min; m/z=489.1 [M+H]$^+$; Total running time 7 min.

Compound 4

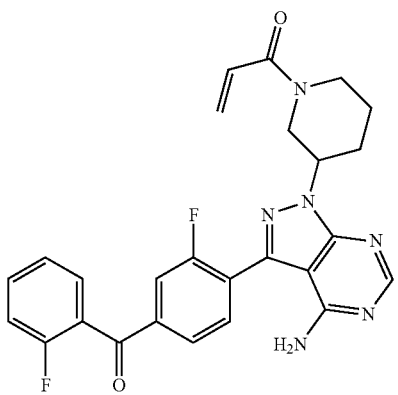 [SMILES: C=CC(=O)N1CCCC(n2nc(-c3ccc(C(=O)c4ccccc4F)cc3F)c3c(N)ncnc32)C1]

1-(3-(4-amino-3-(2-fluoro-4-(2-fluorobenzoyl)phenyl)-1H-pyrazolo[3,4-d]pyrimidin-1-yl)piperidin-1-yl)prop-2-en-1-one Step A:

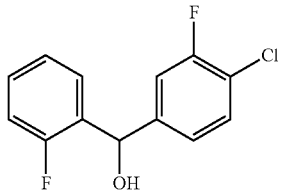 [SMILES: OC(c1ccc(Cl)c(F)c1)c1ccccc1F]

(4-chloro-3-fluorophenyl)(2-fluorophenyl)methanol

Procedure:

A solution of 4-chloro-3-fluorophenyl magnesium bromide in THF (2 M, 19.3 mL, 38.6 mmol, 1.2 eq.) was added dropwise to a solution of 2-fluorobenzaldehyde (3.6 g, 32.0 mmol, 1.0 eq.) in tetrahydrofuran (10 mL) at −78° C. The reaction mixture was stirred at room temperature for 2 hours, then cooled to 0° C. and quenched with saturated ammonium chloride solution. The mixture was extracted with ethyl acetate (30 mL×3). The combined organic phases were dried over anhydrous sodium sulfate, and then filtered. The filtrate was concentrated to give the crude product, which was purified by silica gel column chromatography (eluent:petroleum ether:ethyl acetate=1:0 to 1:1) to give the title compound (2.2 g, yield: 25%).

Step B:

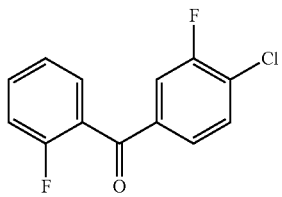 [SMILES: O=C(c1ccc(Cl)c(F)c1)c1ccccc1F]

(4-chloro-3-fluorophenyl)(2-fluorophenyl)methanone

Procedure:

Tetrapropylammonium perruthenate (455 mg, 1.3 mmol, 0.15 eq.), N-methyl morpholine oxide (2.0 g, 17.3 mmol, 2.0 eq.) and 4 Å molecular sieves (1.0 g) were added to a solution of (4-chloro-3-fluorophenyl)(2-fluorophenyl)methanol (2.2 g, 8.66 mmol, 1.0 eq.) in dichloromethane (20 mL). The reaction mixture was stirred at room temperature for 2 hours, and then concentrated. The obtained crude product was purified by silica gel column chromatography (eluent:petroleum ether:ethyl acetate=1:0~1:1) to give the title compound (2.0 g, yield: 92%).

Step C:

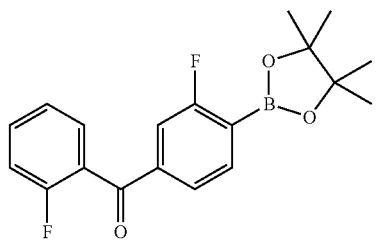 [SMILES: CC1(C)OB(c2ccc(C(=O)c3ccccc3F)cc2F)OC1(C)C]

(3-fluoro-4-(4,4,5,5-tetramethyl-1,3,2-dioxaborolan-2-yl)phenyl)(2-fluorophenyl)methanone Procedure:
(4-chloro-3-fluorophenyl)(2-fluorophenyl)methanone (1.5 g, 5.94 mmol, 1.0 eq.), bis(pinacolato)diboron (3.3 g, 13.08 mmol, 2.2 eq.), potassium acetate (1.74 g, 17.8 mmol, 3.0 eq.), tris(dibenzylideneacetone)dipalladium (540 mg, 0.59 mmol, 0.1 eq.) and 2-dicyclohexyl phosphino-2', 4', 6'-triisopropyl biphenyl (1.14 g, 2.37 mmol, 0.4 eq.) were dissolved in 1,4-dioxane (10 mL), and then stirred at 110° C. under microwave irradiation for 1 hours. The reaction mixture was filtered through Celite. The filtrate was concentrated to give the crude product (2.0 g, yield: 100%), which was used directly in the next step.

Step D:

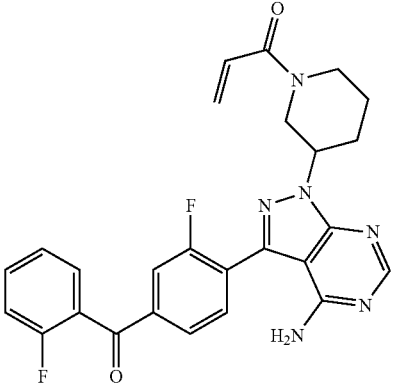 [SMILES: C=CC(=O)N1CCCC(n2nc(-c3ccc(C(=O)c4ccccc4F)cc3F)c3c(N)ncnc32)C1]

1-(3-(4-amino-3-(2-fluoro-4-(2-fluorobenzoyl)phenyl)-1H-pyrazolo[3,4-d]pyrimidin-1-yl)piperidin-1-yl)prop-2-en-1-one Procedure:
(3-fluoro-4-(4,4,5,5-tetramethyl-1,3,2-dioxaborolan-2-yl)phenyl)(2-fluorophenyl)methanone (2.0 g, 5.81 mmol, 2.3 eq.), 1-(3-(4-amino-3-iodo-1H-pyrazolo[3,4-d]pyrimidin-1-yl)piperidin-1-yl)prop-2-en-1-one (1.0 g, 2.51 mmol, 1.0 eq.), sodium carbonate (798 mg, 7.53 mmol, 3.0 eq.) and Pd(PPh$_3$)$_4$ (300 mg, 0.25 mmol, 0.1 eq.) were dissolved in 1,4-dioxane/water (20 mL, 1/1, v/v). The reaction mixture was stirred at 85° C. for 30 minutes under nitrogen atmosphere with microwave irradiation. The reaction solution was diluted with water (20 mL), and then extracted with ethyl acetate (20 mL×3). The combined organic phases were dried over anhydrous sodium sulfate and filtered. The filtrate was concentrated to give the crude product, which was purified by HPLC (C18 reverse phase column, mobile phase: acetonitrile/water/0.5% HCl, gradient 10%-100% (volume ratio)) to give the title compound hydrochloride (70 mg, yield: 6%).

LC/MS (Method: UFLC): RT=2.156 min; m/z=489.2 [M+H]$^+$; Total running time 4 min.

Compound 5

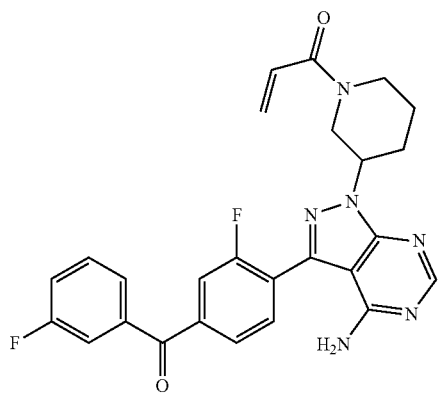 [SMILES: C=CC(=O)N1CCCC(n2nc(-c3ccc(C(=O)c4cccc(F)c4)cc3F)c3c(N)ncnc32)C1]

1-(3-(4-amino-3-(2-fluoro-4-(3-fluorobenzoyl)phenyl)-1H-pyrazolo[3,4-d]pyrimidin-1-yl)piperidin-1-yl)prop-2-en-1-one Step A:

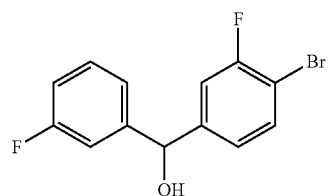 [SMILES: OC(c1cccc(F)c1)c1ccc(Br)c(F)c1]

(4-bromo-3-fluorophenyl)(3-fluorophenyl)methanol

Procedure:

A solution of 3-fluorophenyl magnesium bromide in THF (1 M, 75 mL, 75 mmol, 1.5 eq.) was added dropwise to a solution of 4-bromo-3-fluorobenzaldehyde (10.0 g, 49.2 mmol, 1.0 eq.) in tetrahydrofuran (100 mL) at −78° C. The reaction mixture was stirred at room temperature for 2 hours, then cooled to 0° C. and quenched with saturated ammonium chloride solution. The mixture was extracted with ethyl acetate (100 mL×3). The combined organic phases were dried over anhydrous sodium sulfate, and then filtered. The filtrate was concentrated to give the crude product, which was purified by silica gel column chromatography (eluent: petroleum ether:ethyl acetate=1:0 to 1:1) to give the title compound (2.0 g, yield: 13%).

Step B:

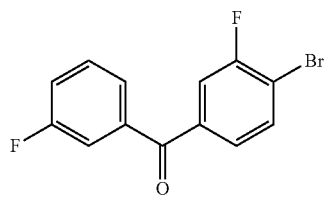 [SMILES: O=C(c1cccc(F)c1)c1ccc(Br)c(F)c1]

(4-bromo-3-fluorophenyl)(3-fluorophenyl)methanone

Procedure:

Tetrapropylammonium perruthenate (350 mg, 1.0 mmol, 0.15 eq.), N-methyl morpholine oxide (1.56 g, 13.4 mmol, 2.0 eq.) and 4 A molecular sieves (1.0 g) were added to a solution of (4-bromo-3-fluorophenyl)(3-fluorophenyl)methanol (2.0 g, 6.69 mmol, 1.0 eq.) in dichloromethane (20 mL). The reaction mixture was stirred at room temperature for 2 hours, and then concentrated. The obtained crude product was purified by silica gel column chromatography (eluent:petroleum ether:ethyl acetate=1:0~1:1) to give the title compound (1.95 g, yield: 98%).

Step C:

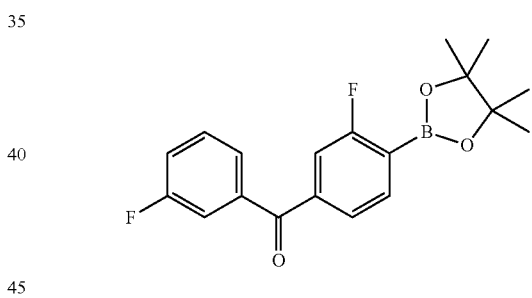

(3-fluoro-4-(4,4,5,5-tetramethyl-1,3,2-dioxaborolan-2-yl)phenyl)(3-fluorophenyl)methanone Procedure:

(4-bromo-3-fluorophenyl)(3-fluorophenyl)methanone (1.9 g, 6.4 mmol, 1.0 eq.), bis(pinacolato)diboron (2.1 g, 8.3 mmol, 1.2 eq.), potassium acetate (1.9 g, 19.2 mmol, 3.0 eq.), tris(dibenzylideneacetone)dipalladium (585 mg, 0.64 mmol, 0.1 eq.) and 2-dicyclohexyl phosphino-2',4',6'-triisopropyl biphenyl (1.21 g, 2.56 mmol, 0.4 eq.) were dissolved in 1,4-dioxane (10 mL), and then stirred at 110° C. under microwave irradiation for 1 hours. The reaction mixture was filtered through celite. The filtrate was concentrated to give the crude product (2.2 g, yield: 100%), which was used directly in the next step.

Step D:

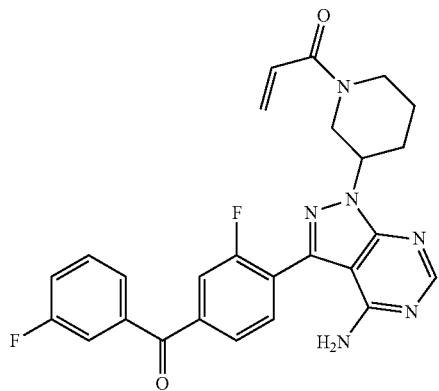 [SMILES: C=CC(=O)N1CCCC(n2nc(-c3ccc(C(=O)c4cccc(F)c4)cc3F)c3c(N)ncnc32)C1]

1-(3-(4-amino-3-(2-fluoro-4-(3-fluorobenzoyl)phenyl)-1H-pyrazolo[3,4-d]pyrimidin-1-yl)piperidin-1-yl)prop-2-en-1-one Procedure:
(3-fluoro-4-(4,4,5,5-tetramethyl-1,3,2-dioxaborolan-2-yl)phenyl)(3-fluorophenyl)methanone (2.5 g, 7.3 mmol, 2.0 eq.), 1-(3-(4-amino-3-iodo-1H-pyrazolo[3,4-d]pyrimidin-1-yl)piperidin-1-yl)prop-2-en-1-one (1.4 g, 3.6 mmol, 1.0 eq.), sodium carbonate (1.14 g, 10.8 mmol, 3.0 eq.) and Pd(PPh$_3$)$_4$ (416 mg, 0.36 mmol, 0.1 eq.) were dissolved in 1,4-dioxane/water (20 mL, 1/1, v/v). The reaction mixture was stirred at 85° C. for 30 minutes under nitrogen atmosphere with microwave irradiation. The reaction solution was diluted with water (50 mL), and then extracted with ethyl acetate (50 mL×3). The combined organic phases were dried over anhydrous sodium sulfate and filtered. The filtrate was concentrated to give the crude product, which was purified by HPLC (C18 reverse phase column, mobile phase: acetonitrile/water/0.5% HCl, gradient 10%-100% (volume ratio)) to give the title compound hydrochloride (150 mg, yield: 4%).

LC/MS (Method: UFLC): RT=0.787 min; m/z=489.1 [M+H]$^+$; Total running time 1.5 min.

$^1$H NMR (400 MHz, CDCl$_3$) δ 8.43 (s, 1H), 7.78-7.73 (m, 3H), 7.65-7.53 (m, 3H), 7.35-7.25 (m, 1H), 6.64-6.57 (m, 1H), 6.35-6.28 (m, 1H), 5.76-5.66 (m, 1H), 5.48 (br, 2H), 4.99-4.90 (m, 1.5H), 4.60-4.56 (m, 0.5H), 4.25-4.22 (m, 0.5H), 4.07-4.05 (m, 0.5H), 3.81-3.77 (m, 0.5H), 3.45-3.41 (m, 0.5H), 3.28-3.20 (m, 0.5H), 2.99-2.94 (m, 0.5H), 2.44-2.32 (m, 2H), 2.06-2.01 (m, 1H), 1.80-1.76 (m, 1H).

Compound 6

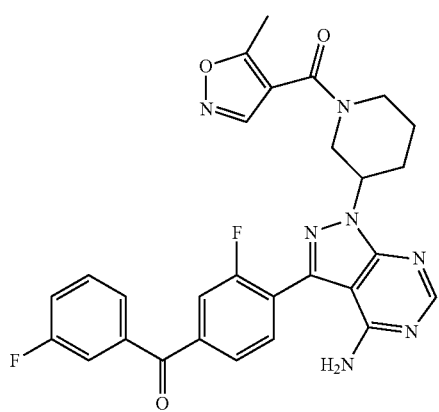 [SMILES: Cc1oncc1C(=O)N1CCCC(n2nc(-c3ccc(C(=O)c4cccc(F)c4)cc3F)c3c(N)ncnc32)C1]

(3-(4-amino-3-(2-fluoro-4-(3-fluorobenzoyl)phenyl)-1H-pyrazolo[3,4-d]pyrimidin-1-yl)piperidin-1-yl)(5-methylisoxazol-4-yl)methanone Step A:

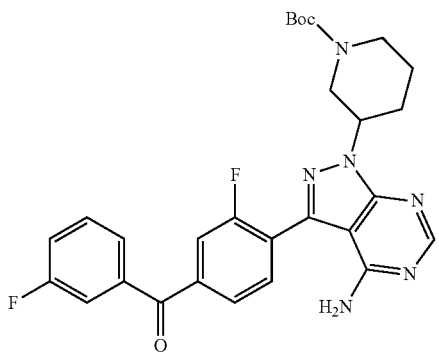 [SMILES: CC(C)(C)OC(=O)N1CCCC(n2nc(-c3ccc(C(=O)c4cccc(F)c4)cc3F)c3c(N)ncnc32)C1]

tert-butyl 3-(4-amino-3-(2-fluoro-4-(3-fluorobenzoyl)phenyl)-1H-pyrazolo[3,4-d]pyrimidin-1-yl)piperidine-1-carboxylate Procedure:
(3-fluoro-4-(4,4,5,5-tetramethyl-1,3,2-dioxaborolan-2-yl)phenyl)(3-fluorophenyl)methanone (1.16 g, 3.38 mmol, 2.0 eq.), tert-butyl 3-(4-amino-3-iodo-1H-pyrazolo[3,4-d]pyrimidin-1-yl)piperidine-1-carboxylate (0.75 g, 1.69 mmol, 1.0 eq.), sodium carbonate (358 mg, 3.38 mmol, 2.0 eq.) and Pd(PPh$_3$)$_4$ (196 mg, 0.17 mmol, 0.1 eq.) were dissolved in 1,4-dioxane (10 mL). The reaction mixture was stirred at 85° C. for 30 minutes under nitrogen atmosphere with microwave irradiation. The reaction solution was diluted with water (50 mL), and then extracted with ethyl acetate (50 mL×3). The combined organic phases were dried over anhydrous sodium sulfate and filtered. The filtrate was concentrated to give the crude product, which was purified by silica gel column chromatography (eluent:ethyl acetate: petroleum ether=1:1) to give the title compound (500 mg, yield: 55%).

Step B:

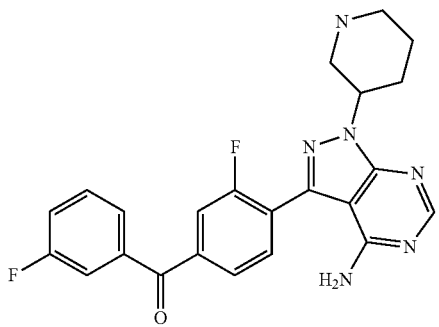 [SMILES: Nc1ncnc2c1c(-c1ccc(C(=O)c3cccc(F)c3)cc1F)nn2C1CCCNC1]

(4-(4-amino-1-(piperidin-3-yl)-1H-pyrazolo[3,4-d]pyrimidin-3-yl)-3-fluorophenyl)(3-fluorophenyl)methanone Procedure:

4M HCl/EtOAc (5 mL) was added to a solution of tert-butyl 3-(4-amino-3-(2-fluoro-4-(3-fluorobenzoyl)phenyl)-1H-pyrazolo[3,4-d]pyrimidin-1-yl)piperidine-1-carboxylate (500 mg, 0.94 mol) in dicloromethane (5 mL) at 0° C. The reaction mixture was stirred at room temperature for 1 h and concentrated to give the title compound hydrochloride (440 mg, yield: 99%).

Step C:

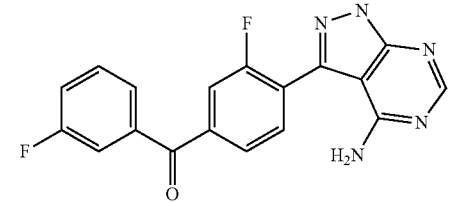

(3-(4-amino-3-(2-fluoro-4-(3-fluorobenzoyl)phenyl)-1H-pyrazolo[3,4-d]pyrimidin-1-yl)piperidin-1-yl)(5-methylisoxazol-4-yl)methanone Procedure:

5-methylisoxazole-4-carboxylic acid (15 mg, 0.11 mmol, 1.1 eq.), HATU (60 mg, 0.15 mmol, 1.5 eq.) and DIPEA (38 mg, 0.3 mmol, 3.0 eq.) were added to a solution of (4-(4-amino-1-(piperidin-3-yl)-1H-pyrazolo[3,4-d]pyrimidin-3-yl)-3-fluorophenyl)(3-fluorophenyl)methanone (45 mg, 0.1 mmol, 1.0 eq.) in dichloromethane (10 mL). The reaction mixture was stirred at room temperature for 12 hours, and concentrated to give the crude product, which was purified by HPLC (C18 reverse phase column, mobile phase: acetonitrile/water/0.5% HCl, eluent gradient 10%-100% (volume ratio)) to give the title compound hydrochloride (44 mg, yield: 81%).

LC/MS (Method: UFLC): RT=2.976 min; m/z=544.3 [M+H]⁺; Total running time 7 min.

Compound 7

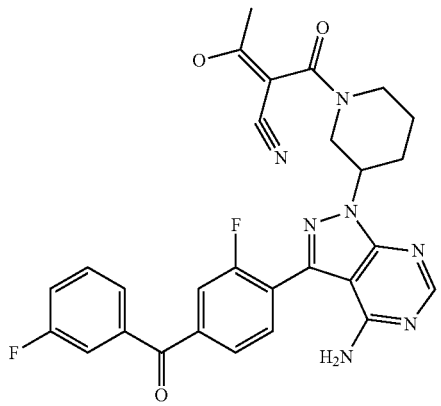 [SMILES: C/C(O)=C(/C#N)C(=O)N1CCCC(n2nc(-c3ccc(C(=O)c4cccc(F)c4)cc3F)c3c(N)ncnc32)C1]

(E)-2-(3-(4-amino-3-(2-fluoro-4-(3-fluorobenzoyl)phenyl)-1H-pyrazolo[3,4-d]pyrimidin-1-yl)piperidine-1-carbonyl)-3-hydroxybut-2-enenitrile Procedure:

Triethylamine (17 mg, 0.16 mmol, 3.0 eq.) was added to a solution of (3-(4-amino-3-(2-fluoro-4-(3-fluorobenzoyl)phenyl)-1H-pyrazolo[3,4-d]pyrimidin-1-yl)piperidin-1-yl)(5-methylisoxazol-4-yl)methanone (30 mg, 0.055 mmol, 1.0 eq.) in tetrahydrofuran (10 mL). The reaction was stirred at room temperature for 12 hours and concentrated to give the title compound (26 mg, yield: 83%).

LC/MS (Method: UFLC): RT=1.089 min; m/z=544.3 [M+H]⁺; Total running time 2 min.

Compound 8

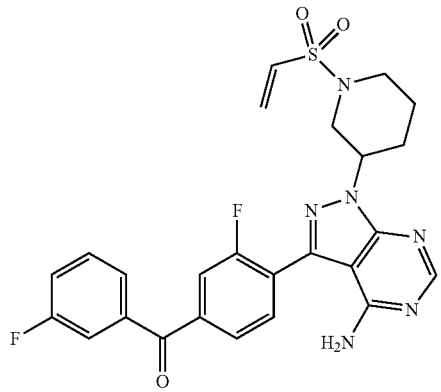 [SMILES: C=CS(=O)(=O)N1CCCC(n2nc(-c3ccc(C(=O)c4cccc(F)c4)cc3F)c3c(N)ncnc32)C1]

(4-(4-amino-1-(1-(vinylsulfonyl)piperidin-3-yl)-1H-pyrazolo[3,4-d]pyrimidin-3-yl)-3-fluorophenyl)(3-fluorophenyl)methanone Procedure:

2-chloroethanesulfonyl chloride (16 mg, 0.1 mmol, 1.0 eq.) and triethylamine (50 mg, 0.5 mmol, 5.0 eq.) were added to a solution of (4-(4-amino-1-(piperidin-3-yl)-1H-pyrazolo[3,4-d]pyrimidin-3-yl)-3-fluorophenyl)(3-fluorophenyl)methanone (45 mg, 0.1 mmol, 1.0 eq.) in dichloromethane (10 mL). The reaction mixture was stirred at room temperature for 12 hours, and concentrated to give the crude product, which was purified by HPLC (C18 reverse phase column, mobile phase: acetonitrile/water, eluent gradient 10%-100% (volume ratio)) to give the title compound (2 mg, yield: 4%).

LC/MS (Method: UFLC): RT=2.030 min; m/z=525.1 [M+H]⁺; Total running time 3 min.

Compound 9

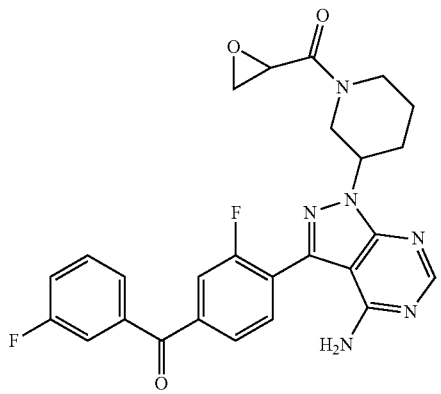 [SMILES: Nc1ncnc2c1c(-c1ccc(C(=O)c3cccc(F)c3)cc1F)nn2C1CCCN(C(=O)C2CO2)C1]

(3-(4-amino-3-(2-fluoro-4-(3-fluorobenzoyl)phenyl)-1H-pyrazolo[3,4-d]pyrimidin-1-yl)piperidin-1-yl)(oxiran-2-yl)methanone Procedure:

Potassium oxirane-2-carboxylate (19 mg, 0.15 mmol, 1.0 eq.), PyBrop (84 mg, 0.18 mmol, 1.2 eq.) and DIPEA (38 mg, 0.3 mmol, 2.0 eq.) were added to a solution of (4-(4-amino-1-(piperidin-3-yl)-1H-pyrazolo[3,4-d]pyrimidin-3-yl)-3-fluorophenyl)(3-fluorophenyl)methanone (65 mg, 0.15 mmol, 1.0 eq.) in DMF (2 mL). The reaction was stirred 90° C. for 12 hours. After cooling to room temperature, the reaction mixture was diluted with saturated brine (10 mL) and extracted with ethyl acetate (10 mL×2). The combined organic phases were dried over anhydrous sodium sulfate and filtered. The filtrate was concentrated to give the crude product, which was purified by HPLC (C18 reverse phase column, mobile phase: acetonitrile/water/0.5% HCl, eluent gradient 10%-100% (volume ratio)) to give the title compound hydrochloride (38 mg, yield: 51%).

LC/MS (Method: UFLC): RT=4.157 min; m/z=505.2 [M+H]$^+$; Total running time 7 min.

Compound 10

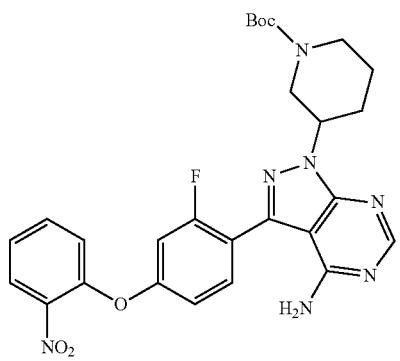 [SMILES: CC(C)(C)OC(=O)N1CCCC(n2nc(-c3ccc(Oc4ccccc4[N+](=O)[O-])cc3F)c3c(N)ncnc32)C1]

tert-butyl 3-(4-amino-3-(2-fluoro-4-(2-nitrophenoxy)phenyl)-1H-pyrazolo[3,4-d]pyrimidin-1-yl)piperidine-1-carboxylate Step A:

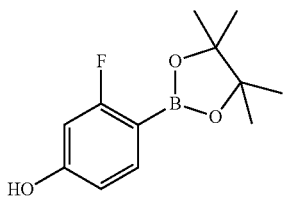 [SMILES: CC1(C)OB(c2ccc(O)cc2F)OC1(C)C]

3-fluoro-4-(4,4,5,5-tetramethyl-1,3,2-dioxaborolan-2-yl)phenol

Procedure:

4-bromo-3-fluorophenol (0.5 g, 2.62 mmol, 1.0 eq.), bis(pinacolato)diboron (0.86 g, 3.41 mmol, 1.3 eq.), potassium acetate (490 mg, 5.02 mmol, 3.0 eq.), X-phos (125 mg, 0.26 mmol, 0.1 eq.) and Pd$_2$(dba)$_3$ (0.24 g, 0.26 mmol, 0.1 eq.) were dissolved in 1,4-dioxane (10 mL). The resulting mixture was stirred at 90° C. under nitrogen for 1 hour. The reaction mixture was filtered through celite. The filtrate was concentrated to give the crude product (0.62 g, yield: 99%), which was used directly in the next step.

Step B:

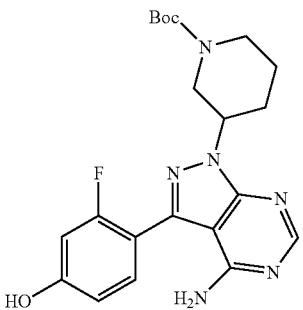 [SMILES: CC(C)(C)OC(=O)N1CCCC(n2nc(-c3ccc(O)cc3F)c3c(N)ncnc32)C1]

tert-butyl 3-(4-amino-3-(2-fluoro-4-hydroxyphenyl)-1H-pyrazolo[3,4-d]pyrimidin-1-yl)piperidine-1-carboxylate Procedure:

3-fluoro-4-(4,4,5,5-tetramethyl-1,3,2-dioxaborolan-2-yl)phenol (268 mg, 1.13 mmol, 2.0 eq.), tert-butyl 3-(4-amino-3-iodo-1H-pyrazolo[3,4-d]pyrimidin-1-yl)piperidine-1-carboxylate (250 mg, 0.56 mmol, 1.0 eq.), potassium phosphate (239 mg, 1.13 mmol, 2.0 eq.) and Pd-118 (18 mg, 0.028 mmol, 0.05 eq.) were dissolved in 1,4-dioxane/water (11 mL, 10/1, v/v). The reaction mixture was stirred at 60° C. for 14 minutes under nitrogen atmosphere. After cooled to room temperature, the reaction was diluted with ice-water (10 mL), and then extracted with ethyl acetate (10 mL×3). The combined organic phases were dried over anhydrous sodium sulfate and filtered. The filtrate was concentrated to give the crude product, which was purified by thin layer chromatography (developer: ethyl acetate) to give the title compound (150 mg, yield: 62%).

Step C:

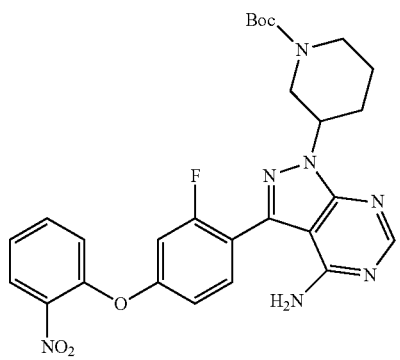 [SMILES: CC(C)(C)OC(=O)N1CCCC(n2nc(-c3ccc(Oc4ccccc4[N+](=O)[O-])cc3F)c3c(N)ncnc32)C1]

tert-butyl 3-(4-amino-3-(2-fluoro-4-(2-nitrophenoxy)phenyl)-1H-pyrazolo[3,4-d]pyrimidin-1-yl)piperidine-1-carboxylate Procedure:

2-fluoro-nitrobenzene (20 mg, 0.14 mmol, 1.2 eq.) and potassium carbonate (32 mg, 0.233 mmol, 2.0 eq.) were added to a solution of tert-butyl 3-(4-amino-3-(2-fluoro-4-hydroxyphenyl)-1H-pyrazolo[3,4-d]pyrimidin-1-yl)piperidine-1-carboxylate (50 mg, 0.117 mmol, 1.0 eq.) in DMF (2 mL). The reaction mixture was stirred at 100° C. for 14 hours. After cooling to room temperature, the mixture was filtered, and the filter cake washed with ethyl acetate. The filtrate was concentrated to give the crude product by HPLC (C18 reverse phase column, mobile phase: acetonitrile/water/0.7% NH$_4$HCO$_3$, gradient: 10% to 100% (volume ratio)) to give the title compound (8 mg, yield: 12%).

LC/MS (Method: UFLC): RT=3.320 min; m/z=550.4 [M+H]$^+$; Total running time 7 min.

Compound 11

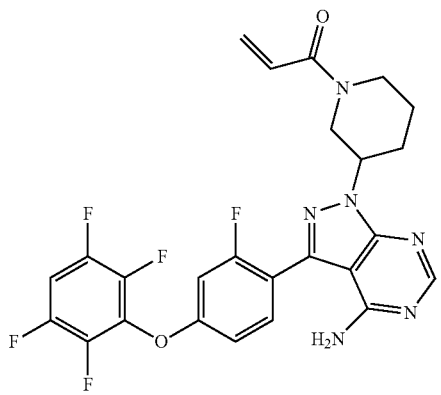

1-(3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one Step A:

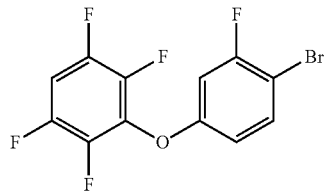

3-(4-bromo-3-fluorophenoxy)-1,2,4,5-tetrafluorobenzene

Procedure:

Potassium carbonate (68.0 g, 492.1 mmol, 2.0 eq.) and 1,2,3,4,5-pentafluorophenyl (49.6 g, 295.3 mmol, 1.2 eq.) were added to a solution of 4-bromo-3-fluorophenol (47.0 g, 246.1 mmol, 1.0 eq.) in DMF (500 mL). The reaction was stirred for 12 hours at 100° C., and then concentrated under reduced pressure. The residue was dissolved in ethyl acetate (300 mL), washed with water (100 mL×2) and saturated brine (100 mL). The organic phase was dried over anhydrous sodium sulfate, and concentrated to give the title compound (78 g, yield: 93%).

Step B:

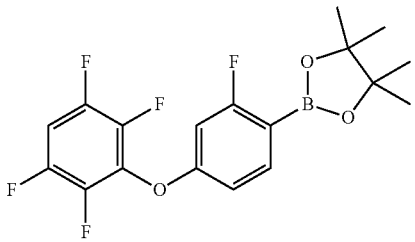 [SMILES: CC1(C)OB(c2ccc(Oc3c(F)c(F)cc(F)c3F)cc2F)OC1(C)C]

2-(2-fluoro-4-(2,3,5,6-tetrafluorophenoxy)phenyl)-4,4,5,5-tetramethyl-1,3,2-dioxaborolane Procedure:

3-(4-bromo-3-fluorophenoxy)-1,2,4,5-tetrafluorobenzene (73 g, 215.3 mmol, 1.0 eq.), bis(pinacolato)diboron (65.6 g, 258.4 mmol, 1.2 eq.), potassium acetate (31.6 g, 322.9 mmol, 1.5 eq.) and (1,1'-bis(diphenylphosphino)ferrocene)dichloropalladium (9.4 g, 12.8 mmol, 0.06 eq.) were dissolved in 1,4-dioxane (1 L). The resulting mixture was at stirred 80° C. under nitrogen for 14 hours. After cooling to room temperature, the reaction mixture was filtered through Celite. The filtrate was concentrated to give the crude product, which was purified by silica gel column chromatography (eluent:petroleum ether) to give the title compound (60 g, yield: 72%).

Step C:

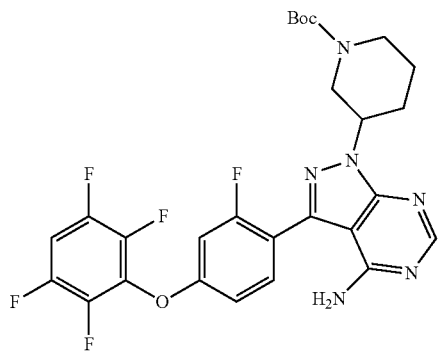 [SMILES: CC(C)(C)OC(=O)N1CCCC(n2nc(-c3ccc(Oc4c(F)c(F)cc(F)c4F)cc3F)c3c(N)ncnc32)C1]

tert-butyl 3-(4-amino-3-(2-fluoro-4-(2,3,5,6-tetra-
fluorophenoxy)phenyl)-1H-pyrazolo[3,4-d]pyrimi-
din-1-yl)piperidine-1-carboxylate Procedure:
tert-butyl 3-(4-amino-3-iodo-1H-pyrazolo[3,4-d]pyrimi-din-1-yl)piperidine-1-carboxylate (7.6 g, 17.1 mmol, 1.0 eq.), 2-(2-fluoro-4-(2,3,5,6-tetrafluorophenoxy)phenyl)-4,4,5,5-tetramethyl-1,3,2-dioxaborolane (8.6 g, 22.3 mmol, 1.3 eq.), potassium phosphate (7.3 g, 34.2 mmol, 2.0 eq.) and Pd-118 (0.56 g, 0.855 mmol, 0.05 eq.) were dissolved in 1,4-dioxane/water (240 mL, 5/1, v/v). The reaction mixture was stirred at 60° C. for 12 hours under nitrogen atmosphere. The reaction solution was poured into ice-water (300 mL), and then extracted with ethyl acetate (100 mL×4). The combined organic phases were dried over anhydrous sodium sulfate and filtered. The filtrate was concentrated to give the crude product, which was purified by silica gel column chromatography (eluent:ethyl acetate) to give the title compound (6.8 g, yield: 69%).

Step D:

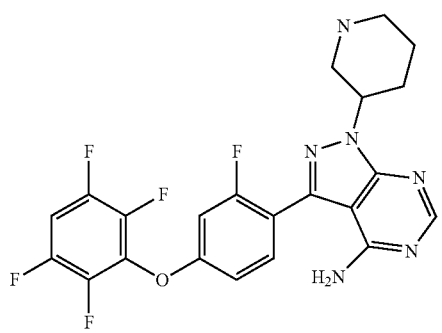 [SMILES: Nc1ncnc2c1c(-c1ccc(Oc3c(F)c(F)cc(F)c3F)cc1F)nn2C1CCCNC1]

3-(2-fluoro-4-(2,3,5,6-tetrafluorophenoxy)phenyl)-1-
(piperidin-3-yl)-1H-pyrazolo[3,4-d]pyrimidin-4-
amine Procedure:
4M HCl/EtOAc (20 mL) was added to a solution of tert-butyl 3-(4-amino-3-(2-fluoro-4-(2,3,5,6-tetrafluorophenoxy)phenyl)-1H-pyrazolo[3,4-d]pyrimidin-1-yl)piperidine-1-carboxylate (6.8 g, 11.8 mmol) in ethyl acetate (50 mL) at 0° C. The reaction mixture was stirred at room temperature for 1 h and concentrated to give the title compound hydrochloride (5.2 g, yield: 86%).

Step E:

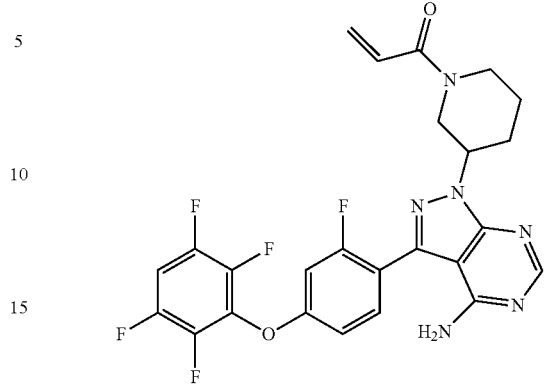

1-(3-(4-amino-3-(2-fluoro-4-(2,3,5,6-tetrafluorophe-
noxy)phenyl)-1H-pyrazolo[3,4-d]pyrimidin-1-yl)
piperidin-1-yl)prop-2-en-1-one Procedure:
Triethylamine (887 mg, 8.7 mmol, 3.0 eq.) and acrylic chloride (0.26 g, 2.9 mmol, 1.0 eq.) were added subsequently to a solution of 3-(2-fluoro-4-(2,3,5,6-tetrafluorophenoxy)phenyl)-1-(piperidin-3-yl)-1H-pyrazolo[3,4-d]pyrimidin-4-amine (1.5 g, 2.9 mmol, 1.0 eq.) in dichloromethane (10 mL). The reaction mixture was stirred at 0° C. for 1 hour, and then quenched with water (5 mL), diluted with dichloromethane (50 mL), washed with water (30 mL×2) and saturated brine (30 mL). The organic layer was dried over anhydrous sodium sulfate and filtered. The filtrate was concentrated to give the crude product, which was purified by silica gel column chromatography (eluent: petroleum ether:ethyl acetate=1:0~1:1) to give the title compound (0.94 g, yield: 64%).

LC/MS (Method: UFLC): RT=3.130 min; m/z=531.1 [M+H]$^+$; Total running time 7 min.

$^1$H NMR (400 MHz, DMSO-$d_6$) δ 8.22 (s, 1H), 8.00-7.91 (m, 1H), 7.55-7.46 (m, 1H), 7.27 (dd, J=2.4, 10.8 Hz, 1H), 7.12 (dd, J=2.4, 8.8 Hz, 1H), 6.88-6.65 (m, 1H), 6.13-6.02 (m, 1H), 5.70-5.56 (m, 1H), 4.71-4.65 (m, 1H), 4.54-4.51 (m, 0.5H), 4.20-4.17 (m, 1H), 4.07-4.04 (m, 0.5H), 3.67-3.60 (m, 0.5H), 3.17-3.12 (m, 1H), 2.98-2.94 (m, 0.5H), 2.26-2.21 (m, 1H), 2.11-2.06 (m, 1H), 1.92-1.89 (m, 1H), 1.58-1.54 (m, 1H).

Compound 12

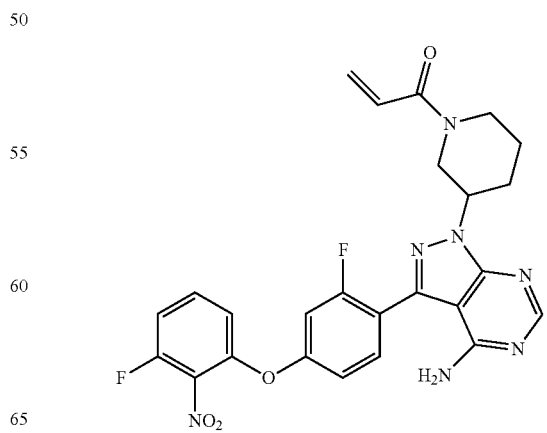

1-(3-(4-amino-3-(2-fluoro-4-(3-fluoro-2-nitro phenoxy)phenyl)-1H-pyrazolo[3,4-d]pyrimidin-1-yl)piperidin-1-yl)prop-2-en-1-one Step A:

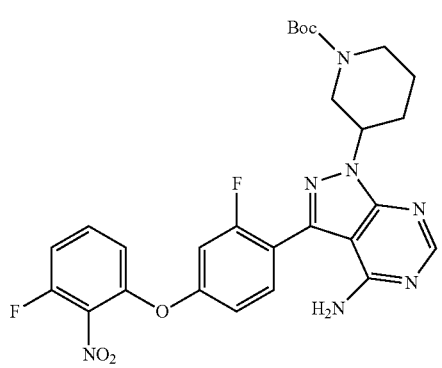 [SMILES: CC(C)(C)OC(=O)N1CCCC(n2nc(-c3ccc(Oc4cccc(F)c4[N+](=O)[O-])cc3F)c3c(N)ncnc32)C1]

tert-butyl 3-(4-amino-3-(2-fluoro-4-(3-fluoro-2-nitrophenoxy)phenyl)-1H-pyrazolo[3,4-d]pyrimidin-1-yl)piperidine-1-carboxylate Procedure:

1,3-difluoro-2-nitrobenzene (222.8 mg, 1.4 mmol, 3.0 eq.) and potassium carbonate (96.8 mg, 0.7 mmol, 1.5 eq.) were added to a solution of tert-butyl 3-(4-amino-3-(2-fluoro-4-hydroxyphenyl)-1H-pyrazolo[3,4-d]pyrimidin-1-yl)piperidine-1-carboxylate (200 mg, 0.467 mmol, 1.0 eq.) in acetonitrile (5 mL). The reaction mixture was stirred at 60° C. for 12 hours. After cooling to room temperature, the mixture was poured into water (10 mL), and then extracted with ethyl acetate (10 mL×3). The combined organic phases were dried over anhydrous sodium sulfate and filtered. The filtrate was concentrated to give the crude product, which was purified by thin layer chromatography (developer: ethyl acetate) to give the title compound (90 mg, yield: 34%).

Step B:

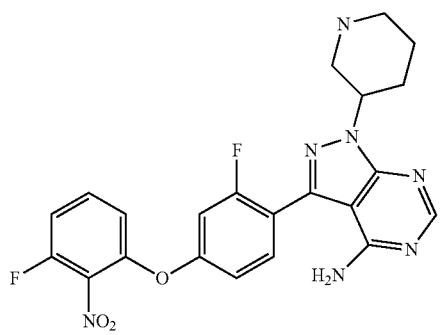 [SMILES: Nc1ncnc2c1c(-c1ccc(Oc3cccc(F)c3[N+](=O)[O-])cc1F)nn2C1CCCNC1]

3-(2-fluoro-4-(3-fluoro-2-nitrophenoxy)phenyl)-1-(piperidin-3-yl)-1H-pyrazolo[3,4-d]pyrimidin-4-amine Procedure:

4M HCl/EtOAc (1 mL) was added to a solution of tert-butyl 3-(4-amino-3-(2-fluoro-4-(3-fluoro-2-nitrophenoxy)phenyl)-1H-pyrazolo[3,4-d]pyrimidin-1-yl)piperidine-1-carboxylate (90 mg, 0.16 mmol) in dichloromethane (5 mL) at 0° C. The reaction mixture was stirred at room temperature for 1 h and concentrated to give the title compound hydrochloride (75 mg, yield: 94%).

Step C:

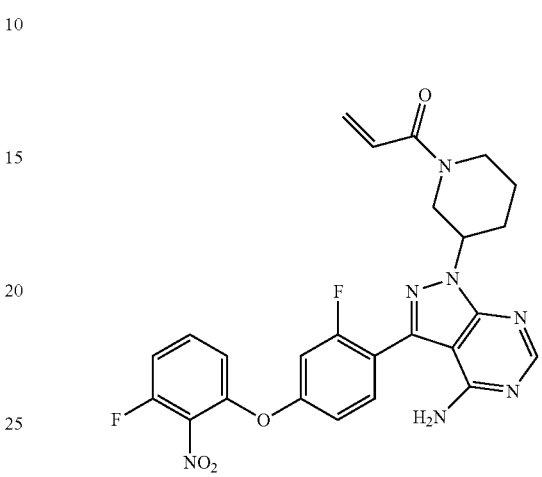

1-(3-(4-amino-3-(2-fluoro-4-(3-fluoro-2-nitrophenoxy)phenyl)-1H-pyrazolo[3,4-d]pyrimidin-1-yl)piperidin-1-yl)prop-2-en-1-one Procedure:

Triethylamine (45 mg, 0.45 mmol, 3.0 eq.) and acrylic chloride (13 mg, 0.15 mmol, 1.0 eq.) were added subsequently to a solution of 3-(2-fluoro-4-(3-fluoro-2-nitrophenoxy)phenyl)-1-(piperidin-3-yl)-1H-pyrazolo[3,4-d]pyrimidin-4-amine (75 mg, 0.15 mmol, 1.0 eq.) in dichloromethane (2 mL). The reaction mixture was stirred at 0° C. for 1 hour, and then quenched with water (5 mL), diluted with dichloromethane (10 mL), washed with water (5 mL) and saturated brine (5 mL). The organic layer was dried over anhydrous sodium sulfate and filtered. The filtrate was concentrated to give the crude product, which was purified by silica gel column chromatography (eluent:dichloromethane:methanol=5:1) to give the title compound (19 mg, yield: 24%).

LC/MS (Method: UFLC): RT=2.538 min; m/z=522.3 [M+H]$^+$; Total running time 7 min.

$^1$H NMR (400 MHz, DMSO-d$_6$) δ 8.21 (s, 1H), 7.71-7.55 (m, 2H), 7.43 (t, J=9.2 Hz, 1H), 7.33 (d, J=8.8 Hz, 1H), 7.22 (d, J=8.8 Hz, 1H), 7.14 (d, J=7.2 Hz, 1H), 6.88-6.67 (m, 1H), 6.13-6.02 (m, 1H), 5.70-5.56 (m, 1H), 4.69-4.53 (m, 1.5H), 4.21-4.05 (m, 1.5H), 3.68-3.61 (m, 0.5H), 3.21-3.18 (m, 1H), 3.05-2.99 (m, 0.5H), 2.24-2.13 (m, 2H), 1.92-1.89 (m, 1H), 1.59-1.54 (m, 1H).

Compound 13

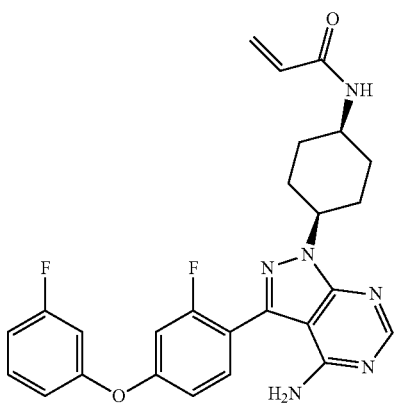 [SMILES: C=CC(=O)N[C@H]1CC[C@@H](n2nc(-c3ccc(Oc4cccc(F)c4)cc3F)c3c(N)ncnc32)CC1]

N-((1s,4s)-4-(4-amino-3-(2-fluoro-4-(3-fluorophenoxy)phenyl)-1H-pyrazolo[3,4-d]pyrimidin-1-yl)cyclohexyl)acrylamide Step A:

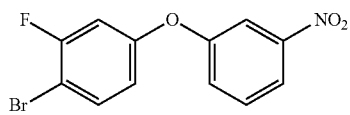 [SMILES: Nc1cccc(Oc2ccc(Br)c(F)c2)c1]

1-(3-fluoro-4-bromophenoxy)-3-nitrobenzene

Procedure:
Potassium carbonate (58 g, 420 mmol, 2.0 eq.) and 1-fluoro-3-nitrobenzene (29.6 g, 210 mmol, 1.0 eq.) were added to a solution of 4-bromo-3-fluorophenol (40 g, 210 mmol, 1.0 eq.) in DMF (400 mL). The reaction was stirred for 12 hours at 90° C., and then concentrated under reduced pressure. The residue was diluted with water (300 mL), extracted with ethyl acetate (300 mL×3). The combined organic phases were dried over anhydrous sodium sulfate and filtered. The filtrate was concentrated to give the title compound (65 g, yield: 100%).

Step B:

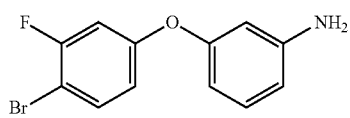

3-(4-bromo-3-fluorophenoxy)benzenamine

Procedure:
Chloride ammonium (28 g, 525 mmol, 2.5 eq.) and iron powder (58.8 g, 1.05 mol, 5.0 eq.) were added to a solution of 1-(4-bromo-3-fluorophenoxy)-3-nitrobenzene (65 g, 210 mmol, 1.0 eq.) in ethanol (300 mL) and water (60 mL). The reaction solution was refluxed under nitrogen for 12 hours. After cooled to room temperature, the reaction was filtered through celite. The filtrate was concentrated to give the crude product, which was purified by HPLC (C18 reverse phase column, mobile phase: acetonitrile/water/0.7% NH$_4$HCO$_3$, gradient: 10%-100% (volume ratio)) to give the title compound (19 g, yield: 23%).

Step C:

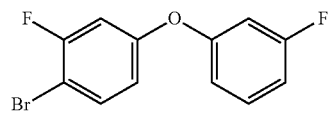 [SMILES: Fc1cccc(Oc2ccc(Br)c(F)c2)c1]

1-bromo-2-fluoro-4-(3-fluorophenoxy)benzene

Procedure:
3-(4-bromo-3-fluorophenoxy)aniline (9 g, 32 mmol, 1.0 eq.) was added portionwise to pyridine-hydrogen fluoride solution (30 mL) at −10° C. The resulting reaction mixture was stirred at 0° C. for 30 minutes, and then sodium nitrite (2.42 g, 35 mmol, 1.1 eq.) was added portionwise at −10° C. The reaction was stirred at 20° C. for 30 minutes, then at 60° C. for 14 hours. After cooling to room temperature, the reaction solution was poured into ice-ethanol (50 mL). A saturated solution of NaHCO$_3$ (50 mL) was added, and then extracted with ethyl acetate (50 mL×3). The combined organic phases were dried over anhydrous sodium sulfate and filtered. The filtrate was concentrated to give the crude, which was purified by silica gel column chromatography (eluent:petroleum ether) to give the title compound (5.8 g, yield: 64%).

Step D:

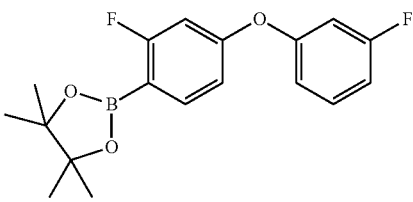 [SMILES: CC1(C)OB(c2ccc(Oc3cccc(F)c3)cc2F)OC1(C)C]

2-(2-fluoro-4-(3-fluorophenoxy)phenyl)-4,4,5,5-tetramethyl-1,3,2-dioxaborolane

Procedure:
1-bromo-2-fluoro-4-(3-fluorophenoxy)benzene (5.8 g, 20 mmol, 1.0 eq.), bis(pinacolato)diboron (6.1 g, 24 mmol, 1.2 eq.), potassium acetate (3.9 g, 40 mmol, 2.0 eq.) and (1,1'-bis(diphenylphosphino)ferrocene)dichloropalladium (0.89 g, 1.2 mmol, 0.06 eq.) were dissolved in 1,4-dioxane (100 mL). The resulting mixture was at stirred 85° C. under nitrogen for 14 hours. After cooling to room temperature, the reaction mixture was filtered through celite. The filtrate was concentrated to give the crude product, which was purified by silica gel column chromatography (eluent:petroleum ether) to give the title compound (6.5 g, yield: 100%).

Step E:

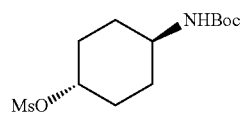

(1r,4r)-4-(tert-butoxycarbonyl)cyclohexyl methanesulfonate

Procedure:

Triethylamine (7 g, 70 mmol, 3.0 eq.) and methanesulfonyl chloride (2.9 g, 25.5 mmol, 1.1 eq.) were subsequently added to a solution of tert-butyl (1r,4r)-4-hydroxycyclohexylcarbamate (5.0 g, 23.2 mmol, 1.0 eq.) in dichloromethane (100 mL) at 0° C. The reaction was stirred at 20° C. for 1 hour, quenched with saturated NaHCO$_3$ (100 mL), and then extracted with dichloromethane (200 mL×3). The combined organic phases were dried over anhydrous sodium sulfate and filtered. The filtrate was concentrated to give the title compound (6.0 g, yield: 88%).

Step F:

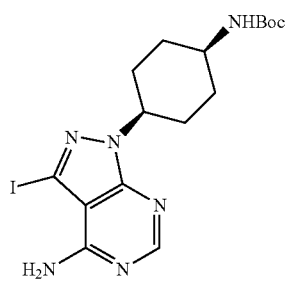 [SMILES: CC(C)(C)OC(=O)N[C@H]1CC[C@@H](n2nc(I)c3c(N)ncnc32)CC1]

tert-butyl (1s,4s)-4-(4-amino-3-iodo-1H-pyrazolo[3,4-d]pyrimidin-1-yl)cyclohexylcarbamate Procedure:

Cesium carbonate (8.8 g, 27.6 mmol, 2.0 eq.) and (1r,4r)-4-(tert-butoxycarbonyl)cyclohexyl methanesulfonate (6.0 g, 20.5 mmol, 1.5 eq.) were added to a solution of 3-iodo-1H-pyrazolo[3,4-d]pyrimidin-4-amine (3.6 g, 13.6 mmol, 1.0 eq.) in DMF (50 mL) at 0° C. The reaction solution was stirred at 80° C. overnight, filtered through celite, and concentrated to give the crude product, which was purified by silica gel column chromatography (eluent:ethyl acetate) to give the title compound (4 g, yield: 64%).

Step G:

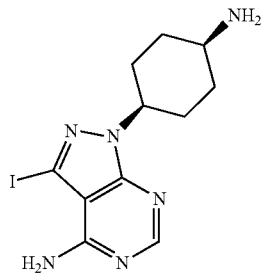 [SMILES: Nc1ncnc2c1c(I)nn2[C@H]1CC[C@@H](N)CC1]

1-((1s,4s)-4-aminocyclohexyl)-3-iodo-1H-pyrazolo[3,4-d]pyrimidin-4-amine

Procedure:

4M HCl/EtOAc (20 mL) was added to a solution of tert-butyl (1s,4s)-4-(4-amino-3-iodo-1H-pyrazolo[3,4-d]pyrimidin-1-yl)cyclohexylcarbamate (4 g, 8.73 mmol) in dichloromethane (20 mL) at 0° C. The reaction mixture was stirred at room temperature for 1 h and concentrated to give the title compound hydrochloride (2.5 g, yield: 73%).

Step H:

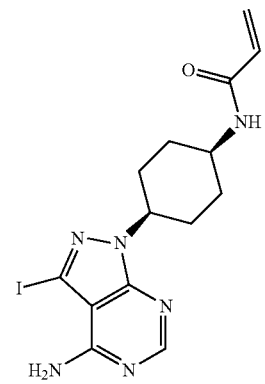 [SMILES: C=CC(=O)N[C@H]1CC[C@@H](n2nc(I)c3c(N)ncnc32)CC1]

N-((1s,4s)-4-(4-amino-3-iodo-1H-pyrazolo[3,4-d]pyrimidin-1-yl)cyclohexyl)acrylamide Procedure:

Triethylamine (1.9 g, 19 mmol, 3.0 eq.) and acrylic chloride (570 mg, 6.3 mmol, 1.0 eq.) were subsequently added to a solution of 1-((1s,4s)-4-aminocyclohexyl)-3-iodo-1H-pyrazolo[3,4-d]pyrimidin-4-amine (2.5 g, 6.3 mmol, 1.0 eq.) in dichloromethane (50 mL) at 0° C. The reaction mixture was stirred at 0° C. for 1 hour, and then quenched with saturated NaHCO$_3$ (30 mL). The aqueous phase was extracted with dichloromethane (50 mL×2). The combined organic layers were dried over anhydrous sodium sulfate and filtered. The filtrate was concentrated to give the crude product, which was purified by silica gel column chromatography (eluent:ethyl acetate) to give the title compound (2.0 g, yield: 77%).

Step I:

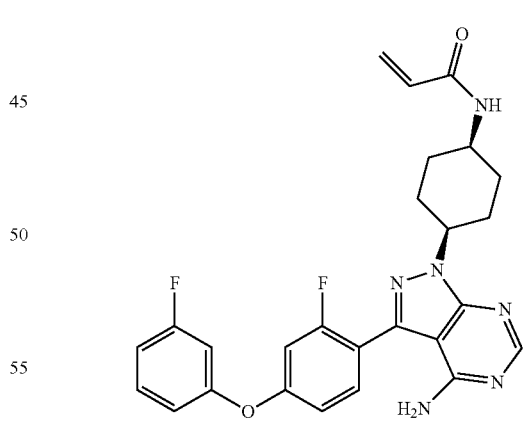

N-((1s,4s)-4-(4-amino-3-(2-fluoro-4-(3-fluorophenoxy)phenyl)-1H-pyrazolo[3,4-d]pyrimidin-1-yl)cyclohexyl)acrylamide Procedure:

The compound N-((1s,4s)-4-(4-amino-3-iodo-1H-pyrazolo[3,4-d]pyrimidin-1-yl)cyclohexyl)acrylamide (250 mg, 0.6 mmol, 1.0 eq.), 2-(2-fluoro-4-(3-fluorophenoxy)phenyl)-4,4,5,5-tetramethyl-1,3,2-dioxaborolane (400 mg, 1.2 mmol, 2.eq.), sodium carbonate (200 mg, 1.8 mmol, 3.0 eq.) and Pd(PPh$_3$)$_4$ (70 mg, 0.06 mmol, 0.1 eq.) were dissolved in 1,4-dioxane/water (10 mL, 1/1, v/v). The reaction solution was stirred at 80° C. for 40 minutes under nitrogen atmosphere with microwave irradiation. After cooling to room temperature, the reaction mixture was extracted with ethyl acetate (10 mL×3). The combined organic phases were dried over anhydrous sodium sulfate, and concentrated to give the crude product, which was purified by thin layer chromatography (developer: ethyl acetate) to give the title compound (75 mg, yield: 23%).

LC/MS (Method: UFLC): RT=2.856 min; m/z=491.3 [M+H]$^+$; Total running time 7 min.

$^1$H NMR (400 MHz, DMSO-d$_6$) δ 8.22 (s, 1H), 8.14 (d, 1H), 7.58-7.44 (m, 2H), 7.14-6.96 (m, 6H), 6.42-6.35 (m, 1H), 6.09-6.04 (m, 1H), 5.56-5.52 (m, 1H), 4.77-4.73 (m, 1H), 3.99-3.95 (m, 1H), 2.25-2.15 (m, 2H), 1.88-1.72 (m, 6H).

Compound 14

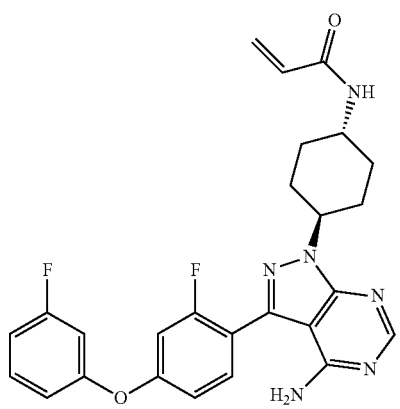 [SMILES: C=CC(=O)N[C@H]1CC[C@H](n2nc(-c3ccc(Oc4cccc(F)c4)cc3F)c3c(N)ncnc32)CC1]

N-((1r,4r)-4-(4-amino-3-(2-fluoro-4-(3-fluorophenoxy)phenyl)-1H-pyrazolo[3,4-d]pyrimidin-1-yl)cyclohexyl)acrylamide Step A:

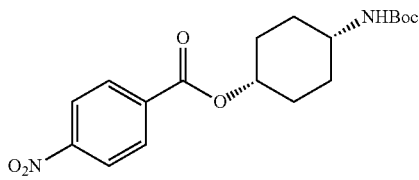 [SMILES: CC(C)(C)OC(=O)N[C@H]1CC[C@@H](OC(=O)c2ccc([N+](=O)[O-])cc2)CC1]

(1s,4s)-4-(tert-butoxycarbonyl)cyclohexyl 4-nitrobenzoate

Procedure:
Tert-butyl (1r,4r)-4-hydroxycyclohexylcarbamate (4.4 g, 20.4 mmol, 1.0 eq.), 4-nitrobenzoic acid (8.4 g, 50.3 mmol, 2.5 eq.) and triphenylphosphine (8.0 g, 30.5 mmol, 1.5 eq.) were dissolved in toluene (240 mL) and tetrahydrofuran (20 mL). Diethyl azodicarboxylate (7.1 g, 40.8 mmol, 2.0 eq.) was added to the resulting mixture. The reaction was stirred at room temperature for 12 hours under nitrogen atmosphere and concentrated under reduced pressure. Dichloromethane (500 mL) was added to the residue, stirred for 30 minutes, and then filtered. The filtrate was concentrated to give the crude product, which was purified by silica gel column chromatography (eluent:petroleum ether:ethyl acetate=10:1 to 1:1) to give the title compound (4.0 g, yield: 54%).

Step B:

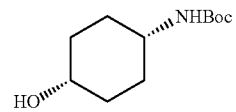

tert-butyl (1s,4s)-4-hydroxycyclohexylcarbamate

Procedure:
(1s,4s)-4-(tert-butoxycarbonyl)cyclohexyl 4-nitrobenzoate (4.0 g, 11.0 mmol) was dissolved in tetrahydrofuran (50 mL) and NaOH solution (2N, 100 mL), and then refluxed for 12 hours. The reaction solution was diluted with water (50 mL), and extracted with methyl tert-butyl ether (50 mL×3). The combined organic phases were dried over anhydrous sodium sulfate and filtered. The filtrate was concentrated to give the title compound (1.0 g, yield: 40%).

Step C:

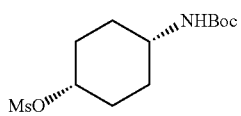

(1s,4s)-4-(tert-butoxycarbonyl)cyclohexyl methanesulfonate

Procedure:
Triethylamine (1.4 g, 14.0 mmol, 3.0 eq.) and methanesulfonyl chloride (0.8 g, 7.0 mmol, 1.5 eq.) were added sequentially to a solution of tert-butyl (1s,4s)-4-hydroxycyclohexylcarbamate (1.0 g, 4.6 mmol, 1.0 eq.) in dichloromethane (30 mL) at 0° C. The reaction was stirred at 0° C. for 1 hour, quenched with water (5 mL), washed with water (30 mL×2) and brine (30 mL). The organic phase was dried over anhydrous sodium sulfate and filtered. The filtrate was concentrated to give the title compound (860 mg, yield: 64%).

Step D:

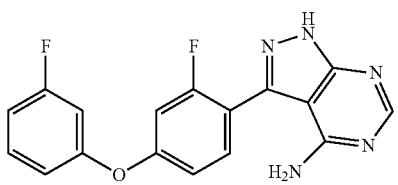 [SMILES: Nc1ncnc2[nH]nc(-c3ccc(Oc4cccc(F)c4)cc3F)c12]

147

3-(2-fluoro-4-(3-fluorophenoxy)phenyl)-1H-pyrazolo[3,4-d]pyrimidin-4-amine

Procedure:

3-iodo-1H-pyrazolo[3,4-d]pyrimidin-4-amine (2.3 g, 8.8 mmol, 1.0 eq.), 2-(2-fluoro-4-(3-fluorophenoxy)phenyl)-4,4,5,5-tetramethyl-1,3,2-dioxaborolane (5.8 g, 17.6 mmol, 2.0 eq.), potassium phosphate (3.7 g, 17.6 mmol, 2.0 eq.) and Pd-118 (570 mg, 0.88 mmol, 0.1 eq.) were dissolved in 1,4-dioxane/H₂O (40 mL, 1/1, v/v). The reaction mixture was stirred at 80° C. for 40 minutes under nitrogen atmosphere with microwave irradiation. After cooling to room temperature, the reaction solution was extracted with ethyl acetate (50 mL×3). The combined organic phases were dried over anhydrous sodium sulfate and filtered. The filtrate was concentrated to give the crude product, which was purified by silica gel column chromatography (eluent:ethyl acetate) to give the title compound (700 mg, yield: 23%).

Step E:

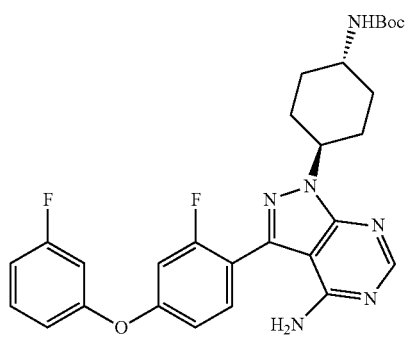 [SMILES: CC(C)(C)OC(=O)N[C@H]1CC[C@H](n2nc(-c3ccc(Oc4cccc(F)c4)cc3F)c3c(N)ncnc32)CC1]

tert-butyl (1r,4r)-4-(4-amino-3-(2-fluoro-4-(3-fluorophenoxy)phenyl)-1H-pyrazolo[3,4-d]pyrimidin-1-yl)cyclohexylcarbamate Procedure:

Cesium carbonate (385 mg, 1.18 mmol, 2.0 eq.) and (1s,4s)-4-(tert-butoxycarbonyl)cyclohexyl methanesulfonate (346 mg, 1.18 mmol, 2.0 eq.) were added to a solution of 3-(2-fluoro-4-(3-fluorophenoxy)phenyl)-1H-pyrazolo[3,4-d]pyrimidin-4-amine (200 mg, 0.59 mmol, 1.0 eq.) in DMF (10 mL). The reaction was stirred at 80° C. for 12 hours, cooled to room temperature and filtered. The filtrate was concentrated to give the crude product, which was purified by thin layer chromatography (developer: ethyl acetate) to give the title compound (70 mg, yield: 23%).

Step F:

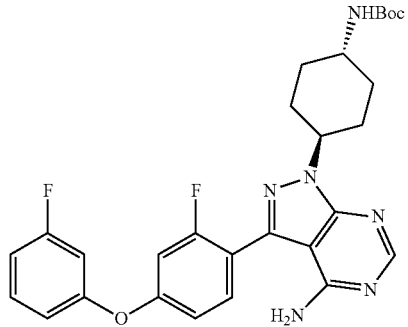 [SMILES: CC(C)(C)OC(=O)N[C@H]1CC[C@H](n2nc(-c3ccc(Oc4cccc(F)c4)cc3F)c3c(N)ncnc32)CC1]

148

1-((1r,4r)-4-aminocyclohexyl)-3-(2-fluoro-4-(3-fluorophenoxy)phenyl)-1H-pyrazolo[3,4-d]pyrimidin-4-amine Procedure:

4M HCl/EtOAc (1.0 mL) was added to a solution of tert-butyl (1r,4r)-4-(4-amino-3-(2-fluoro-4-(3-fluorophenoxy)phenyl)-1H-pyrazolo[3,4-d]pyrimidin-1-yl)cyclohexylcarbamate (70 mg, 0.13 mmol) in ethyl acetate (10 mL) at 0° C. The reaction mixture was stirred at room temperature for 1 h and concentrated to give the title compound hydrochloride (61 mg, yield: 100%).

Step G:

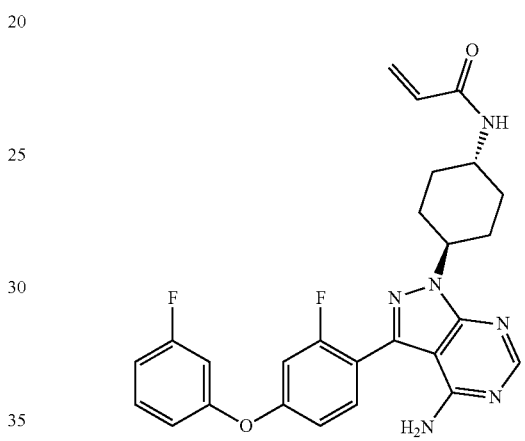

N-((1r,4r)-4-(4-amino-3-(2-fluoro-4-(3-fluorophenoxy)phenyl)-1H-pyrazolo[3,4-d]pyrimidin-1-yl)cyclohexyl)acrylamide Procedure:

Triethylamine (40 mg, 0.39 mmol, 3.0 eq.) and acrylic chloride (23 mg, 0.26 mmol, 2.0 eq.) were added subsequently to a solution of 1-((1r,4r)-4-aminocyclohexyl)-3-(2-fluoro-4-(3-fluorophenoxy)phenyl)-1H-pyrazolo[3,4-d]pyrimidin-4-amine (61.5 mg, 0.13 mmol, 1.0 eq.) in dichloromethane (5 mL) at 0° C. The reaction mixture was stirred at 0° C. for 1 hour, and then quenched with water (5 mL), diluted with dichloromethane (10 mL), washed with water (5 mL×2) and brine (5 mL). The organic layer was dried over anhydrous sodium sulfate and filtered. The filtrate was concentrated to give the crude product, which was purified by HPLC (C18 reverse phase column, mobile phase: acetonitrile/water/0.5% HCl, gradient: 10% to 100% (volume ratio)) to give the title compound hydrochloride (6.3 mg, yield: 10%).

LC/MS (Method: UFLC): RT=0.811 min; m/z=491.1 [M+H]⁺; Total running time 1.5 min.

Compound 15

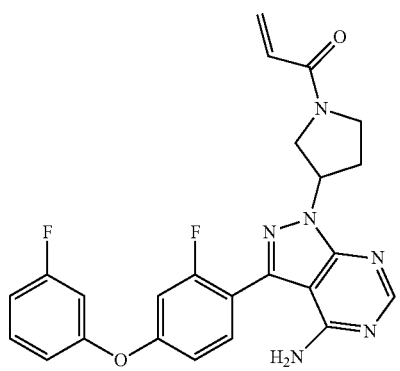 [SMILES: C=CC(=O)N1CCC(n2nc(-c3ccc(Oc4cccc(F)c4)cc3F)c3c(N)ncnc32)C1]

1-(3-(4-amino-3-(2-fluoro-4-(3-fluorophenoxy)phenyl)-1H-pyrazolo[3,4-d]pyrimidin-1-yl)pyrrolidin-1-yl)prop-2-en-1-one Step A:

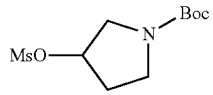

tert-butyl 3-(methylsulfonyloxy)pyrrolidine-1-carboxylate

Procedure:

Triethylamine (35 g, 346 mmol, 2.1 eq.) and methanesulfonyl chloride (36.6 g, 321 mmol, 1.9 eq.) were added subsequently to a solution of tert-butyl 3-hydroxypyrrolidine-1-carboxylate (30.0 g, 163 mmol, 1.0 eq.) in dichloromethane (200 mL) at 0° C. The reaction was stirred at 0° C. for 3 hours, quenched with water (20 mL), washed with water (100 mL×2) and brine (100 mL). The organic phase was dried over anhydrous sodium sulfate and filtered. The filtrate was concentrated to give the title compound (45.6 g, yield: 100%).

Step B:

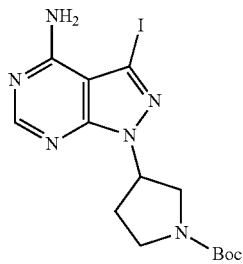 [SMILES: CC(C)(C)OC(=O)N1CCC(n2nc(I)c3c(N)ncnc32)C1]

tert-butyl 3-(4-amino-3-iodo-1H-pyrazolo[3,4-d]pyrimidin-1-yl)pyrrolidine-1-carboxylate Procedure:

Cesium carbonate (37 g, 115 mmol, 3.0 eq.) and 3-iodo-1H-pyrazolo[3,4-d]pyrimidin-4-amine (10 g, 38 mmol, 1.0 eq.) were added to a solution of 3-(methylsulfonyloxy)pyrrolidine-1-carboxylate (35 g, 134 mmol, 3.5 eq.) in DMF (300 mL). The reaction was stirred at 85° C. for 12 h, cooled to room temperature and filtered. The filtrate was concentrated to give the crude product, which was purified by silica gel column chromatography (eluent:petroleum ether:ethyl acetate=1:1) to give the title compound (7.0 g, yield: 44%).

Step C:

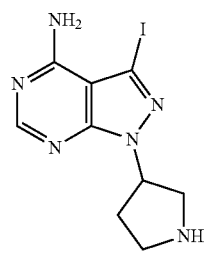 [SMILES: Nc1ncnc2c1c(I)nn2C1CCNC1]

3-iodo-1-(pyrrolidin-3-yl)-1H-pyrazolo[3,4-d]pyrimidin-4-amine

Procedure:

4M HCl/EtOAc (10.0 mL) was added to a solution of tert-butyl 3-(4-amino-3-iodo-1H-pyrazolo[3,4-d]pyrimidin-1-yl)pyrrolidine-1-carboxylate (7.0 g, 16 mmol) in dichloromethane (100 mL) at 0° C. The reaction mixture was stirred at room temperature for 1 h and concentrated to give the title compound hydrochloride (5.3 g, yield: 100%).

Step D:

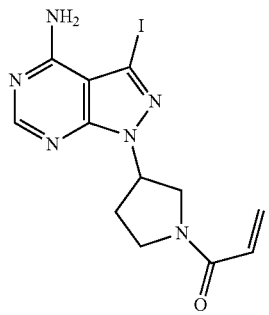 [SMILES: C=CC(=O)N1CCC(n2nc(I)c3c(N)ncnc32)C1]

1-(3-(4-amino-3-iodo-1H-pyrazolo[3,4-d]pyrimidin-1-yl)pyrrolidin-1-yl)prop-2-en-1-one Procedure:

Triethylamine (4.8 g, 48 mmol, 3.0 eq.) and acrylic chloride (750 mg, 8.0 mmol, 0.5 eq.) were subsequently added to a solution of 3-iodo-1-(pyrrolidin-3-yl)-1H-pyrazolo[3,4-d]pyrimidin-4-amine (5.3 g, 16 mmol, 1.0 eq.) in dichloromethane (50 mL) at 0° C. The reaction mixture was stirred at 0° C. for 1 hour, and then quenched with saturated NaHCO$_3$ (10 mL), washed with water (30 mL×2) and brine (30 mL). The organic layer was dried over anhydrous sodium sulfate and filtered. The filtrate was concentrated to give the crude product, which was purified by silica gel column chromatography (eluent:ethyl acetate) to give the title compound (1.5 g, yield: 50%).

Step E:

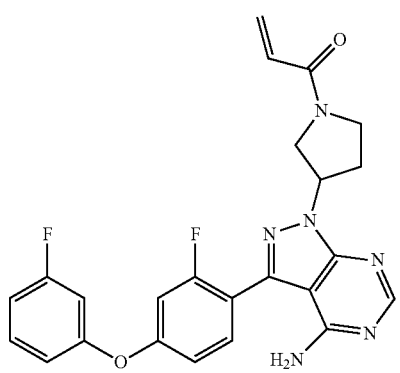 [SMILES: C=CC(=O)N1CCC(n2nc(-c3ccc(Oc4cccc(F)c4)cc3F)c3c(N)ncnc32)C1]

1-(3-(4-amino-3-(2-fluoro-4-(3-fluorophenoxy)phenyl)-1H-pyrazolo[3,4-d]pyrimidin-1-yl)pyrrolidin-1-yl)prop-2-en-1-one Procedure:

1-(3-(4-amino-3-iodo-1H-pyrazolo[3,4-d]pyrimidin-1-yl)pyrrolidin-1-yl)prop-2-en-1-one (250 mg, 0.65 mmol, 1.0 eq.), 2-(2-fluoro-4-(3-fluorophenoxy)phenyl)-4,4,5,5-tetramethyl-1,3,2-dioxaborolane (420 mg, 1.25 mmol, 2.eq.), sodium carbonate (200 mg, 1.88 mmol, 3.0 eq.) and Pd(PPh$_3$)$_4$ (72 mg, 0.06 mmol, 0.1 eq.) were dissolved in 1,4-dioxane/water (10 mL, 1/1, v/v). The reaction solution was stirred at 85° C. for 40 minutes under nitrogen atmosphere with microwave irradiation. After cooling to room temperature, the reaction mixture was diluted with water (10 mL), and then extracted with ethyl acetate (10 mL×3). The combined organic phases were dried over anhydrous sodium sulfate, and concentrated to give the crude product, which was purified by silica gel chromatography column (eluent: ethyl acetate) to give the title compound (65 mg, yield: 24%).

LC/MS (Method: UFLC): RT=2.754 min; m/z=463.3 [M+H]$^+$; Total running time 7 min.

$^1$H NMR (400 MHz, DMSO-d$_6$) δ 8.25 (s, 1H), 7.56-7.43 (m, 2H), 7.13-6.98 (m, 6H), 6.68-6.52 (m, 1H), 6.16-6.08 (m, 1H), 5.68-5.64 (m, 1H), 5.55-5.43 (m, 1H), 4.14-4.09 (m, 0.5H), 3.97-3.56 (m, 4.5H), 2.55-2.34 (m, 2H).

Compounds 16 and 17

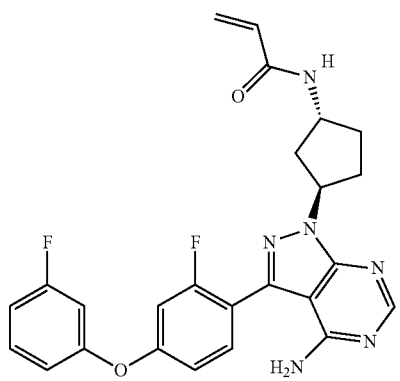

N-((1r,3r)-3-(4-amino-3-(2-fluoro-4-(3-fluorophenoxy)phenyl)-1H-pyrazolo[3,4-d]pyrimidin-1-yl)cyclopentyl)acrylamide

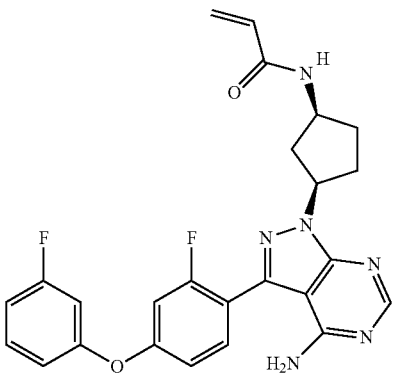

N-((1s,3r)-3-(4-amino-3-(2-fluoro-4-(3-fluorophenoxy)phenyl)-1H-pyrazolo[3,4-d]pyrimidin-1-yl)cyclopentyl)acrylamide Step A:

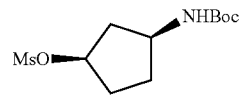

(1r,3s)-3-(tert-butoxycarbonyl)cyclopentyl methanesulfonate

Procedure:

Triethylamine (3.14 g, 31.05 mmol, 2.5 eq.) and methanesulfonyl chloride (3.5 g, 24.84 mmol, 1.2 eq.) were added sequentially to a solution of tert-butyl (1s,3r)-3-hydroxycyclopentylcarbamate (2.5 g, 12.42 mmol, 1.0 eq.) in dichloromethane (25 mL) at 0° C. The reaction was stirred at room temperature for 14 hours, quenched with water (20 mL), and then extracted with dichloromethane (25 mL×2). The combined organic phases were dried over anhydrous sodium sulfate and filtered. The filtrate was concentrated to give the title compound (2.5 g, yield: 72%).

Step B:

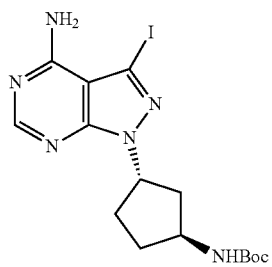 [SMILES: CC(C)(C)OC(=O)N[C@H]1CC[C@H](n2nc(I)c3c(N)ncnc32)C1]

tert-butyl (1S,3 S)-3-(4-amino-3-iodo-1H-pyrazolo[3,4-d]pyrimidin-1-yl)cyclopentylcarbamate Procedure:

Cesium carbonate (8.75 g, 26.85 mmol, 3.0 eq.) and 3-iodo-1H-pyrazolo[3,4-d]pyrimidin-4-amine (1.87 g, 7.16 mmol, 0.8 eq.) were added to a solution of (1r,3s)-3-(tert-butoxycarbonyl)cyclopentyl methanesulfonate (2.5 g, 8.95 mmol, 1.0 eq.) in DMF (30 mL) at 0° C. The reaction solution was stirred at 85° C. for 12 hours. After cooling to room temperature, the mixture was filtered through celite and concentrated. Ethyl acetate (100 mL) was added to the residue, washed with water (50 mL×2) and brine (50 mL). The organic phase was dried over anhydrous sodium sulfate and filtered. The filtrate was concentrated to give the crude product, which was purified by silica gel column chromatography (eluent:petroleum ether:ethyl acetate=1:1) to give the title compound (500 mg, yield: 13%).

Step C:

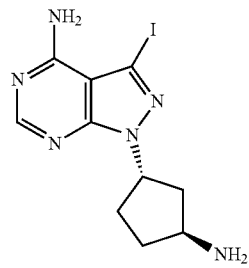 [SMILES: Nc1ncnc2c1c(I)nn2[C@H]1CC[C@H](N)C1]

1-((1s,3 s)-3-aminocyclopentyl)-3-iodo-1H-pyrazolo[3,4-d]pyrimidin-4-amine

Procedure:

4M HCl/EtOAc (10.0 mL) was added to a solution of tert-butyl (1s,3s)-3-(4-amino-3-iodo-1H-pyrazolo[3,4-d]pyrimidin-1-yl)cyclopentylcarbamate (500 mg, 1.13 mmol) in ethyl acetate (20 mL) at 0° C. The reaction mixture was stirred at room temperature for 1 h and concentrated to give the title compound hydrochloride (500 mg, yield: 100%).

Step D:

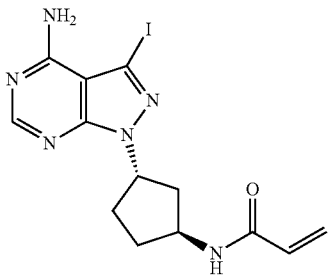 [SMILES: C=CC(=O)N[C@H]1CC[C@H](n2nc(I)c3c(N)ncnc32)C1]

N-((1S,3 S)-3-(4-amino-3-iodo-1H-pyrazolo[3,4-d]pyrimidin-1-yl)cyclopentyl)acrylamide Procedure:

Triethylamine (170 mg, 1.7 mmol, 3.0 eq.) and acrylic chloride (51 mg, 0.56 mmol, 1.1 eq.) were added subsequently to a solution of 1-((1s,3s)-3-aminocyclopentyl)-3-iodo-1H-pyrazolo[3,4-d]pyrimidin-4-amine (215 mg, 0.56 mmol, 1.0 eq.) in dichloromethane (15 mL) at 0° C. The reaction mixture was stirred at 0° C. for 1 hour, and then quenched with saturated NaHCO₃ (10 mL). The organic layer was extracted with dichloromethane (5 mL×2). The combined organic layers were dried over anhydrous sodium sulfate and filtered. The filtrate was concentrated to give the crude product, which was purified by silica gel column chromatography (eluent:petroleum ether:ethyl acetate=1:1) to give the title compound (100 mg, yield: 45%).

Step E:

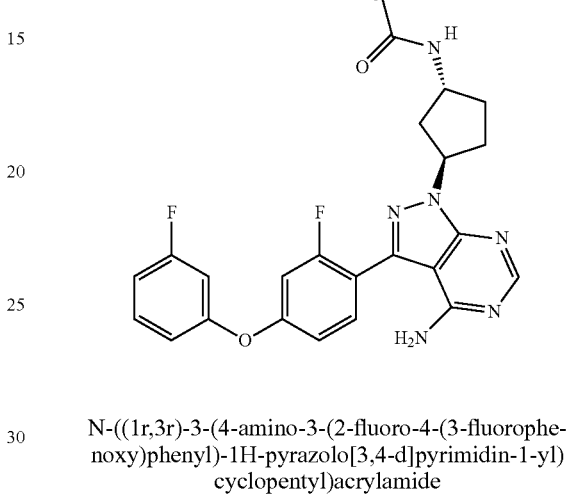

N-((1r,3r)-3-(4-amino-3-(2-fluoro-4-(3-fluorophenoxy)phenyl)-1H-pyrazolo[3,4-d]pyrimidin-1-yl)cyclopentyl)acrylamide

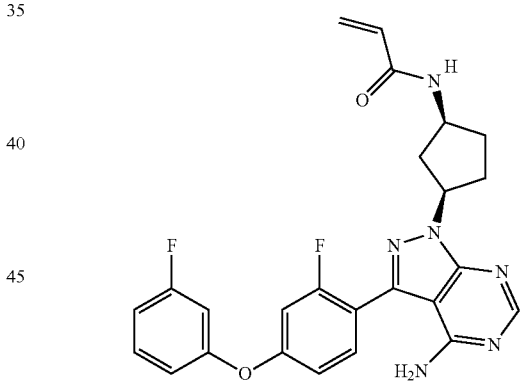

N-((1s,3r)-3-(4-amino-3-(2-fluoro-4-(3-fluorophenoxy)phenyl)-1H-pyrazolo[3,4-d]pyrimidin-1-yl)cyclopentyl)acrylamide Procedure:

N-((1s,3 s)-3-(4-amino-3-iodo-1H-pyrazolo[3,4-d]pyrimidin-1-yl)cyclopentyl)acrylamide (70 mg, 0.175 mmol, 1.0 eq.), 2-(2-fluoro-4-(3-fluorophenoxy)phenyl)-4,4,5,5-tetramethyl-1,3,2-dioxaborolane (116.8 mg, 0.35 mmol, 1.1 eq.), sodium carbonate (93 mg, 0.875 mmol, 3.0 eq.) and Pd(PPh₃)₄ (20 mg, 0.017 mmol, 0.1 eq.) were dissolved in 1,4-dioxane/water (10 mL, 1/1, v/v). The reaction solution was stirred at 85° C. for 40 minutes under nitrogen atmosphere with microwave irradiation. After cooling to room temperature, the reaction mixture was diluted with water (10 mL), and then extracted with ethyl acetate (10 mL×3). The combined organic phases were dried over anhydrous sodium sulfate, and concentrated to give the crude product, which was purified by HPLC (C18 reverse phase column, mobile phase: acetonitrile/water/0.5% HCl, gradient: 10% to 100% (volume ratio)) to give Compound 16 hydrochloride (11 mg, yield: 5%) and Compound 17 hydrochloride (3.8 mg, yield: 2%).

Compound 16:

LC/MS (Method: UFLC): RT=3.693 min; m/z=477.1 [M+H]$^+$; Total running time 7 min.

Compound 17:

LC/MS (Method: UFLC): RT=3.766 min; m/z=477.1 [M+H]$^+$; Total running time 7 min.

Compound 18

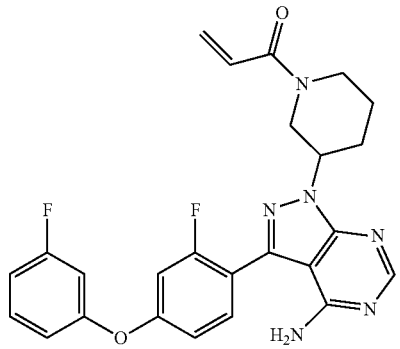 [SMILES: C=CC(=O)N1CCCC(n2nc(-c3ccc(Oc4cccc(F)c4)cc3F)c3c(N)ncnc32)C1]

1-(3-(4-amino-3-(2-fluoro-4-(3-fluorophenoxy)phenyl)-1H-pyrazolo[3,4-d]pyrimidin-1-yl)piperidin-1-yl)prop-2-en-1-one Procedure:

1-(3-(4-amino-3-iodo-1H-pyrazolo[3,4-d]pyrimidin-1-yl)piperidin-1-yl)prop-2-en-1-one (250 mg, 0.63 mmol, 1.0 eq.), 2-(2-fluoro-4-(3-fluorophenoxy)phenyl)-4,4,5,5-tetramethyl-1,3,2-dioxaborolane (417 mg, 1.26 mmol, 2.0 eq.), sodium carbonate (200 mg, 1.88 mmol, 3.0 eq.) and Pd(PPh$_3$)$_4$ (37 mg, 0.032 mmol, 0.05 eq.) were dissolved in 1,4-dioxane/water (3 mL, 5/1, v/v). The reaction solution was stirred at 85° C. for 40 minutes under nitrogen atmosphere with microwave irradiation. After cooling to room temperature, the reaction mixture was diluted with water (10 mL), and then extracted with ethyl acetate (10 mL×3). The combined organic phases were dried over anhydrous sodium sulfate, and concentrated to give the crude product, which was purified by thin layer chromatography (developer: ethyl acetate) to give the title compound (25 mg, yield: 4.3%).

LC/MS (Method: UFLC): RT=3.693 min; m/z=477.1 [M+H]$^+$; Total running time 7 min.

$^1$H NMR (400 MHz, DMSO-d$_6$) δ 8.23 (s, 1H), 7.55-7.45 (m, 2H), 7.14-7.00 (m, 5H), 6.85-6.69 (m, 2H), 6.09-6.02 (m, 1H), 6.13-6.02 (m, 1H), 5.70-5.56 (m, 1H), 4.69-4.53 (m, 1.5H), 4.21-4.04 (m, 1.5H), 3.69-3.66 (m, 0.5H), 3.20-3.14 (m, 1H), 2.99-2.94 (m, 0.5H), 2.27-2.12 (m, 2H), 1.92-1.89 (m, 1H), 1.59-1.53 (m, 1H).

Compound 19

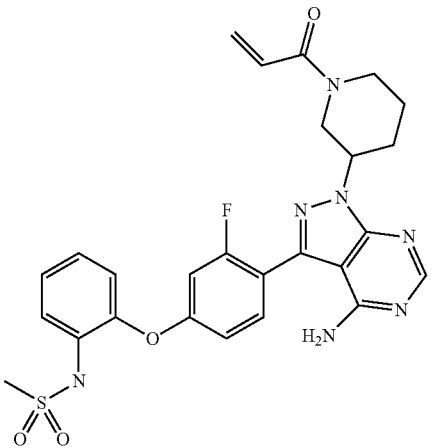 [SMILES: C=CC(=O)N1CCCC(n2nc(-c3ccc(Oc4ccccc4NS(C)(=O)=O)cc3F)c3c(N)ncnc32)C1]

N-(2-(4-(1-(1-acryloylpiperidin-3-yl)-4-amino-1H-pyrazolo[3,4-d]pyrimidin-3-yl)-3-fluorophenoxy)phenyl)methanesulfonamide Step A:

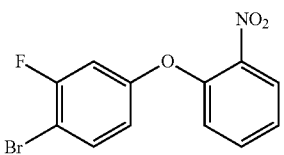 [SMILES: O=[N+]([O-])c1ccccc1Oc1ccc(Br)c(F)c1]

1-(4-bromo-3-fluorophenoxy)-2-nitrobenzene

Procedure:

2-fluoronitrobenzene (44.33 g, 314.14 mmol, 1.2 eq.) and potassium carbonate (72.36 g, 523.57 mmol, 2.0 eq.) were added to a solution of 4-bromo-3-fluorophenol (50 g, 261.78 mmol, 1.0 eq.) in DMF (500 mL). The reaction was stirred at 110° C. for 14 hours. After cooled to room temperature, the mixture was filtered. The filter cake was washed with ethyl acetate. The filtrate was concentrated to give the title compound (81.7 g, yield: 100%).

Step B:

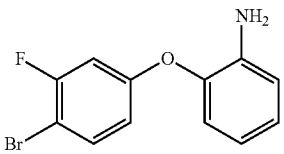 [SMILES: Nc1ccccc1Oc1ccc(Br)c(F)c1]

2-(4-bromo-3-fluorophenoxy)benzenamine

Procedure:

1-(4-bromo-3-fluorophenoxy)-2-nitrobenzene (40 g, 128.17 mmol, 1.0 eq.) was dissolved in ethanol (500 mL). The resulting mixture was degassed with nitrogen three times. 5% Pt/C (4 g, 10%, w/w) was added to the above solution, and then degassed with hydrogen three times. The reaction solution was stirred under hydrogen (50 psi) at room temperature for 12 hours, then filtered through celite. The filtrate was concentrated to give the title compound (36 g, yield: 99%).

Step C:

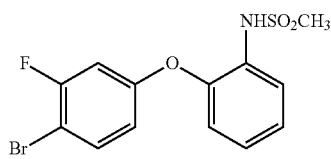

N-(2-(3-fluoro-4-bromophenoxy)phenyl)methanesulfonamide

Procedure:

Triethylamine (1.35 g, 13.29 mmol, 2.5 eq.) and methylsulfonyl chloride (1.22 g, 10.65 mmol, 1.0 eq.) were subsequently added to a solution of 2-(4-bromo-3-fluorophenoxy)aniline (1.5 g, 5.32 mmol, 1.0 eq.) in dichloromethane (25 mL) at 0° C. The reaction was stirred at room temperature for 14 hours, quenched with water (20 mL) and then extracted with dichloromethane (25 mL×2). The combined organic phases were dried over anhydrous sodium sulfate and filtered. The filtrate was concentrated to give the crude product, which was purified by silica gel column chromatography (eluent:petroleum ether:ethyl acetate=3:1) to give the title compound (1.0 g, yield: 52%).

Step D:

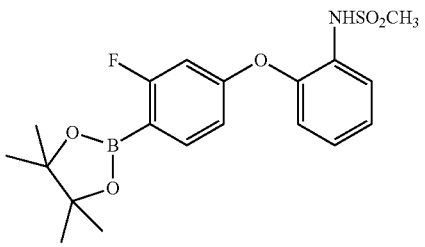

N-(2-(3-fluoro-4-(4,4,5,5-tetramethyl-1,3,2-dioxaborolan-2-yl)phenoxy)phenyl)methanesulfonamide Procedure:

N-(2-(3-fluoro-4-bromophenoxy)phenyl)methanesulfonamide (1.0 g, 2.78 mmol, 1.0 eq.), bis(pinacolato)diboron (0.85 g, 3.33 mmol, 1.2 eq.), potassium acetate (0.95 g, 9.72 mmol, 3.5 eq.) and (1,1'-bis(diphenylphosphino)ferrocene) dichloropalladium (121 mg, 0.16 mmol, 0.06 eq.) were dissolved in 1,4-dioxane (10 mL). The resulting mixture was stirred at 80° C. under nitrogen atmosphere for 12 hours. The reaction mixture was filtered through celite. The filtrate was concentrated to give the crude product (1.13 g, yield: 100%), which was used directly in the next step.

Step E:

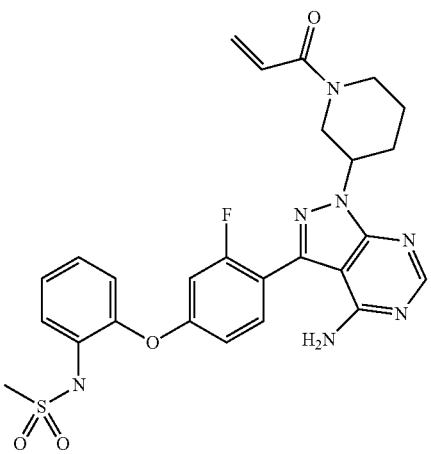 [SMILES: C=CC(=O)N1CCCC(n2nc(-c3ccc(Oc4ccccc4NS(C)(=O)=O)cc3F)c3c(N)ncnc32)C1]

N-(2-(4-(1-(1-acryloylpiperidin-3-yl)-4-amino-1H-pyrazolo[3,4-d]pyrimidin-3-yl)-3-fluorophenoxy) phenyl)methanesulfonamide Procedure:

1-(3-(4-amino-3-iodo-1H-pyrazolo[3,4-d]pyrimidin-1-yl) piperidin-1-yl)prop-2-en-1-one (100 mg, 0.251 mmol, 1.0 eq.), N-(2-(3-fluoro-4-(4,4,5,5-tetramethyl-1,3,2-dioxaborolan-2-yl)phenoxy)phenyl)methanesulfonamide (205 mg, 0.502 mmol, 2.0 eq.), sodium carbonate (2N, 0.25 mL, 0.502 mmol, 2.0 eq.) and Pd(PPh$_3$)$_4$ (29 mg, 0.025 mmol, 0.1 eq.) were dissolved in 1,4-dioxane (2 mL). The reaction solution was stirred at 85° C. for 40 minutes under nitrogen atmosphere with microwave irradiation. After cooling to room temperature, the reaction mixture was diluted with water (10 mL), and then extracted with ethyl acetate (10 mL×3). The combined organic phases were dried over anhydrous sodium sulfate and filtered. The filtrate was concentrated to give the crude product, which was purified by HPLC (C18 reverse phase column, mobile phase: acetonitrile/water/7‰ NH$_4$HCO$_3$, gradient: 10% to 100% (volume ratio)) to give the title compound (5 mg, yield: 4%).

LC/MS (Method: UFLC): RT=2.452 min; m/z=552.4 [M+H]$^+$; Total running time 7 min.

Compound 20

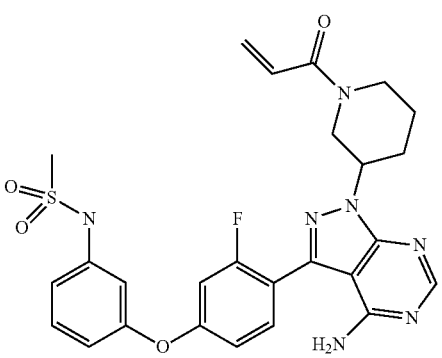 [SMILES: C=CC(=O)N1CCCC(n2nc(-c3ccc(Oc4cccc(NS(C)(=O)=O)c4)cc3F)c3c(N)ncnc32)C1]

N-(3-(4-(1-(1-acryloylpiperidin-3-yl)-4-amino-1H-pyrazolo[3,4-d]pyrimidin-3-yl)-3-fluorophenoxy)phenyl)methanesulfonamide Step A:

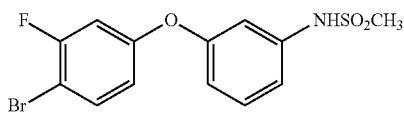

N-(3-(4-bromo-3-fluorophenoxy)phenyl)methanesulfonamide

Procedure:

Triethylamine (2.02 g, 20 mmol, 6.0 eq.) and methylsulfonyl chloride (1.2 g, 10.6 mmol, 3.0 eq.) were subsequently added to a solution of 3-(4-bromo-3-fluorophenoxy)aniline (1.0 g, 3.54 mmol, 1.0 eq.) in dichloromethane (25 mL) at 0° C. The reaction was stirred at room temperature for 14 hours, quenched with water (20 mL) and then extracted with dichloromethane (25 mL×2). The combined organic phases were dried over anhydrous sodium sulfate and filtered. The filtrate was concentrated to give the crude product, which was purified by silica gel column chromatography (eluent: petroleum ether:ethyl acetate=10:1) to give the title compound (1.0 g, yield: 78%).

Step B:

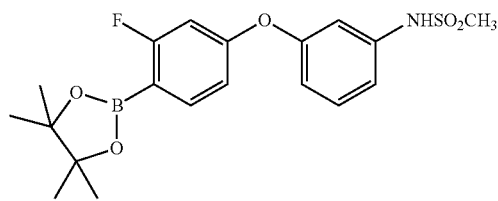

N-(3-(3-fluoro-4-(4,4,5,5-tetramethyl-1,3,2-dioxaborolan-2-yl)phenoxy)phenyl)methanesulfonamide Procedure:

N-(3-(4-bromo-3-fluorophenoxy)phenyl)methanesulfonamide (640 mg, 1.78 mmol, 1.0 eq.), bis(pinacolato)diboron (496 mg, 1.95 mmol, 1.1 eq.), potassium acetate (523 mg, 5.33 mmol, 3.0 eq.) and (1,1'-bis(diphenylphosphino)ferrocene)dichloropalladium (126 mg, 0.178 mmol, 0.1 eq.) were dissolved in 1,4-dioxane (10 mL). The resulting mixture was stirred at 80° C. under nitrogen atmosphere for 12 hours. The reaction mixture was filtered through celite. The filtrate was concentrated to give the crude product (0.8 g, yield: 100%), which was used directly in the next step.

Step C:

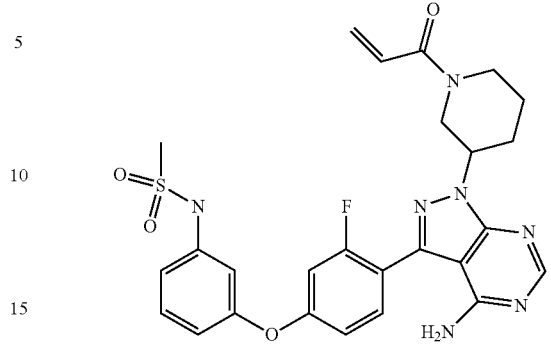

N-(3-(4-(1-(1-acryloylpiperidin-3-yl)-4-amino-1H-pyrazolo[3,4-d]pyrimidin-3-yl)-3-fluorophenoxy)phenyl)methanesulfonamide Procedure:

1-(3-(4-amino-3-iodo-1H-pyrazolo[3,4-d]pyrimidin-1-yl)piperidin-1-yl)prop-2-en-1-one (60 mg, 0.150 mmol, 1.0 eq.), N-(3-(3-fluoro-4-(4,4,5,5-tetramethyl-1,3,2-dioxaborolan-2-yl)phenoxy)phenyl)methanesulfonamide (122 mg, 0.30 mmol, 2.0 eq.), sodium carbonate (64 mg, 0.6 mmol, 4.0 eq.) and Pd(PPh$_3$)$_4$ (17 mg, 0.015 mmol, 0.1 eq.) were dissolved in 1,4-dioxane (6 mL, 1/1, v/v). The reaction solution was stirred at 85° C. for 40 minutes under nitrogen atmosphere with microwave irradiation. After cooling to room temperature, the reaction mixture was diluted with water (10 mL), and then extracted with ethyl acetate (10 mL×3). The combined organic phases were dried over anhydrous sodium sulfate, and concentrated to give the crude product, which was purified by HPLC (C18 reverse phase column, mobile phase: acetonitrile/water/0.5% HCl, gradient: 10% to 100% (volume ratio)) to give the title compound hydrochloride (16 mg, yield: 22%).

LC/MS (Method: UFLC): RT=0.775 min; m/z=552.1 [M+H]$^+$; Total running time 1.5 min.

Compound 21

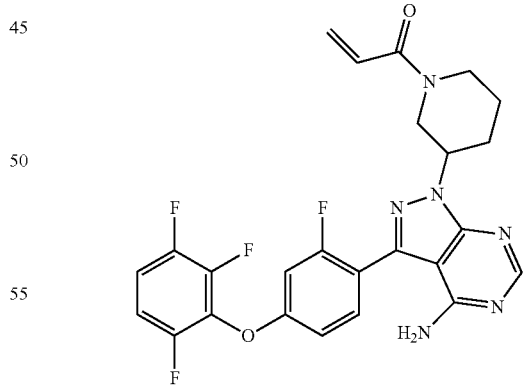

1-(3-(4-amino-3-(2-fluoro-4-(2,3,6-trifluorophenoxy)phenyl)-1H-pyrazolo[3,4-d]pyrimidin-1-yl)piperidin-1-yl)prop-2-en-1-one Procedure:

1,2,3,4-fluorobenzene (20 mg, 0.13 mmol, 1.0 eq.) and potassium carbonate (35 mg, 0.26 mmol, 2.0 eq.) were added to a solution of 1-(3-(4-amino-3-(2-fluoro-4-hydroxyphenyl)-1H-pyrazolo[3,4-d]pyrimidin-1-yl)piperidin-1-yl)prop-2-en-1-one (50 mg, 0.13 mmol, 1.0 eq.) in DMF (5 mL). The reaction was stirred at 100° C. and for 4 hours. After cooled to room temperature, the reaction mixture was diluted with water (10 mL), and then extracted with ethyl acetate (10 mL×3). The combined organic phases were dried over anhydrous sodium sulfate and filtered. The filtrate was concentrated to give the crude product, which was purified by HPLC (C18 reverse phase column, mobile phase: acetonitrile/water, gradient: 10%-100% (volume ratio)) to give the title compound (10 mg, yield: 15%).

LC/MS (Method: UFLC): RT=2.993 min; m/z=513.2 [M+H]$^+$; Total running time 7 min.

Compound 22

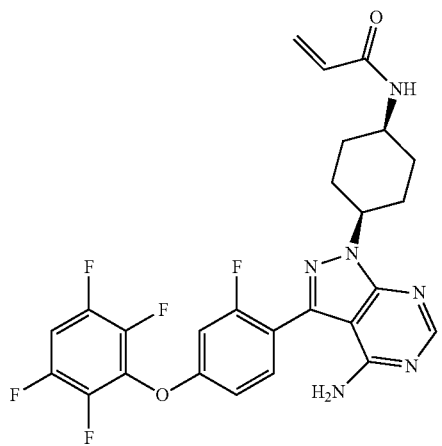 [SMILES: C=CC(=O)N[C@H]1CC[C@@H](n2nc(-c3ccc(Oc4c(F)c(F)cc(F)c4F)cc3F)c3c(N)ncnc32)CC1]

N-((1s,4s)-4-(4-amino-3-(2-fluoro-4-(2,3,5,6-tetrafluorophenoxy)phenyl)-1H-pyrazolo[3,4-d]pyrimidin-1-yl)cyclohexyl)acrylamide Step A:

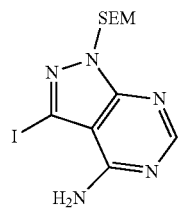

3-iodo-1-((2-(trimethyl silyl)ethoxy)methyl)-1H-pyrazolo[3,4-d]pyrimidin-4-amine Procedure:

NaH (13.8 g, 345 mmol, 1.5 eq.) was added to a solution of 3-iodo-1H-pyrazolo[3,4-d]pyrimidin-4-amine (60 g, 230 mmol, 1.0 eq.) in DMF (1.24 L) and DMSO (180 mL) at 0° C. The reaction was stirred at 0° C. for 30 min, then SEMCl (42 g, 253 mmol, 1.1 eq.) was added. The reaction was stirred overnight at room temperature, poured into ice water (500 mL) and extracted with ethyl acetate (500 mL×3). The combined organic phases were dried over anhydrous sodium sulfate and filtered. The filtrate was concentrated to give the crude product, which was purified by silica gel column chromatography (eluent:petroleum ether:ethyl acetate=10:1 to 1:1) to give the title compound (10 g, yield: 44%).

Step B:

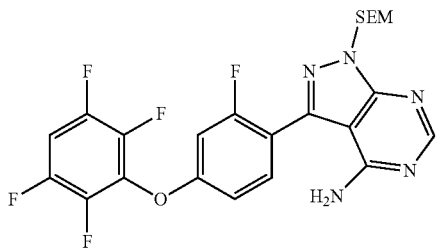 [SMILES: C[Si](C)(C)CCOCn1nc(-c2ccc(Oc3c(F)c(F)cc(F)c3F)cc2F)c2c(N)ncnc21]

3-(2-fluoro-4-(2,3,5,6-tetrafluorophenoxy)phenyl)-1-((2-(trimethylsilyl)ethoxy)methyl)-1H-pyrazolo[3,4-d]pyrimidin-4-amine Procedure:

3-iodo-1-((2-(trimethyl silyl)ethoxy)methyl)-1H-pyrazolo[3,4-d]pyrimidin-4-amine (40 g, 102 mmol, 1.0 eq.), 2-(2-fluoro-4-(2,3,5,6-tetrafluorophenoxy)phenyl)-4,4,5,5-tetramethyl-1,3,2-dioxaborolane (50 g, 129 mmol, 1.3 eq.), potassium phosphate (40 g, 189 mmol, 1.8 eq.) and Pd-118 (3.0 g, 5.0 mmol, 0.05 eq.) were dissolved in 1,4-dioxane/water (1400 mL, 5/1, v/v). The reaction solution was stirred at 60° C. for 12 hours under nitrogen atmosphere. After cooling to room temperature, the reaction mixture was filtered through celite. The filtrate was extracted with ethyl acetate (500 mL×4). The combined organic phases were dried over anhydrous sodium sulfate, and concentrated to give the crude product, which was purified by silica gel column chromatography (eluent:petroleum ether:ethyl acetate=10:1 to 1:1) to give the title compound (25 g, yield: 46%).

Step C:

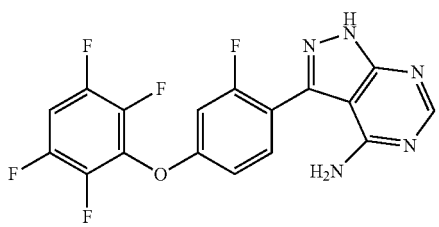 [SMILES: Nc1ncnc2[nH]nc(-c3ccc(Oc4c(F)c(F)cc(F)c4F)cc3F)c12]

3-(2-fluoro-4-(2,3,5,6-tetrafluorophenoxy)phenyl)-1H-pyrazolo[3,4-d]pyrimidin-4-amine Procedure:

4M HCl/EtOAc (200 mL) was added to a solution of 3-(2-fluoro-4-(2,3,5,6-tetrafluorophenoxy)phenyl)-1-((2-(trimethylsilyl)ethoxy)methyl)-1H-pyrazolo[3,4-d]pyrimidin-4-amine (25 g, 48 mmol, 1.0 eq.) in ethyl acetate (50 mL) at 0° C. The reaction mixture was stirred at 60° C. for 14 hours and concentrated under reduced pressure. Water (100 mL) and saturated NaHCO$_3$ (100 mL) were added to the residue, and then was extracted with ethyl acetate (300 mL×3). The combined organic phases were dried over anhydrous sodium sulfate, and concentrated to give the title compound (13 g, yield: 69%).

Step D:

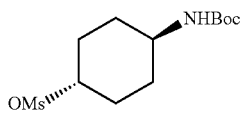 [SMILES: CC(C)(C)OC(=O)N[C@H]1CC[C@H](OS(C)(=O)=O)CC1]

(1r,4r)-4-(tert-butoxycarbonyl)cyclohexyl methanesulfonate

Procedure:
Triethylamine (7.16 g, 70.7 mmol, 3.0 eq.) and methanesulfonyl chloride (5.4 g, 45 mmol, 2.05 eq.) were subsequently added to a solution of tert-butyl (1r,4r)-4-hydroxycyclohexylcarbamate (5.08 g, 23.6 mmol, 1.0 eq.) in dichloromethane (50 mL) at 0° C. The reaction was stirred at room temperature for 14 hours, quenched with water (60 mL), and then extracted with dichloromethane (50 mL×2). The combined organic phases were dried over anhydrous sodium sulfate and filtered. The filtrate was concentrated to give the title compound (6.0 g, yield: 87%).

Step E:

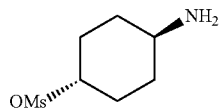 [SMILES: CS(=O)(=O)O[C@H]1CC[C@H](N)CC1]

(1r,4r)-4-aminocyclohexyl methanesulfonate

Procedure:
4M HCl/EtOAc (10 mL) was added to a solution of (1r,4r)-4-(tert-butoxycarbonyl)cyclohexyl methanesulfonate (4 g, 13.63 mmol) in ethyl acetate (40 mL) at 0° C. The reaction mixture was stirred at room temperature for 1 h and concentrated to give the title compound hydrochloride (3.2 g, yield: 100%).

Step F:

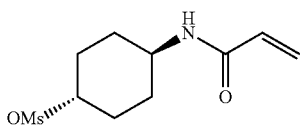 [SMILES: C=CC(=O)N[C@H]1CC[C@H](OS(C)(=O)=O)CC1]

(1r,4r)-4-acrylamidocyclohexyl methanesulfonate

Procedure:
Triethylamine (1.03 g, 10.19 mmol, 3.0 eq.) and acrylic chloride (307 mg, 3.4 mmol, 1.0 eq.) were subsequently added to a solution of (1r,4r)-4-aminocyclohexyl methanesulfonate (780 mg, 3.4 mmol, 1.0 eq.) in dichloromethane (15 mL) at 0° C. The reaction mixture was stirred at 0° C. for 1 hour, and then quenched with saturated $NaHCO_3$ (10 mL). The aqueous phase was extracted with dichloromethane (5 mL×2). The combined organic layers were dried over anhydrous sodium sulfate and filtered. The filtrate was concentrated to give the title compound (780 mg, yield: 93%).

Step G:

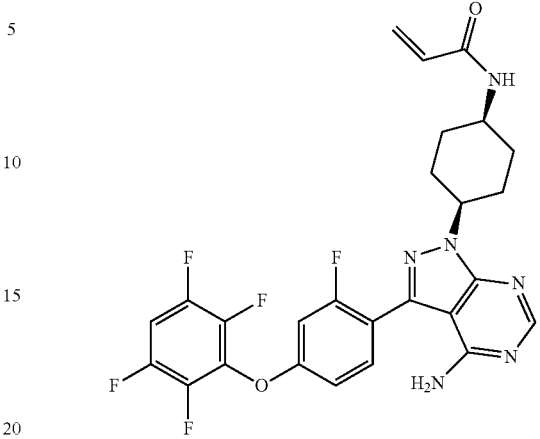

N-((1s,4s)-4-(4-amino-3-(2-fluoro-4-(2,3,5,6-tetrafluorophenoxy)phenyl)-1H-pyrazolo[3,4-d]pyrimidin-1-yl)cyclohexyl)acrylamide Procedure:
(1r,4r)-4-acrylamidocyclohexyl methanesulfonate (49 mg, 0.198 mmol, 1.3 eq.) and cesium carbonate (130.5 mg, 0.305 mmol, 2.0 eq.) were added to a solution of 3-(2-fluoro-4-(2,3,5,6-fluorophenoxy)phenyl)-1H-pyrazolo[3,4-d]pyrimidin-4-amine (60 mg, 0.152 mmol, 1.0 eq.) in DMF (2 mL). The reaction was stirred at 90° C. for 4 hours, diluted with water (10 mL) and extracted with ethyl acetate (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.5% HCl, gradient 10%-100% (volume ratio)) to give the title compound hydrochloride (2 mg, yield: 2%).

LC/MS (Method: UFLC): RT=0.816 min; m/z=544.9 $[M+H]^+$; Total running time 1.5 min.

Compounds 23 and 24

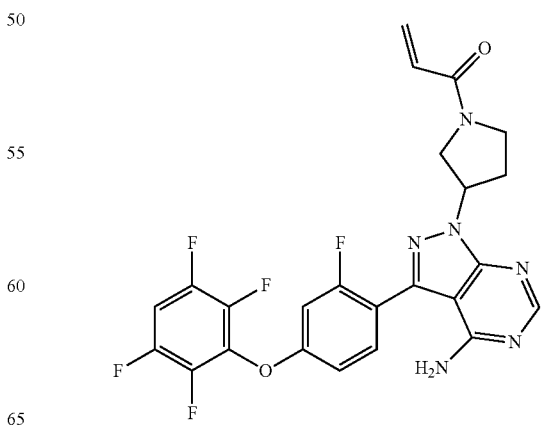

1-(3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one

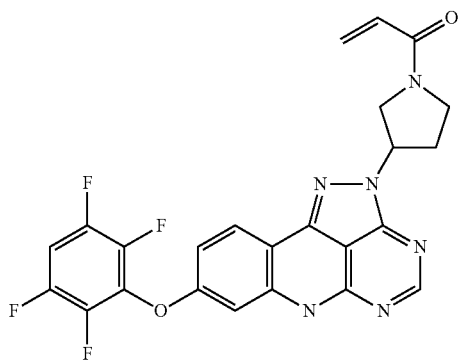 [SMILES: C=CC(=O)N1CCC(n2nc3c4c(ncnc42)Nc2cc(Oc4c(F)c(F)cc(F)c4F)ccc2-3)C1]

Step A:

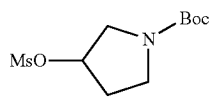

tert-butyl 3-(methylsulfonyloxy)pyrrolidine-1-carboxylate

Procedure:

Triethylamine (4.8 g, 48 mmol, 3.0 eq.) and methanesulfonyl chloride (3.7 g, 32 mmol, 2.0 eq.) were subsequently added to a solution of tert-butyl 3-hydroxypyrrolidine-1-carboxylate (3.0 g, 16 mmol, 1.0 eq.) in dichloromethane (50 mL) at 0° C. The reaction was stirred at room temperature for 2 hours, quenched with water (60 mL), and then extracted with dichloromethane (50 mL×2). The combined organic phases were dried over anhydrous sodium sulfate and filtered. The filtrate was concentrated to give the title compound (4.0 g, yield: 95%).

Step B:

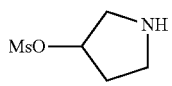

pyrrolidin-3-yl methanesulfonate

Procedure:

4M HCl/EtOAc (10 mL) was added to a solution of tert-butyl 3-(methylsulfonyloxy)pyrrolidine-1-carboxylate (4.0 g, 15 mmol) in ethyl acetate (40 mL). The reaction mixture was stirred at room temperature for 1 h and concentrated to give the title compound hydrochloride (2.5 g, yield: 100%).

Step C:

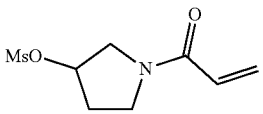

1-acryloylpyrrolidin-3-yl methanesulfonate

Procedure:

Triethylamine (4.5 g, 45 mmol, 3.0 eq.) and acrylic chloride (1.01 g, 12 mmol, 0.8 eq.) were added subsequently to a solution of pyrrolidin-3-yl methanesulfonate (2.5 g, 15 mmol, 1.0 eq.) in dichloromethane (305 mL) at 0° C. The reaction mixture was stirred at 0° C. for 1 hour, and then quenched with saturated NaHCO$_3$ (10 mL). The aqueous phase was extracted with dichloromethane (5 mL×2). The combined organic layers were dried over anhydrous sodium sulfate and filtered. The filtrate was concentrated to give the title compound (2.5 g, yield: 83%).

Step D:

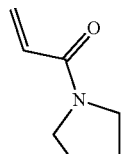
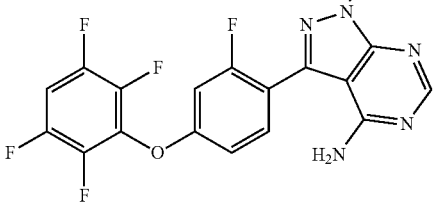

1-(3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one

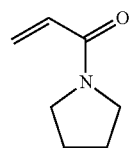
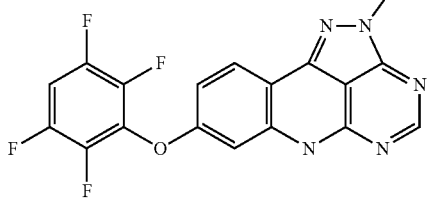

Procedure:

1-acryloylpyrrolidin-3-yl methanesulfonate (62 mg, 0.306 mmol, 2.0 eq.) and cesium carbonate (149 mg, 0.459 mmol, 3.0 eq.) were added to a solution of 3-(2-fluoro-4-(2,3,5,6-fluorophenoxy)phenyl)-1H-pyrazolo[3,4-d]pyrimidin-4-amine (60 mg, 0.152 mmol, 1.0 eq.) in DMF (2 mL). The reaction was stirred at 90° C. for 4 hours, diluted with water (10 mL) and extracted with ethyl acetate (10 mL×3). The combined organic phases were dried over anhydrous sodium sulfate and filtered. The filtrate was concentrated to give the crude product, which was purified by HPLC (C18 reverse phase column, mobile phase: acetonitrile/water, gradient 10%-100% (volume ratio)) to give Compound 23 (18 mg, yield: 11%) and Compound 24 (3.5 mg, yield: 2%).

Compound 23:
LC/MS (Method: UFLC): RT=2.780 min; m/z=517.1 [M+H]$^+$; Total running time 7 min.
$^1$H NMR (400 MHz, CDCl$_3$) δ 8.35 (s, 1H), 7.55-7.48 (m, 1H), 7.10-7.03 (m, 1H), 6.93-6.88 (m, 2H), 6.43-6.39 (m, 1H), 5.73-5.57 (m, 2H), 5.47-5.43 (m, 1H), 4.15-3.96 (m, 3H), 3.82-3.73 (m, 1H), 2.70-2.42 (m, 2H).

Compound 24:
LC/MS (Method: UFLC): RT=0.813 min; m/z=497.0 [M+H]$^+$; Total running time 1.5 min.

Compound 25

5.49-5.41 (m, 1H), 4.47-4.42 (m, 1H), 2.34-2.25 (m, 3.5H), 2.04-1.96 (m, 1.5H), 1.62-1.59 (m, 1H).

Compound 26

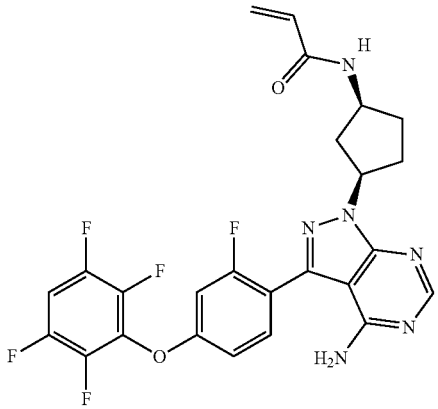

N-((1s,3r)-3-(4-amino-3-(2-fluoro-4-(2,3,5,6-tetrafluorophenoxy)phenyl)-1H-pyrazolo[3,4-d]pyrimidin-1-yl)cyclopentyl)acrylamide Step A:

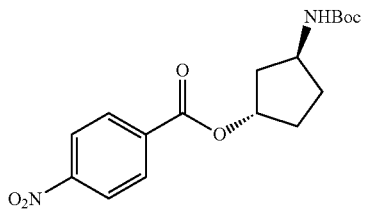 [SMILES: CC(C)(C)OC(=O)N[C@H]1CC[C@H](OC(=O)c2ccc([N+](=O)[O-])cc2)C1]

(1s,3 s)-3-(tert-butoxycarbonyl)cyclopentyl 4-nitrobenzoate

Procedure:
Tert-butyl (1s,3r)-3-hydroxycyclopentylcarbamate (2.25 g, 11.2 mmol, 1.0 eq.), 4-nitrobenzoic acid (4.67 g, 28.0 mmol, 2.5 eq.) and triphenylphosphine (4.4 g, 16.8 mmol, 1.5 eq.) were dissolved in toluene (50 mL) and tetrahydrofuran (12 mL). Diethyl azodicarboxylate (3.0 g, 16.8 mmol, 1.5 eq.) was added to the resulting mixture. The reaction was stirred at room temperature for 12 hours under nitrogen atmosphere and concentrated under reduced pressure. Dichloromethane (500 mL) was added to the residue, and stirred for 30 minutes, then filtered. The filtrate was concentrated to give the crude product, which was purified by silica gel column chromatography (eluent:petroleum ether: ethyl acetate=10:1 to 1:1) to give the title compound (0.6 g, yield: 15%).

Step B:

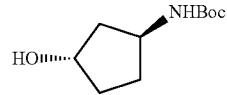

N-((1r,3r)-3-(4-amino-3-(2-fluoro-4-(2,3,5,6-tetrafluorophenoxy)phenyl)-1H-pyrazolo[3,4-d]pyrimidin-1-yl)cyclopentyl)acrylamide Procedure:
N-((1r,3r)-3-(4-amino-3-iodo-1H-pyrazolo[3,4-d]pyrimidin-1-yl)cyclopentyl)acrylamide (70 mg, 0.17 mmol, 1.0 eq.), 2-(2-fluoro-4-(2,3,5,6-tetrafluorophenoxy)phenyl)-4,4,5,5-tetramethyl-1,3,2-dioxaborolane (135 mg, 0.35 mmol, 2.0 eq.), sodium carbonate (56 mg, 0.52 mmol, 3.0 eq.) and Pd(PPh$_3$)$_4$ (20 mg, 0.0175 mmol, 0.1 eq) was dissolved in 1,4-dioxane (10 mL, 1/1, v/v) in. The reaction mixture was stirred at 85° C. for 40 minutes with microwave irradiation under nitrogen atmosphere, diluted with water (10 mL) and extracted with ethyl acetate (10 mL×3). The combined organic phase with anhydrous sodium sulfate and filtered. The filtrate was concentrated to give the crude product, which was purified by HPLC (C18 reverse phase column, mobile phase: acetonitrile/water/0.5% HCl, gradient: 10%-100% (volume ratio)) to give the title compound hydrochloride (4 mg, yield: 4%).

LC/MS (Method: UFLC): RT=3.935 min; m/z=531.1 [M+H]$^+$; Total running time 7 min.
$^1$H NMR (400 MHz, DMSO-d$_6$) δ 8.33 (s, 1H), 8.30 (d, J=7.2 Hz, 1H), 7.99-7.90 (m, 1H), 7.60 (t, J=8.4 Hz, 1H), 7.30 (dd, J=2.4, 10.8 Hz, 1H), 7.14 (dd, J=2.8, 8.4 Hz, 1H), 6.21-6.17 (m, 1H), 6.08-6.04 (m, 1H), 5.58-5.55 (m, 1H), tert-butyl (1s,3 s)-3-hydroxycyclopentylcarbamate Procedure:

Potassium carbonate (177 mg, 1.28 mmol, 1.5 eq.) was added to a solution of (1s,3s)-3-(tert-butoxycarbonyl)cyclopentyl-4-nitrobenzoate (300 mg, 0.86 mmol) in methanol (5 mL). The resulting mixture was stirred at room temperature for 2 hours. The reaction solution was diluted with water (10 mL), and extracted with methyl tert-butyl ether (10 mL×3). The combined organic phases were dried over anhydrous sodium sulfate, and concentrated to give the title compound (180 mg, yield: 90%).

Step C:

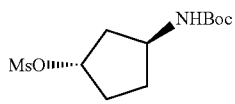

(1s,3 s)-3-(tert-butoxycarbonyl)cyclopentyl methanesulfonate

Procedure:

Triethylamine (180 mg, 1.79 mmol, 2.0 eq.) and methanesulfonyl chloride (204 mg, 1.79 mmol, 2.0 eq.) were subsequently added to a solution of tert-butyl (1s,3s)-3-hydroxycyclopentylcarbamate (180 mg, 0.895 mmol, 1.0 eq.) in dichloromethane (3 mL) at 0° C. The reaction was stirred at 0° C. for 1 hour, quenched with water (5 mL). The aqueous layer was washed with dichloromethane (5 mL×2). The combined organic phases were dried over anhydrous sodium sulfate and filtered. The filtrate was concentrated to give the title compound (200 mg, yield: 80%).

Step D:

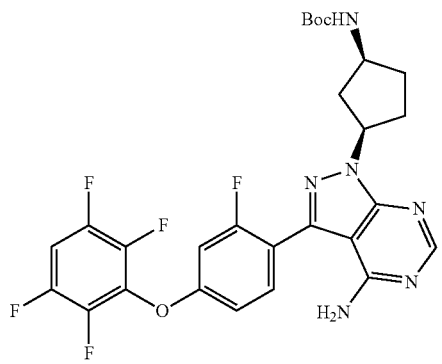 [SMILES: CC(C)(C)OC(=O)N[C@H]1CC[C@@H](n2nc(-c3ccc(Oc4c(F)c(F)cc(F)c4F)cc3F)c3c(N)ncnc32)C1]

tert-butyl (1S,3R)-3-(4-amino-3-(2-fluoro-4-(2,3,5,6-tetrafluorophenoxy)phenyl)-1H-pyrazolo[3,4-d]pyrimidin-1-yl)cyclopentylcarbamate Procedure:

Cesium carbonate (66 mg, 0.202 mmol, 2.0 eq.) and 3-(2-fluoro-4-(2,3,5,6-tetrafluorophenoxy)phenyl)-1H-pyrazolo[3,4-d]pyrimidin-4-amine (40 mg, 0.101 mmol, 1.0 eq.) were added to a solution of (1s,3s)-3-(tert-butoxycarbonyl)cyclopentyl methanesulfonate (56 mg, 0.202 mmol, 2.0 eq.) in DMF (1 mL). The reaction was stirred at 85° C. 12 h, cooled to room temperature and filtered. The filtrate was concentrated to give the crude product, which was purified by silica gel column chromatography (eluent:petroleum ether:ethyl acetate=1:1) to give the title compound (9 mg, yield: 15%).

Step E:

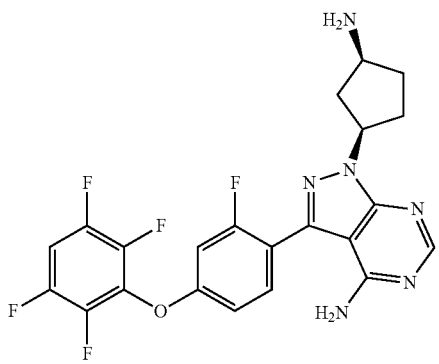 [SMILES: Nc1ncnc2c1c(-c1ccc(Oc3c(F)c(F)cc(F)c3F)cc1F)nn2[C@@H]1CC[C@H](N)C1]

1-((1r,3 s)-3-aminocyclopentyl)-3-(2-fluoro-4-(2,3,5,6-tetrafluorophenoxy)phenyl)-1H-pyrazolo[3,4-d]pyrimidin-4-amine Procedure:

4M HCl/EtOAc (1.0 mL) was added to a solution of tert-butyl (1r,4r)-4-(4-amino-3-(2-fluoro-4-(3-fluorophenoxy)phenyl)-1H-pyrazolo[3,4-d]pyrimidin-1-yl)cyclohexylcarbamate (9 mg, 0.015 mmol) in ethyl acetate (1 mL) at 0° C. The reaction mixture was stirred at room temperature for 1 h and concentrated to give the title compound hydrochloride (8 mg, yield: 100%).

Step F:

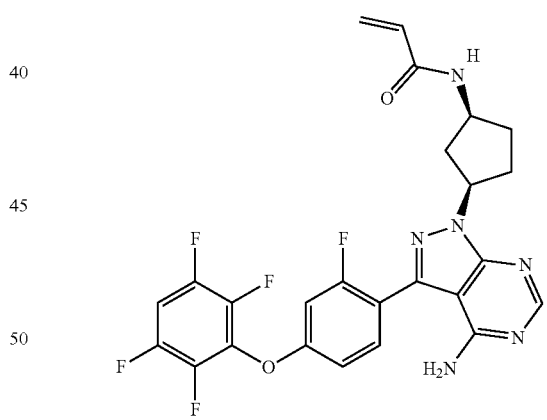

N-((1s,3r)-3-(4-amino-3-(2-fluoro-4-(2,3,5,6-tetrafluorophenoxy)phenyl)-1H-pyrazolo[3,4-d]pyrimidin-1-yl)cyclopentyl)acrylamide Procedure:

Triethylamine (3.0 mg, 0.03 mmol, 2.0 eq.) and acryloyl chloride (1.5 mg, 0.017 mmol, 1.1 eq.) were added subsequently to a solution of 1-((1r,3s)-3-aminocyclopentyl)-3-(2-fluoro-4-(2,3,5,6-tetrafluorophenoxy)phenyl)-1H-pyrazolo[3,4-d]pyrimidin-4-amine (8 mg, 0.015 mmol, 1.0 eq.) in dichloromethane (1 mL) at 0° C. The reaction mixture was stirred at 0° C. for 1 hour, quenched with water (5 mL), and then extracted with dichloromethane (5 mL×3). The combined organic layers were dried over anhydrous sodium sulfate and filtered. The filtrate was concentrated to give the crude product, which was purified by HPLC (C18 reverse phase column, mobile phase: acetonitrile/water/0.5% HCl, gradient: 10% to 100% (volume ratio)) to give the title compound hydrochloride (1.0 mg, yield: 12%).

LC/MS (Method: UFLC): RT=2.424 min; m/z=531.2 [M+H]$^+$; Total running time 3 min.

Compound 27

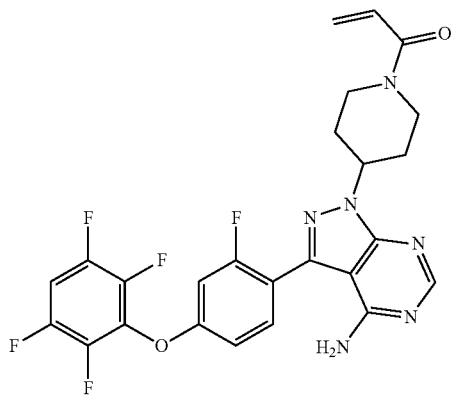 [SMILES: C=CC(=O)N1CCC(n2nc(-c3ccc(Oc4c(F)c(F)cc(F)c4F)cc3F)c3c(N)ncnc32)CC1]

1-(4-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one Procedure:

Potassium carbonate (42 mg, 0.304 mmol, 2.0 eq.) and 1-acryloylpiperidin-4-yl methanesulfonate (71 mg, 0.304 mmol, 2.0 eq.) were added to a solution of 3-(2-fluoro-4-(2,3,5,6-tetrafluorophenoxy)phenyl)-1H-pyrazolo[3,4-d]pyrimidin-4-amine (60 mg, 0.152 mmol, 1.0 eq.) in DMF (1 mL). The reaction was stirred at 85° C. for 3 hours, cooled to room temperature and filtered. The filtrate was concentrated to give the crude product, which was purified by HPLC (C18 reverse phase column, mobile phase: acetonitrile/water/0.5% HCl, gradient: 10% to 100% (volume ratio)) to give the title compound hydrochloride (1.1 mg, yield: 1.3%).

LC/MS (Method: UFLC): RT=2.834 min; m/z=531.1 [M+H]$^+$; Total running time 7 min.

Compound 28

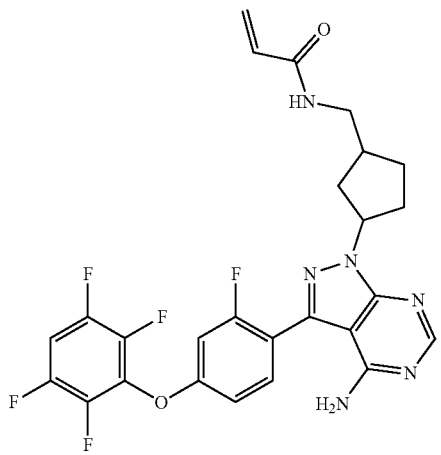 [SMILES: C=CC(=O)NCC1CCC(n2nc(-c3ccc(Oc4c(F)c(F)cc(F)c4F)cc3F)c3c(N)ncnc32)C1]

N-((3-(4-amino-3-(2-fluoro-4-(2,3,5,6-tetrafluorophenoxy)phenyl)-1H-pyrazolo[3,4-d]pyrimidin-1-yl)cyclopentyl)methyl)acrylamide Step A:

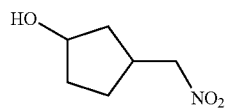

3-(nitromethyl)cyclopentanol

Procedure:

NaBH$_4$ (1.06 g, 27.94 mmol, 2.0 eq.) was added to a solution of 3-(nitromethyl)cyclopentanone (2.0 g, 14.0 mmol, 1.0 eq.) in methanol (20 mL) at 0° C. The reaction was stirred at 0° C. for 2 hours, quenched with water (2 mL), and concentrated to dryness to give the title compound (2.0 g, yield: 98%).

Step B:

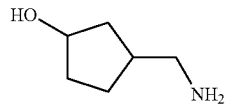

3-(aminomethyl)cyclopentanol

Procedure:

Raney nickel (200 mg, 10%) was added to a solution of 3-(nitromethyl)cyclopentanol (2.0 g, 13.8 mmol, 1.0 eq.) in ethanol (30 mL) under nitrogen atmosphere. The reaction was purged with hydrogen three times, and then stirred at 50° C. under hydrogen (50 psi) for 12 hours. After cooling to room temperature, the reaction solution was filtered through celite. The filtrate was concentrated to give the title compound (1.5 g, yield: 94%).

Step C:

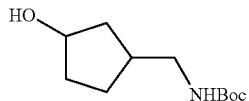

tert-butyl (3-hydroxycyclopentyl)methylcarbamate

Procedure:

(Boc)$_2$O (3.1 g, 14.33 mmol, 1.1 eq.) and triethylamine (3.95 g, 39.07 mmol, 3.0 eq.) were added to a solution of 3-(aminomethyl)cyclopentanol (1.5 g, 13.0 mmol, 1.0 eq.) in dichloromethane (20 mL). The reaction was stirred for 12 hours at 20° C., and concentrated to give the crude product, which was purified by silica gel column chromatography (eluent:petroleum ether:ethyl acetate=1:0~7:3) to give the title compound (0.7 g, yield rate: 25%).

Step D:

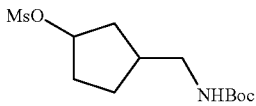

3-((tert-butoxycarbonyl)methyl)cyclopentyl methanesulfonate

Procedure:

Triethylamine (0.98 g, 9.75 mmol, 3.0 eq.) and methanesulfonyl chloride (0.74 g, 6.5 mmol, 2.0 eq.) were subsequently added to a solution of tert-butyl (3-hydroxycyclopentyl)methylcarbamate (0.7 g, 3.25 mmol, 1.0 eq.) in dichloromethane (25 mL) at 0° C. The reaction was stirred at 20° C. for 14 hours, quenched with saturated NaHCO₃ (20 mL), then extracted with dichloromethane (20 mL×3). The combined organic phases were dried over anhydrous sodium sulfate, and concentrated to give the title compound (0.76 g, yield: 80%).

Step E:

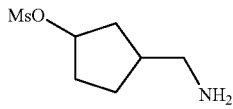

3-(aminomethyl)cyclopentyl methanesulfonate

Procedure:

4M HCl/EtOAc (10 mL) was added to a solution of 3-((tert-butoxycarbonyl)methyl)cyclopentyl methanesulfonate (760 mg, 2.59 mmol) in dichloromethane (20 mL) at 0° C. The reaction mixture was stirred at room temperature for 1 h and concentrated to give the title compound hydrochloride (590 mg, yield: 100%).

Step F:

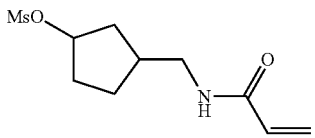 [SMILES: C=CC(=O)NCC1CCC(OS(C)(=O)=O)C1]

3-(acrylamidomethyl)cyclopentyl methanesulfonate

Procedure:

Triethylamine (530 mg, 5.3 mmol, 2.0 eq.) and acryloyl chloride (280 mg, 3.2 mmol, 1.2 eq.) were subsequently added to a solution of 3-(aminomethyl)cyclopentyl methanesulfonate (590 mg, 2.6 mmol, 1.0 eq.) in dichloromethane (15 mL) at 0° C. The reaction mixture was stirred at 0° C. for 2 hour, and then quenched with saturated NaHCO₃ (10 mL). The aqueous layer was extracted with dichloromethane (10 mL×2). The combined organic layers were dried over anhydrous sodium sulfate and filtered. The filtrate was concentrated to give the title compound (400 mg, yield: 60%).

Step G:

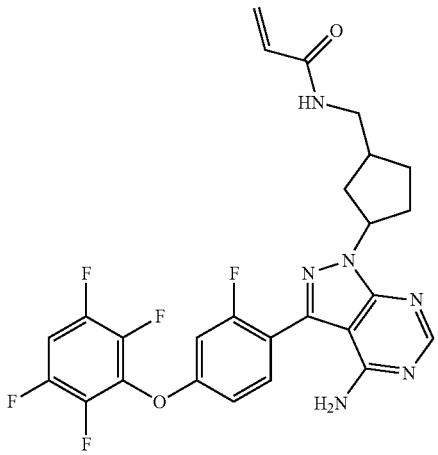 [SMILES: C=CC(=O)NCC1CCC(n2nc(-c3ccc(Oc4c(F)c(F)cc(F)c4F)cc3F)c3c(N)ncnc32)C1]

N-((3-(4-amino-3-(2-fluoro-4-(2,3,5,6-tetrafluorophenoxy)phenyl)-1H-pyrazolo[3,4-d]pyrimidin-1-yl)cyclopentyl)methyl)acrylamide Procedure:

Potassium carbonate (98 mg, 0.712 mmol, 4.0 eq.) and 3-(acrylamidomethyl)cyclopentyl methanesulfonate (131 mg, 0.534 mmol, 3.0 eq.) were added to a solution of 3-(2-fluoro-4-(2,3,5,6-tetrafluorophenoxy)phenyl)-1H-pyrazolo[3,4-d]pyrimidin-4-amine (70 mg, 0.178 mmol, 1.0 eq.) in DMF (1 mL). The reaction was stirred at 90° C. for 12 hours, cooled to room temperature and filtered. The filtrate was concentrated to give the crude product, which was purified by HPLC (C18 reverse phase column, mobile phase: acetonitrile/water/0.5% HCl, gradient: 10% to 100% (volume ratio)) to give the title compound hydrochloride (1.6 mg, yield: 0.6%).

LC/MS (Method: UFLC): RT=2.920 min; m/z=545.1 [M+H]⁺; Total running time 7 min.

Compound 29

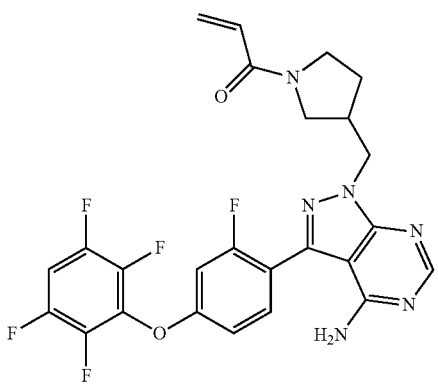 [SMILES: C=CC(=O)N1CCC(Cn2nc(-c3ccc(Oc4c(F)c(F)cc(F)c4F)cc3F)c3c(N)ncnc32)C1]

1-(3-((4-amino-3-(2-fluoro-4-(2,3,5,6-tetrafluorophenoxy)phenyl)-1H-pyrazolo[3,4-d]pyrimidin-1-yl)methyl)pyrrolidin-1-yl)prop-2-en-1-one Step A:

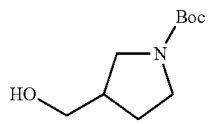

tert-butyl 3-(hydroxymethyl)pyrrolidine-1-carboxylate

Procedure:

BH$_3$ (1 M, 90 mL, 90 mmol, 3.0 eq.) was dropwise added to a solution of 1-(tert-butoxycarbonyl)pyrrolidine-3-carboxylic acid (6.45 g, 30 mmol, 1.0 eq.) in tetrahydrofuran (30 mL) at 0° C. After completion of the addition, the reaction solution was allowed to warm to room temperature, and stirred at 45° C. for 2 hours. The reaction was quenched with HCl (3N, 5 mL) at 0° C., diluted with water (100 mL), and then extracted with ethyl acetate (200 mL×2). The combined organic phases were washed with saturated NaHCO$_3$ (100 mL), dried over anhydrous sodium sulfate, and concentrated to give the title compound (4.0 g, yield: 67%).

Step B:

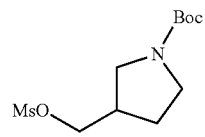

tert-butyl 3-((methylsulfonyloxy)methyl)pyrrolidine-1-carboxylate

Procedure:

Triethylamine (3.02 g, 30.0 mmol, 3.0 eq.) and methanesulfonyl chloride (2.28 g, 20 mmol, 2.0 eq.) were subsequently added to a solution of tert-butyl 3-(hydroxymethyl)pyrrolidine-1-carboxylate (0.7 g, 3.25 mmol, 1.0 eq.) in dichloromethane (20 mL) at 0° C. The reaction was stirred at 0° C. for 1 hours, quenched with water (20 mL), then extracted with dichloromethane (10 mL×2). The combined organic phases were dried over anhydrous sodium sulfate and filtered. The filtrate was concentrated to give the title compound (2.5 g, yield: 90%).

Step C:

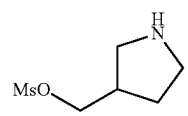 [SMILES: CS(=O)(=O)OCC1CCNC1]

pyrrolidin-3-ylmethyl methanesulfonate

Procedure:

4M HCl/EtOAc (10 mL) was added to a solution of tert-butyl 3-((methylsulfonyloxy)methyl)pyrrolidine-1-carboxylate (2.5 g, 8.9 mmol) in ethyl acetate (40 mL) at 0° C. The reaction mixture was stirred at room temperature for 1 h and concentrated to give the title compound hydrochloride (1.9 g, yield: 100%).

Step D:

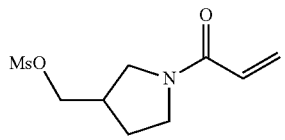

(1-acryloylpyrrolidin-3-yl)methyl methanesulfonate

Procedure:

Triethylamine (2.7 g, 26.7 mmol, 3.0 eq.) and acryloyl chloride (0.97 g, 10.7 mmol, 1.1 eq.) were subsequently added to a solution of pyrrolidin-3-ylmethyl methanesulfonate (1.9 g, 8.9 mmol, 1.0 eq.) in dichloromethane (30 mL) at 0° C. The reaction mixture was stirred at 0° C. for 1 hour, and then quenched with saturated NaHCO$_3$ (10 mL). The aqueous layer was extracted with dichloromethane (10 mL×3). The combined organic layers were dried over anhydrous sodium sulfate and filtered. The filtrate was concentrated to give the title compound (1.5 g, yield: 65%).

Step E:

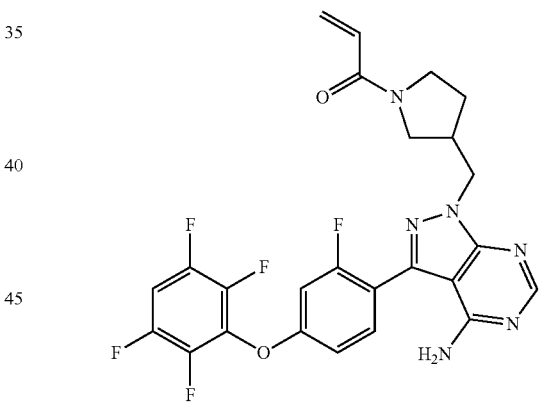

1-(3-((4-amino-3-(2-fluoro-4-(2,3,5,6-tetrafluorophenoxy)phenyl)-1H-pyrazolo[3,4-d]pyrimidin-1-yl)methyl)pyrrolidin-1-yl)prop-2-en-1-one Procedure:

Potassium carbonate (42 mg, 0.305 mmol, 2.0 eq.) and (1-acryloylpyrrolidin-3-yl)methyl methanesulfonate (46 mg, 0.198 mmol, 1.3 eq.) were added to a solution of 3-(2-fluoro-4-(2,3,5,6-tetrafluorophenoxy)phenyl)-1H-pyrazolo[3,4-d]pyrimidin-4-amine (60 mg, 0.152 mmol, 1.0 eq.) in DMF (2 mL). The reaction was stirred at 90° C. for 4 hours, cooled to room temperature and filtered. The filtrate was concentrated to give the crude product, which was purified by HPLC (C18 reverse phase column, mobile phase: acetonitrile/water/0.5% HCl, gradient: 10% to 100% (volume ratio)) to give the title compound hydrochloride (6 mg, yield: 7%).

LC/MS (Method: UFLC): RT=3.891 min; m/z=531.2 [M+H]⁺; Total running time 7 min.

Compound 30

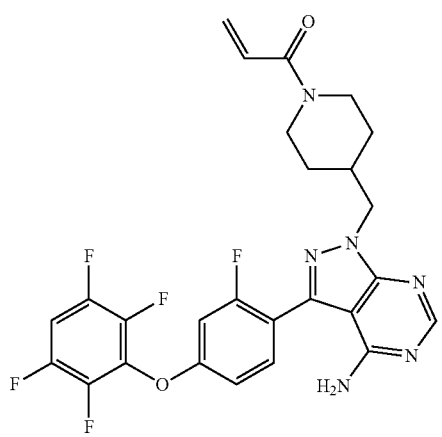 [SMILES: C=CC(=O)N1CCC(Cn2nc(-c3ccc(Oc4c(F)c(F)cc(F)c4F)cc3F)c3c(N)ncnc32)CC1]

1-(4-((4-amino-3-(2-fluoro-4-(2,3,5,6-tetrafluorophenoxy)phenyl)-1H-pyrazolo[3,4-d]pyrimidin-1-yl)methyl)piperidin-1-yl)prop-2-en-1-one Step A:

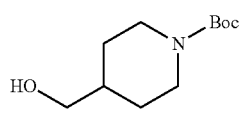

tert-butyl 4-(hydroxymethyl)piperidine-1-carboxylate

Procedure:

A solution of LiAlH₄ (520 mg, 0.013 mmol, 0.7 eq.) in tetrahydrofuran (15 mL) was added dropwise to a solution of 1-tert-butyl 4-ethyl piperidine-1,4-dicarboxylate (5.0 g, 19.0 mmol, 1.0 eq.) in tetrahydrofuran (15 mL) at 0° C. After completion of the addition, the reaction solution was stirred at 0° C. for 2 hours. The reaction was quenched with water (1 mL), and then 15% NaOH (1 mL) was added. After stirring for 10 min, water (1 mL) was added to the resulting mixture, and dried over anhydrous sodium sulfate for 30 min. The mixture was filtered through celite. The filtrate was concentrated to give the title compound (4.0 g, yield: 96%).

Step B:

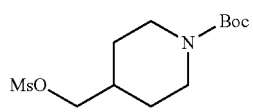

tert-butyl 4-((methylsulfonyloxy)methyl)piperidine-1-carboxylate

Procedure:

Triethylamine (3.76 g, 37.2 mmol, 2.0 eq.) and methanesulfonyl chloride (3.19 g, 27.9 mmol, 1.5 eq.) were subsequently added to a solution of tert-butyl 4-(hydroxymethyl)piperidine-1-carboxylate (4.0 g, 18.6 mmol, 1.0 eq.) in dichloromethane (25 mL) at 0° C. The reaction was stirred at 20° C. for 14 hours, quenched with water (20 mL), then extracted with dichloromethane (50 mL×3). The combined organic phases were dried over anhydrous sodium sulfate and filtered. The filtrate was concentrated to give the title compound (4.5 g, yield: 83%).

Step C:

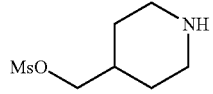 [SMILES: CS(=O)(=O)OCC1CCNCC1]

piperidin-4-ylmethyl methanesulfonate

Procedure:

4M HCl/EtOAc (20 mL) was added to a solution of tert-butyl 4-((methylsulfonyloxy)methyl)piperidine-1-carboxylate (4.5 g, 13.5 mmol) in dichloromethane (20 mL) at 0° C. The reaction mixture was stirred at room temperature for 1 h and concentrated to give the title compound hydrochloride (3.5 g, yield: 95%).

Step D:

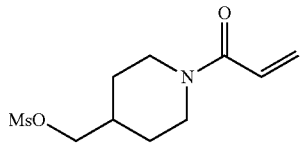 [SMILES: C=CC(=O)N1CCC(COS(C)(=O)=O)CC1]

(1-acryloylpiperidin-4-yl)methyl methanesulfonate

Procedure:

Triethylamine (4.63 g, 45.7 mmol, 3.0 eq.) and acryloyl chloride (1.38 g, 15.2 mmol, 1.0 eq.) were subsequently added to a solution of piperidin-4-ylmethyl methanesulfonate (3.5 g, 15.2 mmol, 1.0 eq.) in dichloromethane (15 mL) at 0° C. The reaction mixture was stirred at 0° C. for 2 hour, and then quenched with water (60 mL). The aqueous layer was extracted with dichloromethane (100 mL×3). The combined organic layers were dried over anhydrous sodium sulfate and filtered. The filtrate was concentrated to give the title compound (2.5 g, yield: 66%).

Step E:

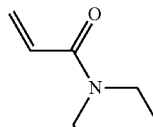
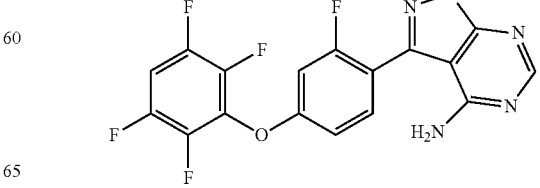

1-(4-((4-amino-3-(2-fluoro-4-(2,3,5,6-tetrafluorophenoxy)phenyl)-1H-pyrazolo[3,4-d]pyrimidin-1-yl)methyl)piperidin-1-yl)prop-2-en-1-one Procedure:

Potassium carbonate (42 mg, 0.304 mmol, 2.0 eq.) and (1-acryloylpiperidin-4-yl)methyl methanesulfonate (75 mg, 0.304 mmol, 2.0 eq.) were added to a solution of 3-(2-fluoro-4-(2,3,5,6-tetrafluorophenoxy)phenyl)-1H-pyrazolo[3,4-d]pyrimidin-4-amine (60 mg, 0.152 mmol, 1.0 eq.) in DMF (2 mL). The reaction was stirred at 80° C. for 3 hours, cooled to room temperature and filtered. The filtrate was concentrated to give the crude product, which was purified by HPLC (C18 reverse phase column, mobile phase: acetonitrile/water/0.5% HCl, gradient: 10% to 100% (volume ratio)) to give the title compound hydrochloride (5 mg, yield: 6%).

LC/MS (Method: UFLC): RT=2.820 min; m/z=545.1 [M+H]$^+$; Total running time 7 min.

Compound 31

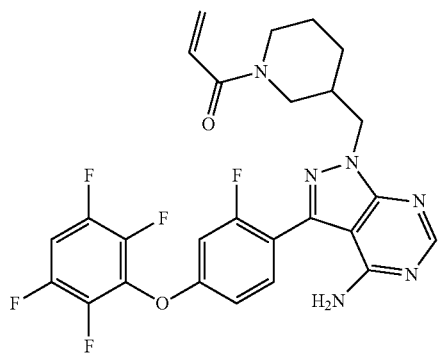 [SMILES: C=CC(=O)N1CCCC(Cn2nc(-c3ccc(Oc4c(F)c(F)cc(F)c4F)cc3F)c3c(N)ncnc32)C1]

1-(3-((4-amino-3-(2-fluoro-4-(2,3,5,6-tetrafluorophenoxy)phenyl)-1H-pyrazolo[3,4-d]pyrimidin-1-yl)methyl)piperidin-1-yl)prop-2-en-1-one Step A:

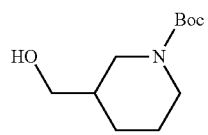

tert-butyl 3-(hydroxymethyl)piperidine-1-carboxylate

Procedure:

LiAlH$_4$ (580 mg, 15.3 mmol, 0.7 eq.) was added to a solution of 1-(tert-butoxycarbonyl)piperidine-3-carboxylic acid (5.0 g, 21.8 mmol, 1.0 eq.) in tetrahydrofuran (30 mL) at 0° C. After completion of the addition, the reaction solution was stirred at 0° C. for 2 hours. The reaction was quenched with water (1 mL), and then 15% NaOH (1 mL) was added. After stirring for 10 min, water (1 mL) was added to the resulting mixture, and dried over anhydrous sodium sulfate for 30 min. The mixture was filtered through celite. The filtrate was concentrated to give the title compound (3.9 g, yield: 93%).

Step B:

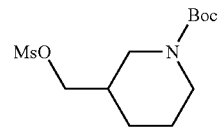

tert-butyl 3-((methylsulfonyloxy)methyl)piperidine-1-carboxylate

Procedure:

Triethylamine (1.9 g, 18.6 mmol, 2.0 eq.) and methanesulfonyl chloride (2.12 g, 18.6 mmol, 2.0 eq.) were subsequently added to a solution of tert-butyl 3-(hydroxymethyl)piperidine-1-carboxylate (2.0 g, 18.6 mmol, 1.0 eq.) in dichloromethane (20 mL) at 0° C. The reaction was stirred at 0° C. for 1 hours, quenched with water (20 mL), then extracted with dichloromethane (10 mL×2). The combined organic phases were dried over anhydrous sodium sulfate, and concentrated to give the title compound (2.5 g, yield: 92%).

Step C:

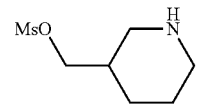

piperidin-3-ylmethyl methanesulfonate

Procedure:

4M HCl/EtOAc (10 mL) was added to a solution of tert-butyl 3-((methylsulfonyloxy)methyl)piperidine-1-carboxylate (2.5 g, 8.5 mmol) in ethyl acetate (40 mL) at 0° C. The reaction mixture was stirred at room temperature for 1 h and concentrated to give the title compound hydrochloride (1.93 g, yield: 98%).

Step D:

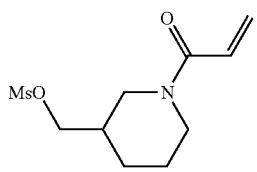 [SMILES: C=CC(=O)N1CCCC(COS(C)(=O)=O)C1]

(1-acryloylpiperidin-3-yl)methyl methanesulfonate

Procedure:

Triethylamine (1.67 g, 16.6 mmol, 2.0 eq.) and acryloyl chloride (0.82 g, 9.1 mmol, 1.1 eq.) were subsequently added to a solution of piperidin-3-ylmethyl methanesulfonate (1.93 g, 8.3 mmol, 1.0 eq.) in dichloromethane (30 mL) at 0° C. The reaction mixture was stirred at 0° C. for 1 hour, and then quenched with saturated NaHCO$_3$ (10 mL). The aqueous layer was extracted with dichloromethane (10 mL×3). The combined organic layers were dried over anhydrous sodium sulfate and filtered. The filtrate was concentrated to give the title compound (1.5 g, yield: 71%).

Step E:

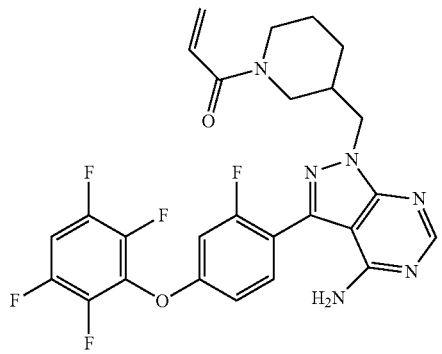 [SMILES: C=CC(=O)N1CCCC(Cn2nc(-c3ccc(Oc4c(F)c(F)cc(F)c4F)cc3F)c3c(N)ncnc32)C1]

1-(3-((4-amino-3-(2-fluoro-4-(2,3,5,6-tetrafluoro-phenoxy)phenyl)-1H-pyrazolo[3,4-d]pyrimidin-1-yl)methyl)piperidin-1-yl)prop-2-en-1-one Procedure:

Cesium carbonate (99 mg, 0.304 mmol, 2.0 eq.) and (1-acryloylpiperidin-3-yl)methyl methanesulfonate (75 mg, 0.304 mmol, 2.0 eq.) were added to a solution of 3-(2-fluoro-4-(2,3,5,6-tetrafluorophenoxy)phenyl)-1H-pyrazolo[3,4-d]pyrimidin-4-amine (60 mg, 0.152 mmol, 1.0 eq.) in DMF (2 mL). The reaction was stirred at 80° C. for 12 hours, cooled to room temperature and filtered. The filtrate was concentrated to give the crude product, which was purified by HPLC (C18 reverse phase column, mobile phase: acetonitrile/water/0.5% HCl, gradient: 10% to 100% (volume ratio)) to give the title compound hydrochloride (2 mg, yield: 2%).

LC/MS (Method: UFLC): RT=2.947 min; m/z=545.1 [M+H]$^+$; Total running time 7 min.

Compound 32

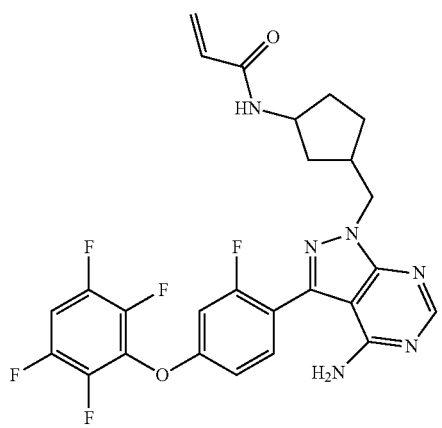 [SMILES: C=CC(=O)NC1CCC(Cn2nc(-c3ccc(Oc4c(F)c(F)cc(F)c4F)cc3F)c3c(N)ncnc32)C1]

N-(3-((4-amino-3-(2-fluoro-4-(2,3,5,6-tetrafluoro-phenoxy)phenyl)-1H-pyrazolo[3,4-d]pyrimidin-1-yl)methyl)cyclopentyl)acrylamide Step A:

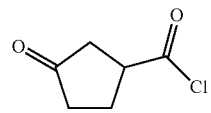

3-oxocyclopentanecarbonyl chloride

Procedure:

DMF (3 drops) and oxalyl chloride (3.8 g, 30 mmol, 3.0 eq.) was added dropwise to 3-oxo-1-cyclopentanecarboxylic acid (1.28 g, 10 mmol, 1.0 eq.) in dichloromethane (30 mL) at 0° C. The reaction was stirred at room temperature for 2 hours, and concentrated to give the title compound (1.2 g, yield: 82%).

Step B:

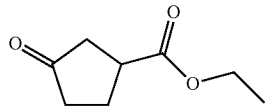

ethyl 3-oxocyclopentanecarboxylate

Procedure:

Triethylamine (3.8 g, 30 mmol, 2.0 eq.) and ethanol (754 mg, 16.37 mmol, 2.0 eq.) were subsequently added dropwise solution of 3-oxocyclopentanecarbonyl chloride (1.28 g, 8.2 mmol, 1.0 eq.) in dichloromethane (20 mL) at 0° C. The reaction was stirred at room temperature for 2 hours, quenched with water (20 mL). The aqueous phase was extracted with methylene chloride (10 mL×2). The combined organic phases were dried over anhydrous sodium sulfate, and concentrated to give the crude product, which was purified by silica gel column chromatography (eluent: petroleum ether:ethyl acetate=1:1) to give the title compound (0.6 g, yield: 47%).

Step C:

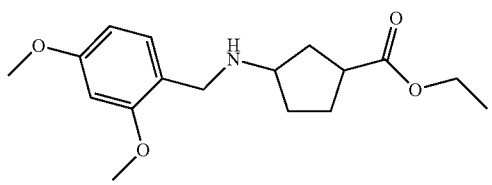 [SMILES: CCOC(=O)C1CCC(NCc2ccc(OC)cc2OC)C1]

ethyl 3-(2,4-dimethoxybenzylamino)cyclopentan-ecarboxylate

Procedure:

2,4-dimethoxybenzyl amine (556 mg, 4.66 mmol, 1.0 eq.), sodium triacetoxyborohydride (446 mg, 3.32 mmol, 1.4 eq.) and acetic acid (200 mg, 3.32 mmol, 1.0 eq.) were added to a solution of ethyl 3-oxocyclopentanecarboxylate (520 mg, 3.32 mmol, 1.0 eq.) in tetrahydrofuran (5 mL) at 0° C. The reaction was stirred at room temperature for 14 hours, quenched with saturated NaHCO₃ (10 mL). The aqueous phase was extracted with ethyl acetate (10 mL×2). The combined organic phases were dried over anhydrous sodium sulfate, and concentrated to give the crude product, which was purified by silica gel column chromatography (eluent: petroleum ether:ethyl acetate=1:1) to give the title compound (250 mg, yield: 44%).

Step D:

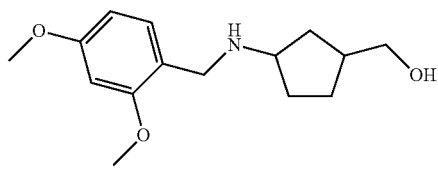 [SMILES: COc1ccc(CNC2CCC(CO)C2)c(OC)c1]

(3-(2,4-dimethoxybenzylamino)cyclopentyl)methanol

Procedure:

LiAlH₄ (17 mg, 0.445 mmol, 0.7 eq.) was added to a solution of ethyl 3-(2,4-dimethoxybenzylamino)cyclopentanecarboxylate (200 mg, 0.65 mmol, 1.0 eq.) in tetrahydrofuran (5 mL) at 0° C. After completion of the addition, the reaction solution was stirred at 0° C. for 2 hours. The reaction was quenched with water (0.2 mL), and then 15% NaOH (0.2 mL) was added. After stirring for 10 min, water (0.6 mL) was added to the resulting mixture, and dried over anhydrous sodium sulfate. The mixture was filtered through celite. The filtrate was concentrated to give the title compound (150 mg, yield: 87%).

Step E:

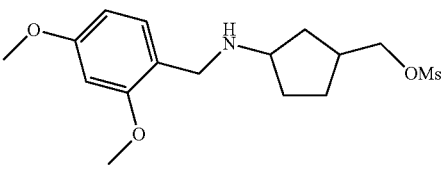 [SMILES: COc1ccc(CNC2CCC(COS(C)(=O)=O)C2)c(OC)c1]

(3-(2,4-dimethoxybenzylamino)cyclopentyl)methyl methanesulfonate

Procedure:

Triethylamine (171 mg, 1.7 mmol, 3.0 eq.) and methanesulfonyl chloride (129 mg, 1.13 mmol, 2.0 eq.) were subsequently added to a solution of (3-(2,4-dimethoxybenzylamino)cyclopentyl)methanol (150 mg, 0.566 mmol, 1.0 eq.) in dichloromethane (20 mL) at 0° C. The reaction was stirred at room temperature for 14 hours, quenched with water (10 mL), then extracted with dichloromethane (10 mL×2). The combined organic phases were dried over anhydrous sodium sulfate, and concentrated to give the title compound (194 mg, yield: 100%).

Step F:

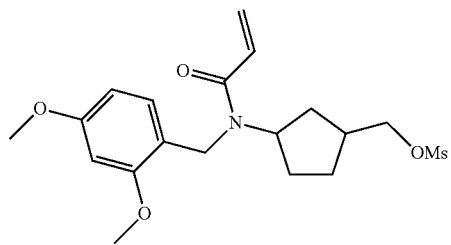 [SMILES: C=CC(=O)N(Cc1ccc(OC)cc1OC)C1CCC(COS(C)(=O)=O)C1]

(3-(N-(2,4-dimethoxybenzyl)acrylamido)cyclopentyl)methyl methanesulfonate

Procedure:

Triethylamine (220 mg, 2.18 mmol, 3.0 eq.) and acryloyl chloride (79 mg, 0.873 mmol, 1.2 eq.) were subsequently added to a solution of (3-(2,4-dimethoxybenzylamino)cyclopentyl)methyl methanesulfonate (250 mg, 0.727 mmol, 1.0 eq.) in dichloromethane (10 mL) at 0° C. The reaction mixture was stirred at 0° C. for 1 hour, and then quenched with saturated NaHCO₃ (10 mL). The aqueous layer was extracted with dichloromethane (10 mL×3). The combined organic layers were dried over anhydrous sodium sulfate and filtered. The filtrate was concentrated to give the title compound (200 mg, yield: 69%).

Step G:

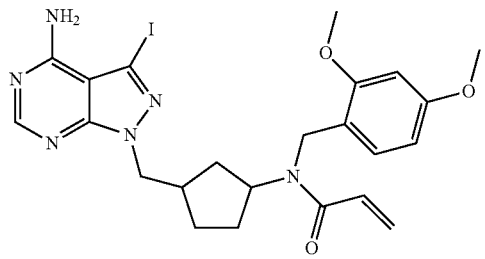 [SMILES: C=CC(=O)N(Cc1ccc(OC)cc1OC)C1CCC(Cn2nc(I)c3c(N)ncnc32)C1]

N-(2,4-dimethoxybenzyl)-N-(3-((4-amino-3-iodo-1H-pyrazolo[3,4-d]pyrimidin-1-yl)methyl)cyclopentyl)acrylamide Procedure:

Potassium carbonate (79 mg, 0.57 mmol, 2.5 eq.) and 3-iodo-1H-pyrazolo[3,4-d]pyrimidin-4-amine (60 mg, 0.23 mmol, 1.0 eq.) were added to a solution of (3-(N-(2,4-dimethoxybenzyl)acrylamido)cyclopentyl)methyl methanesulfonate (137 mg, 0.34 mmol, 1.5 eq.) in DMF (5 mL) was added. The reaction was stirred at 90° C. for 12 hours, cooled to room temperature and filtered. The filter cake was washed with ethyl acetate. The filtrate was concentrated to give the crude product, which was purified by thin layer chromatography (developer:petroleum ether:ethyl acetate=1:3) to give the title compound (60 mg, yield: 62%).

Step H:

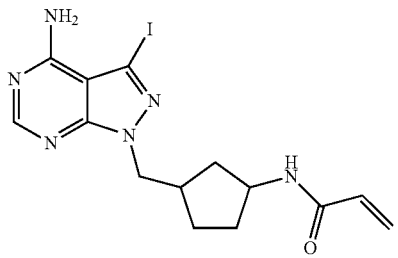 [SMILES: C=CC(=O)NC1CCC(Cn2nc(I)c3c(N)ncnc32)C1]

N-(3-((4-amino-3-iodo-1H-pyrazolo[3,4-d]pyrimidin-1-yl)methyl)cyclopentyl)acrylamide Procedure:

Et₃SiH (0.5 mL) was added to a solution of N-(2,4-dimethoxybenzyl)-N-(3-((4-amino-3-iodo-1H-pyrazolo[3,4-d]pyrimidin-1-yl)methyl)cyclopentyl)acrylamide (60 mg, 0.14 mmol, 1.0 eq.) in trifluoroacetic acid (3 mL) was added. The reaction mixture was refluxed for 3 hours, and concentrated under reduced pressure. The residue was dissolved in ethyl acetate (10 mL), washed with saturated NaHCO₃ (10 mL) and brine (10 mL), dried over anhydrous sodium sulfate and filtered. The filtrate was concentrated to give the crude product, which was purified by thin layer chromatography (developer:petroleum ether:ethyl acetate=1:3) to give the title compound (15 mg, yield: 35%).

Step I:

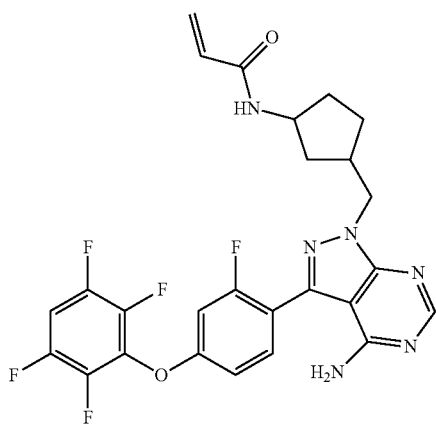 [SMILES: C=CC(=O)NC1CCC(Cn2nc(-c3ccc(Oc4c(F)c(F)cc(F)c4F)cc3F)c3c(N)ncnc32)C1]

N-(3-((4-amino-3-(2-fluoro-4-(2,3,5,6-tetrafluorophenoxy)phenyl)-1H-pyrazolo[3,4-d]pyrimidin-1-yl)methyl)cyclopentyl)acrylamide Procedure:

N-(3-((4-amino-3-iodo-1H-pyrazolo[3,4-d]pyrimidin-1-yl)methyl)cyclopentyl)acrylamide (15 mg, 0.036 mmol, 1.0 eq.), 2-(2-fluoro-4-(2,3,5,6-tetrafluorophenoxy)phenyl)-4,4,5,5-tetramethyl-1,3,2-dioxaborolane (21 mg, 0.054 mmol, 1.5 eq.), potassium carbonate (17 mg, 0.127 mmol, 3.0 eq.) and Pd(PPh₃)₄ (4 mg, 0.0036 mmol, 0.1 eq.) were dissolved in 1,4-dioxane (8 mL, 3/1, v/v). The reaction mixture was stirred at 85° C. for 30 minutes with microwave irradiation under nitrogen atmosphere, diluted with water (10 mL) and extracted with ethyl acetate (10 mL×3). The combined organic phase with anhydrous sodium sulfate and filtered. The filtrate was concentrated to give the crude product, which was purified by thin layer chromatography (developer:petroleum ether:ethyl acetate=1:3) to give the title compound (5 mg, yield: 40%).

LC/MS (Method: UFLC): RT=0.810 min; m/z=545.0 [M+H]⁺; Total running time 1.5 min.

Compounds 33 and 34

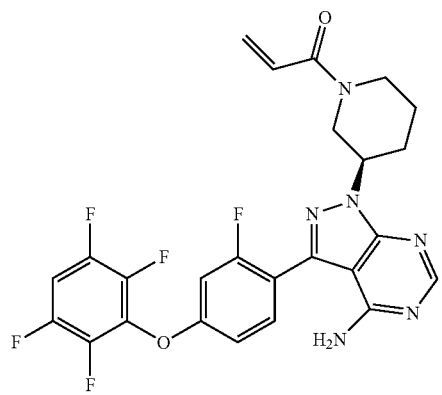 [SMILES: C=CC(=O)N1CCC[C@@H](n2nc(-c3ccc(Oc4c(F)c(F)cc(F)c4F)cc3F)c3c(N)ncnc32)C1]

1-((R)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one

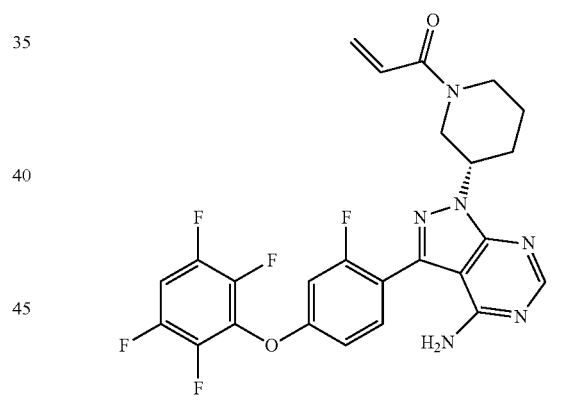

1-((S)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one Procedure:

1-(3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one (750 mg) was separated by supercritical fluid chromatogram (Chiralcel OJ, 20 μm; Supercritical CO₂:C₂H₅OH (0.2% DEA), v/v, 200 ml/min) to give 1-((R)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one (280 mg, ee: 100%) and 1-((S)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one (330 mg, ee: 98%).

Compound 33:

LC/MS (Method: UFLC): RT=3.002 min; m/z=531.1 [M+H]⁺; Total running time 7 min.

¹H NMR (400 MHz, CDCl₃) δ 8.36 (s, 1H), 7.58 (t, J=8.4 Hz, 1H), 7.09-7.04 (m, 1H), 6.94-6.88 (m, 2H), 6.62-6.54 (m, 1H), 6.32-6.25 (m, 1H), 5.73-5.63 (m, 1H), 5.56-5.51 (m, 1H), 4.90-4.85 (m, 1.5H), 4.59-4.56 (m, 0.5H), 4.21-4.17 (m, 0.5H), 4.04-4.01 (m, 0.5H), 3.76-3.71 (m, 0.5H), 3.40-3.35 (m, 0.5H), 3.22-3.15 (m, 0.5H), 2.93-2.87 (m, 0.5H), 2.39-2.27 (m, 2H), 2.04-1.68 (m, 2H).

Compound 34:

LC/MS (Method: UFLC): RT=3.006 min; m/z=531.1 [M+H]⁺; Total running time 7 min.

¹H NMR (400 MHz, CD₃OD) δ 8.24 (s, 1H), 7.62 (t, J=8.4 Hz, 1H), 7.50-7.45 (m, 1H), 7.09-7.01 (m, 2H), 6.85-6.63 (m, 1H), 6.21-6.09 (m, 1H), 5.77-5.61 (m, 1H), 4.63-4.59 (m, 1H), 4.23-4.07 (m, 1.5H), 3.90-3.85 (m, 0.5H), 3.51-3.45 (m, 0.5H), 3.34-3.17 (m, 1.5H), 2.40-2.23 (m, 2H), 2.08-2.05 (m, 1H), 1.75-1.71 (m, 1H).

Compound 35

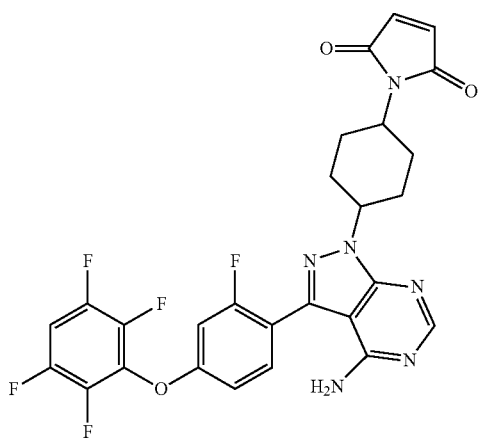 [SMILES: Nc1ncnc2c1c(-c1ccc(Oc3c(F)c(F)cc(F)c3F)cc1F)nn2C1CCC(N2C(=O)C=CC2=O)CC1]

1-(4-(4-amino-3-(2-fluoro-4-(2,3,5,6-tetrafluorophenoxy)phenyl)-1H-pyrazolo[3,4-d]pyrimidin-1-yl)cyclohexyl)-1H-pyrrole-2,5-dione Step A:

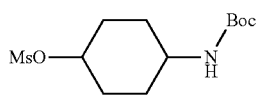

4-(tert-butoxycarbonyl)cyclohexyl methanesulfonate

Procedure:

Triethylamine (9.4 g, 92 mmol, 2.0 eq.) and methanesulfonyl chloride (10.5 g, 92 mmol, 2.0 eq.) were subsequently added to a solution of tert-butyl 4-hydroxycyclohexylcarbamate (10 g, 46 mmol, 1.0 eq.) in dichloromethane (100 mL) at 0° C. The reaction was stirred at room temperature for 14 hours, quenched with saturated NaHCO₃ (50 mL). The aqueous layer was extracted with dichloromethane (30 mL×2). The combined organic phases were dried over anhydrous sodium sulfate, and concentrated to give the title compound (11 g, yield: 80%).

Step B:

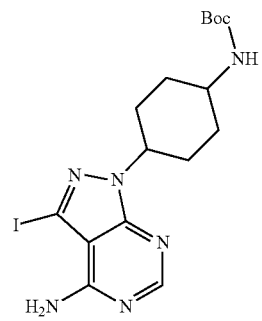 [SMILES: CC(C)(C)OC(=O)NC1CCC(n2nc(I)c3c(N)ncnc32)CC1]

tert-butyl 4-(4-amino-3-iodo-1H-pyrazolo[3,4-d]pyrimidin-1-yl)cyclohexylcarbamate Procedure:

Cesium carbonate (5.0 g, 15.3 mmol, 2.0 eq) and 4-(tert-butoxycarbonyl)cyclohexyl methanesulfonate (4.5 g, 15.3 mmol, 2.0 eq) were added to a solution of 3-iodo-1H-pyrazolo[3,4-d]pyrimidin-4-amine (2.0 g, 7.66 mmol, 1.0 eq.) in DMF (10 mL). The reaction was stirred at 80° C. for 12 hours. After cooled to room temperature, the reaction was filtered, and the filter cake was washed with ethyl acetate. The filtrate was concentrated to give the crude product, which was purified by silica gel column chromatography (eluent:petroleum ether:ethyl acetate=1:1) to give the title compound (1.1 g, yield: 31%).

Step C:

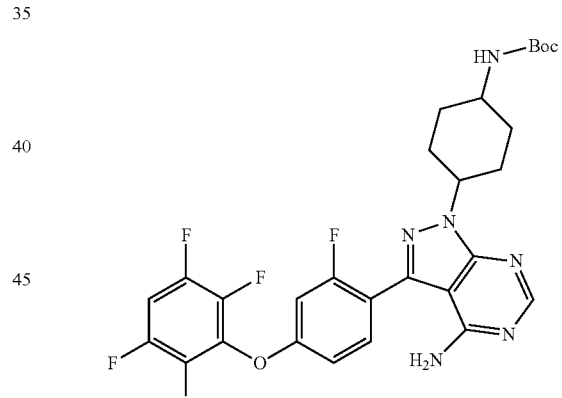

tert-butyl 4-(4-amino-3-(2-fluoro-4-(2, 3,5,6-tetrafluorophenoxy)phenyl)-1H-pyrazolo[3,4-d]pyrimidin-1-yl)cyclohexylcarbamate Procedure:

Tert-butyl 4-(4-amino-3-iodo-1H-pyrazolo[3,4-d]pyrimidin-1-yl)cyclohexylcarbamate (0.82 g, 1.79 mmol, 1.0 eq.), 2-(2-fluoro-4-(2,3,5,6-tetrafluorophenoxy)phenyl)-4,4,5,5-tetramethyl-1,3,2-dioxaborolane (1.0 g, 2.69 mmol, 1.5 eq.), potassium phosphate (0.76 g, 3.68 mmol, 2.0 eq.) and Pd-118 (58 mg, 0.089 mmol, 0.05 eq.) were dissolved in 1,4-dioxane/water (10 mL, 5/1, v/v). The reaction was stirred at 80° C. for 12 hours under nitrogen atmosphere. The reaction solution was diluted with water (10 mL) and extracted with ethyl acetate (10 mL×3). The combined organic phases were dried over anhydrous sodium sulfate, and concentrated to give the crude product, which was purified by thin layer chromatography (developer:petroleum ether:ethyl acetate=1:3) to give the title compound (800 mg, yield: 80%).

Step D:

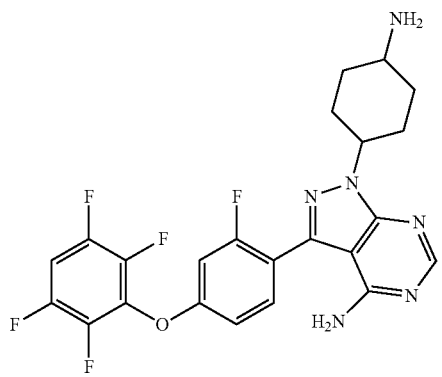 [SMILES: Nc1ncnc2c1c(-c1ccc(Oc3c(F)c(F)cc(F)c3F)cc1F)nn2C1CCC(N)CC1]

1-(4-aminocyclohexyl)-3-(2-fluoro-4-(2,3,5,6-tetra-fluorophenoxy)phenyl)-1H-pyrazolo[3,4-d]pyrimidin-4-amine Procedure:

4M HCl/EtOAc (5 mL) was added to a solution of tert-butyl 4-(4-amino-3-(2-fluoro-4-(2,3,5,6-tetrafluorophenoxy)phenyl)-1H-pyrazolo[3,4-d]pyrimidin-1-yl)cyclohexylcarbamate (800 mg, 1.35 mmol) in ethyl acetate (10 mL) at 0° C. The reaction mixture was stirred at room temperature for 1 h and concentrated to give the title compound hydrochloride (600 mg, yield: 90%).

Step E:

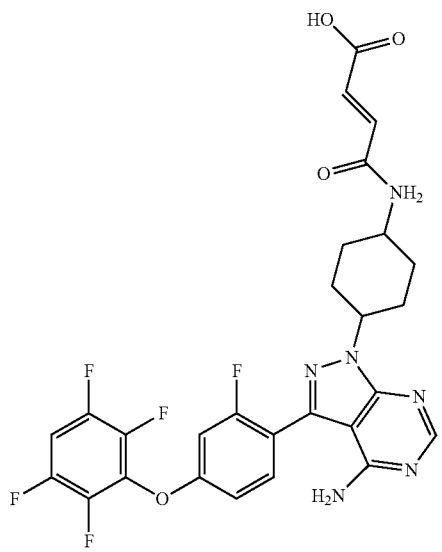 [SMILES: Nc1ncnc2c1c(-c1ccc(Oc3c(F)c(F)cc(F)c3F)cc1F)nn2C1CCC(NC(=O)/C=C/C(=O)O)CC1]

4-(4-(4-amino-3-(2-fluoro-4-(2,3,5,6-tetrafluorophenoxy)phenyl)-1H-pyrazolo[3,4-d]pyrimidin-1-yl) cyclohexylamino)-4-oxobut-2-enoic acid Procedure:

A mixture of triethylamine (41 mg, 0.408 mmol, 2.0 eq.) and maleic anhydride (20 mg, 204 mmol, 1.0 eq.) in dichloromethane (0.2 mL) was added dropwise to a solution of 1-(4-aminocyclohexyl)-3-(2-fluoro-4-(2,3,5,6-tetrafluorophenoxy)phenyl)-1H-pyrazolo[3,4-d]pyrimidin-4-amine (100 mg, 0.204 mmol, 1.0 eq.) in dichloromethane (1 mL) at 0° C. The reaction was stirred at room temperature for 14 hours, quenched with water (10 mL) and then extracted with dichloromethane (10 mL×3). The combined organic phases were dried over anhydrous sodium sulfate, and concentrated to give the title compound (100 mg, yield: 83%).

Step F:

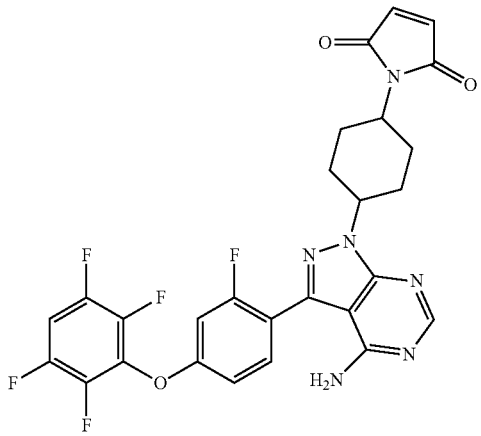

1-(4-(4-amino-3-(2-fluoro-4-(2,3,5,6-tetrafluorophenoxy)phenyl)-1H-pyrazolo[3,4-d]pyrimidin-1-yl) cyclohexyl)-1H-pyrrole-2,5-dione Procedure:

4-(4-(4-amino-3-(2-fluoro-4-(2,3,5,6-tetrafluorophenoxy)phenyl)-1H-pyrazolo[3,4-d]pyrimidin-1-yl)cyclohexylamino)-4-oxobut-2-enoic acid (50 mg, 0.085 mmol, 1.0 eq.) was dissolved in PPA (0.5 mL). The reaction was stirred at 110° C. for 4 hours, and then poured into ice water (5 mL) to quench the reaction. The mixture was extracted with ethyl acetate (5 mL×3). The combined organic phases were dried over anhydrous sodium sulfate, and concentrated to give the crude product, which was purified by HPLC (C18 reverse phase column, mobile phase: acetonitrile/water/ 0.5% HCl, gradient elution 10%-100% (volume ratio)) to give the title compound (1.5 mg, yield: 3%).

LC/MS (Method: UFLC): RT=4.399 min; m/z=571.1 $[M+H]^+$; Total running time 7 min.

Compound 36

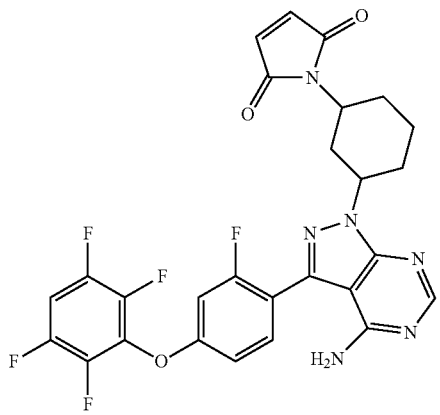 [SMILES: Nc1ncnc2c1c(-c1ccc(Oc3c(F)c(F)cc(F)c3F)cc1F)nn2C1CCCC(N2C(=O)C=CC2=O)C1]

1-(3-(4-amino-3-(2-fluoro-4-(2,3,5,6-tetrafluorophenoxy)phenyl)-1H-pyrazolo[3,4-d]pyrimidin-1-yl)cyclohexyl)-1H-pyrrole-2,5-dione Step A:

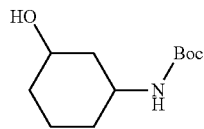

tert-butyl 3-hydroxycyclohexylcarbamate

Procedure:

Sodium borohydride (710 mg, 18.8 mmol, 2.0 eq.) was added to a solution of tert-butyl 3-oxocyclohexylcarbamate (2.0 g, 9.38 mmol, 1.0 eq.) in methanol (20 mL) at 0° C. The reaction was stirred at room temperature for 14 hours, quenched with water (20 mL) and extracted with ethyl acetate (30 mL×3). The combined organic phases were dried over anhydrous sodium sulfate, and concentrated to give the title compound (2.0 g, yield: 100%).

Step B:

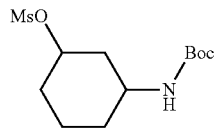

3-(tert-butoxycarbonyl)cyclohexyl methanesulfonate

Procedure:

Triethylamine (1.41 g, 13.9 mmol, 3.0 eq.) and methanesulfonyl chloride (798 mg, 6.97 mmol, 1.5 eq.) were subsequently added to a solution of tert-butyl 3-hydroxycyclohexylcarbamate (1.0 g, 4.64 mmol, 1.0 eq.) in dichloromethane (10 mL) at 0° C. The reaction was stirred at room temperature for 14 hours, quenched with saturated NaHCO$_3$ (10 mL), then extracted with dichloromethane (10 mL×2). The combined organic phases were dried over anhydrous sodium sulfate, and concentrated to give the title compound (1.36 g, yield: 100%).

Step C:

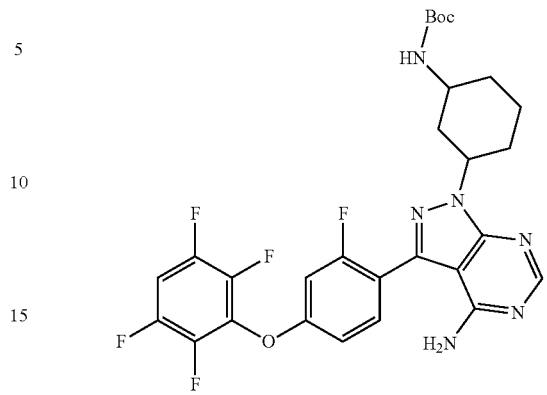

tert-butyl 3-(4-amino-3-(2-fluoro-4-(2,3,5,6-tetrafluorophenoxy)phenyl)-1H-pyrazolo[3,4-d]pyrimidin-1-yl)cyclohexylcarbamate Procedure:

Cesium carbonate (116 mg, 0.356 mmol, 2.0 eq) and 3-(tert-butoxycarbonyl)cyclohexyl methanesulfonate (105 mg, 0.356 mmol, 2.0 eq) were added to a solution of 3-(2-fluoro-4-(2,3,5,6-tetrafluorophenoxy)phenyl)-1H-pyrazolo[3,4-d]pyrimidin-4-amine (70 mg, 0.178 mmol, 1.0 eq.) in DMF (3 mL). The reaction was stirred at 80° C. for 3 hours, cooled to room temperature and filtered. The filter cake washed with ethyl acetate. The filtrate was concentrated to give the crude product, which was purified by thin layer chromatography (developer:petroleum ether:ethyl acetate=1:1) to give the title compound (35 mg, yield: 33%).

Step D:

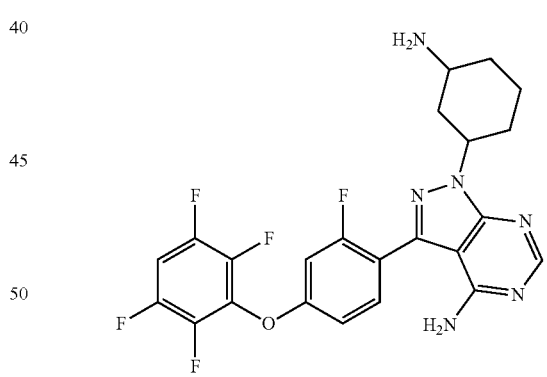

1-(3-aminocyclohexyl)-3-(2-fluoro-4-(2,3,5,6-tetrafluorophenoxy)phenyl)-1H-pyrazolo[3,4-d]pyrimidin-4-amine Procedure:

4M HCl/EtOAc (2 mL) was added to a solution of tert-butyl 3-(4-amino-3-(2-fluoro-4-(2,3,5,6-tetrafluorophenoxy)phenyl)-1H-pyrazolo[3,4-d]pyrimidin-1-yl)cyclohexylcarbamate (34 mg, 0.058 mmol, 1.0 eq.) in ethyl acetate (5 mL) at 0° C. The reaction mixture was stirred at room temperature for 2 hours and concentrated to give the title compound hydrochloride (30 mg, yield: 100%).

Step E:

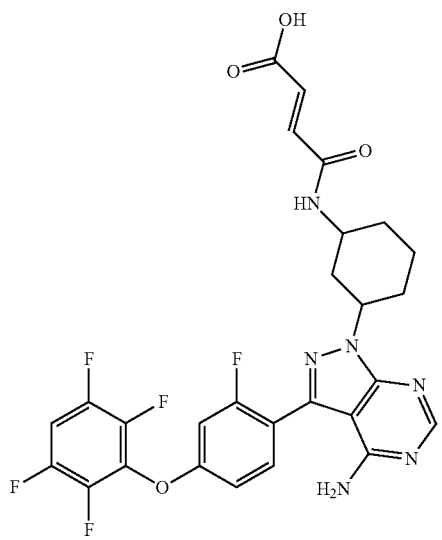 [SMILES: Nc1ncnc2c1c(-c1ccc(Oc3c(F)c(F)cc(F)c3F)cc1F)nn2C1CCCC(NC(=O)/C=C/C(=O)O)C1]

(E)-4-(3-(4-amino-3-(2-fluoro-4-(2,3,5,6-tetrafluoro-phenoxy)phenyl)-1H-pyrazolo[3,4-d]pyrimidin-1-yl)cyclohexylamino)-4-oxobut-2-enoic acid Procedure:

A mixture of triethylamine (29.3 mg, 0.29 mmol, 5.0 eq.) and maleic anhydride (5.69 mg, 0.058 mmol, 1.0 eq.) in dichloromethane (0.2 mL) was added dropwise to a solution of 1-(3-aminocyclohexyl)-3-(2-fluoro-4-(2,3,5,6-tetrafluorophenoxy)phenyl)-1H-pyrazolo[3,4-d]pyrimidin-4-amine (30 mg, 0.058 mmol, 1.0 eq.) in dichloromethane (3 mL) at 0° C. The reaction was stirred at room temperature for 14 hours, quenched with water (10 mL) and then extracted with dichloromethane (10 mL×3). The combined organic phases were dried over anhydrous sodium sulfate, and concentrated to give the title compound (16 mg, yield: 47%).

Step F:

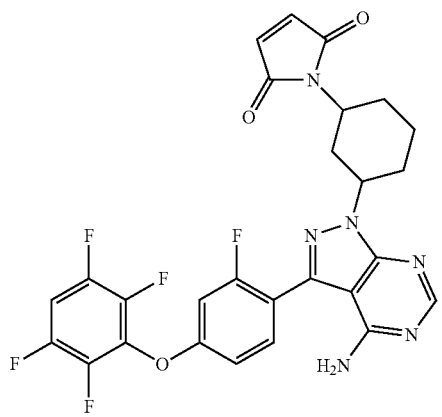 [SMILES: Nc1ncnc2c1c(-c1ccc(Oc3c(F)c(F)cc(F)c3F)cc1F)nn2C1CCCC(N2C(=O)C=CC2=O)C1]

1-(3-(4-amino-3-(2-fluoro-4-(2,3,5,6-tetrafluorophenoxy)phenyl)-1H-pyrazolo[3,4-d]pyrimidin-1-yl)cyclohexyl)-1H-pyrrole-2,5-dione Procedure:

4-(3-(4-amino-3-(2-fluoro-4-(2,3,5,6-tetrafluorophenoxy)phenyl)-1H-pyrazolo[3,4-d]pyrimidin-1-yl)cyclohexylamino)-4-oxobut-2-enoic acid (16 mg, 0.028 mmol, 1.0 eq.) was dissolved in PPA (5 mL). The reaction was stirred at 110° C. for 16 hours, and then poured into ice water (10 mL) to quench the reaction. The mixture was extracted with ethyl acetate (10 mL×3). The combined organic phases were dried over anhydrous sodium sulfate, and concentrated to give the crude product, which was purified by HPLC (C18 reverse phase column, mobile phase: acetonitrile/water, gradient elution 10%-100% (volume ratio)) to give the title compound (0.8 mg, yield: 5%).

LC/MS (Method: UFLC): RT=4.429 min; m/z=571.1 [M+H]$^+$; Total running time 7 min.

Compound 37

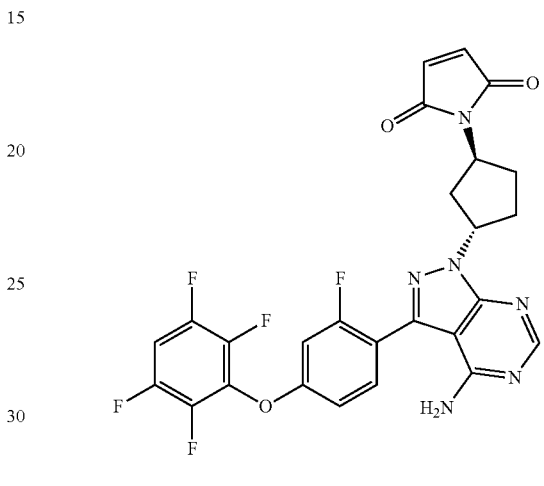

1-((1S,3 S)-3-(4-amino-3-(2-fluoro-4-(2,3,5,6-tetrafluorophenoxy)phenyl)-1H-pyrazolo[3,4-d]pyrimidin-1-yl)cyclopentyl)-1H-pyrrole-2,5-dione Step A:

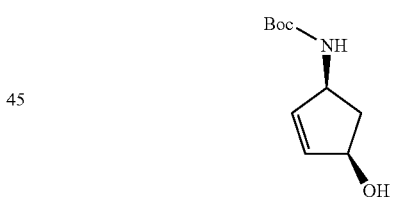

tert-butyl (1s,4r)-4-hydroxycyclopent-2-enylcarbamate

Procedure:

Mo(Co)$_6$ (1.6 g, 6.08 mmol, 1.0 eq.) was added to a solution of tert-butyl 3-oxa-2-aza-bicyclo[2.2.1]hept-5-ene-2-carboxylate (6.0 g, 30.4 mmol, 5.0 eq.) in acetonitrile/water (10 mL, 20/1, v/v). Sodium borohydride (2.3 g, 60.8 mmol, 10.0 eq.) was added in one portion to the above solution at 30° C. The reaction was stirred at 60° C. for 12 hours, cooled to room temperature, and filtered through celite. The filtrate was concentrated to give the crude product, which was purified by silica gel column chromatography (eluent:petroleum ether:ethyl acetate=1:0~1:1) to give the title compound (2.0 g, yield: 33%)

Step B:

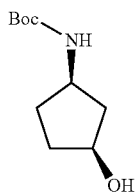 [SMILES: CC(C)(C)OC(=O)N[C@@H]1CC[C@H](O)C1]

tert-butyl (1r, 3s)-3-hydroxycyclopentylcarbamate

Procedure:
tert-butyl (1s, 4r)-4-hydroxycyclopent-2-enylcarbamate (2.0 g, 10 mmol) was dissolved in methanol (20 mL), the reaction flask was purged with nitrogen air three times. 10% Pd/C (0.2 g, 10%, w/w) was added to the above solution, and then replaced with hydrogen three times. The reaction solution was stirred at room temperature under hydrogen atmosphere (1 atm) for 14 hours, and filtered through celite. The filtrate was concentrated to give the title compound (1.9 g, yield: 95%).

Step C:

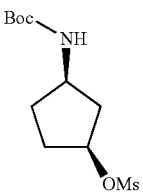 [SMILES: CC(C)(C)OC(=O)N[C@@H]1CC[C@H](OS(C)(=O)=O)C1]

(1s,3r)-3-(tert-butoxycarbonyl)cyclopentyl methanesulfonate

Procedure:
Triethylamine (350 mg, 3.48 mmol, 2.0 eq.) and methanesulfonyl chloride (397 mg, 3.48 mmol, 2.0 eq.) were subsequently added to a solution of tert-butyl (1r, 3s)-3-hydroxycyclopentylcarbamate (350 mg, 1.74 mmol, 1.0 eq.) in dichloromethane (10 mL) at 0° C. The reaction was stirred at room temperature for 14 hours, quenched with saturated NaHCO₃ (10 mL). The aqueous layer was extracted with dichloromethane (10 mL×2). The combined organic phases were dried over anhydrous sodium sulfate, and concentrated to give the title compound (400 mg, yield: 83%).

Step D:

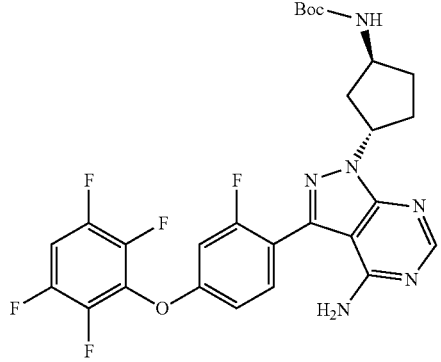 [SMILES: CC(C)(C)OC(=O)N[C@H]1CC[C@H](n2nc(-c3ccc(Oc4c(F)c(F)cc(F)c4F)cc3F)c3c(N)ncnc32)C1]

tert-butyl (1s,3 s)-3-(4-amino-3-(2-fluoro-4-(2,3,5,6-tetrafluorophenoxy)phenyl)-1H-pyrazolo[3,4-d]pyrimidin-1-yl)cyclopentylcarbamate Procedure:
Cesium carbonate (160 mg, 0.508 mmol, 2.0 eq.) and (1s,3r)-3-(tert-butoxycarbonyl)cyclopentyl methanesulfonate (150 mg, 0.508 mmol, 2.0 eq.) were added to a solution of 3-(2-fluoro-4-(2,3,5,6-tetrafluorophenoxy)phenyl)-1H-pyrazolo[3,4-d]pyrimidin-4-amine (100 mg, 0.254 mmol, 1.0 eq.) in DMF (3 mL). The reaction was stirred at 80° C. for 12 hours, cooled to room temperature and filtered. The filter cake washed with ethyl acetate. The filtrate was concentrated to give the crude product, which was purified by thin layer chromatography (developer:petroleum ether: ethyl acetate=1:1) to give the title compound (60 mg, yield: 41%).

Step E:

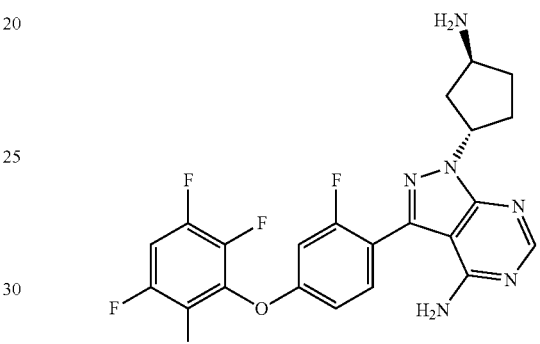

1-((1s,3 s)-3-aminocyclopentyl)-3-(2-fluoro-4-(2,3,5,6-tetrafluorophenoxy)phenyl)-1H-pyrazolo[3,4-d]pyrimidin-4-amine Procedure:
4M HCl/EtOAc (2 mL) was added to a solution of tert-butyl (1s,3s)-3-(4-amino-3-(2-fluoro-4-(2,3,5,6-tetrafluorophenoxy)phenyl)-1H-pyrazolo[3,4-d]pyrimidin-1-yl) cyclopentylcarbamate (60 mg, 0.104 mmol) in ethyl acetate (5 mL) at 0° C. The reaction mixture was stirred at room temperature for 0.5 h and concentrated to give the title compound hydrochloride (41 mg, yield: 82%).

Step F:

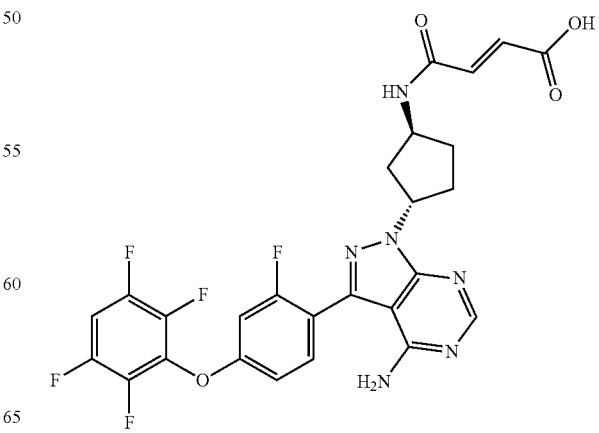

4-((1s,3 s)-3-(4-amino-3-(2-fluoro-4-(2,3,5,6-tetra-fluorophenoxy)phenyl)-1H-pyrazolo[3,4-d]pyrimidin-1-yl)cyclopentylamino)-4-oxobut-2-enoic acid Procedure:

A mixture of triethylamine (16 mg, 0.16 mmol, 2.0 eq.) and maleic anhydride (8 mg, 0.08 mmol, 1.1 eq.) in dichloromethane (0.2 mL) was added dropwise to a solution of 1-((1s,3s)-3-aminocyclopentyl)-3-(2-fluoro-4-(2,3,5,6-tetrafluorophenoxy)phenyl)-1H-pyrazolo[3,4-d]pyrimidin-4-amine (41 mg, 0.08 mmol, 1.0 eq.) in dichloromethane (0.5 mL) at 0° C. The reaction was stirred at room temperature for 14 hours, quenched with water (10 mL) and then extracted with dichloromethane (10 mL×3). The combined organic phases were dried over anhydrous sodium sulfate, and concentrated to give the title compound (40 mg, yield: 87%).

Step G:

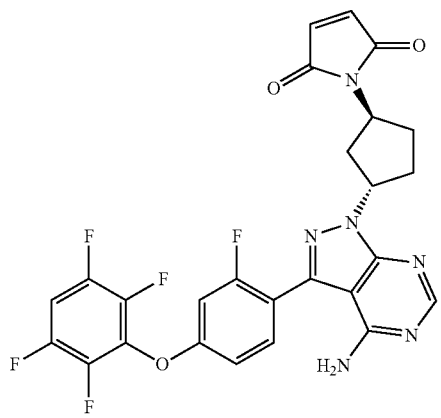 [SMILES: Nc1ncnc2c1c(-c1ccc(Oc3c(F)c(F)cc(F)c3F)cc1F)nn2[C@H]1CC[C@H](N2C(=O)C=CC2=O)C1]

1-((1S,3 S)-3-(4-amino-3-(2-fluoro-4-(2,3,5,6-tetra-fluorophenoxy)phenyl)-1H-pyrazolo[3,4-d]pyrimidin-1-yl)cyclopentyl)-1H-pyrrole-2,5-dione Procedure:

4-((1s,3 s)-3-(4-amino-3-(2-fluoro-4-(2,3,5,6-tetrafluorophenoxy)phenyl)-1H-pyrazolo[3,4-d]pyrimidin-1-yl)cyclopentylamino)-4-oxobut-2-enoic acid (40 mg, 0.069 mmol, 1.0 eq.) was dissolved in PPA (0.5 mL). The reaction was stirred at 110° C. for 4 hours, and then poured into ice water (10 mL) to quench the reaction. The mixture was extracted with ethyl acetate (10 mL×3). The combined organic phases were dried over anhydrous sodium sulfate, and concentrated to give the crude product, which was purified by HPLC (C18 reverse phase column, mobile phase: acetonitrile/water/0.5% HCl, gradient elution 10%-100% (volume ratio)) to give the title compound (0.7 mg, yield: 2%).

LC/MS (Method: UFLC): RT=4.370 min; m/z=557.1 [M+H]$^+$; Total running time 7 min.

Compound 38

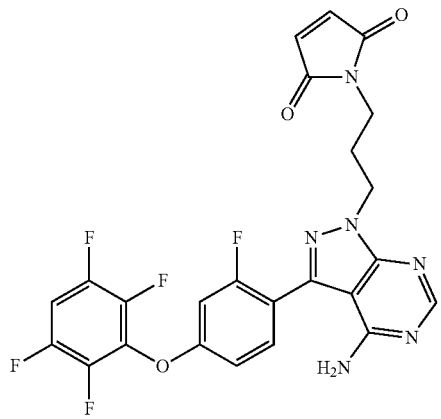 [SMILES: Nc1ncnc2c1c(-c1ccc(Oc3c(F)c(F)cc(F)c3F)cc1F)nn2CCCN1C(=O)C=CC1=O]

1-(3-(4-amino-3-(2-fluoro-4-(2,3,5,6-tetrafluorophenoxy)phenyl)-1H-pyrazolo[3,4-d]pyrimidin-1-yl)propyl)-1H-pyrrole-2,5-dione Step A:

3-(tert-butoxycarbonyl)propyl methanesulfonate

Procedure:

Triethylamine (4.5 g, 44.6 mol, 3.0 eq.) and methanesulfonyl chloride (3.37 g, 29.6 mmol, 2.0 eq.) were subsequently added to a solution of 3-(tert-butoxycarbonyl)propyl methanesulfonate (2.6 g, 14.8 mmol, 1.0 eq.) in dichloromethane (30 mL) at 0° C. The reaction was stirred at room temperature for 14 hours, quenched with saturated NaHCO$_3$ (50 mL). The aqueous layer was extracted with dichloromethane (50 mL×2). The combined organic phases were dried over anhydrous sodium sulfate, and concentrated to give the title compound (2.7 g, yield: 100%).

Step B:

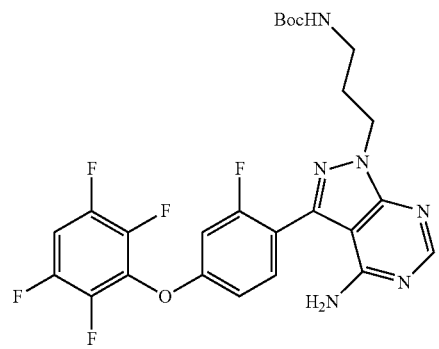 [SMILES: CC(C)(C)OC(=O)NCCCn1nc(-c2ccc(Oc3c(F)c(F)cc(F)c3F)cc2F)c2c(N)ncnc21]

tert-butyl 3-(4-amino-3-(2-fluoro-4-(2,3,5,6-tetrafluorophenoxy)phenyl)-1H-pyrazolo[3,4-d]pyrimidin-1-yl)propylcarbamate Procedure:

Potassium carbonate (60 mg, 0.44 mmol, 3.0 eq.) and 3-(tert-butoxycarbonyl)propyl methanesulfonate (140 mg, 0.553 mmol, 3.6 eq.) were added to a solution of 3-(2-fluoro-4-(2,3,5,6-tetrafluorophenoxy)phenyl)-1H-pyrazolo[3,4-d]pyrimidin-4-amine (60 mg, 0.153 mmol, 1.0 eq.) in DMF (3 mL). The reaction was stirred at 90° C. for 12 hours, cooled to room temperature and filtered. The filter cake washed with ethyl acetate. The filtrate was concentrated to give the crude product, which was purified by thin layer chromatography (developer:petroleum ether:ethyl acetate=1:1) to give the title compound (50 mg, yield: 61%).

Step C:

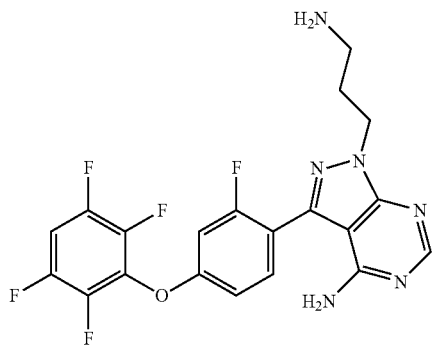 [SMILES: NCCCn1nc(-c2ccc(Oc3c(F)c(F)cc(F)c3F)cc2F)c2c(N)ncnc21]

1-(3-aminopropyl)-3-(2-fluoro-4-(2,3,5,6-tetrafluorophenoxy)phenyl)-1H-pyrazolo[3,4-d]pyrimidin-4-amine Procedure:

4M HCl/EtOAc (2 mL) was added to a solution of tert-butyl 3-(4-amino-3-(2-fluoro-4-(2,3,5,6-tetrafluorophenoxy)phenyl)-1H-pyrazolo[3,4-d]pyrimidin-1-yl)propylcarbamate (50 mg, 0.09 mmol) in dichloromethane (5 mL) at 0° C. The reaction mixture was stirred at room temperature for 0.5 h and concentrated to give the title compound hydrochloride (42 mg, yield: 100%).

Step D:

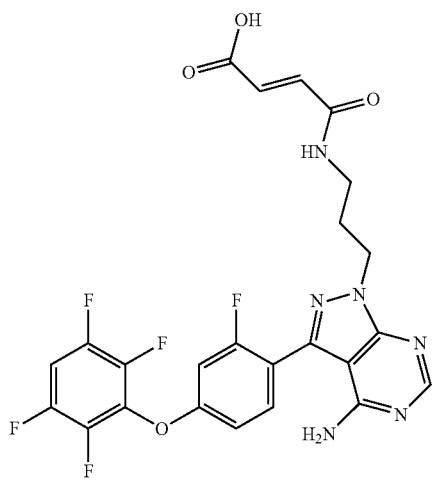 [SMILES: Nc1ncnc2c1c(-c1ccc(Oc3c(F)c(F)cc(F)c3F)cc1F)nn2CCCNC(=O)/C=C/C(=O)O]

(E)-4-(3-(4-amino-3-(2-fluoro-4-(2,3,5,6-tetrafluorophenoxy)phenyl)-1H-pyrazolo[3,4-d]pyrimidin-1-yl)propylamino)-4-oxobut-2-enoic acid Procedure:

A mixture of triethylamine (33 mg, 0.33 mmol, 3.0 eq.) and maleic anhydride (11 mg, 0.11 mmol, 1.0 eq.) in dichloromethane (0.2 mL) was added dropwise to a solution of 1-(3-aminopropyl)-3-(2-fluoro-4-(2,3,5,6-tetrafluorophenxy)phenyl)-1H-pyrazolo[3,4-d]pyrimidin-4-amine (50 mg, 0.11 mmol, 1.0 eq.) in dichloromethane (5 mL) at 0° C. The reaction was stirred at room temperature for 3 hours, quenched with water (10 mL) and then extracted with dichloromethane (10 mL×3). The combined organic phases were dried over anhydrous sodium sulfate, and concentrated to give the title compound (60 mg, yield: 100%).

Step E:

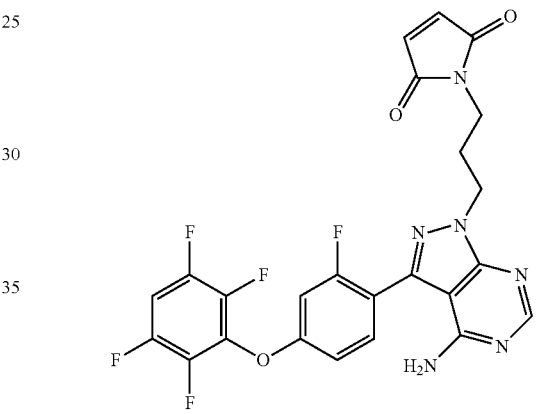

1-(3-(4-amino-3-(2-fluoro-4-(2,3,5,6-tetrafluorophenoxy)phenyl)-1H-pyrazolo[3,4-d]pyrimidin-1-yl)propyl)-1H-pyrrole-2,5-dione Procedure:

(E)-4-(3-(4-amino-3-(2-fluoro-4-(2,3,5,6-tetrafluorophenoxy)phenyl)-1H-pyrazolo[3,4-d]pyrimidin-1-yl)propylamino)-4-oxobut-2-enoic acid (450 mg, 1.28 mmol, 1.0 eq.) was dissolved in PPA (5 mL). The reaction was stirred at 120° C. for 4 hours, and then poured into ice water (10 mL) to quench the reaction. The mixture was extracted with ethyl acetate (10 mL×3). The combined organic phases were dried over anhydrous sodium sulfate, and concentrated to give the crude product, which was purified by HPLC (C18 reverse phase column, mobile phase: acetonitrile/water/0.5% HCl, gradient elution 10%-100% (volume ratio)) to give the title compound (3.5 mg, yield: 6%).

LC/MS (Method: UFLC): RT=2.902 min; m/z=531.1 [M+H]$^+$; Total running time 7 min.

Compound 39

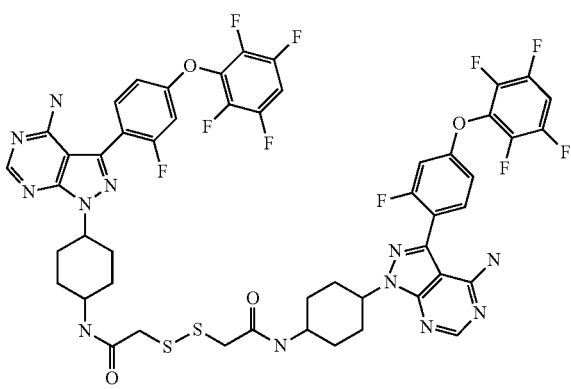 [SMILES: Nc1ncnc2c1c(-c1ccc(Oc3c(F)c(F)cc(F)c3F)cc1F)nn2C1CCC(NC(=O)CSSCC(=O)NC2CCC(n3nc(-c4ccc(Oc5c(F)c(F)cc(F)c5F)cc4F)c4c(N)ncnc43)CC2)CC1]

Step A:

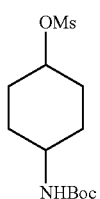 [SMILES: CC(C)(C)OC(=O)NC1CCC(OS(C)(=O)=O)CC1]

4-(tert-butoxycarbonyl)cyclohexyl methanesulfonate

Procedure:
Triethylamine (9.3 g, 92 mmol, 2.0 eq.) and methanesulfonyl chloride (10.5 g, 92 mmol, 2.0 eq.) were subsequently added to a solution of tert-butyl 4-hydroxycyclohexylcarbamate (10.0 g, 46 mmol, 1.0 eq.) in dichloromethane (100 mL) at 0° C. The reaction was stirred at 20° C. for 14 hours, quenched with saturated NaHCO₃ (10 mL). The aqueous layer was extracted with dichloromethane (200 mL×3). The combined organic phases were dried over anhydrous sodium sulfate, and concentrated to give the title compound (11 g, yield: 81%).

Step B:

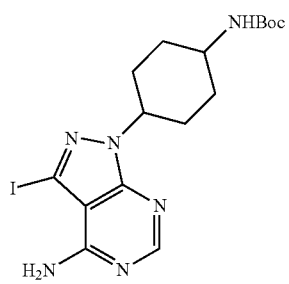 [SMILES: CC(C)(C)OC(=O)NC1CCC(n2nc(I)c3c(N)ncnc32)CC1]

tert-butyl 4-(4-amino-3-iodo-1H-pyrazolo[3,4-d]pyrimidin-1-yl)cyclohexylcarbamate Procedure:
Cesium carbonate (4.9 g, 15.3 mmol, 2.0 eq.) and 4-(tert-butoxycarbonyl)cyclohexyl methanesulfonate (4.5 g, 15.3 mmol, 2.0 eq) were added to a solution of 3-iodo-1H-pyrazolo[3,4-d]pyrimidin-4-amine (2.0 g, 7.66 mmol, 1.0 eq.) in DMF (10 mL). The reaction was stirred at 80° C. for 12 hours. After cooled to room temperature, the reaction was filtered, and the filter cake was washed with ethyl acetate. The filtrate was concentrated to give the crude product, which was purified by silica gel column chromatography (eluent:petroleum ether:ethyl acetate=4:1) to give the title compound (1.1 g, yield: 31%).

Step C:

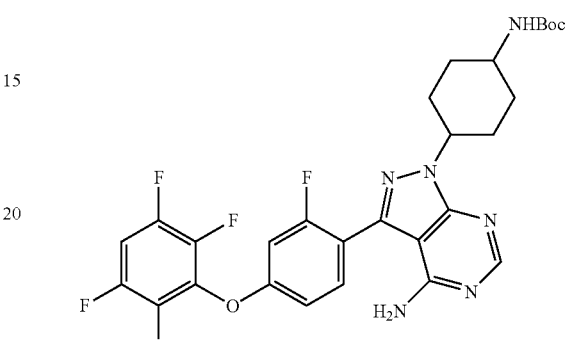

tert-butyl 4-(4-amino-3-(2-fluoro-4-(2,3,5,6-tetrafluorophenoxy)phenyl)-1H-pyrazolo[3,4-d]pyrimidin-1-yl)cyclohexylcarbamate Procedure:
Tert-butyl 4-(4-amino-3-iodo-1H-pyrazolo[3,4-d]pyrimidin-1-yl)cyclohexylcarbamate (0.82 g, 1.79 mmol, 1.0 eq.), 2-(2-fluoro-4-(2,3,5,6-tetrafluorophenoxy)phenyl)-4,4,5,5-tetramethyl-1,3,2-dioxaborolane (1.0 g, 2.69 mmol, 1.5 eq.), potassium phosphate (0.76 g, 3.68 mmol, 2.0 eq.) and Pd-118 (58 mg, 0.089 mmol, 0.05 eq.) were dissolved in 1,4-dioxane/water (9 mL, 5/1, v/v). The reaction was stirred at 80° C. for 12 hours under nitrogen atmosphere. The reaction solution was diluted with water (10 mL) and extracted with ethyl acetate (10 mL×4). The combined organic phases were dried over anhydrous sodium sulfate, and concentrated to give the crude product, which was purified by silica gel column chromatography (eluent:ethyl acetate) to give the title compound (0.8 g, yield: 80%).

Step D:

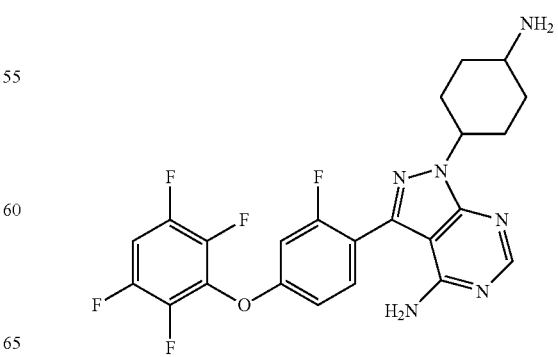

1-(4-aminocyclohexyl)-3-(2-fluoro-4-(2,3,5,6-tetra-fluorophenoxy)phenyl)-1H-pyrazolo[3,4-d]pyrimi-din-4-amine Procedure:

4M HCl/EtOAc (5 mL) was added to a solution of tert-butyl 4-(4-amino-3-(2-fluoro-4-(2,3,5,6-tetrafluorophenoxy)phenyl)-1H-pyrazolo[3,4-d]pyrimidin-1-yl)cyclohexylcarbamate (800 mg, 1.35 mmol) in ethyl acetate (5 mL) at 0° C. The reaction mixture was stirred at room temperature for 1 h and concentrated to give the title compound hydrochloride (600 mg, yield: 90%).

Step E:

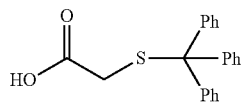 [SMILES: O=C(O)CSC(c1ccccc1)(c1ccccc1)c1ccccc1]

2-(tritylthio)acetic acid

Procedure:

Triphenylmethyl chloride (2.79 g, 10 mol, 1.0 eq.) and BF$_3$.Et$_2$O (2 mL) was added dropwise to a solution of thioglycolic acid (0.92 g, 10 mmol, 1.0 eq.) in dichloromethane (30 mL) and acetic acid (6 mL). The reaction solution was stirred at room temperature for 1 hour and concentrated under reduced pressure. The residue was dissolved in ethyl acetate (30 mL), washed with water (20 mL) and brine (20 mL). The organic phase was dried over anhydrous sodium sulfate and filtered. The filtrate was concentrated to give the title compound (2.8 g, yield: 84%).

Step F:

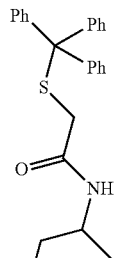

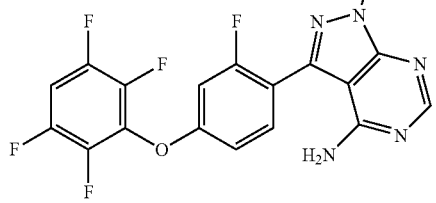

N-(4-(4-amino-3-(2-fluoro-4-(2,3,5,6-tetrafluorophenoxy)phenyl)-1H-pyrazolo[3,4-d]pyrimidin-1-yl)cyclohexyl)-2-(tritylthio)acetamide Procedure:

2-(tritylthio)acetic acid (65 mg, 0.195 mmol, 1.2 eq.), DIPEA (42 mg, 0.326 mmol, 2.0 eq.) and HATU (139 mg, 0.244 mmol, 1.5 eq.) were added to a solution of 1-(4-aminocyclohexyl)-3-(2-fluoro-4-(2,3,5,6-tetrafluorophenoxy)phenyl)-1H-pyrazolo[3,4-d]pyrimidin-4-amine (80 mg, 0.163 mmol, 1.0 eq.) in dichloromethane (3 mL) at 0° C. The reaction was stirred at room temperature for 2 hours, diluted with methylene chloride (30 mL), washed with water (20 mL) and brine (20 mL). The organic phase was dried over anhydrous sodium sulfate, and concentrated to give the title compound (80 mg, yield: 62%).

Step G:

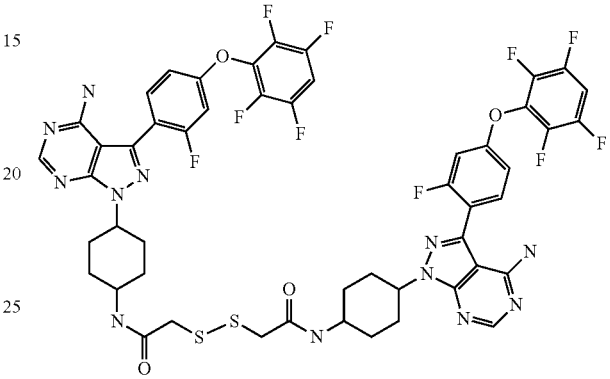

Procedure:

Et$_3$SiH (2 drops) was added to a solution of N-(4-(4-amino-3-(2-fluoro-4-(2,3,5,6-tetrafluorophenoxy)phenyl)-1H-pyrazolo[3,4-d]pyrimidin-1-yl)cyclohexyl)-2-(tritylthio)acetamide (80 mg, 0.1 mmol) in TFA (0.5 mL). The reaction was stirred at room temperature for 1 hour, quenched with water (10 mL), extracted with ethyl acetate (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.5% HCl, gradient: 10%-100% (volume ratio)) to give the title compound (5 mg, yield: 4%).

LC/MS (Method: UFLC): RT=3.442 min; m/z=564.5 [M/2]$^+$; Total running time 7 min.

Compound 40

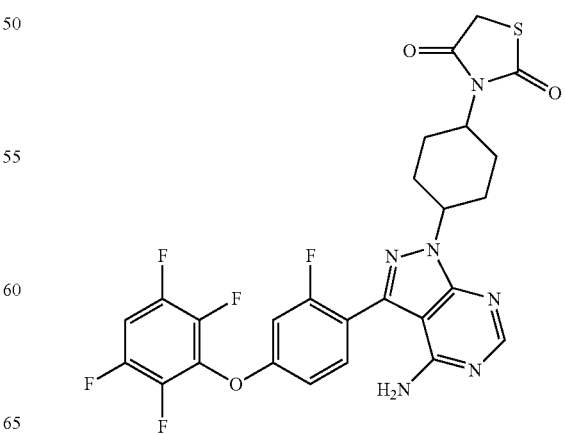

3-(4-(4-amino-3-(2-fluoro-4-(2,3,5,6-tetrafluorophenoxy)phenyl)-1H-pyrazolo[3,4-d]pyrimidin-1-yl)cyclohexyl)thiazolidine-2,4-dione Step A:

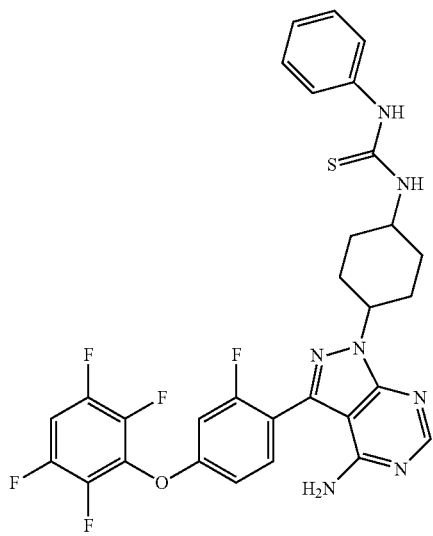 [SMILES: Nc1ncnc2c1c(-c1ccc(Oc3c(F)c(F)cc(F)c3F)cc1F)nn2C1CCC(NC(=S)Nc2ccccc2)CC1]

1-(4-(4-amino-3-(2-fluoro-4-(2,3,5,6-tetrafluorophenoxy)phenyl)-1H-pyrazolo[3,4-d]pyrimidin-1-yl)cyclohexyl)-3-phenylthiourea Procedure:
phenyl isothiocyanate (24.8 mg, 0.184 mmol, 0.9 eq.) was added to a solution of 1-(4-aminocyclohexyl)-3-(2-fluoro-4-(2,3,5,6-tetrafluorophenoxy)phenyl)-1H-pyrazolo[3,4-d]pyrimidin-4-amine (100 mg, 0.204 mmol, 1.0 eq.) in dichloromethane (3 mL). The reaction solution was stirred at room temperature for 2 hours, and concentrated, which was purified by thin layer chromatography (developer:petroleum ether:ethyl acetate=1:1) to give the title compound (100 mg, yield: 79%).

Step B:

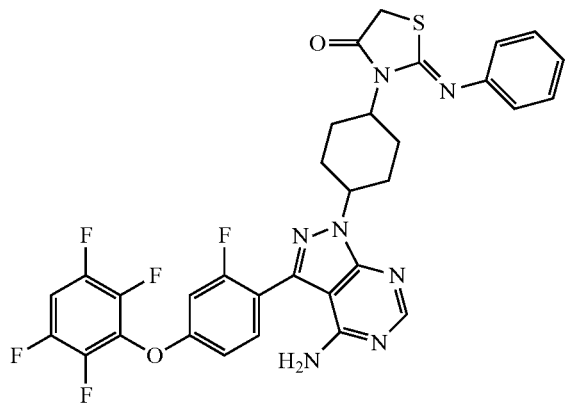 [SMILES: Nc1ncnc2c1c(-c1ccc(Oc3c(F)c(F)cc(F)c3F)cc1F)nn2C1CCC(N2C(=O)CS/C2=N\c2ccccc2)CC1]

(Z)-3-(4-(4-amino-3-(2-fluoro-4-(2,3,5,6-tetrafluorophenoxy)phenyl)-1H-pyrazolo[3,4-d]pyrimidin-1-yl)cyclohexyl)-2-(phenylimino)thiazolidin-4-one Procedure:
Chloroacetic acid (17.4 mg, 0.184 mmol, 2.3 eq.) and sodium acetate (3.94 mg, 0.048 mmol, 0.6 eq.) were added to a solution of 1-(4-(4-amino-3-(2-fluoro-4-(2,3,5,6-tetrafluorophenoxy)phenyl)-1H-pyrazolo[3,4-d]pyrimidin-1-yl)cyclohexyl)-3-phenylthiourea (50 mg, 0.08 mmol, 1.0 eq.) in ethanol (3 mL). The reaction was stirred at 110° C. 6 hours, cooled to room temperature and concentrated. The obtained crude product was purified by thin layer chromatography (developer:petroleum ether:ethyl acetate=1:1) to give the title compound (20 mg, yield: 38%).

Step C:

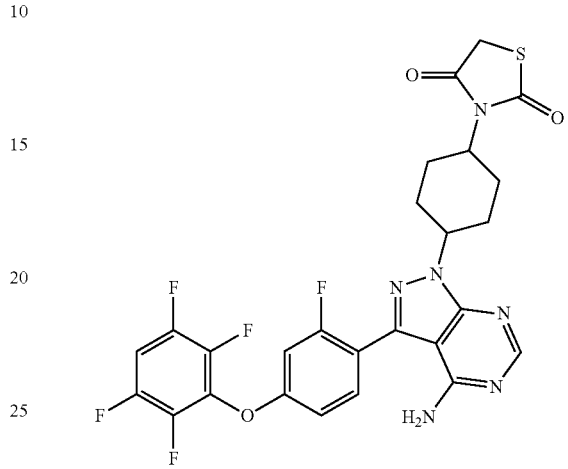

3-(4-(4-amino-3-(2-fluoro-4-(2,3,5,6-tetrafluorophenoxy)phenyl)-1H-pyrazolo[3,4-d]pyrimidin-1-yl)cyclohexyl)thiazolidine-2,4-dione Procedure:
A solution of (Z)-3-(4-(4-amino-3-(2-fluoro-4-(2,3,5,6-tetrafluorophenoxy)phenyl)-1H-pyrazolo[3,4-d]pyrimidin-1-yl)cyclohexyl)-2-(phenylimino)thiazolidin-4-one (20 mg, 0.03 mmol) in conc. HCl (5 mL) was stirred at 110° C. for 6 hours and concentrated. The obtained crude product was purified by HPLC (C18 reverse phase column, mobile phase: acetonitrile/water/0.5% HCl, gradient: 10%-100% (volume ratio)) to give the title compound (2 mg, yield: 12%).

LC/MS (Method: UFLC): RT=3.794 min; m/z=591.1 [M+H]$^+$; Total running time 7 min.

Compound 41

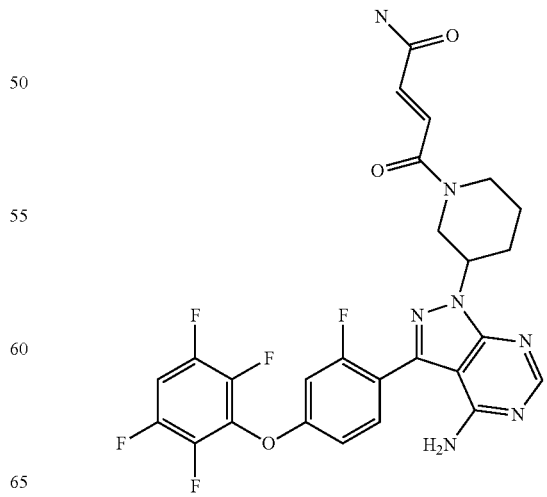

(E)-4-(3-(4-amino-3-(2-fluoro-4-(2,3,5,6-tetrafluorophenoxy)phenyl)-1H-pyrazolo[3,4-d]pyrimidin-1-yl)piperidin-1-yl)-4-oxobut-2-enamide Procedure:

3-(2-fluoro-4-(2,3,5,6-tetrafluorophenoxy)phenyl)-1-(piperidin-3-yl)-1H-pyrazolo[3,4-d]pyrimidin-4-amine (48 mg, 0.1 mmol, 1.0 eq.), DIPEA (26 mg, 0.2 mmol, 2.0 eq.) and HATU (50 mg, 0.0.15 mmol, 1.5 eq.) was added to a solution of (E)-4-amino-4-oxobut-2-enoic acid (15 mg, 0.15 mmol, 1.5 eq.) in dichloromethane (3 mL) at 0° C. The reaction was stirred at room temperature for 16 hours, diluted with dichloromethane (30 mL), washed with saturated NaHCO₃ (20 mL) and brine (20 mL). The organic phase was dried over anhydrous sodium sulfate and concentrated to give the crude product, which was purified by HPLC (C18 reverse phase column, mobile phase: acetonitrile/water/0.5% HCl, gradient: 10%-100% (volume ratio)) to give the title compound hydrochloride (5 mg, yield: 10%).

LC/MS (Method: UFLC): RT=0.791 min; m/z=574.0 [M+H]$^+$; Total running time 1.5 min.

Compound 42

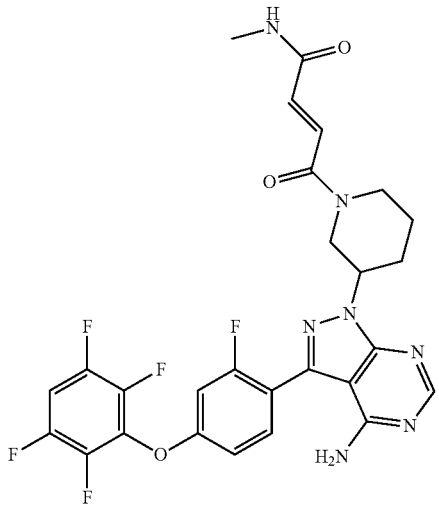 [SMILES: CNC(=O)/C=C/C(=O)N1CCCC(n2nc(-c3ccc(Oc4c(F)c(F)cc(F)c4F)cc3F)c3c(N)ncnc32)C1]

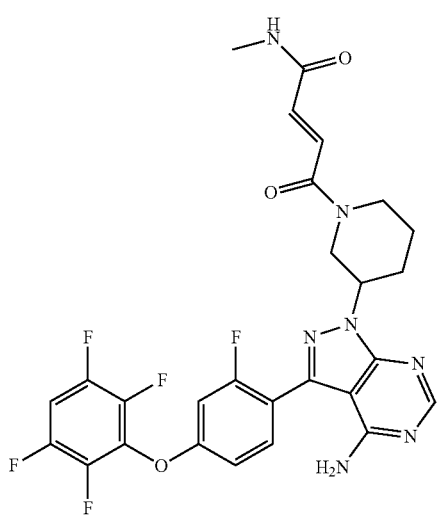

(E)-4-(3-(4-amino-3-(2-fluoro-4-(2,3,5,6-tetrafluorophenoxy)phenyl)-1H-pyrazolo[3,4-d]pyrimidin-1-yl)piperidin-1-yl)-N-methyl-4-oxobut-2-enamide Step A:

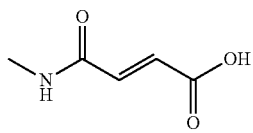

(E)-4-(methylamino)-4-oxobut-2-enoic acid

Procedure:

A solution of maleic anhydride (500 mg, 5.1 mmol, 1.0 eq.) in methylamine (2 M tetrahydrofuran solution, 10 mL) was stirred at room temperature for 1 hour, and concentrated give the title compound (658 mg, yield: 100%).

Step B:

(E)-4-(3-(4-amino-3-(2-fluoro-4-(2,3,5,6-tetrafluorophenoxy)phenyl)-1H-pyrazolo[3,4-d]pyrimidin-1-yl)piperidin-1-yl)-N-methyl-4-oxobut-2-enamide Procedure:

3-(2-fluoro-4-(2,3,5,6-tetrafluorophenoxy)phenyl)-1-(piperidin-3-yl)-1H-pyrazolo[3,4-d]pyrimidin-4-amine (150 mg, 0.315 mmol, 1.0 eq.), DIPEA (163 mg, 1.26 mmol, 4.0 eq.) and HATU (180 mg, 0.472 mmol, 1.5 eq.) were added to a solution of (E)-4-(methylamino)-4-oxobut-2-enoic acid (40 mg, 0.315 mmol, 1.0 eq.) in dichloromethane (3 mL) at 0° C. The reaction was stirred at room temperature for 16 hours, diluted with dichloromethane (30 mL), washed with saturated NaHCO₃ (20 mL) and brine (20 mL). The organic phase was dried over anhydrous sodium sulfate and concentrated to give the crude product, which was purified by HPLC (C18 reverse phase column, mobile phase: acetonitrile/water/0.5% HCl, gradient: 10%-100% (volume ratio)) to give the title compound hydrochloride (44 mg, yield: 24%).

LC/MS (Method: UFLC): RT=2.723 min; m/z=588.2 [M+H]$^+$; Total running time 7 min.

$^1$H NMR (400 MHz, DMSO-d₆) δ 8.59-8.53 (m, 1H), 8.25-8.20 (m, 1H), 7.97-7.92 (m, 1H), 7.65-7.57 (m, 1H), 7.34-7.31 (m, 1H), 7.16-7.12 (m, 1H), 6.41-6.28 (m, 1H), 6.06-5.95 (m, 1H), 5.00-4.80 (m, 1.5H), 4.61-4.58 (m, 0.5H), 4.35-4.32 (m, 0.5H), 3.90-3.87 (m, 1H), 3.69-3.66 (m, 0.5H), 3.52-3.49 (m, 0.5H), 3.15-3.09 (m, 1H), 2.66-2.64 (m, 3H), 2.53-2.47 (m, 2H), 2.16-2.12 (m, 1H), 1.75-1.71 (m, 1H).

Compound 43

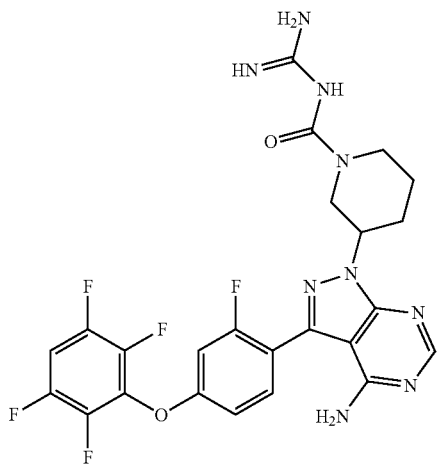 [SMILES: N=C(N)NC(=O)N1CCCC(n2nc(-c3ccc(Oc4c(F)c(F)cc(F)c4F)cc3F)c3c(N)ncnc32)C1]

N-[3-[4-amino-3-[2-fluoro-4-(2,3,5,6-trifluorophenoxy)phenyl]-1H-pyrazolo[3,4-d]pyrimidin-1-yl]piperidine-1-carbonyl] formamidine Procedure:
CDI (25 mg, 0.15 mmol, 1.5 eq.) was added to a solution of 3-(2-fluoro-4-(2,3,5,6-tetrafluorophenoxy)phenyl)-1-(piperidin-3-yl)-1H-pyrazolo[3,4-d]pyrimidin-4-amine (48 mg, 0.1 mmol, 1.0 eq.) in DMF (5 mL). The reaction was stirred at 70° C. for 2 hours, and then guanidine carbonate (11 mg, 0.06 mmol, 0.6 eq.) was added. The resulting mixture was stirred at 70° C. for 3 hours. After cooling to room temperature, the reaction mixture was concentrated to give the crude product, which was purified by HPLC (C18 reverse phase column, mobile phase: acetonitrile/water/0.5% HCl, gradient 10% to 100% (volume ratio)) to give the title compound (13 mg, yield: 23%).

LC/MS (Method: UFLC): RT=0.749 min; m/z=562.0 [M+H]$^+$; Total running time 1.5 min.

$^1$H NMR (400 MHz, CD$_3$OD) δ 8.44 (s, 1H), 7.72 (t, J=8.4 Hz, 1H), 7.53-7.48 (m, 1H), 7.13-7.07 (m, 2H), 5.10-5.06 (m, 1H), 4.30-4.27 (m, 1H), 3.98-3.86 (m, 2H), 3.47-3.42 (m, 1H), 2.37-2.31 (m, 2H), 2.12-2.07 (m, 1H), 1.81-1.78 (m, 1H).

Compound 44

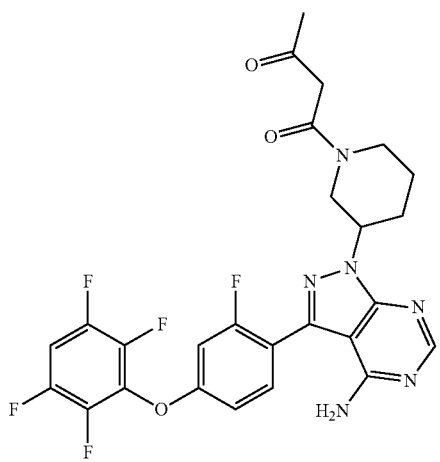 [SMILES: CC(=O)CC(=O)N1CCCC(n2nc(-c3ccc(Oc4c(F)c(F)cc(F)c4F)cc3F)c3c(N)ncnc32)C1]

1-(3-(4-amino-3-(2-fluoro-4-(2,3,5,6-tetrafluorophenoxy)phenyl)-1H-pyrazolo[3,4-d]pyrimidin-1-yl)piperidin-1-yl)butane-1,3-dione Procedure:
Tert-butyl acetoacetate (24 mg, 0.15 mmol, 1.5 eq.) and triethylamine (30 mg, 0.3 mmol, 3.0 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (48 mg, 0.1 mmol, 1.0 eq.) in toluene (3 mL). The reaction mixture was stirred at 90° C. for 16 hours. After cooling to room temperature, the mixture was concentrated to give the crude product, which was purified by HPLC (C18 reverse phase column, mobile phase: acetonitrile/water/0.5% HCl, gradient 10% to 100% (volume ratio)) to give the title compound (15 mg, yield: 27%).

LC/MS (Method: UFLC): RT=2.778 min; m/z=561.0 [M+H]$^+$; Total running time 7 min.

Compound 45

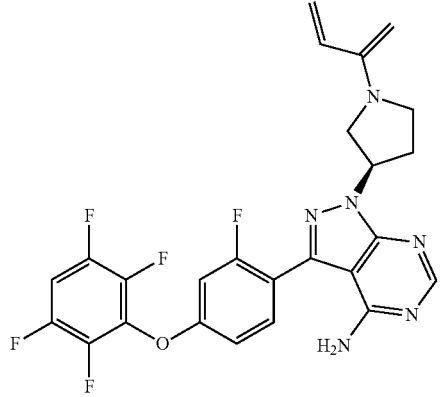 [SMILES: C=CC(=C)N1CC[C@@H](n2nc(-c3ccc(Oc4c(F)c(F)cc(F)c4F)cc3F)c3c(N)ncnc32)C1]

1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one Method 1:
Step A:

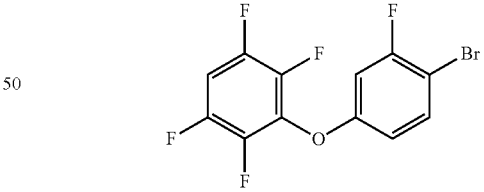

3-(4-bromo-3-fluorophenoxy)-1,2,4,5-tetrafluorobenzene

Procedure:
Potassium carbonate (34.0 g, 246 mmol, 2.0 eq.) and 1,2,3,4,5-pentafluorophenyl (24.8 g, 147 mmol, 1.2 eq.) were added to a solution of 4-bromo-3-fluorophenol (23.5 g, 123 mmol, 1.0 eq.) in DMF (250 mL). The reaction solution was stirred at 100° C. overnight, and concentrated under reduced pressure. The residue was dissolved in ethyl acetate and water. The aqueous phase was extracted with ethyl acetate (200 mL×3). The combined organic phases were dried over anhydrous sodium sulfate, and concentrated to give the title compound (39 g, yield: 93%).

Step B:

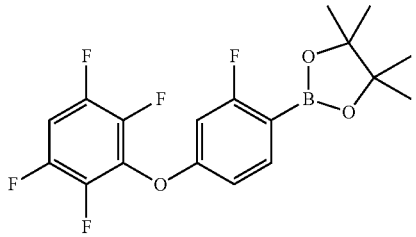 [SMILES: CC1(C)OB(c2ccc(Oc3c(F)c(F)cc(F)c3F)cc2F)OC1(C)C]

2-(2-fluoro-4-(2,3,5,6-tetrafluorophenoxy)phenyl)-4,4,5,5-tetramethyl-1,3,2-dioxaborolane Procedure:

3-(4-bromo-3-fluorophenoxy)-1,2,4,5-tetrafluorobenzene (36.5 g, 107.6 mmol, 1.0 eq.), bis(pinacolato)diboron (32.8 g, 129.2 mmol, 1.2 eq.), potassium acetate (37 g, 377 mmol, 3.5 eq.) and (1,1'-bis(diphenylphosphino)ferrocene)dichloropalladium (4.7 g, 6.45 mmol, 0.06 eq.) were dissolved in 1,4-dioxane (500 mL), and then stirred at 80° C. under nitrogen for 4 hours. The reaction mixture was filtered through celite. The filtrate was concentrated to give the crude product, which was purified by silica gel chromatography column to give the title compound (30 g, yield: 72%).

Step C:

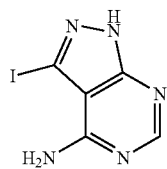

3-iodo-1H-pyrazolo[3,4-d]pyrimidin-4-amine

Procedure:

NIS (250 g, 1.11 mol, 1.5 eq.) was added to a solution of 1H-pyrazolo[3,4-d]pyrimidin-4-amine (100 g, 0.74 mol, 1.0 eq.) in DMF (800 mL). The reaction was stirred at 80~85° C. for 16 hours under nitrogen atmosphere. The reaction mixture was filtered, and the filter cake was washed with ethanol (1000 mL×3) to give the title compound (184 g, yield: 95%).

Step D:

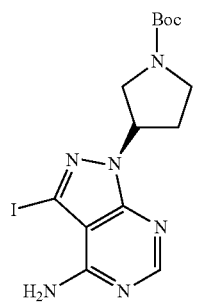

(R)-tert-butyl 3-(4-amino-3-iodo-1H-pyrazolo[3,4-d]pyrimidin-1-yl)pyrrolidine-1-carboxylate Procedure:

DIAD (27.6 g, 137.5 mmol, 1.5 eq.) was dropwise added to a solution of 3-iodo-1H-pyrazolo[3,4-d]pyrimidin-4-amine (24 g, 92 mmol, 1.0 eq.), tert-butyl (3S)-3-hydroxycyclopentylcarbamate (26 g, 137.5 mmol, 1.5 eq) and PPh$_3$ (36 g, 137.5 mmol, 1.5 eq.) in tetrahydrofuran (720 mL) at 0° C. under nitrogen atmosphere. The reaction was stirred for 1 hour at 0° C., then stirred overnight at room temperature. After the removal of solvent under reduced pressure, acetonitrile (200 mL) was added to the reaction flask, and then stirred at room temperature for 2 hours. The resulting mixture was filtered, and the filter cake was washed with acetonitrile (20 mL) and to give the title compound (25 g, yield: 63%).

Step E:

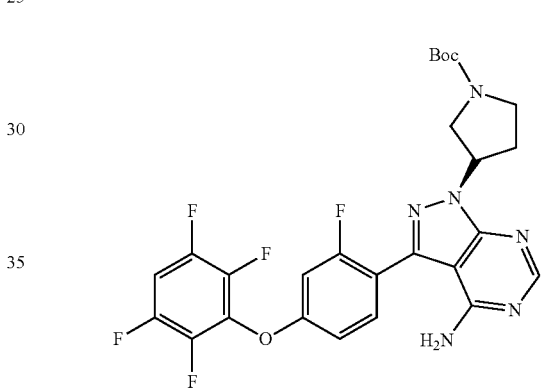

(3R)-tert-butyl 3-(4-amino-3-(2-fluoro-4-(2,3,5,6-tetrafluorophenoxy)phenyl)-1H-pyrazolo[3,4-d]pyrimidin-1-yl)pyrrolidine-1-carboxylate Procedure:

(R)-tert-butyl 3-(4-amino-3-iodo-1H-pyrazolo[3,4-d]pyrimidin-1-yl)pyrrolidine-1-carboxylate (25 g, 58 mmol, 1.0 eq.), 2-(2-fluoro-4-(2,3,5,6-tetrafluorophenoxy)phenyl)-4,4,5,5-tetramethyl-1,3,2-dioxaborolane (30 g, 75.4 mmol, 1.3 eq.), potassium phosphate (25 g, 116 mmol, 2.0 eq.) and Pd-118 (750 mg, 1.16 mmol, 0.02 eq.) were dissolved in 1,4-dioxane/water (600 mL, 5/1, v/v). The reaction mixture was stirred at 60° C. overnight under nitrogen atmosphere. After cooling to room temperature, the reaction was filtered through celite. After the removal of the solvent, water (300 mL) was added to the residue, and then extracted with ethyl acetate (300 mL×3). The combined organic phases were dried over anhydrous sodium sulfate, and concentrated to give the title compound (60 g, crude).

Step F:

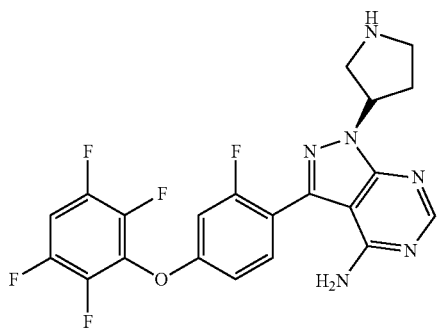

3-(2-fluoro-4-(2,3,5,6-tetrafluorophenoxy)phenyl)-1-((R)-pyrrolidin-3-yl)-1H-pyrazolo[3,4-d]pyrimidin-4-amine Procedure:

4M HCl/EtOAc (100 mL) was added to a solution of (3R)-tert-butyl 3-(4-amino-3-(2-fluoro-4-(2,3,5,6-tetrafluorophenoxy)phenyl)-1H-pyrazolo[3,4-d]pyrimidin-1-yl)pyrrolidine-1-carboxylate (60 g, crude) in ethyl acetate (100 mL) at 0° C. The reaction mixture was stirred at room temperature for 1 h and concentrated to give the title compound hydrochloride. Water (500 mL) was added to the obtained product, and extracted with ethyl acetate (300 mL×3). The aqueous layer was adjusted pH=9 and extracted with ethyl acetate (300 mL×3). The combined organic layers were dried over anhydrous sodium sulfate, and concentrated to give the title compound (24 g, yield: 90%, 2 steps).

Step G:

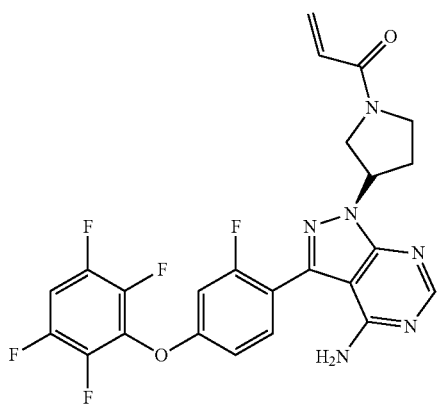

1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one Procedure:

NaOH (10%, 94 mL) was added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (23.5 g, 50.75 mmol, 1.0 eq.) in tetrahydrofuran (470 mL) at −5° C., followed by dropwise addition of acryloyl chloride (5.97 g, 66 mmol, 1.3 eq.). The reaction was stirred at −5° C. for 1 hour, quenched with saturated brine (100 mL), and extracted with ethyl acetate (200 mL×3). The combined organic phases were dried over anhydrous sodium sulfate, and concentrated to give the crude product, which was purified by silica gel column chromatography (eluent:petroleum ether:ethyl acetate=3:1 to 1:1) to afford the crude product, which was dissolved in methanol (500 mL) and filtered. Water (1500 mL) was added to the stirring filtrate, followed by stirring for 2 hours and filtered. The filter cake was dried under reduced pressure to give the title compound (16.5 g, yield: 63%).

LC/MS (Method: UFLC): RT=3.764 min; m/z=517.0 [M+H]+; Total running time 7 min.

$^1$H NMR (400 MHz, CD$_3$OD) δ 8.45 (s, 1H), 7.70 (t, J=8.4 Hz, 1H), 7.55-7.46 (m, 1H), 7.12-7.05 (m, 2H), 6.70-6.55 (m, 1H), 6.33-6.26 (m, 1H), 5.81-5.75 (m, 1H), 4.23-3.83 (m, 5H), 2.68-2.55 (m, 2H).

Method 2:

Procedure:

NaOH (216 mg, 5.40 mmol, 2.5 eq.) was added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (1.0 g, 2.16 mmol, 1.0 eq.) in tetrahydrofuran (50 mL) and water (10 mL) at 0° C., followed by dropwise addition of a solution of 3-chloropropionyl chloride (288 mg, 2.27 mmol, 1.05 eq.) in tetrahydrofuran (10 mL). The reaction was stirred at 0° C. for 1 hour, and then stirred at 60° C. for 12 hours. After cooling to room temperature, saturated brine (100 mL) was added to the reaction, and extracted with ethyl acetate (50 mL×3). The combined organic phases were dried over anhydrous sodium sulfate, and concentrated to give the crude product, which was purified by silica gel column chromatography (eluent:petroleum ether:ethyl acetate=3:1 to 1:1) to give the title compound (0.8 g, yield: 71%).

Method 3:

Procedure:

(R)-1-(3-(4-amino-3-iodo-1H-pyrazolo[3,4-d]pyrimidin-1-yl)pyrrolidin-1-yl)prop-2-en-1-one (100 g, 0.26 mmol, 1.0 eq.), 2-(2-fluoro-4-(2,3,5,6-tetrafluorophenoxy)phenyl)-4,4,5,5-tetramethyl-1,3,2-dioxaborolane (120 mg, 0.31 mmol, 1.2 eq.), sodium carbonate (55 mg, 0.52 mmol, 2.0 eq.) and Pd(PPh$_3$)$_4$ (30 mg, 0.026 mmol, 0.01 eq) were dissolved in 1,4-dioxane/water (5 mL, 1/1, v/v). The reaction was stirred at 80° C. for 30 minutes under microwave irradiation. After cooling to room temperature, the reaction was filtered through celite. The filtrate was concentrated to give the crude product, which was purified by HPLC (C18 reverse phase column, mobile phase: acetonitrile/water/0.5% HCl, gradient: 10% to 100% (volume ratio)) to give the title compound (38 mg, yield: 28%).

Method 4:

Compounds 45 and 46

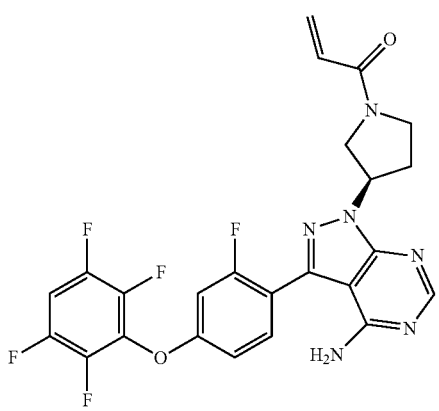 [SMILES: C=CC(=O)N1CC[C@@H](n2nc(-c3ccc(Oc4c(F)c(F)cc(F)c4F)cc3F)c3c(N)ncnc32)C1]

215

1-((R)-3-(4-amino-3-(2-fluoro-4-(2,3,5,6-tetrafluoro-phenoxy)phenyl)-1H-pyrazolo[3,4-d]pyrimidin-1-yl)pyrrolidin-1-yl)prop-2-en-1-one

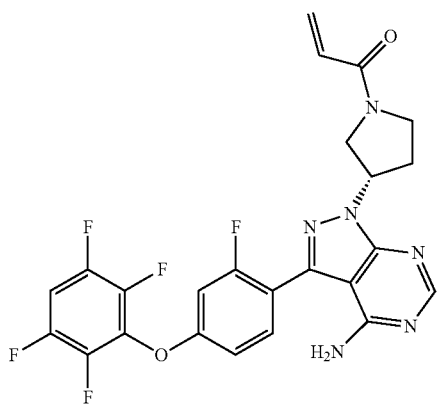 [SMILES: C=CC(=O)N1CC[C@H](n2nc(-c3ccc(Oc4c(F)c(F)cc(F)c4F)cc3F)c3c(N)ncnc32)C1]

1-((S)-3-(4-amino-3-(2-fluoro-4-(2,3,5,6-tetrafluoro-phenoxy)phenyl)-1H-pyrazolo[3,4-d]pyrimidin-1-yl)pyrrolidin-1-yl)prop-2-en-1-one Step A:

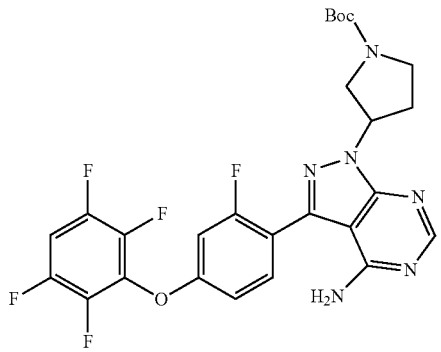 [SMILES: CC(C)(C)OC(=O)N1CCC(n2nc(-c3ccc(Oc4c(F)c(F)cc(F)c4F)cc3F)c3c(N)ncnc32)C1]

tert-butyl 3-(4-amino-3-(2-fluoro-4-(2,3,5,6-tetra-fluorophenoxy)phenyl)-1H-pyrazolo[3,4-d]pyrimi-din-1-yl)pyrrolidine-1-carboxylate Procedure:

tert-butyl 3-(4-amino-3-iodo-1H-pyrazolo[3,4-d]pyrimi-din-1-yl)pyrrolidine-1-carboxylate (8 g, 18 mmol, 1.0 eq.), 2-(2-fluoro-4-(2,3,5,6-tetrafluorophenoxy)phenyl)-4,4,5,5-tetramethyl-1,3,2-dioxaborolane (10.7 g, 27 mmol, 1.5 eq.), potassium phosphate (7.6 g, 36 mmol, 2.0 eq.) and Pd-118 (1.2 g, 1.8 mmol, 0.1 eq.) was dissolved in 1,4-dioxane/water (180 mL, 5/1, v/v). The reaction was stirred at 60° C. for 14 hours under nitrogen atmosphere. After cooling to room temperature, the reaction mixture was poured into ice water (50 mL) and extracted with ethyl acetate (100 mL×3). The combined organic phases were dried over anhydrous sodium sulfate, and concentrated to give the crude product, which was purified by silica gel column chromatography (eluent:ethyl acetate:petroleum ether=1:1) to give the title compound (2.5 g, yield: 25%).

216

Step B:

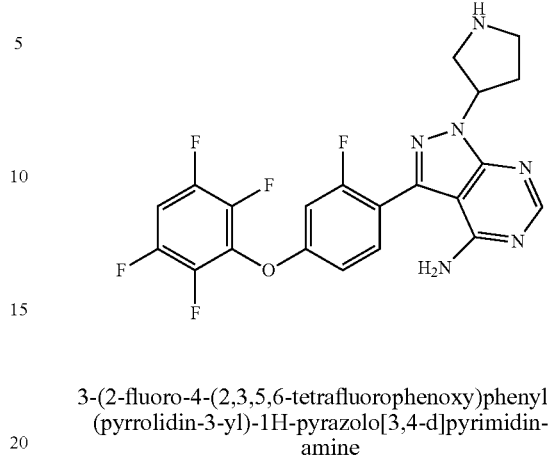

3-(2-fluoro-4-(2,3,5,6-tetrafluorophenoxy)phenyl)-1-(pyrrolidin-3-yl)-1H-pyrazolo[3,4-d]pyrimidin-4-amine Procedure:

4M HCl/EtOAc (20 mL) was added to a solution of tert-butyl 3-(4-amino-3-(2-fluoro-4-(2,3,5,6-tetrafluorophe-noxy)phenyl)-1H-pyrazolo[3,4-d]pyrimidin-1-yl)pyrroli-dine-1-carboxylate (2.5 g, 4.4 mmol) in dichloromethane (20 mL) at 0° C. The reaction mixture was stirred at room temperature for 1 h and concentrated to give the title compound hydrochloride (2.2 g, yield: 100%).

Step C:

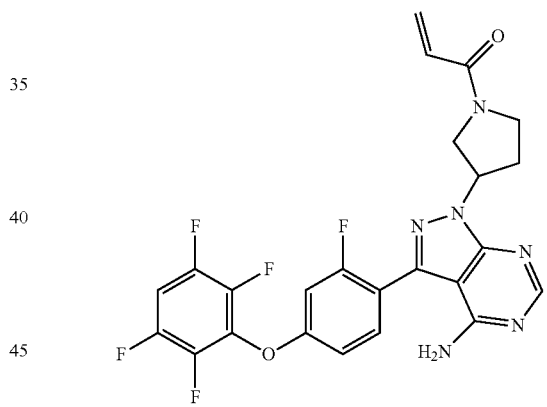

1-(3-(4-amino-3-(2-fluoro-4-(2,3,5,6-tetrafluorophe-noxy)phenyl)-1H-pyrazolo[3,4-d]pyrimidin-1-yl)pyrrolidin-1-yl)prop-2-en-1-one Procedure:

Triethylamine (1.4 g, 12.8 mmol, 3.0 eq.) and acryloyl chloride (0.38 g, 4.2 mmol, 0.95 eq.) were subsequently added dropwise to a solution of 3-(2-fluoro-4-(2,3,5,6-tet-rafluorophenoxy)phenyl)-1-(pyrrolidin-3-yl)-1H-pyrazolo[3,4-d]pyrimidin-4-amine (2.2 g, 4.4 mmol, 1.0 eq.) in dichloromethane (50 mL) at 0° C. The reaction was stirred at 0° C. for 1 hour, and then quenched with water (30 mL). The aqueous phase was extracted with methylene chloride (30 mL×3). The combined organic phases were dried over anhydrous sodium sulfate, and concentrated to give the crude product, which was purified by silica gel column chromatography (eluent:ethyl acetate) to give the title compound (1.0 g, yield: 45%).

LC/MS (Method: UFLC): RT=2.810 min; m/z=517.1 [M+H]⁺; Total running time 7 min.

Step D:

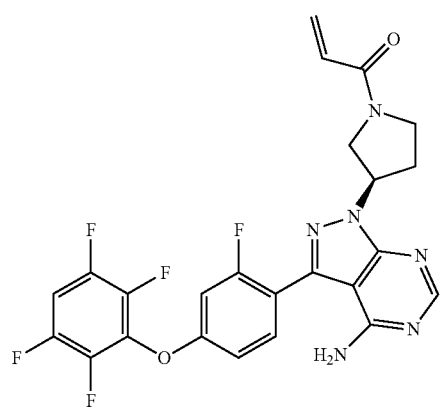 [SMILES: C=CC(=O)N1CC[C@@H](n2nc(-c3ccc(Oc4c(F)c(F)cc(F)c4F)cc3F)c3c(N)ncnc32)C1]

1-((R)-3-(4-amino-3-(2-fluoro-4-(2,3,5,6-tetrafluoro-phenoxy)phenyl)-1H-pyrazolo[3,4-d]pyrimidin-1-yl)pyrrolidin-1-yl)prop-2-en-1-one

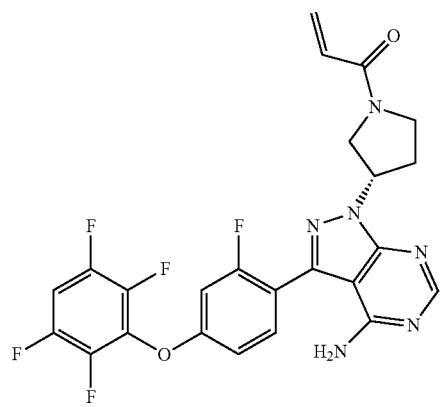 [SMILES: C=CC(=O)N1CC[C@H](n2nc(-c3ccc(Oc4c(F)c(F)cc(F)c4F)cc3F)c3c(N)ncnc32)C1]

1-((S)-3-(4-amino-3-(2-fluoro-4-(2,3,5,6-tetrafluoro-phenoxy)phenyl)-1H-pyrazolo[3,4-d]pyrimidin-1-yl)pyrrolidin-1-yl)prop-2-en-1-one Procedure:

1-(3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one was separated by supercritical fluid chromatogram to give Compound 45 (270 mg) and Compound 46 (320 mg).

Compound 46

LC/MS (Method: UFLC): RT=2.808 min; m/z=517.1 [M+H]⁺; Total running time 7 min.

Compound 47

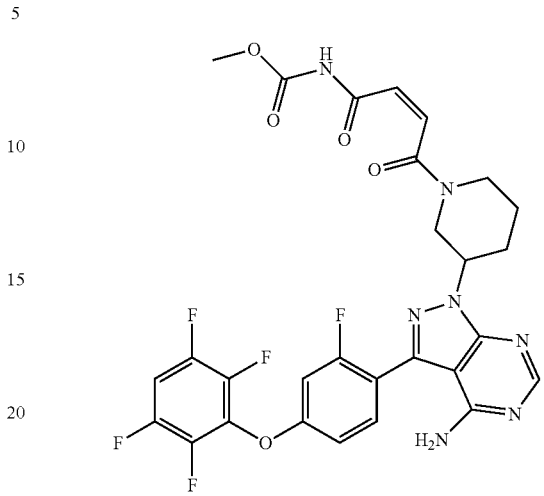

(Z)-methyl 4-(3-(4-amino-3-(2-fluoro-4-(2,3,5,6-tetrafluorophenoxy)phenyl)-1H-pyrazolo[3,4-d]pyrimidin-1-yl)piperidin-1-yl)-4-oxobut-2-enoylcarbamate Procedure:

Methyl 2,5-dioxo-2H-pyrrole-1(5H)-carboxylate (17 mg, 0.11 mmol, 1.1 eq.) and sodium bicarbonate (17 mg, 0.2 mmol, 2.0 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (48 mg, 0.1 mmol, 1.0 eq.) in 1,4-dioxane/water (3 mL/1 mL) at 0° C. The reaction was stirred at 20° C. for 2 hours, diluted with water (5 mL), and extracted with ethyl acetate (10 mL×3). The combined organic phases were dried over anhydrous sodium sulfate, and concentrated to give the drude product, which was purified by thin layer chromatography (developer:petroleum ether:ethyl acetate=1:3) to afford the title compound (40 mg, yield: 67%).

LC/MS (Method: UFLC): RT=0.775 min; m/z=632.1 [M+H]⁺; Total running time 1.5 min.

¹H NMR (400 MHz, CDCl₃) δ 8.36 (s, 1H), 7.58-7.54 (m, 1H), 7.15-7.06 (m, 1H), 6.96-6.90 (m, 2H), 6.77-6.73 (m, 1H), 6.65-6.55 (m, 1H), 4.63-4.59 (m, 1H), 4.99-4.94 (m, 1H), 4.85-4.80 (m, 0.5H), 4.57-4.54 (m, 0.5H), 4.04-4.00 (m, 0.5H), 3.88-3.77 (m, 4H), 3.50-3.44 (m, 0.5H), 3.26-3.22 (m, 0.5H), 2.98-2.95 (m, 0.5H), 2.34-2.26 (m, 1H), 2.03-1.96 (m, 2H), 1.85-1.81 (m, 1H).

Compound 48

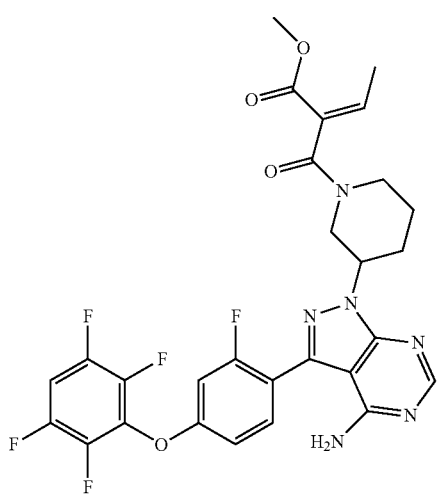 [SMILES: C/C=C(\C(=O)OC)C(=O)N1CCCC(n2nc(-c3ccc(Oc4c(F)c(F)cc(F)c4F)cc3F)c3c(N)ncnc32)C1]

(Z)-methyl 2-(3-(4-amino-3-(2-fluoro-4-(2,3,5,6-tetrafluorophenoxy)phenyl)-1H-pyrazolo[3,4-d]pyrimidin-1-yl)piperidine-1-carbonyl)but-2-enoate Step A:

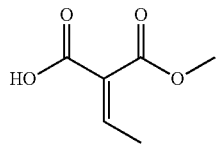

(Z)-2-(methoxycarbonyl)but-2-enoic acid

Procedure:

Lithium hydroxide monohydrate (0.265 g, 6.32 mmol, 1.0 eq.) was added to a solution of dimethyl 2-ethylidenemalonate (1.0 g, 6.32 mmol, 1.0 eq.) in tetrahydrofuran/water (20 mL, 1/1, v/v). The reaction was stirred at room temperature for 14 hours and concentrated. The residue was dissolved in water (10 mL), adjusted with 2 N HCl to pH=1, and then extracted with ethyl acetate (20 mL×3). The combined organic phases were dried over anhydrous sodium sulfate, and concentrated to give the title compound (0.6 g, yield: 63%).

Step B:

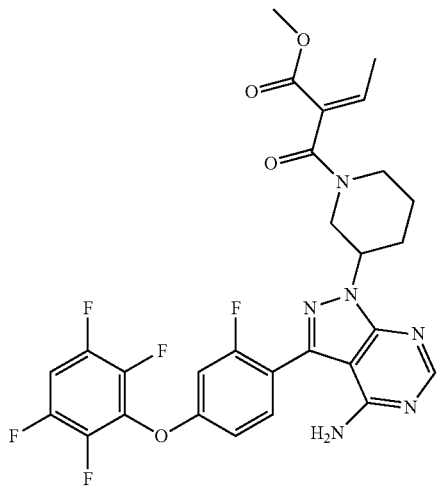 [SMILES: C/C=C(\C(=O)OC)C(=O)N1CCCC(n2nc(-c3ccc(Oc4c(F)c(F)cc(F)c4F)cc3F)c3c(N)ncnc32)C1]

(Z)-methyl 2-(3-(4-amino-3-(2-fluoro-4-(2,3,5,6-tetrafluorophenoxy)phenyl)-1H-pyrazolo[3,4-d]pyrimidin-1-yl)piperidine-1-carbonyl)but-2-enoate Procedure:

3-(2-fluoro-4-(2,3,5,6-tetrafluorophenoxy)phenyl)-1-(piperidin-3-yl)-1H-pyrazolo[3,4-d]pyrimidin-4-amine (48 mg, 0.1 mmol, 1.0 eq.), DIPEA (52 mg, 0.4 mmol, 4.0 eq.) and HATU (57 mg, 0.15 mmol, 1.5 eq.) were added to a solution of (Z)-2-(methoxycarbonyl)but-2-enoic acid (22 mg, 0.15 mmol, 1.5 eq.) in dichloromethane (3 mL) at 0° C. The reaction was stirred at room temperature for 16 hours, and concentrated to give the crude product, which was purified by HPLC (C18 reverse phase column, mobile phase: acetonitrile/water/0.5% HCl, gradient: 10%-100% (volume ratio)) to give the title compound hydrochloride (2.4 mg, yield: 4%).

LC/MS (Method: UFLC): RT=3.540 min; m/z=603.2 [M+H]$^+$; Total running time 7 min.

Compound 49

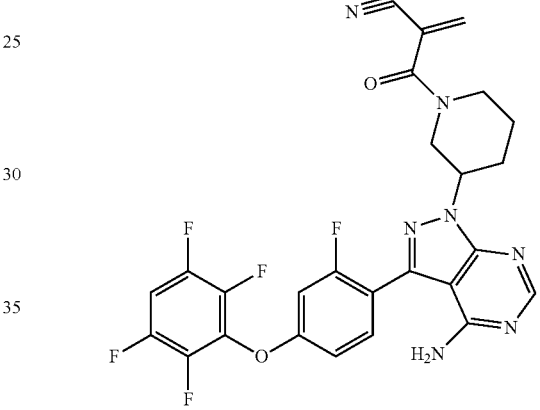

2-(3-(4-amino-3-(2-fluoro-4-(2,3,5,6-tetrafluorophenoxy)phenyl)-1H-pyrazolo[3,4-d]pyrimidin-1-yl)piperidine-1-carbonyl)acrylonitrile Step A:

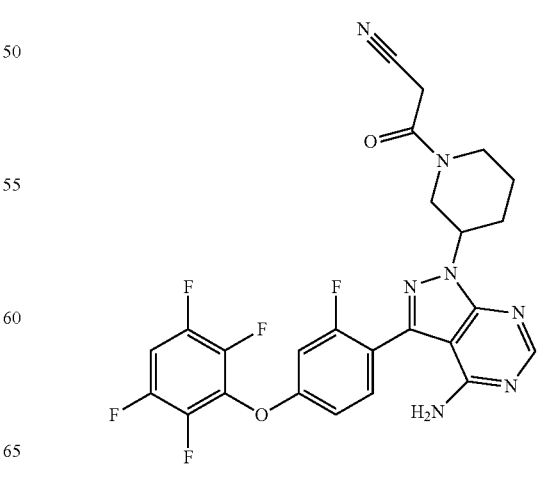

3-(3-(4-amino-3-(2-fluoro-4-(2,3,5,6-tetrafluorophenoxy)phenyl)-1H-pyrazolo[3,4-d]pyrimidin-1-yl)piperidin-1-yl)-3-oxopropanenitrile Procedure:

3-(2-fluoro-4-(2,3,5,6-tetrafluorophenoxy)phenyl)-1-(piperidin-3-yl)-1H-pyrazolo[3,4-d]pyrimidin-4-amine (100 mg, 0.21 mmol, 1.0 eq.), DIPEA (108 mg, 0.84 mmol, 4.0 eq.) and HATU (120 mg, 0.31 mmol, 1.5 eq.) were added to a solution of 2-cyanoacetic acid (27 mg, 0.31 mmol, 1.5 eq.) in dichloromethane (10 mL) at 0° C. The reaction was stirred at room temperature for 16 hours, and concentrated to give the crude product, which was purified by silica gel column chromatography (eluent:ethyl acetate) to give the title compound (100 mg, yield: 88%).

Step B:

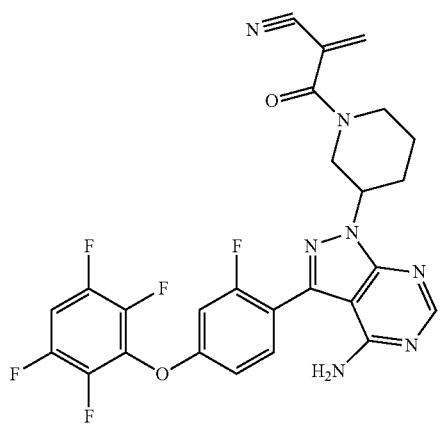 [SMILES: C=C(C#N)C(=O)N1CCCC(n2nc(-c3ccc(Oc4c(F)c(F)cc(F)c4F)cc3F)c3c(N)ncnc32)C1]

2-(3-(4-amino-3-(2-fluoro-4-(2,3,5,6-tetrafluorophenoxy)phenyl)-1H-pyrazolo[3,4-d]pyrimidin-1-yl)piperidine-1-carbonyl)acrylonitrile Procedure:

A mixture of paraformaldehyde (6 mg, 0.2 mmol, 2.0 eq.) and piperidine (0.2 mg, 0.002 mmol, 0.02 eq.) in methanol (10 mL) was refluxed for 1.5 hours. After cooled to room temperature was added 3-(3-(4-amino-3-(2-fluoro-4-(2,3,5,6-tetrafluorophenoxy)phenyl)-1H-pyrazolo[3,4-d]pyrimidin-1-yl)piperidin-1-yl)-3-oxopropanenitrile (54 mg, 0.1 mmol, 1.0 eq.), and then refluxed for 16 hours. After the removal of solvent under reduced pressure, toluene (10 mL) and p-toluenesulfonic acid monohydrate (0.2 mg, 0.001 mmol, 0.01 eq.) were added to the residue. The resulting mixture was refluxed for 3 hours. After cooling to room temperature, the mixture was concentrated to give the crude product, which was purified by HPLC (C18 reverse phase column, mobile phase: acetonitrile/water/0.5% HCl, gradient: 10% to 100% (volume ratio)) to give the title compound (0.7 mg, yield: 1%).

Compound 50

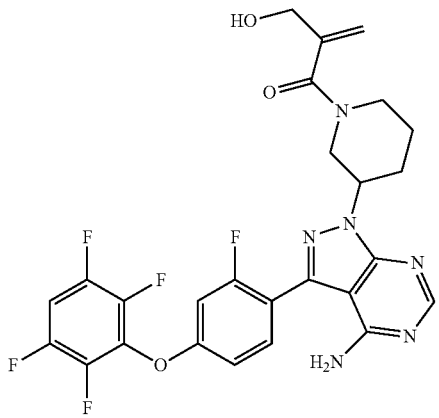 [SMILES: C=C(CO)C(=O)N1CCCC(n2nc(-c3ccc(Oc4c(F)c(F)cc(F)c4F)cc3F)c3c(N)ncnc32)C1]

1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-(hydroxymethyl)prop-2-en-1-one Step A:

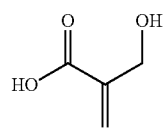

2-(hydroxymethyl)acrylic acid

Procedure:

Lithium hydroxide monohydrate (145 mg, 3.46 mmol, 5.0 eq.) was added to a solution of ethyl 2-(hydroxymethyl)acrylate (90 mg, 0.69 mmol, 1.0 eq.) in tetrahydrofuran/methanol/water (3 mL, 1/1/1, v/v/v). The reaction was stirred at room temperature for 14 hours, and concentrated. The residue was dissolved in water (10 mL), adjusted with 2 N HCl to pH=5, and then extracted with ethyl acetate (20 mL×3). The combined organic phases were dried over anhydrous sodium sulfate, and concentrated to give the title compound (70 mg, yield: 100%).

Step B:

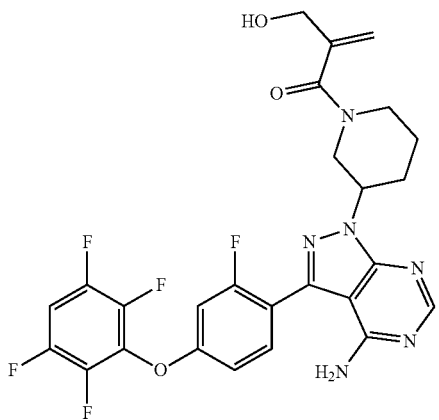 [SMILES: C=C(CO)C(=O)N1CCCC(n2nc(-c3ccc(Oc4c(F)c(F)cc(F)c4F)cc3F)c3c(N)ncnc32)C1]

1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-(hydroxymethyl)prop-2-en-1-one Procedure:

3-(2-fluoro-4-(2,3,5,6-tetrafluorophenoxy)phenyl)-1-(piperidin-3-yl)-1H-pyrazolo[3,4-d]pyrimidin-4-amine (257 mg, 0.54 mmol, 1.0 eq.), DIPEA (253 mg, 1.96 mmol, 4.0 eq.) and HATU (279 mg, 0.75 mmol, 1.5 eq.) were added to a solution of 2-(hydroxymethyl)acrylic acid (50 mg, 0.49 mmol, 1.0 eq.) in dichloromethane (3 mL) at 0° C. The reaction was stirred at room temperature for 16 hours, and concentrated to give the crude product, which was purified by HPLC (C18 reverse phase column, mobile phase: acetonitrile/water/0.5% HCl, gradient: 10%-100% (volume ratio)) to give the title compound hydrochloride (52 mg, yield: 20%).

LC/MS (Method: UFLC): RT=2.799 min; m/z=561.2 [M+H]$^+$; Total running time 7 min.

$^1$H NMR (400 MHz, DMSO-$d_6$) δ 9.51 (br, 1H), 8.62 (br, 2H), 7.98-7.95 (m, 1H), 7.62 (t, J=8.4 Hz, 1H), 7.33-7.30 (m, 1H), 7.17-7.15 (m, 1H), 5.33-5.27 (m, 1H), 5.11-5.05 (m, 1H), 4.87-4.82 (m, 1H), 4.46-3.94 (m, 2H), 3.60-3.07 (m, 2H), 2.22-2.16 (m, 2H), 1.90-1.87 (m, 1H), 1.65-1.60 (m, 1H).

Compound 51

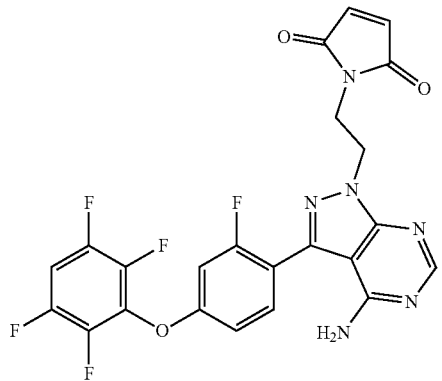 [SMILES: Nc1ncnc2c1c(-c1ccc(Oc3c(F)c(F)cc(F)c3F)cc1F)nn2CCN1C(=O)C=CC1=O]

1-(2-(4-amino-3-(2-fluoro-4-(2,3,5,6-tetrafluorophenoxy)phenyl)-1H-pyrazolo[3,4-d]pyrimidin-1-yl)ethyl)-1H-pyrrole-2,5-dione Procedure:

Compound 51 was synthesized by following the method aforementioned.

LC/MS (Method: UFLC): RT=2.774 min; m/z=517.1 [M+H]$^+$; Total running time 7 min.

Compound 52

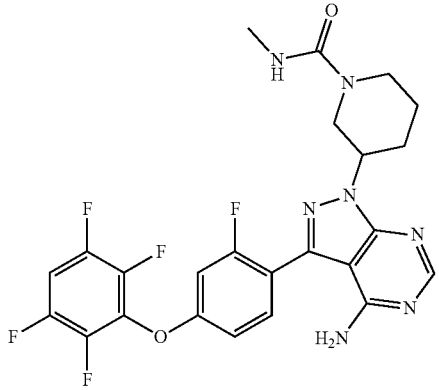 [SMILES: CNC(=O)N1CCCC(n2nc(-c3ccc(Oc4c(F)c(F)cc(F)c4F)cc3F)c3c(N)ncnc32)C1]

3-(4-amino-3-(2-fluoro-4-(2,3,5,6-tetrafluorophenoxy)phenyl)-1H-pyrazolo[3,4-d]pyrimidin-1-yl)-N-methylpiperidine-1-carboxamide Procedure:

N,N'-carbonyldiimidazole (109 mg, 0.63 mmol, 2.0 eq.) was added to methylamine (0.16 mL, 0.31 mmol, 1.0 eq, 2.0 M solution in tetrahydrofuran) in tetrahydrofuran (2 mL). The reaction solution was stirred at room temperature for 1 hour, followed by the addition of 3-(2-fluoro-4-(2,3,5,6-tetrafluorophenoxy)phenyl)-1-(piperidin-3-yl)-1H-pyrazolo[3,4-d]pyrimidin-4-amine (150 mg, 0.31 mmol, 1.0 eq.). The reaction was stirred for 16 hours at room temperature, and concentrated to give the crude product, which was purified by HPLC (C18 reverse phase column, mobile phase: acetonitrile/water/7‰ NH$_4$HCO$_3$, gradient: 10%-100% (volume ratio)) to give the title compound (92 mg, yield: 55%).

LC/MS (Method: UFLC): RT=2.724 min; m/z=534.0 [M+H]$^+$; Total running time 7 min.

$^1$H NMR (400 MHz, DMSO-$d_6$) δ 8.21 (s, 1H), 7.55 (t, J=8.4 Hz, 1H), 7.27 (dd, J=2.4, 8.8 Hz, 1H), 7.11 (dd, J=2.4, 8.8 Hz, 1H), 6.50 (d, J=4.4 Hz, 1H), 4.64-4.58 (m, 1H), 4.14-4.10 (m, 1H), 3.95-3.92 (m, 1H), 3.17-3.11 (m, 1H), 2.75-2.65 (m, 1H), 2.55-2.54 (m, 3H), 2.08-2.05 (m, 2H), 1.79-1.76 (m, 1H), 1.55-1.50 (m, 1H).

Compound 53

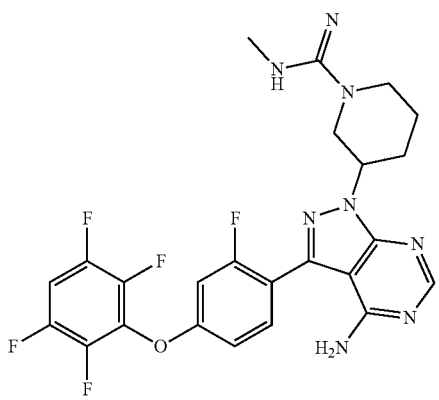 [SMILES: CNC(=N)N1CCCC(n2nc(-c3ccc(Oc4c(F)c(F)cc(F)c4F)cc3F)c3c(N)ncnc32)C1]

3-[4-amino-3-[2-fluoro-4-(2,3,5,6-fluorophenoxy)
phenyl]-1H-pyrazolo[3,4-d]pyrimidine-1-yl]piperi-
dine-1-carboxamidine Procedure:

A mixture of 3-(2-fluoro-4-(2,3,5,6-tetrafluorophenoxy) phenyl)-1-(piperidin-3-yl)-1H-pyrazolo[3,4-d]pyrimidin-4-amine (50 mg, 0.1 mmol, 1.0 eq.), N-methyl-1-pyrazole carboxamidine (25 mg, 0.2 mmol, 2.0 eq.) and DIPEA (77 mg, 0.6 mmol, 6.0 eq.) in DMF (2 mL) was stirred at 150° C. for 20 minutes under microwave irradiation. After cooling to room temperature, diluted with water (5 mL), extracted with ethyl acetate (5 mL×3). The combined organic phases were dried over anhydrous sodium sulfate, and concentrated to give the crude product, which was purified by HPLC (C18 reverse phase column, mobile phase: acetonitrile/water/0.5% HCl, gradient: 10% to 100% (by volume ratio)) to give the title compound hydrochloride (6 mg, yield: 13%).

LC/MS (Method: UFLC): RT=0.781 min; m/z=533.1 [M+H]$^+$; Total running time 1.5 min.

Compound 54

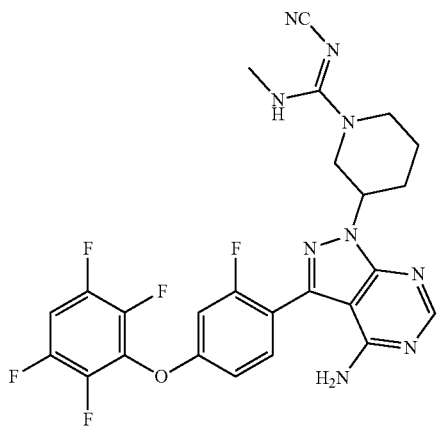 [SMILES: CN/C(=N\C#N)N1CCCC(n2nc(-c3ccc(Oc4c(F)c(F)cc(F)c4F)cc3F)c3c(N)ncnc32)C1]

3-[4-amino-3-[2-fluoro-4-(2,3,5,6-fluorophenoxy) phenyl]-1H-pyrazolo[3,4-d]pyrimidine-1-yl]-N'-cyano-N-methyl-piperidine-1-carboxamidine Procedure:

DIPEA (40 mg, 0.315 mmol, 3.0 eq.) and diphenyl N-cyanocarbonimidate (25 mg, 0.1 mmol, 1.0 eq.) were added to methylamine (2 M tetrahydrofuran solution, 0.05 mL, 0.1 mmol, 1.0 eq.) in DMF (2 mL). The reaction was stirred at 20° C. for 1 hour and then 3-(2-fluoro-4-(2,3,5,6-tetrafluorophenoxy)phenyl)-1-(piperidin-3-yl)-1H-pyrazolo[3,4-d]pyrimidin-4-amine (50.0 mg, 0.105 mmol, 1.0 eq.) was added. The reaction solution was stirred at 120° C. for 1 hour under microwave irradiation, and then concentrated to give the crude product, which was purified by HPLC (C18 reverse phase column, mobile phase: acetonitrile/water/0.5% HCl, gradient: 10% to 100% (volume ratio)) to give the title compound hydrochloride (4.5 mg, yield: 8%).

LC/MS (Method: UFLC): RT=2.689 min; m/z=558.0 [M+H]$^+$; Total running time 7 min.

Compound 55

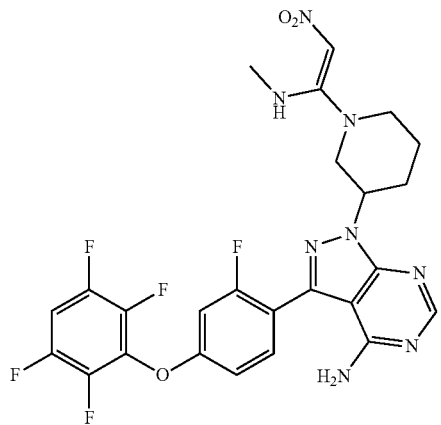 [SMILES: CN/C(=C\[N+](=O)[O-])N1CCCC(n2nc(-c3ccc(Oc4c(F)c(F)cc(F)c4F)cc3F)c3c(N)ncnc32)C1]

1-[3-[4-amino-3-[2-fluoro-4-(2,3,5,6-three-fluoro-phenoxy)phenyl]-1H-pyrazolo[3,4-d] pyrimidin-1-yl]-1-piperidinyl]-1-(methylamino)-2-nitro ethylene Step A:

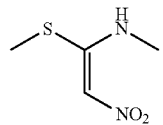

N-methyl-1-methylthio-2-nitroethyleneamine

Procedure:

Methylamine (31 mg, 2.0 mmol, 1.0 eq.) was added to a solution of 1,1-bis(methylthio)-2-nitroethene (330 mg, 2.0 mmol, 1.0 eq.) in ethanol (10 mL). The reaction was stirred at 80° C. for 14 h, cooled to room temperature, diluted with water (10 mL), and then extracted with dichloromethane (10 mL×3). The combined organic phase was dried over anhydrous sodium sulfate and concentrated to give the title compound (200 mg, yield: 68%).

Step B:

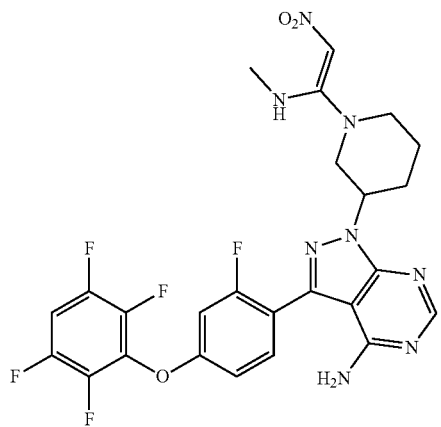 [SMILES: CN/C(=C\[N+](=O)[O-])N1CCCC(n2nc(-c3ccc(Oc4c(F)c(F)cc(F)c4F)cc3F)c3c(N)ncnc32)C1]

1-[3-[4-amino-3-[2-fluoro-4-(2,3,5,6-three-fluoro-phenoxy)phenyl]-1H-pyrazolo[3,4-d] pyrimidin-1-yl]-1-piperidinyl]-1-(methylamino)-2-nitro ethylene Procedure:

A mixture of 3-(2-fluoro-4-(2,3,5,6-tetrafluorophenoxy)phenyl)-1-(piperidin-3-yl)-1H-pyrazolo[3,4-d]pyrimidin-4-amine (60 mg, 0.13 mmol, 1.0 eq.) and N-methyl-1-methylthio-2-nitroethyleneamine (22 mg, 0.15 mmol, 1.2 eq.) in ethanol (10 mL) was refluxed for 14 hours. After cooling to room temperature, the reaction mixture was diluted with water (10 mL), then extracted with dichloromethane (10 mL×3). The combined organic phases were dried over anhydrous sodium sulfate, and concentrated to give the crude product, which was purified by HPLC (C18 reverse phase column, mobile phase: acetonitrile/water/0.5% HCl, gradient: 10%-100% (by volume ratio)) to give the title compound hydrochloride (9.3 mg, yield: 13%).

LC/MS (Method: UFLC): RT=2.343 min; m/z=577.0 [M+H]$^+$; Total running time 7 min.

Compound 56

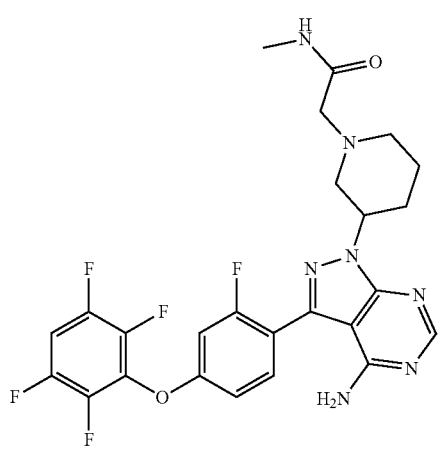 [SMILES: CNC(=O)CN1CCCC(n2nc(-c3ccc(Oc4c(F)c(F)cc(F)c4F)cc3F)c3c(N)ncnc32)C1]

2-(3-(4-amino-3-(2-fluoro-4-(2,3,5,6-tetrafluorophenoxy)phenyl)-1H-pyrazolo[3,4-d]pyrimidin-1-yl)piperidin-1-yl)-N-methylacetamide Procedure:

2-bromo-N-methyl-acetamide (32 mg, 0.21 mmol, 2.0 eq.), carbonate potassium (29 mg, 0.21 mmol, 2.0 eq.) and sodium iodide (2 mg, 0.01 mmol, 0.1 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (50 mg, 0.1 mmol, 1.0 eq.) in ethanol (2 mL). The reaction was refluxed for 2 hours, and concentrated to give the crude product, which was purified by HPLC (C18 reverse phase column, mobile phase: acetonitrile/water/0.6% NH$_4$HCO$_3$, gradient: 10% to 100% (volume ratio)) to give the title compound (4.5 mg, yield: 20%).

LC/MS (Method: UFLC): RT=2.302 min; m/z=548.1 [M+H]$^+$; Total running time 7 min.

Compound 57

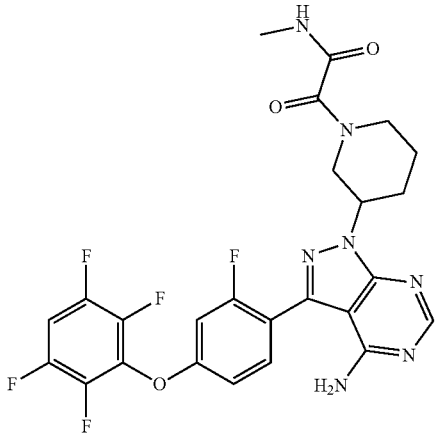 [SMILES: CNC(=O)C(=O)N1CCCC(n2nc(-c3ccc(Oc4c(F)c(F)cc(F)c4F)cc3F)c3c(N)ncnc32)C1]

2-(3-(4-amino-3-(2-fluoro-4-(2,3,5,6-tetrafluorophenoxy)phenyl)-1H-pyrazolo[3,4-d]pyrimidin-1-yl)piperidin-1-yl)-N-methyl-2-oxoacetamide Procedure:

Triethylamine (38 mg, 0.38 mmol, 3.0 eq.) and oxalyl chloride (20 mg, 0.16 mmol, 1.25 eq.) was added to a solution of 3-(2-fluoro-4-(2,3,5,6-tetrafluorophenoxy)phenyl)-1-(piperidin-3-yl)-1H-pyrazolo[3,4-d]pyrimidin-4-amine (60 mg, 0.13 mmol, 1.0 eq.) in dichloromethane (2 mL) at 0° C. The reaction was stirred at 0° C. for 10 min, and then methyl amine (6 mg, 0.19 mmol, 1.5 eq) was added. The reaction was stirred at room temperature for 2 hours, and concentrated to give the crude product, which was purified by HPLC (C18 reverse phase column, mobile phase: acetonitrile/water/0.5% HCl, gradient: 10%-100% (by volume ratio)) to give the title compound hydrochloride (9.0 mg, yield: 6%).

LC/MS (Method: UFLC): RT=2.748 min; m/z=562.1 [M+H]$^+$; Total running time 7 min.

Compound 58

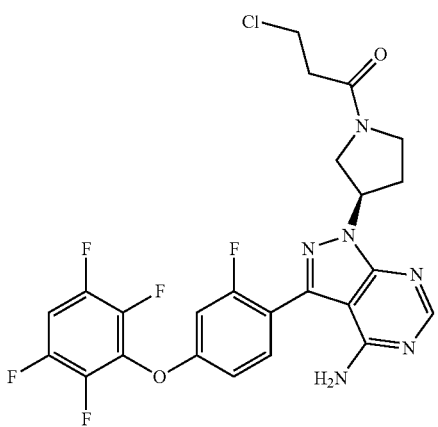 [SMILES: Nc1ncnc2c1c(-c1ccc(Oc3c(F)c(F)cc(F)c3F)cc1F)nn2[C@@H]1CCN(C(=O)CCCl)C1]

1-((R)-3-(4-amino-3-(2-fluoro-4-(2,3,5,6-tetrafluoro-phenoxy)phenyl)-1H-pyrazolo[3,4-d]pyrimidin-1-yl)pyrrolidin-1-yl)-3-chloropropan-1-one Procedure:

Triethylamine (66 mg, 0.649 mmol, 3.0 eq.) and chloropropionyl chloride (33 mg, 0.26 mmol, 1.2 eq.) were added dropwise to a solution of 3-(2-fluoro-4-(2,3,5,6-tetrafluorophenoxy)phenyl)-1-(piperidin-3-yl)-1H-pyrazolo[3,4-d]pyrimidin-4-amine (100 mg, 0.22 mmol, 1.0 eq.) in dichloromethane (3 mL) at −5° C. The reaction was stirred at 0° C. for 2 hours, quenched with water (10 mL), and extracted with methylene chloride (20 mL×3). The combined organic layers were and concentrated to dryness to give the crude product, which was purified by HPLC (C18 reverse phase column, mobile phase: acetonitrile/water/0.5% HCl, gradient: 10%-100% (by volume ratio)) to give the title compound hydrochloride (4.0 mg, yield: 3%).

LC/MS (Method: UFLC): RT=3.929 min; m/z=553.1 [M+H]$^+$; Total running time 7 min.

$^1$H NMR (400 MHz, CD$_3$OD) δ 8.44 (s, 1H), 7.02 (t, J=8.4 Hz, 1H), 7.51-7.48 (m, 1H), 7.10-7.03 (m, 2H), 5.74-5.67 (m, 1H), 4.13-4.11 (m, 1H), 4.00-3.97 (m, 2H), 3.82-3.78 (m, 3H), 2.90-2.84 (m, 2H), 2.62-2.53 (m, 2H).

Compound 59

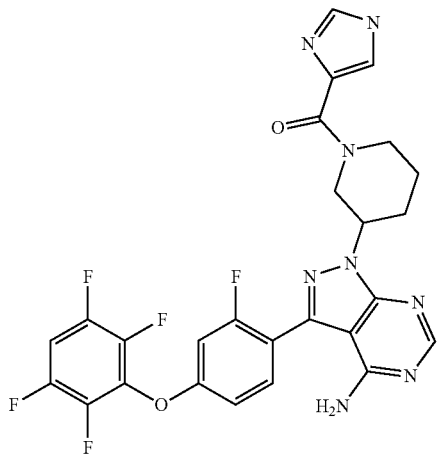 [SMILES: Nc1ncnc2c1c(-c1ccc(Oc3c(F)c(F)cc(F)c3F)cc1F)nn2C1CCCN(C(=O)c2c[nH]cn2)C1]

(3-(4-amino-3-(2-fluoro-4-(2,3,5,6-tetrafluorophenoxy)phenyl)-1H-pyrazolo[3,4-d]pyrimidin-1-yl)piperidin-1-yl)(1H-imidazol-4-yl)methanone Procedure:

Imidazole-4-carboxylic acid (17 mg, 0.15 mmol, 1.2 eq.), DIPEA (49 mg, 0.38 mmol, 3.0 eq.) and HATU (53 mg, 0.14 mmol, 1.1 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (60 mg, 0.13 mmol, 1.0 eq.) in dichloromethane (2 mL) at 0° C. The reaction was stirred at 20° C. for 30 minutes, and concentrated to give the crude product, which was purified by HPLC (C18 reverse phase column, mobile phase: acetonitrile/water/0.5% HCl, gradient: 10%-100% (volume ratio)) to give the title compound hydrochloride (25.0 mg, yield: 35%).

LC/MS (Method: UFLC): RT=2.368 min; m/z=571.1 [M+H]$^+$; Total running time 7 min.

Compound 60

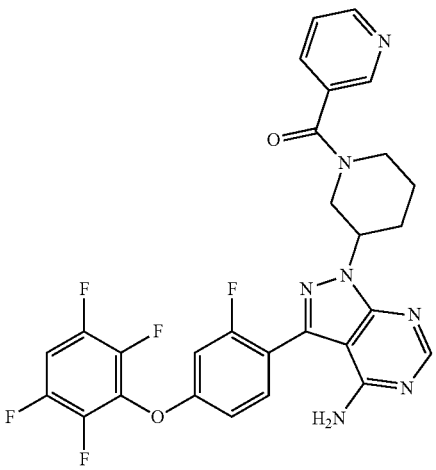 [SMILES: Nc1ncnc2c1c(-c1ccc(Oc3c(F)c(F)cc(F)c3F)cc1F)nn2C1CCCN(C(=O)c2cccnc2)C1]

(3-(4-amino-3-(2-fluoro-4-(2,3,5,6-tetrafluorophenoxy)phenyl)-1H-pyrazolo[3,4-d]pyrimidin-1-yl)piperidin-1-yl)(pyridin-3-yl)methanone Procedure:

Nicotinic acid (19 mg, 0.15 mmol, 1.2 eq.), DIPEA (49 mg, 0.38 mmol, 3.0 eq.) and HATU (53 mg, 0.14 mmol, 1.1 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (60 mg, 0.13 mmol, 1.0 eq.) in dichloromethane (3 mL) at 0° C. The reaction was stirred at 20° C. for 30 minutes, and concentrated to give the crude product, which was purified by HPLC (C18 reverse phase column, mobile phase: acetonitrile/water/0.5% HCl, gradient: 10%-100% (volume ratio)) to give the title compound hydrochloride (20 mg, yield: 27%).

LC/MS (Method: UFLC): RT=3.672 min; m/z=582.0 [M+H]$^+$; Total running time 7 min.

$^1$H NMR (400 MHz, CD$_3$OD) δ 9.06-8.93 (m, 2H), 8.69 (br, 1H), 8.50 (br, 1H), 8.18-8.10 (m, 1H), 7.77-7.71 (m, 1H), 7.53-7.48 (m, 1H), 7.15-7.08 (m, 2H), 5.34-5.23 (m, 1H), 4.61-4.58 (m, 0.5H), 4.43-4.40 (m, 0.5H), 3.99-3.68 (m, 2H), 3.48-3.46 (m, 1H), 2.42-2.37 (m, 2H), 2.15-2.09 (m, 1H), 1.95-1.87 (m, 1H).

Compound 61

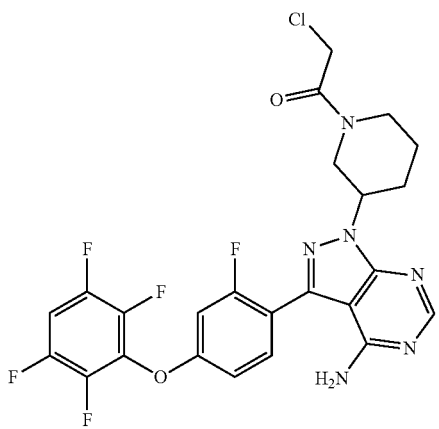 [SMILES: Nc1ncnc2c1c(-c1ccc(Oc3c(F)c(F)cc(F)c3F)cc1F)nn2C1CCCN(C(=O)CCl)C1]

1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-chloroethanone Procedure:

2-chloroacetic acid (14 mg, 0.13 mmol, 1.0 eq.), triethylamine (19 mg, 0.19 mmol, 1.5 eq.) and HATU (53 mg, 0.14 mmol, 1.1 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (60 mg, 0.13 mmol, 1.0 eq.) in dichloromethane (2 mL) at 0° C. The reaction was stirred at 20° C. for 30 minutes, and concentrated to give the crude product, which was purified by HPLC (C18 reverse phase column, mobile phase: acetonitrile/water, gradient: 10%-100% (volume ratio)) to give the title compound (16 mg, yield: 31%).

LC/MS (Method: UFLC): RT=3.046 min; m/z=553.1 [M+H]$^+$; Total running time 7 min.

$^1$H NMR (400 MHz, CD$_3$OD) δ 8.35 (s, 1H), 7.98-7.93 (m, 1H), 7.58-7.54 (m, 1H), 7.31 (dd, J=2.4, 11.2 Hz, 1H), 7.15 (dd, J=2.4, 8.8 Hz, 1H), 4.90-4.86 (m, 0.5H), 7-4.73-4.70 (m, 0.5H), 4.48-4.39 (m, 2H), 4.27-4.04 (m, 1.5H), 3.82-3.66 (m, 1H), 3.23-3.17 (m, 1H), 2.95-2.90 (m, 0.5H), 2.27-2.13 (m, 2H), 1.94-1.75 (m, 2H).

Compound 62

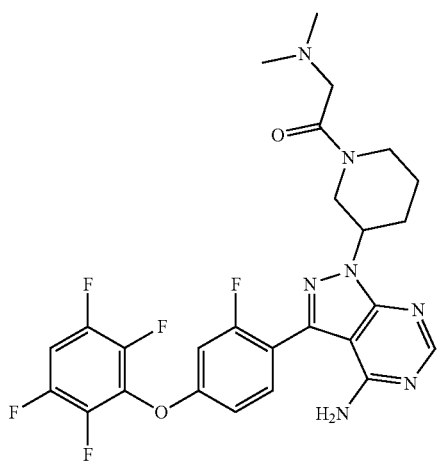 [SMILES: CN(C)CC(=O)N1CCCC(n2nc(-c3ccc(Oc4c(F)c(F)cc(F)c4F)cc3F)c3c(N)ncnc32)C1]

1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-(dimethylamino)ethanone Procedure:

N,N-dimethylglycine (16 mg, 0.15 mmol, 1.2 eq.), DIPEA (49 mg, 0.38 mmol, 3.0 eq.) and HATU (53 mg, 0.14 mmol, 1.1 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (60 mg, 0.13 mmol, 1.0 eq.) in dichloromethane (2 mL) at 0° C. The reaction was stirred at 20° C. for 30 minutes, and concentrated to give the crude product, which was purified by HPLC (C18 reverse phase column, mobile phase: acetonitrile/water/0.6% NH$_4$HCO$_3$, gradient: 10%-100% (volume ratio)) to give the title compound (30 mg, yield: 42%).

LC/MS (Method: UFLC): RT=2.301 min; m/z=562.1 [M+H]$^+$; Total running time 7 min.

$^1$H NMR (400 MHz, DMSO-d$_6$) δ 8.24-8.21 (m, 1H), 7.98-7.90 (m, 1H), 7.56-7.50 (m, 1H), 7.27-7.24 (m, 1H), 7.11-7.09 (m, 1H), 4.83-4.75 (m, 0.5H), 4.66-4.57 (m, 0.5H), 4.44-4.41 (m, 0.5H), 4.20-4.00 (m, 1.5H), 3.59-3.56 (m, 0.5H), 3.45-3.40 (m, 1H), 3.16-3.10 (m, 2H), 2.90-2.83 (m, 0.5H), 2.16-2.08 (m, 8H), 1.89-1.85 (m, 1H), 1.67-1.45 (m, 1H).

Compound 63

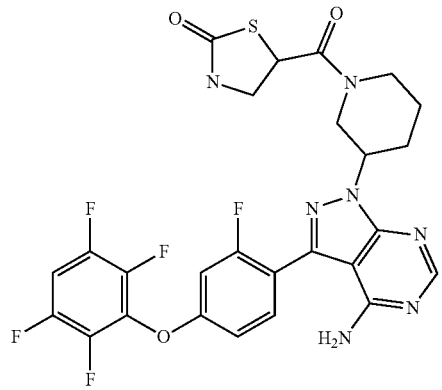 [SMILES: Nc1ncnc2c1c(-c1ccc(Oc3c(F)c(F)cc(F)c3F)cc1F)nn2C1CCCN(C(=O)C2CNC(=O)S2)C1]

5-(3-(4-amino-3-(2-fluoro-4-(2,3,5,6-tetrafluorophenoxy)phenyl)-1H-pyrazolo[3,4-d]pyrimidin-1-yl)piperidine-1-carbonyl)thiazolidin-2-one Procedure:

2-oxothiazolidine-5-carboxylic acid (26 mg, 0.19 mmol, 1.5 eq.), DIPEA (49 mg, 0.38 mmol, 3.0 eq.) and HATU (72 mg, 0.19 mmol, 1.5 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (60 mg, 0.13 mmol, 1.0 eq.) in dichloromethane (2 mL) at 0° C. The reaction was stirred at 20° C. for 12 hours, and concentrated to give the crude product, which was purified by HPLC (C18 reverse phase column, mobile phase: acetonitrile/water/0.6% NH$_4$HCO$_3$, gradient: 10%-100% (volume ratio)) to give the title compound (4 mg, yield: 6%).

LC/MS (Method: UFLC): RT=2.805 min; m/z=606.1 [M+H]$^+$; Total running time 7 min.

Compound 64

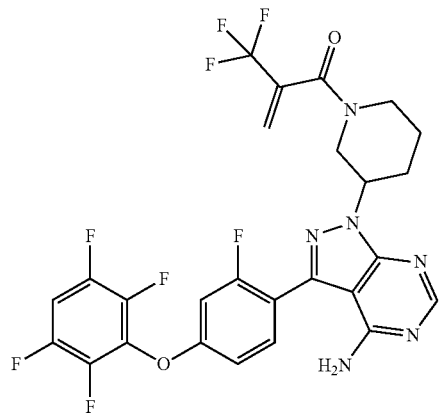 [SMILES: C=C(C(=O)N1CCCC(n2nc(-c3ccc(Oc4c(F)c(F)cc(F)c4F)cc3F)c3c(N)ncnc32)C1)C(F)(F)F]

1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-(trifluoromethyl)prop-2-en-1-one Procedure:

2-(trifluoromethyl)acrylic acid (26 mg, 0.19 mmol, 1.5 eq.), DIPEA (49 mg, 0.38 mmol, 3.0 eq.) and HATU (72 mg, 0.19 mmol, 1.5 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (60 mg, 0.13 mmol, 1.0 eq.) in dichloromethane (2 mL) at 0° C. The reaction was stirred at 20° C. for 12 hours, and concentrated to give the crude product, which was purified by HPLC (C18 reverse phase column, mobile phase: acetonitrile/water/0.6% NH$_4$HCO$_3$, gradient: 10%-100% (volume ratio)) to give the title compound (2.9 mg, yield: 4%).

LC/MS (Method: UFLC): RT=3.310 min; m/z=599.1 [M+H]$^+$; Total running time 7 min.

Compounds 65 and 66

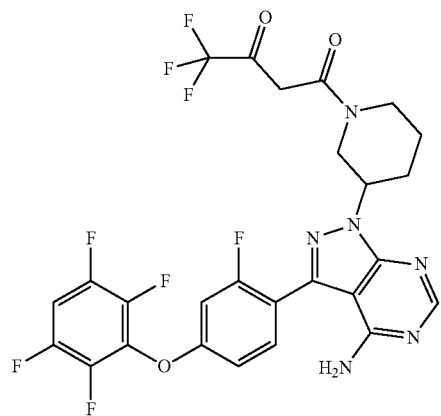 [SMILES: Nc1ncnc2c1c(-c1ccc(Oc3c(F)c(F)cc(F)c3F)cc1F)nn2C1CCCN(C(=O)CC(=O)C(F)(F)F)C1]

1-(3-(4-amino-3-(2-fluoro-4-(2,3,5,6-tetrafluorophenoxy)phenyl)-1H-pyrazolo[3,4-d]pyrimidin-1-yl)piperidin-1-yl)-4,4,4-trifluorobutane-1,3-dione

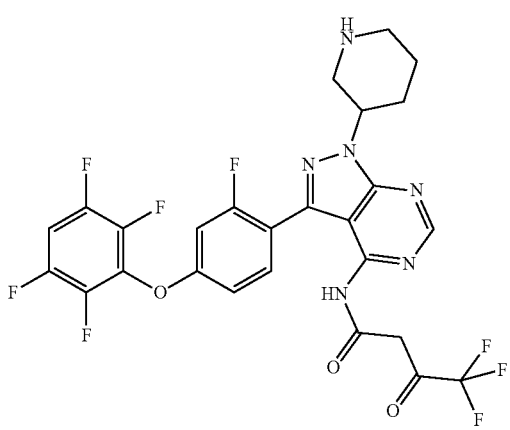 [SMILES: O=C(CC(=O)C(F)(F)F)Nc1ncnc2c1c(-c1ccc(Oc3c(F)c(F)cc(F)c3F)cc1F)nn2C1CCCNC1]

4,4,4-trifluoro-N-(3-(2-fluoro-4-(2,3,5,6-tetrafluorophenoxy)phenyl)-1-(piperidin-3-yl)-1H-pyrazolo[3,4-d]pyrimidin-4-yl)-3-oxobutanamide Procedure:

Ethyl 4,4,4-trifluoro-3-oxobutanoate (24 mg, 0.15 mmol, 1.2 eq.) and DIPEA (49 mg, 0.38 mmol, 3.0 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (60 mg, 0.13 mmol, 1.0 eq.) in toluene (2 mL). The reaction was stirred at 20° C. for 0.5 hour, and concentrated to give the crude product, which was purified by HPLC (C18 reverse phase column, mobile phase: acetonitrile/water/0.5% HCl, gradient: 10%-100% (volume ratio)) to give the title compound 65 (5 mg, yield: 6%) and compound 66 (4 mg, yield: 5%).

Compound 65:
LC/MS (Method: UFLC): RT=1.095 min; m/z=615.1 [M+H]$^+$; Total running time2 min.

Compound 66:
LC/MS (Method: UFLC): RT=1.079 min; m/z=615.1 [M+H]$^+$; Total running time2 min.

Compound 67

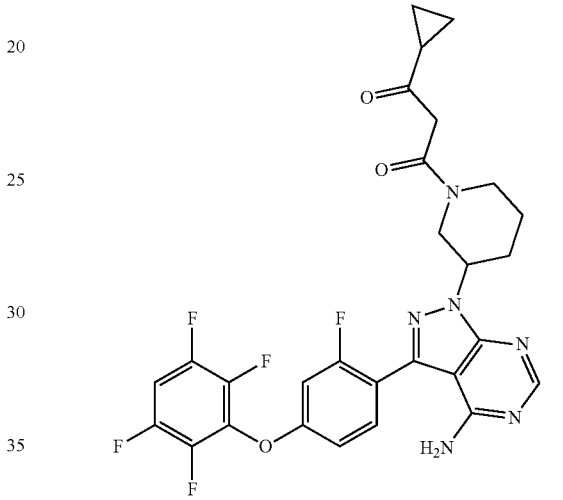

1-(3-(4-amino-3-(2-fluoro-4-(2,3,5,6-tetrafluorophenoxy)phenyl)-1H-pyrazolo[3,4-d]pyrimidin-1-yl)piperidin-1-yl)-3-cyclopropylpropane-1,3-dione Step A:

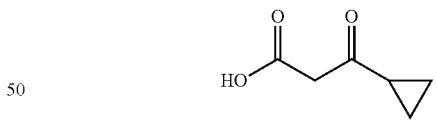

3-cyclopropyl-3-oxopropanoic acid

Procedure:

Lithium hydroxide monohydrate (0.59 g, 14.7 mmol, 2.0 eq.) was added to a solution of methyl 3-cyclopropyl-3-oxopropanoate (1.0 g, 7.03 mmol, 1.0 eq.) in tetrahydrofuran/water/methanol (15 mL, 1/1/1, v/v/v). The reaction was stirred at 20° C. for 14 hours, and concentrated. The residue was dissolved in water (10 mL), adjusted with 2 N HCl to pH=2, and then extracted with ethyl acetate (20 mL×3). The combined organic phases were dried over anhydrous sodium sulfate, and concentrated to give the title compound (0.4 g, yield: 44%).

Step B:

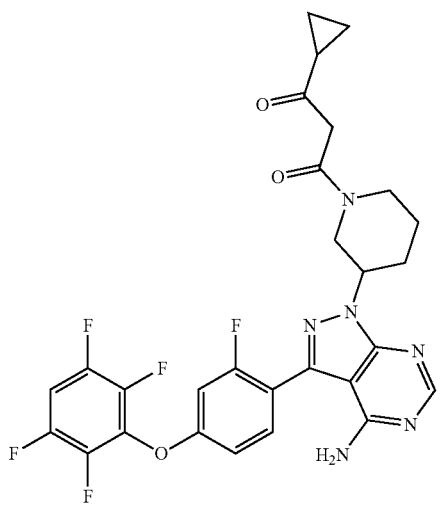 [SMILES: Nc1ncnc2c1c(-c1ccc(Oc3c(F)c(F)cc(F)c3F)cc1F)nn2C1CCCN(C(=O)CC(=O)C2CC2)C1]

1-(3-(4-amino-3-(2-fluoro-4-(2,3,5,6-tetrafluorophenoxy)phenyl)-1H-pyrazolo[3,4-d]pyrimidin-1-yl)piperidin-1-yl)-3-cyclopropylpropane-1,3-dione Procedure:

3-cyclopropyl-3-oxopropanoic acid (19 mg, 0.15 mmol, 1.2 eq.), DIPEA (49 mg, 0.38 mmol, 3.0 eq.) and HATU (72 mg, 0.19 mmol, 1.5 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (60 mg, 0.13 mmol, 1.0 eq.) in dichloromethane (2 mL) at 0° C. The reaction was stirred at 20° C. for 12 hours, and concentrated to give the crude product, which was purified by HPLC (C18 reverse phase column, mobile phase: acetonitrile/water/0.6% $NH_4HCO_3$, gradient: 10%-100% (volume ratio)) to give the title compound (25 mg, yield: 34%).

LC/MS (Method: UFLC): RT=3.003 min; m/z=587.2 [M+H]$^+$; Total running time 7 min.

$^1$H NMR (400 MHz, DMSO-d$_6$) δ 8.24-8.23 (m, 1H), 7.99-7.93 (m, 1H), 7.59-7.54 (m, 1H), 7.29-7.26 (m, 1H), 7.13-7.11 (m, 1H), 4.79-4.63 (m, 1H), 4.53-4.50 (m, 0.5H), 4.28-4.25 (m, 0.5H), 3.86-3.70 (m, 3H), 3.15-3.08 (m, 1.5H), 2.85-2.79 (m, 0.5H), 2.24-1.96 (m, 2H), 1.90-1.85 (m, 1H), 1.65-1.53 (m, 1H), 0.93-0.84 (m, 4H).

Compound 68

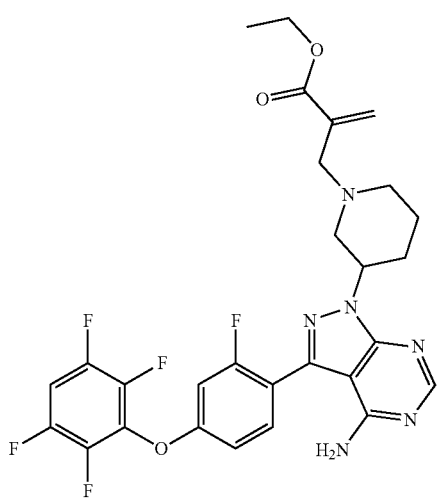 [SMILES: C=C(CN1CCCC(n2nc(-c3ccc(Oc4c(F)c(F)cc(F)c4F)cc3F)c3c(N)ncnc32)C1)C(=O)OCC]

ethyl 2-((3-(4-amino-3-(2-fluoro-4-(2, 3,5,6-tetrafluorophenoxy)phenyl)-1H-pyrazolo[3,4-d]pyrimidin-1-yl)piperidin-1-yl)methyl)acrylate Procedure:

Ethyl 2-(bromomethyl) acrylate (53 mg, 0.28 mmol, 1.2 eq.) and potassium carbonate (63 mg, 0.46 mmol, 2.0 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (110 mg, 0.23 mmol, 1.0 eq.) in DMF (2 mL). The reaction was stirred at 85° C. for 3 hours and filtered. The filter cake was washed with ethyl acetate. The filtrate was concentrated to give the crude product, which was purified by HPLC (C18 reverse phase column, mobile phase: acetonitrile/water/0.5% HCl, gradient: 10%-100% (volume ratio)) to give the title compound (38 mg, yield: 28%).

LC/MS (Method: UFLC): RT=2.654 min; m/z=589.2 [M+H]$^+$; Total running time 7 min.

Compound 69

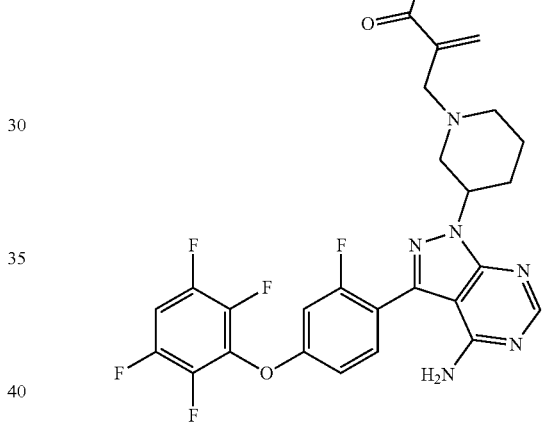

2-((3-(4-amino-3-(2-fluoro-4-(2,3,5,6-tetrafluorophenoxy)phenyl)-1H-pyrazolo[3,4-d]pyrimidin-1-yl)piperidin-1-yl)methyl)-N-methylacrylamide Step A:

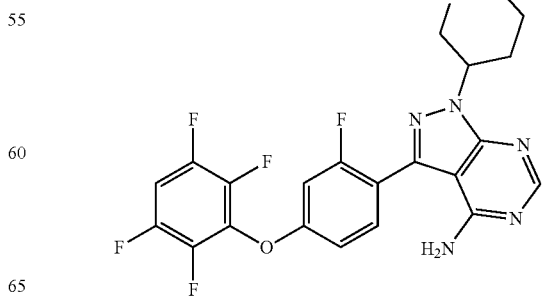

2-((3-(4-amino-3-(2-fluoro-4-(2,3,5,6-tetrafluorophenoxy)phenyl)-1H-pyrazolo[3,4-d]pyrimidin-1-yl)piperidin-1-yl)methyl)acrylic acid Procedure:

Lithium hydroxide monohydrate (3 mg, 0.076 mmol, 1.5 eq.) was added to a solution of ethyl 2-((3-(4-amino-3-(2-fluoro-4-(2,3,5,6-tetrafluorophenoxy)phenyl)-1H-pyrazolo[3,4-d]pyrimidin-1-yl)piperidin-1-yl)methyl)acrylate (30 mg, 0.051 mmol, 1.0 eq.) in tetrahydrofuran/water/methanol (1.5 mL, 1/1/1, v/v/v). The reaction was stirred at 20° C. for 14 hours, and concentrated. The residue was dissolved in water (5 mL), adjusted with 2 N HCl to pH=2, and then extracted with ethyl acetate (5 mL×3). The combined organic phases were dried over anhydrous sodium sulfate, and concentrated to give the title compound (20 mg, yield: 86%).

Step B:

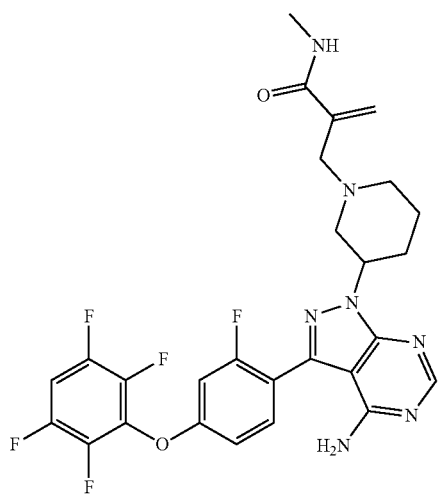 [SMILES: C=C(CN1CCCC(n2nc(-c3ccc(Oc4c(F)c(F)cc(F)c4F)cc3F)c3c(N)ncnc32)C1)C(=O)NC]

2-((3-(4-amino-3-(2-fluoro-4-(2,3,5,6-tetrafluorophenoxy)phenyl)-1H-pyrazolo[3,4-d]pyrimidin-1-yl)piperidin-1-yl)methyl)-N-methylacrylamide Procedure:

Methylamine (1M in THF, 0.072 mL, 0.072 mmol, 2.0 eq.), DIPEA (14 mg, 0.107 mmol, 3.0 eq.) and HATU (20 mg, 0.054 mmol, 1.5 eq.) were added to a solution of 2-((3-(4-amino-3-(2-fluoro-4-(2,3,5,6-tetrafluorophenoxy)phenyl)-1H-pyrazolo[3,4-d]pyrimidin-1-yl)piperidin-1-yl)methyl) acrylic acid (20 mg, 0.036 mmol, 1.0 eq.) in N,N-dimethylformamide (1 mL) at 0° C. The reaction was stirred at 20° C. for 12 hours, and concentrated to give the crude product, which was purified by HPLC (C18 reverse phase column, mobile phase: acetonitrile/water/0.5% HCl, gradient: 10%-100% (volume ratio)) to give the title compound hydrochloride (9 mg, yield: 40%).

LC/MS (Method: UFLC): RT=3.262 min; m/z=574.1 [M+H]⁺; Total running time 7 min.

Compound 70

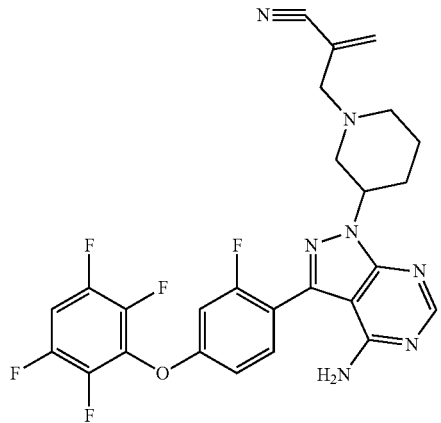 [SMILES: C=C(C#N)CN1CCCC(n2nc(-c3ccc(Oc4c(F)c(F)cc(F)c4F)cc3F)c3c(N)ncnc32)C1]

2-((3-(4-amino-3-(2-fluoro-4-(2,3,5,6-tetrafluorophenoxy)phenyl)-1H-pyrazolo[3,4-d]pyrimidin-1-yl)piperidin-1-yl)methyl)acrylonitrile Procedure:

Cyanoacetic acid (10 mg, 0.12 mmol, 1.0 eq.) and formaldehyde (8.5 mg, 0.28 mmol, 2.4 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (56 mg, 0.12 mmol, 1.0 eq.) in toluene (3 mL). The resulting mixture was refluxed for 12 hours and concentrated to give the crude product, which was purified by HPLC (C18 reverse phase column, mobile phase: acetonitrile/water/0.6‰ NH₄HCO₃, gradient: 10%-100% (volume ratio)) to give the title compound hydrochloride (3.7 mg, yield: 6%).

LC/MS (Method: UFLC): RT=2.458 min; m/z=542.1 [M+H]⁺; Total running time 7 min.

Compound 71

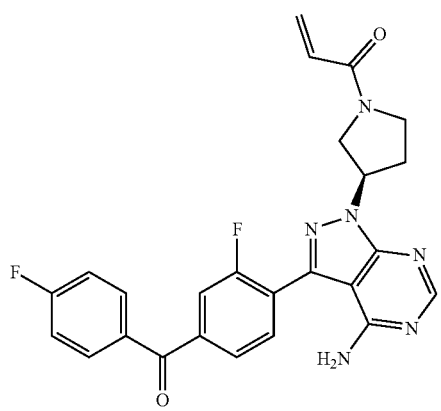 [SMILES: C=CC(=O)N1CC[C@@H](n2nc(-c3ccc(C(=O)c4ccc(F)cc4)cc3F)c3c(N)ncnc32)C1]

1-((R)-3-(4-amino-3-(2-fluoro-4-(4-fluorobenzoyl)phenyl)-1H-pyrazolo[3,4-d]pyrimidin-1-yl)pyrrolidin-1-yl)prop-2-en-1-one Step A:

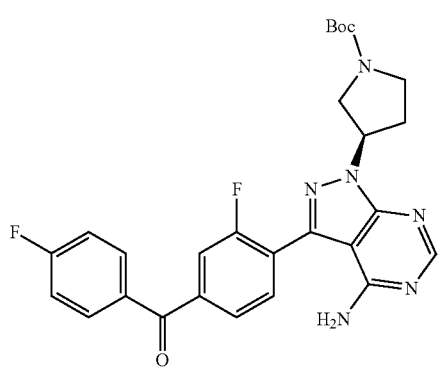 [SMILES: CC(C)(C)OC(=O)N1CC[C@@H](n2nc(-c3ccc(C(=O)c4ccc(F)cc4)cc3F)c3c(N)ncnc32)C1]

(3R)-tert-butyl 3-(4-amino-3-(2-fluoro-4-(4-fluorobenzoyl)phenyl)-1H-pyrazolo[3,4-d]pyrimidin-1-yl)pyrrolidine-1-carboxylate Procedure:

(R)-tert-butyl 3-(4-amino-3-iodo-1H-pyrazolo[3,4-d]pyrimidin-1-yl)pyrrolidine-1-carboxylate (100 mg, 0.232 mmol, 1.0 eq.), (3-fluoro-4-(4,4,5,5-tetramethyl-1,3,2-dioxaborolan-2-yl)phenyl)(4-fluorophenyl)methanone (80 mg, 0.232 mmol, 1.0 eq.), potassium carbonate (96 mg, 0.696 mmol, 3.0 eq.) and Pd(PPh$_3$)$_4$ (26 mg, 0.023 mmol, 0.1 eq.) were dissolved in 1,4-dioxane/water (2.4 mL, 5/1, v/v). The reaction mixture was stirred at 90° C. for 30 minutes under nitrogen atmosphere. After cooling to room temperature, the reaction was diluted with water (10 mL), and then extracted with ethyl acetate (10 mL×3). The combined organic phases were dried over anhydrous sodium sulfate, and concentrated to give the crude product, which was purified by thin layer chromatography (developer:petroleum ether:ethyl acetate=1:1) to give the title compound (20 mg, yield: 17%).

Step B:

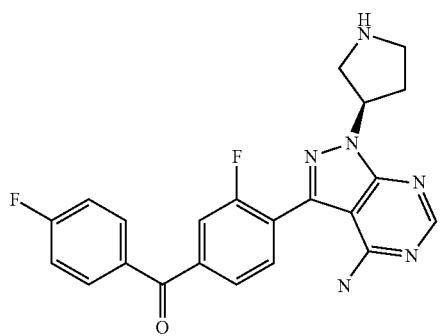 [SMILES: Nc1ncnc2c1c(-c1ccc(C(=O)c3ccc(F)cc3)cc1F)nn2[C@@H]1CCNC1]

(4-(4-amino-1-((R)-pyrrolidin-3-yl)-1H-pyrazolo[3,4-d]pyrimidin-3-yl)-3-fluorophenyl)(4-fluorophenyl)methanone Procedure:

4M HCl/EtOAc (5 mL) was added to a solution of (3R)-tert-butyl 3-(4-amino-3-(2-fluoro-4-(4-fluorobenzoyl)phenyl)-1H-pyrazolo[3,4-d]pyrimidin-1-yl)pyrrolidine-1-carboxylate (20 mg, 0.038 mmol) in dichloromethane (5 mL) at 0° C. The reaction mixture was stirred at room temperature for 1 hour and concentrated to give the title compound hydrochloride (18 mg, yield: 100%).

Step C:

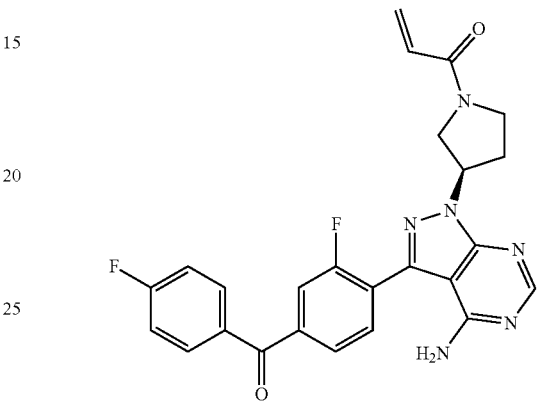

1-((R)-3-(4-amino-3-(2-fluoro-4-(4-fluorobenzoyl)phenyl)-1H-pyrazolo[3,4-d]pyrimidin-1-yl)pyrrolidin-1-yl)prop-2-en-1-one Procedure:

Triethylamine (12 mg, 0.115 mmol, 3.0 eq.) and acrylic acid (3.4 mg, 0.038 mmol, 1.0 eq.) were subsequently added dropwise solution of (4-(4-amino-1-((R)-pyrrolidin-3-yl)-1H-pyrazolo[3,4-d]pyrimidin-3-yl)-3-fluorophenyl)(4-fluorophenyl)methanone (18 mg, 0.038 mmol, 1.0 eq.) in dichloromethane (2 mL) at 0° C. The reaction was stirred at 0° C. for 1 hour, quenched with water (5 mL) and extracted with methylene chloride (5 mL×3). The combined organic phase with anhydrous sodium sulfate and filtered. The filtrate was concentrated to give the crude product, which was purified by HPLC (C18 reverse phase column, mobile phase: acetonitrile/water/0.5% HCl, gradient 10%-100% (volume ratio)) to give the title compound hydrochloride (6.9 mg, yield: 38%).

LC/MS (Method: UFLC): RT=3.424 min; m/z=475.1 [M+H]$^+$; Total running time 7 min.

Compound 72

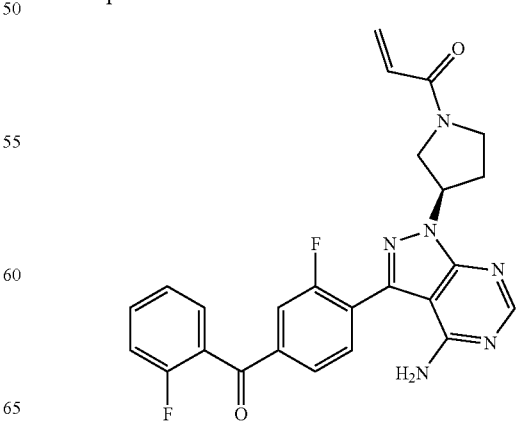

1-((R)-3-(4-amino-3-(2-fluoro-4-(2-fluorobenzoyl)phenyl)-1H-pyrazolo[3,4-d]pyrimidin-1-yl)pyrrolidin-1-yl)prop-2-en-1-one Step A:

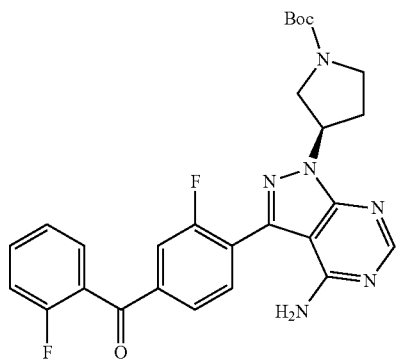 [SMILES: CC(C)(C)OC(=O)N1CC[C@@H](n2nc(-c3ccc(C(=O)c4ccccc4F)cc3F)c3c(N)ncnc32)C1]

(3R)-tert-butyl 3-(4-amino-3-(2-fluoro-4-(2-fluorobenzoyl)phenyl)-1H-pyrazolo[3,4-d]pyrimidin-1-yl)pyrrolidine-1-carboxylate Procedure:
(R)-tert-butyl 3-(4-amino-3-iodo-1H-pyrazolo[3,4-d]pyrimidin-1-yl)pyrrolidine-1-carboxylate (100 mg, 0.232 mmol, 1.0 eq.), (3-fluoro-4-(4,4,5,5-tetramethyl-1,3,2-dioxaborolan-2-yl)phenyl)(2-fluorophenyl)methanone (144 mg, 0.418 mmol, 1.8 eq.), sodium carbonate (74 mg, 0.696 mmol, 3.0 eq.) and Pd(PPh$_3$)$_4$ (26 mg, 0.023 mmol, 0.1 eq.) were dissolved in 1,4-dioxane/water (2.4 mL, 5/1, v/v). The reaction mixture was stirred at 90° C. for 30 minutes under nitrogen atmosphere. After cooling to room temperature, the reaction was diluted with water (10 mL), and then extracted with ethyl acetate (10 mL×3). The combined organic phases were dried over anhydrous sodium sulfate, and concentrated to give the crude product, which was purified by thin layer chromatography (developer:petroleum ether:ethyl acetate=1:1) to give the title compound (40 mg, yield: 33%).

Step B:

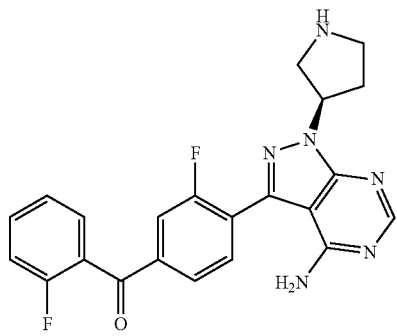 [SMILES: Nc1ncnc2c1c(-c1ccc(C(=O)c3ccccc3F)cc1F)nn2[C@@H]1CCNC1]

(4-(4-amino-1-((R)-pyrrolidin-3-yl)-1H-pyrazolo[3,4-d]pyrimidin-3-yl)-3-fluorophenyl)(2-fluorophenyl)methanone Procedure:
4M HCl/EtOAc (5 mL) was added to a solution of (3R)-tert-butyl 3-(4-amino-3-(2-fluoro-4-(2-fluorobenzoyl)phenyl)-1H-pyrazolo[3,4-d]pyrimidin-1-yl)pyrrolidine-1-carboxylate (40 mg, 0.077 mmol) in dichloromethane (5 mL) at 0° C. The reaction mixture was stirred at room temperature for 1 hour and concentrated to give the title compound hydrochloride (30 mg, yield: 93%).

Step C:

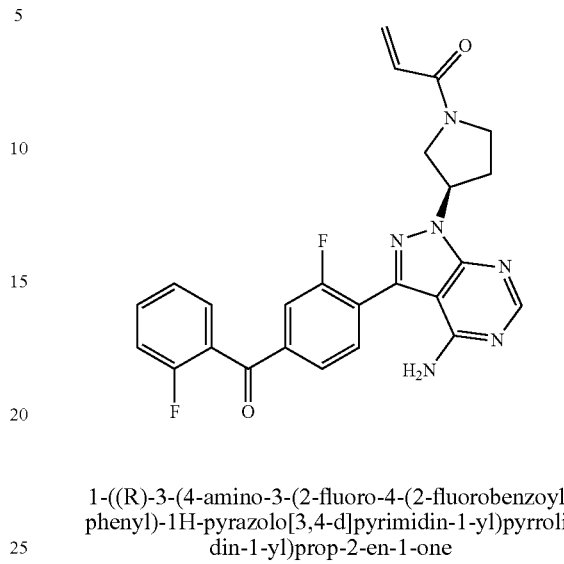

1-((R)-3-(4-amino-3-(2-fluoro-4-(2-fluorobenzoyl)phenyl)-1H-pyrazolo[3,4-d]pyrimidin-1-yl)pyrrolidin-1-yl)prop-2-en-1-one Procedure:
Triethylamine (14 mg, 0.14 mmol, 2.0 eq.) and acrylic acid (7.0 mg, 0.078 mmol, 1.1 eq.) were subsequently added dropwise solution of (4-(4-amino-1-((R)-pyrrolidin-3-yl)-1H-pyrazolo[3,4-d]pyrimidin-3-yl)-3-fluorophenyl)(2-fluorophenyl)methanone (30 mg, 0.071 mmol, 1.0 eq.) in dichloromethane (2 mL) at 0° C. The reaction was stirred at 0° C. for 1 hour, quenched with water (5 mL) and extracted with methylene chloride (5 mL×3). The combined organic phase with anhydrous sodium sulfate and filtered. The filtrate was concentrated to give the crude product, which was purified by HPLC (C18 reverse phase column, mobile phase: acetonitrile/water/0.6% NH$_4$HCO$_3$, gradient 10%-100% (volume ratio)) to give the title compound (4 mg, yield: 15%).

LC/MS (Method: UFLC): RT=2.359 min; m/z=475.1 [M+H]$^+$; Total running time 7 min.

$^1$H NMR (400 MHz, CD$_3$OD) δ 8.29 (s, 1H), 7.76-7.64 (m, 5H), 7.41 (t, J=7.2 Hz, 1H), 7.33 (t, J=8.8 Hz, 1H), 6.70-6.55 (m, 1H), 6.32-6.28 (m, 1H), 5.79-5.76 (m, 1H), 5.65-5.56 (m, 1H), 4.20-4.04 (m, 2.5H), 3.93-3.85 (m, 1H), 3.76-3.73 (m, 0.5H), 2.64-2.49 (m, 2H).

Compound 73

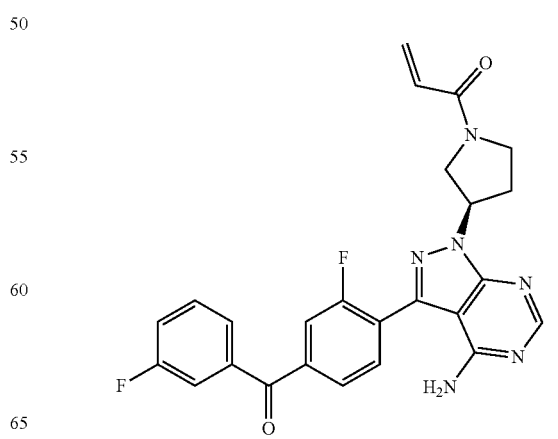

1-((R)-3-(4-amino-3-(2-fluoro-4-(3-fluorobenzoyl)phenyl)-1H-pyrazolo[3,4-d]pyrimidin-1-yl)pyrrolidin-1-yl)prop-2-en-1-one Step A:

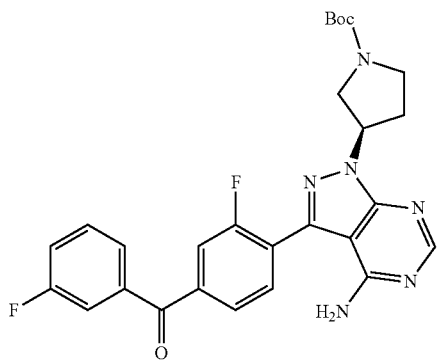 [SMILES: CC(C)(C)OC(=O)N1CC[C@@H](n2nc(-c3ccc(C(=O)c4cccc(F)c4)cc3F)c3c(N)ncnc32)C1]

(3R)-tert-butyl 3-(4-amino-3-(2-fluoro-4-(3-fluorobenzoyl)phenyl)-1H-pyrazolo[3,4-d]pyrimidin-1-yl)pyrrolidine-1-carboxylate Procedure:

(R)-tert-butyl 3-(4-amino-3-iodo-1H-pyrazolo[3,4-d]pyrimidin-1-yl)pyrrolidine-1-carboxylate (140 mg, 0.32 mmol, 1.0 eq.), (3-fluoro-4-(4,4,5,5-tetramethyl-1,3,2-dioxaborolan-2-yl)phenyl)(3-fluorophenyl)methanone (224 mg, 0.64 mmol, 2.0 eq.), sodium carbonate (101 mg, 0.96 mmol, 3.0 eq.) and Pd(PPh$_3$)$_4$ (34 mg, 0.03 mmol, 0.1 eq.) were dissolved in 1,4-dioxane/water (6 mL, 5/1, v/v). The reaction mixture was stirred at 90° C. for 30 minutes under nitrogen atmosphere. After cooling to room temperature, the reaction was diluted with water (10 mL), and then extracted with ethyl acetate (10 mL×3). The combined organic phases were dried over anhydrous sodium sulfate, and concentrated to give the crude product, which was purified by thin layer chromatography (developer:petroleum ether:ethyl acetate=1:1) to give the title compound (50 mg, yield: 23%).

Step B:

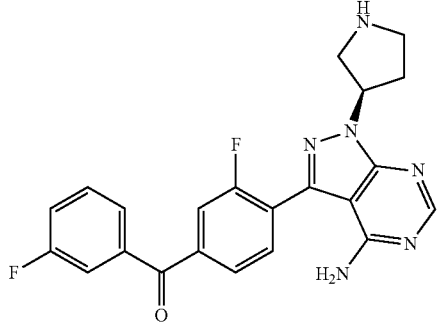 [SMILES: Nc1ncnc2c1c(-c1ccc(C(=O)c3cccc(F)c3)cc1F)nn2[C@@H]1CCNC1]

(4-(4-amino-1-((R)-pyrrolidin-3-yl)-1H-pyrazolo[3,4-d]pyrimidin-3-yl)-3-fluorophenyl)(3-fluorophenyl)methanone Procedure:

4M HCl/EtOAc (5 mL) was added to a solution of (3R)-tert-butyl 3-(4-amino-3-(2-fluoro-4-(3-fluorobenzoyl)phenyl)-1H-pyrazolo[3,4-d]pyrimidin-1-yl)pyrrolidine-1-carboxylate (50 mg, 0.096 mmol) in dichloromethane (5 mL) at 0° C. The reaction mixture was stirred at room temperature for 1 hour and concentrated to give the title compound hydrochloride (40 mg, yield: 99%).

Step C:

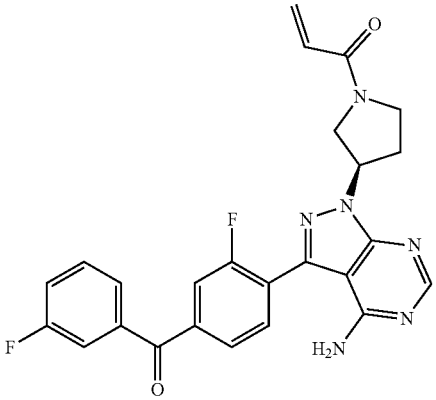 [SMILES: C=CC(=O)N1CC[C@@H](n2nc(-c3ccc(C(=O)c4cccc(F)c4)cc3F)c3c(N)ncnc32)C1]

1-((R)-3-(4-amino-3-(2-fluoro-4-(3-fluorobenzoyl)phenyl)-1H-pyrazolo[3,4-d]pyrimidin-1-yl)pyrrolidin-1-yl)prop-2-en-1-one Procedure:

Triethylamine (19 mg, 0.19 mmol, 2.0 eq.) and acrylic acid (9.5 mg, 0.105 mmol, 1.1 eq.) were subsequently added dropwise solution of (4-(4-amino-1-((R)-pyrrolidin-3-yl)-1H-pyrazolo[3,4-d]pyrimidin-3-yl)-3-fluorophenyl)(3-fluorophenyl)methanone (40 mg, 0.096 mmol, 1.0 eq.) in dichloromethane (2 mL) at 0° C. The reaction was stirred at 0° C. for 1 hour, quenched with water (5 mL) and extracted with methylene chloride (5 mL×3). The combined organic phase with anhydrous sodium sulfate and filtered. The filtrate was concentrated to give the crude product, which was purified by HPLC (C18 reverse phase column, mobile phase: acetonitrile/water/0.5% HCl, gradient 10%-100% (volume ratio)) to give the title compound hydrochloride (0.5 mg, yield: 1%).

LC/MS (Method: UFLC): RT=2.522 min; m/z=475.1 [M+H]$^+$; Total running time 7 min.

Compound 74

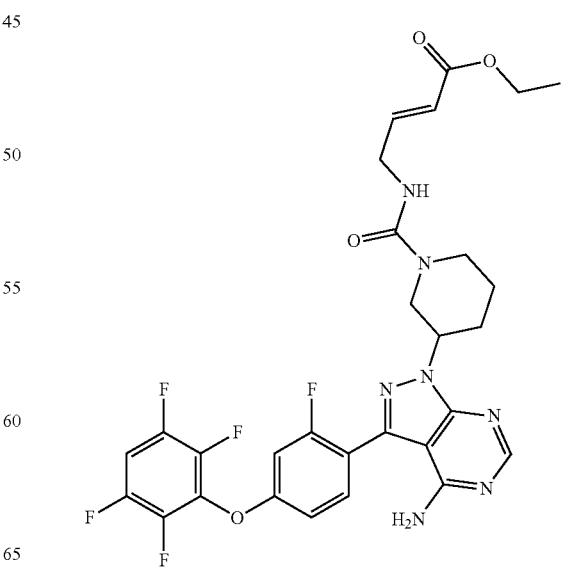

(E)-ethyl 4-(3-(4-amino-3-(2-fluoro-4-(2,3,5,6-tetra-fluorophenoxy)phenyl)-1H-pyrazolo[3,4-d]pyrimidin-1-yl)piperidine-1-carboxamido)but-2-enoate Step A:

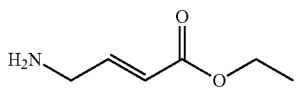

(E)-ethyl 4-aminobut-2-enoate

Procedure:
(E)-ethyl 4-bromobut-2-enoate (1.0 g, 5.18 mmol, 1.0 eq.) in water (10 mL) was added aqueous ammonia solution (10 mL). The reaction was stirred at room temperature for 12 hours, and concentrated to give the title compound (0.7 g, yield: 100%).

Step B:

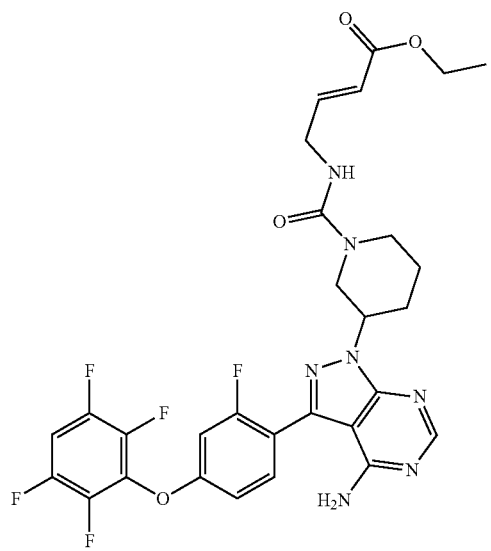 [SMILES: CCOC(=O)/C=C/CNC(=O)N1CCCC(n2nc(-c3ccc(Oc4c(F)c(F)cc(F)c4F)cc3F)c3c(N)ncnc32)C1]

(E)-ethyl 4-(3-(4-amino-3-(2-fluoro-4-(2,3,5,6-tetra-fluorophenoxy)phenyl)-1H-pyrazolo[3,4-d]pyrimidin-1-yl)piperidine-1-carboxamido)but-2-enoate Procedure:
N, N'-carbonyldiimidazole (109 mg, 0.63 mmol, 2.0 eq.) was added to a solution of 3-(2-fluoro-4-(2,3,5,6-tetrafluorophenoxy)phenyl)-1-(piperidin-3-yl)-1H-pyrazolo[3,4-d]pyrimidin-4-amine (48 mg, 0.1 mmol, 1.0 eq.) in DMF (3 mL). The reaction was stirred at 90° C. for 1 hour, followed by addition of (E)-ethyl 4-aminobut-2-enoate (26 mg, 0.2 mmol, 2.0 eq.). The reaction was stirred for 6 hours at 90° C., cooled to room temperature, diluted with water (10 mL), and then extracted with ethyl acetate (10 mL×3). The combined organic phases were dried over anhydrous sodium sulfate, and concentrated to give the crude product, which was purified by thin layer chromatography (developer:petroleum ether:ethyl acetate=1:1) to give the title compound (15 mg, yield: 24%).

LC/MS (Method: UFLC): RT=0.821 min; m/z=632.1 [M+H]+; Total running time 1.5 min.

Compound 75

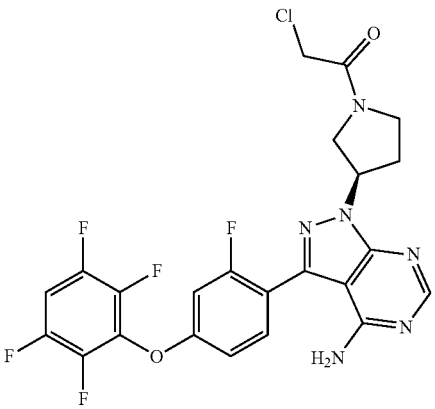 [SMILES: Nc1ncnc2c1c(-c1ccc(Oc3c(F)c(F)cc(F)c3F)cc1F)nn2[C@@H]1CCN(C(=O)CCl)C1]

1-((R)-3-(4-amino-3-(2-fluoro-4-(2,3,5,6-tetrafluoro-phenoxy)phenyl)-1H-pyrazolo[3,4-d]pyrimidin-1-yl)pyrrolidin-1-yl)-2-chloroethanone Procedure:
Triethylamine (44 mg, 0.43 mmol, 2.0 eq.) and chloroacetyl chloride (24 mg, 0.22 mmol, 1.0 eq.) were added dropwise to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (100 mg, 0.22 mmol, 1.0 eq.) in dichloromethane (3 mL) at 0° C. The reaction was stirred at 0° C. for 1 hours, quenched with water (5 mL), and extracted with methylene chloride (5 mL×3). The combined organic layers were and concentrated to dryness to give the crude product, which was purified by HPLC (C18 reverse phase column, mobile phase: acetonitrile/water/7‰ NH4HCO3, gradient: 10%-100% (by volume ratio)) to give the title compound (17 mg, yield: 14%).

LC/MS (Method: UFLC): RT=2.734 min; m/z=539.0 [M+H]+; Total running time 7 min.

Compound 76

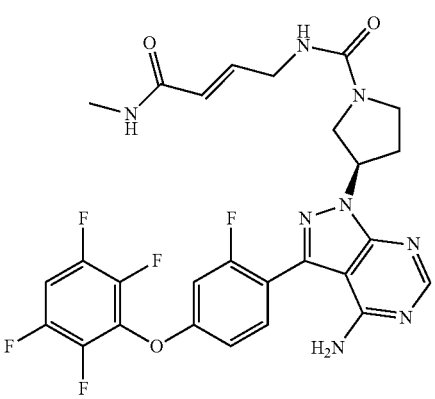 [SMILES: CNC(=O)/C=C/CNC(=O)N1CC[C@@H](n2nc(-c3ccc(Oc4c(F)c(F)cc(F)c4F)cc3F)c3c(N)ncnc32)C1]

247

(3R)-3-(4-amino-3-(2-fluoro-4-(2,3,5,6-tetrafluorophenoxy)phenyl)-1H-pyrazolo[3,4-d]pyrimidin-1-yl)-N-(4-(methylamino)-4-oxobut-2-enyl)pyrrolidine-1-carboxamide Step A:

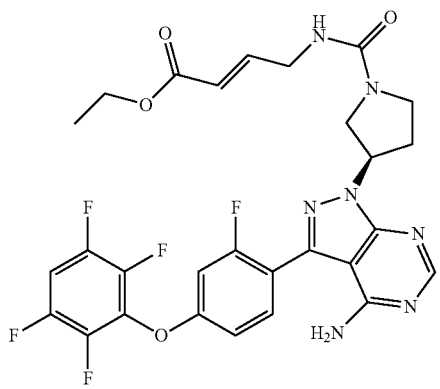 [SMILES: CCOC(=O)/C=C/CNC(=O)N1CC[C@@H](n2nc(-c3ccc(Oc4c(F)c(F)cc(F)c4F)cc3F)c3c(N)ncnc32)C1]

(E)-ethyl 4-((R)-3-(4-amino-3-(2-fluoro-4-(2,3,5,6-tetrafluorophenoxy)phenyl)-1H-pyrazolo[3,4-d]pyrimidin-1-yl)pyrrolidine-1-carboxamido)but-2-enoate Procedure:

N, N'-carbonyldiimidazole (21 mg, 0.13 mmol, 1.0 eq.) was added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (60 mg, 0.13 mmol, 1.0 eq.) in DMF (3 mL). The reaction was stirred at 90° C. for 1 hour, followed by addition of (E)-ethyl 4-aminobut-2-enoate (34 mg, 0.26 mmol, 2.0 eq.). The reaction was stirred for 6 hours at 90° C., cooled to room temperature, diluted with water (10 mL), and then extracted with ethyl acetate (10 mL×3). The combined organic phases were dried over anhydrous sodium sulfate, and concentrated to give the crude product, which was purified by thin layer chromatography (developer:petroleum ether:ethyl acetate=1:1) to give the title compound (30 mg, yield: 37%).

Step B:

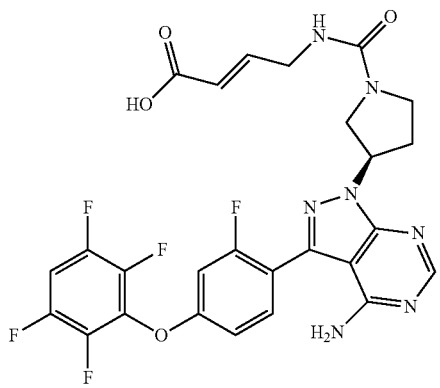 [SMILES: Nc1ncnc2c1c(-c1ccc(Oc3c(F)c(F)cc(F)c3F)cc1F)nn2[C@@H]1CCN(C(=O)NC/C=C/C(=O)O)C1]

(E)-4-((R)-3-(4-amino-3-(2-fluoro-4-(2,3,5,6-tetrafluorophenoxy)phenyl)-1H-pyrazolo[3,4-d]pyrimidin-1-yl)pyrrolidine-1-carboxamido)but-2-enoic acid Procedure:

Lithium hydroxide monohydrate (6 mg, 0.15 mmol, 3.0 eq.) was added to a solution of (E)-ethyl 4-((R)-3-(4-amino-3-(2-fluoro-4-(2,3,5,6-tetrafluorophenoxy)phenyl)-1H-pyrazolo[3,4-d]pyrimidin-1-yl)pyrrolidine-1-carboxamido)but-2-enoate (30 mg, 0.05 mmol, 1.0 eq.) in tetrahydrofuran/water/methanol (3 mL, 1/1/1, v/v/v). The reaction was stirred at 20° C. for 2 hours, and concentrated. The residue was dissolved in water (10 mL), adjusted with 2 N HCl to pH=2, and then extracted with ethyl acetate (20 mL×3). The combined organic phases were dried over anhydrous sodium sulfate, and concentrated to give the title compound (30 mg, yield: 100%).

Step C:

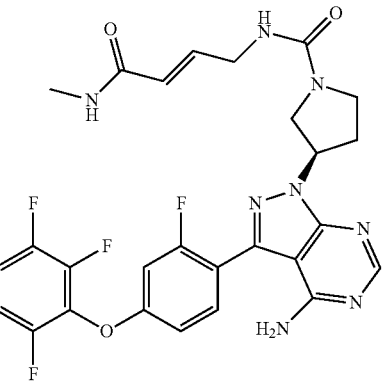

(3R)-3-(4-amino-3-(2-fluoro-4-(2,3,5,6-tetrafluorophenoxy)phenyl)-1H-pyrazolo[3,4-d]pyrimidin-1-yl)-N-(4-(methylamino)-4-oxobut-2-enyl)pyrrolidine-1-carboxamide Procedure:

Methylamine (5 mg, 0.15 mmol, 3.0 eq.) and HATU (29 mg, 0.075 mmol, 1.5 eq.) were added to a solution of (E)-4-((R)-3-(4-amino-3-(2-fluoro-4-(2,3,5,6-tetrafluorophenoxy)phenyl)-1H-pyrazolo[3,4-d]pyrimidin-1-yl)pyrrolidine-1-carboxamido)but-2-enoic acid (30 mg, 0.05 mmol, 1.0 eq.) in dichloromethane (3 mL) at 0° C. The reaction was stirred at 20° C. for 3 hours, and concentrated to give the crude product, which was purified by HPLC (C18 reverse phase column, mobile phase: acetonitrile/water/7‰ $NH_4HCO_3$, gradient: 10%-100% (volume ratio)) to give the title compound (5 mg, yield: 16%).

LC/MS (Method: UFLC): RT=0.854 min; m/z=603.1 [M+H]$^+$; Total running time 1.5 min.

Compound 77

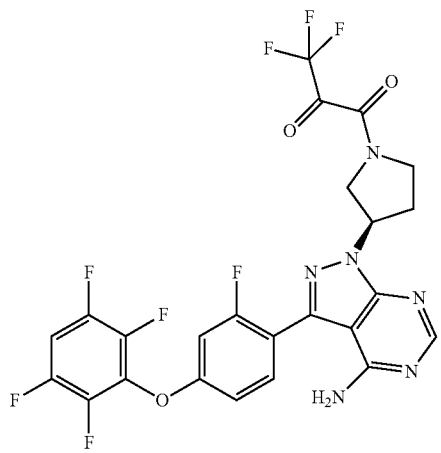 [SMILES: Nc1ncnc2c1c(-c1ccc(Oc3c(F)c(F)cc(F)c3F)cc1F)nn2[C@@H]1CCN(C(=O)C(=O)C(F)(F)F)C1]

1-((R)-3-(4-amino-3-(2-fluoro-4-(2,3,5,6-tetrafluoro-
phenoxy)phenyl)-1H-pyrazolo[3,4-d]pyrimidin-1-yl)
pyrrolidin-1-yl)-3,3,3-trifluoropropane-1,2-dione Procedure:

Ethyl 4,4,4-trifluoro-3-oxobutanoate (44 mg, 0.26 mmol, 1.2 eq.) and DIPEA (84 mg, 0.65 mmol, 3.0 eq.) were added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (100 mg, 0.216 mmol, 1.0 eq.) in toluene (2 mL) at 0° C. The reaction was stirred at 20° C. for 12 hours, and concentrated to give the crude product, which was purified by HPLC (C18 reverse phase column, mobile phase: acetonitrile/water/0.5% HCl, gradient: 10%-100% (volume ratio)) to give the title compound (6.7 mg, yield: 5.3%).

LC/MS (Method: UFLC): RT=4.127 min; m/z=588.9 [M+H]⁺; Total running time 7 min.

Compound 78

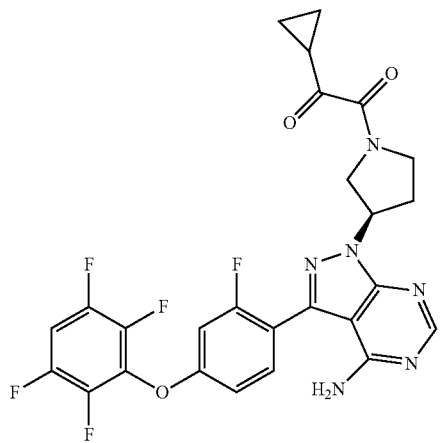 [SMILES: Nc1ncnc2c1c(-c1ccc(Oc3c(F)c(F)cc(F)c3F)cc1F)nn2[C@@H]1CCN(C(=O)C(=O)C2CC2)C1]

1-((R)-3-(4-amino-3-(2-fluoro-4-(2,3,5,6-tetrafluoro-
phenoxy)phenyl)-1H-pyrazolo[3,4-d]pyrimidin-1-yl)
pyrrolidin-1-yl)-2-cyclopropylethane-1,2-dione Step A:

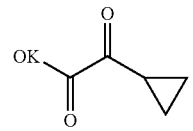

potassium 2-cyclopropyl-2-oxo acetate

Procedure:

Potassium hydroxide (1N, 0.7 mL, 0.70 mmol, 1.0 eq.) was added to a solution of ethyl 2-cyclopropyl-2-oxoacetate (100 mg, 0.70 mmol, 1.0 eq.) in tetrahydrofuran/water (2 mL, 1/1, v/v). The reaction was stirred at 20° C. for 2 hours and concentrated to give the title compound (85 mg, yield: 79%).

Step B:

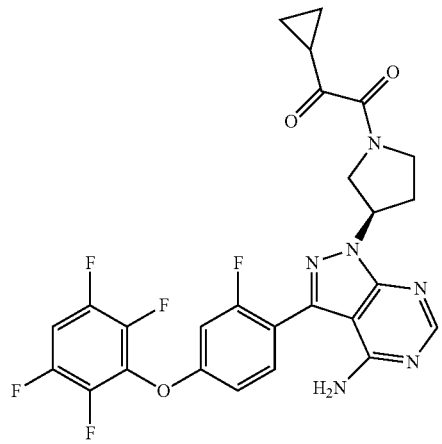 [SMILES: Nc1ncnc2c1c(-c1ccc(Oc3c(F)c(F)cc(F)c3F)cc1F)nn2[C@@H]1CCN(C(=O)C(=O)C2CC2)C1]

1-((R)-3-(4-amino-3-(2-fluoro-4-(2,3,5,6-tetrafluoro-
phenoxy)phenyl)-1H-pyrazolo[3,4-d]pyrimidin-1-yl)
pyrrolidin-1-yl)-2-cyclopropylethane-1,2-dione Procedure:

Potassium 2-cyclopropyl-2-oxo acetate (66 mg, 0.43 mmol, 2.0 eq.), DIPEA (84 mg, 0.65 mmol, 3.0 eq.) and PyBrop (12 mg, 0.24 mmol, 1.1 eq.) were added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (100 mg, 0.22 mmol, 1.0 eq.) in N,N-dimethylformamide (3 mL) at 0° C. The reaction was stirred at 0° C. for 1 hour, and concentrated to give the crude product, which was purified by HPLC (C18 reverse phase column, mobile phase: acetonitrile/water/7‰ NH₄HCO₃, gradient: 10%-100% (volume ratio)) to give the title compound (53 mg, yield: 44%).

LC/MS (Method: UFLC): RT=2.943 min; m/z=559.1 [M+H]⁺; Total running time 7 min.

¹H NMR (400 MHz, CDCl₃) δ 8.37-8.35 (m, 1H), 7.57 (t, J=8.4 Hz, 1H), 7.10-7.05 (m, 1H), 6.95-6.89 (m, 2H), 5.60-5.54 (m, 1H), 4.21-3.88 (m, 3.5H), 3.80-3.72 (m, 0.5H), 2.73-2.48 (m, 3H), 1.25-1.05 (m, 4H).

Compound 79

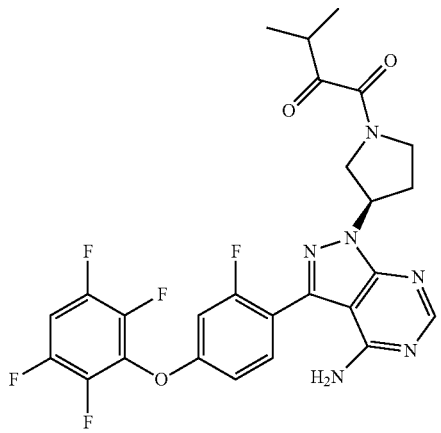 [SMILES: CC(C)C(=O)C(=O)N1CC[C@@H](n2nc(-c3ccc(Oc4c(F)c(F)cc(F)c4F)cc3F)c3c(N)ncnc32)C1]

1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-3-methylbutane-1,2-dione Procedure:

Sodium 3-methyl-2-oxobutanoate (45 mg, 0.32 mmol, 1.5 eq.), DIPEA (84 mg, 0.65 mmol, 3.0 eq.) and PyBrop (100 mg, 0.22 mmol, 1.0 eq.) were added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (100 mg, 0.22 mmol, 1.0 eq.) in N,N-dimethylformamide (3 mL) at 0° C. The reaction was stirred at 0° C. for 1 hour, and concentrated to give the crude product, which was purified by HPLC (C18 reverse phase column, mobile phase: acetonitrile/water/7‰ NH$_4$HCO$_3$, gradient: 10%-100% (volume ratio)) to give the title compound (51 mg, yield: 42%).

LC/MS (Method: UFLC): RT=3.275 min; m/z=561.0 [M+H]$^+$; Total running time 7 min.

$^1$H NMR (400 MHz, CDCl$_3$) δ 8.37-8.36 (m, 1H), 7.55-7.50 (m, 1H), 7.10-7.05 (m, 1H), 6.95-6.88 (m, 2H), 5.60-5.55 (m, 1H), 4.15-3.4 (m, 4H), 3.42-3.37 (m, 1H), 2.58-2.48 (m, 2H), 1.14-1.01 (m, 6H).

Compound 80

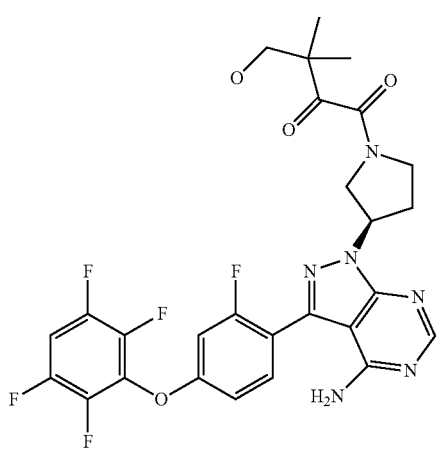 [SMILES: CC(C)(CO)C(=O)C(=O)N1CC[C@@H](n2nc(-c3ccc(Oc4c(F)c(F)cc(F)c4F)cc3F)c3c(N)ncnc32)C1]

1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-4-hydroxy-3,3-dimethylbutane-1,2-dione Procedure:

4,4-dimethyl-dihydrofuran-2,3-dione (15 mg, 0.12 mmol, 2.0 eq.) and DMAP (1.3 mg, 0.01 mmol, 0.1 eq.) were added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.11 mmol, 1.0 eq.) in tetrahydrofuran (3 mL). The reaction was stirred at 70° C. for 3 hours, and concentrated to give the crude product, which was purified by HPLC (C18 reverse phase column, mobile phase: acetonitrile/water, gradient: 10%-100% (volume ratio)) to give the title compound (0.8 mg, yield: 1.3%).

LC/MS (Method: UFLC): RT=4.564 min; m/z=591.2 [M+H]$^+$; Total running time 7 min.

Compound 81

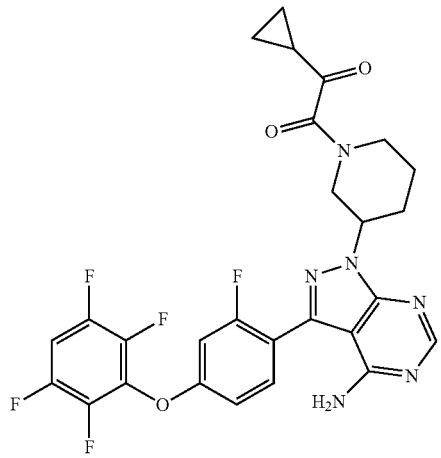 [SMILES: Nc1ncnc2c1c(-c1ccc(Oc3c(F)c(F)cc(F)c3F)cc1F)nn2C1CCCN(C(=O)C(=O)C2CC2)C1]

1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-cyclopropylethane-1,2-dione Procedure:

Potassium 2-cyclopropyl-2-oxo acetate (20 mg, 0.13 mmol, 1.1 eq.), DIPEA (51 mg, 0.39 mmol, 3.0 eq.) and PyBrop (56 mg, 0.12 mmol, 1.0 eq.) were added to a solution of 3-(2-fluoro-4-(2,3,5,6-tetrafluorophenoxy)phenyl)-1-(piperidin-3-yl)-1H-pyrazolo[3,4-d]pyrimidin-4-amine (60 mg, 0.13 mmol, 1.0 eq.) in N,N-dimethylformamide (5 mL) at 0° C. The reaction was stirred at 20° C. for 12 hours, and concentrated to give the crude product, which was purified by HPLC (C18 reverse phase column, mobile phase: acetonitrile/water/0.6‰ NH$_4$HCO$_3$, gradient: 10%-100% (volume ratio)) to give the title compound (17 mg, yield: 6%).

LC/MS (Method: UFLC): RT=2.938 min; m/z=573.5 [M+H]$^+$; Total running time 7 min.

Compound 82

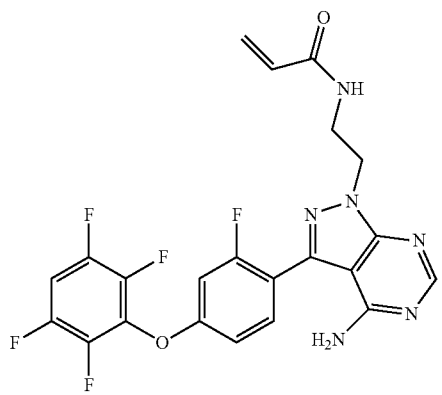 [SMILES: C=CC(=O)NCCn1nc(-c2ccc(Oc3c(F)c(F)cc(F)c3F)cc2F)c2c(N)ncnc21]

N-(2-(4-amino-3-(2-fluoro-4-(2,3,5,6-tetrafluorophenoxy)phenyl)-1H-pyrazolo[3,4-d]pyrimidin-1-yl)ethyl)acrylamide Step A:

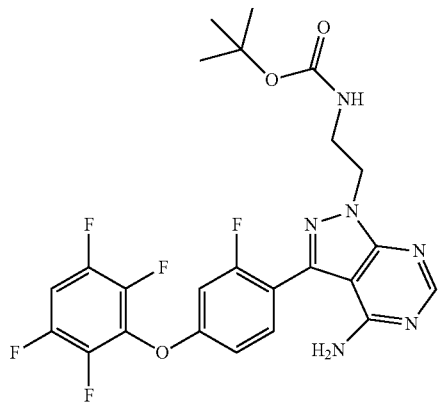 [SMILES: CC(C)(C)OC(=O)NCCn1nc(-c2ccc(Oc3c(F)c(F)cc(F)c3F)cc2F)c2c(N)ncnc21]

tert-butyl 2-(4-amino-3-(2-fluoro-4-(2,3,5,6-tetrafluorophenoxy)phenyl)-1H-pyrazolo[3,4-d]pyrimidin-1-yl)ethylcarbamate Procedure:

tert-butyl 2-bromoethylcarbamate (114 mg, 0.51 mmol, 2.0 eq.), potassium carbonate (70 mg, 0.51 mmol, 2.0 eq.) and sodium iodide (3.8 mg, 0.025 mmol, 0.1 eq.) were added to a solution of 3-(2-fluoro-4-(2,3,5,6-tetrafluorophenoxy)phenyl)-1H-pyrazolo[3,4-d]pyrimidin-4-amine (100 mg, 0.25 mmol, 1.0 eq.) in DMF (2 mL) was added. The reaction was stirred at 80° C. for 14 hours and filtered. The filter cake was washed with ethyl acetate. The filtrate was concentrated to give the crude product, which was purified by silica gel column chromatography (eluent:ethyl acetate) to give the title compound (50 mg, yield: 37%).

Step B:

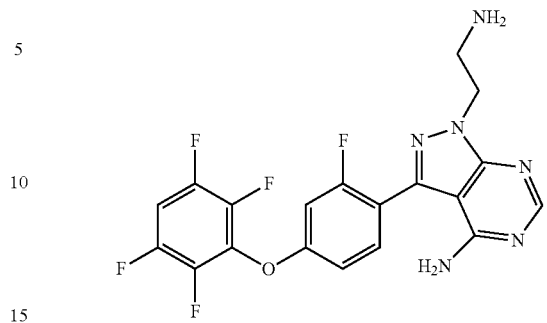

1-(2-aminoethyl)-3-(2-fluoro-4-(2,3,5,6-tetrafluorophenoxy)phenyl)-1H-pyrazolo[3,4-d]pyrimidin-4-amine Procedure:

4M HCl/EtOAc (2 mL) was added to a solution of tert-butyl 2-(4-amino-3-(2-fluoro-4-(2,3,5,6-tetrafluorophenoxy)phenyl)-1H-pyrazolo[3,4-d]pyrimidin-1-yl)ethylcarbamate (50 mg, 0.093 mmol) in dichloromethane (2 mL) at 0° C. The reaction mixture was stirred at room temperature for 1 h and concentrated to give the title compound hydrochloride (44 mg, yield: 100%).

Step C:

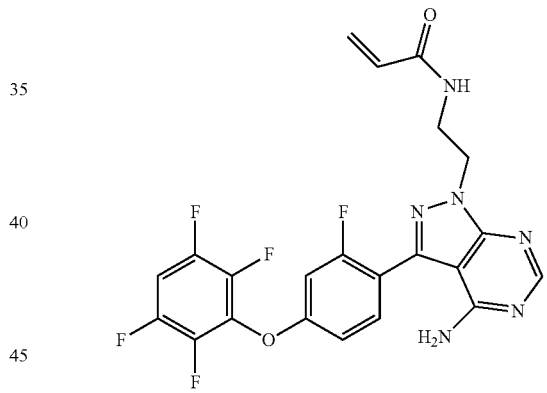

N-(2-(4-amino-3-(2-fluoro-4-(2,3,5,6-tetrafluorophenoxy)phenyl)-1H-pyrazolo[3,4-d]pyrimidin-1-yl)ethyl)acrylamide Procedure:

Triethylamine (28 mg, 0.28 mmol, 3.0 eq.) and acryloyl chloride (8.4 mg, 0.093 mmol, 1.0 eq.) were subsequently added to a solution of 1-(2-aminoethyl)-3-(2-fluoro-4-(2,3,5,6-tetrafluorophenoxy)phenyl)-1H-pyrazolo[3,4-d]pyrimidin-4-amine (44 mg, 0.093 mmol, 1.0 eq.) in dichloromethane (3 mL) at −15° C. The reaction mixture was stirred at −15° C. for 1 hour, and then quenched with water (10 mL). The aqueous layer was extracted with dichloromethane (5 mL×3). The combined organic layers were dried over anhydrous sodium sulfate and filtered. The filtrate was concentrated to give the crude product, which was purified by HPLC (C18 reverse phase column, mobile phase: acetonitrile/water/0.5% HCl, gradient: 10%-100% (volume ratio)) to give the title compound (5 mg, yield: 11%).

LC/MS (Method: UFLC): RT=2.552 min; m/z=491.0 [M+H]$^+$; Total running time 7 min.

Compound 83

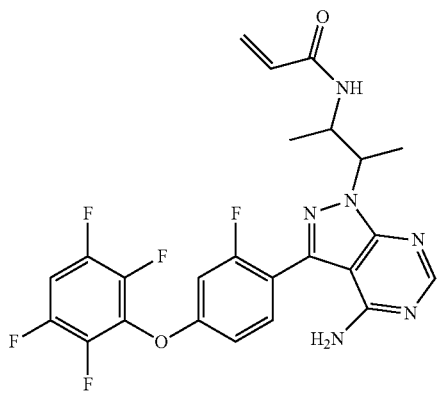 [SMILES: C=CC(=O)NC(C)C(C)n1nc(-c2ccc(Oc3c(F)c(F)cc(F)c3F)cc2F)c2c(N)ncnc21]

N-(3-(4-amino-3-(2-fluoro-4-(2,3,5,6-tetrafluorophenoxy)phenyl)-1H-pyrazolo[3,4-d]pyrimidin-1-yl)butan-2-yl)acrylamide Step A:

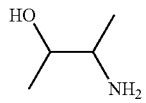

3-aminobutan-2-ol

Procedure:

Ammonium formate (10.8 g, 171.1 mmol, 6.8 eq.) and Pd/C (300 mg) were added to a solution of 3-nitrobutan-2-ol (3.0 g, 25.2 mmol, 1.0 eq.) in methanol (30 mL). The reaction was stirred at room temperature for 18 hours and filtered through celite. The filtrate was concentrated to give compound the title compound (2.0 g, yield: 88%).

Step B:

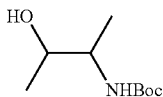

tert-butyl 3-hydroxybutan-2-ylcarbamate

Procedure:

Boc$_2$O (4.9 g, 22.5 mmol, 1.1 eq.) and triethylamine (4.54 g, 45.0 mmol, 2.0 eq.) were added to a solution of 3-aminobutan-2-ol (2.0 g, 22.5 mol, 1.0 eq.) in dichloromethane (20 mL). The reaction was stirred at 20° C. for 16 hours and washed with water (20 mL×2) and brine (20 mL). The organic phase was dried over anhydrous sodium sulfate and filtered. The filtrate was concentrated to give the title compound (600 mg, yield: 14%).

Step C:

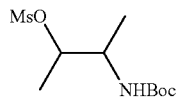

3-(tert-butoxycarbonyl)butan-2-yl methanesulfonate

Procedure:

Triethylamine (640 mg, 6.34 mmol, 2.0 eq.) and methanesulfonyl chloride (540 mg, 4.76 mmol, 1.5 eq.) were subsequently added to a solution of tert-butyl 3-hydroxybutan-2-ylcarbamate (600 mg, 3.17 mmol, 1.0 eq.) in dichloromethane (5 mL) at 0° C. The reaction was stirred at 20° C. for 3 hours, quenched with saturated NaHCO$_3$ (20 mL), and then extracted with dichloromethane (20 mL×2). The combined organic phases were dried over anhydrous sodium sulfate, and concentrated to give the title compound (500 mg, yield: 59%).

Step D:

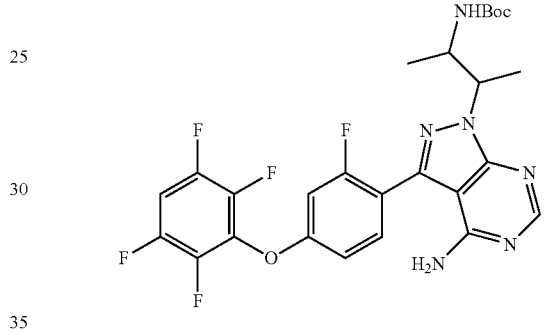

tert-butyl 3-(4-amino-3-(2-fluoro-4-(2,3,5,6-tetrafluorophenoxy)phenyl)-1H-pyrazolo[3,4-d]pyrimidin-1-yl)butan-2-ylcarbamate Procedure:

Cesium carbonate (165 mg, 0.51 mmol, 2.0 eq.) and 3-(tert-butoxycarbonyl)butan-2-yl methanesulfonate (136 mg, 0.51 mmol, 2.0 eq.) were added to a solution of 3-(2-fluoro-4-(2,3,5,6-tetrafluorophenoxy)phenyl)-1H-pyrazolo[3,4-d]pyrimidin-4-amine (100 mg, 0.25 mmol, 1.0 eq.) in DMF (2 mL). The reaction was stirred at 85° C. for 3 hours, cooled to room temperature and filtered. The filtrate was concentrated to give the crude product, which was purified by thin layer chcromotagraphy (developer:petroleum ether:ethyl acetate=1:1) to give the title compound (45 mg, yield: 31%).

Step E:

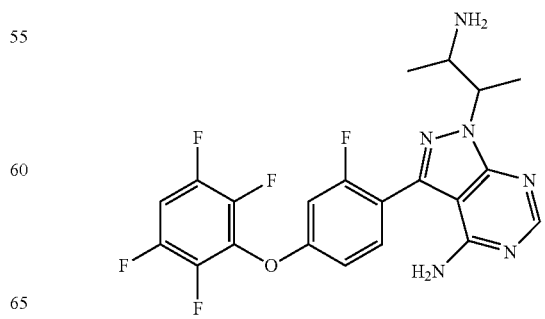

1-(3-aminobutan-2-yl)-3-(2-fluoro-4-(2,3,5,6-tetra-fluorophenoxy)phenyl)-1H-pyrazolo[3,4-d]pyrimidin-4-amine Procedure:

4M HCl/EtOAc (5 mL) was added to a solution of tert-butyl 3-(4-amino-3-(2-fluoro-4-(2,3,5,6-tetrafluorophenoxy)phenyl)-1H-pyrazolo[3,4-d]pyrimidin-1-yl)butan-2-ylcarbamate (45 mg, 0.082 mmol) in ethyl acetate (5 mL) at 0° C. The reaction mixture was stirred at room temperature for 1 h and concentrated to give the title compound hydrochloride (35 mg, yield: 85%).

Step F:

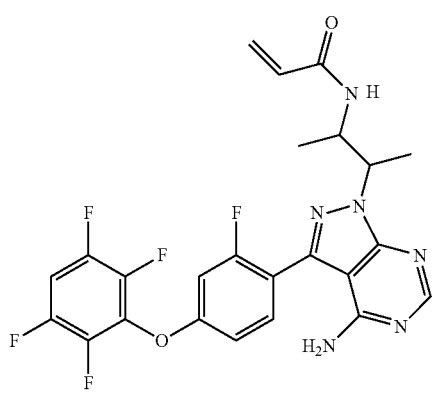

N-(3-(4-amino-3-(2-fluoro-4-(2,3,5,6-tetrafluorophenoxy)phenyl)-1H-pyrazolo[3,4-d]pyrimidin-1-yl)butan-2-yl)acrylamide Procedure:

Triethylamine (15 mg, 0.15 mmol, 2.0 eq.) and acryloyl chloride (7 mg, 0.083 mmol, 1.1 eq.) were subsequently added dropwise to a solution of 1-(3-aminobutan-2-yl)-3-(2-fluoro-4-(2,3,5,6-tetrafluorophenoxy)phenyl)-1H-pyrazolo[3,4-d]pyrimidin-4-amine (35 mg, 0.075 mmol, 1.0 eq.) in dichloromethane (3 mL) at 0° C. The reaction was stirred at 0° C. for 2 hour, and then quenched with water (5 mL). The aqueous phase was extracted with methylene chloride (5 mL×3). The combined organic phases were dried over anhydrous sodium sulfate, and concentrated to give the crude product, which was purified by HPLC (C18 reverse phase column, mobile phase: acetonitrile/water/0.5% HCl, gradient: 10%-100% (volume ratio)) to give the title compound (3.0 mg, yield: 8%).

LC/MS (Method: UFLC): RT=4.038 min; m/z=519.1 [M+H]$^+$; Total running time 7 min.

Compound 84

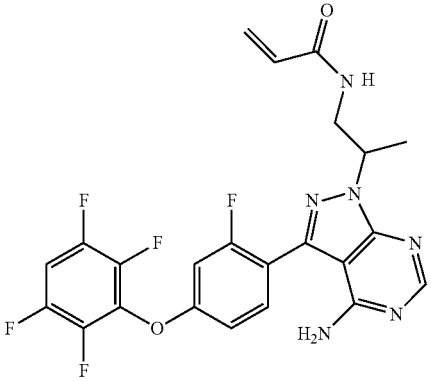

N-(2-(4-amino-3-(2-fluoro-4-(2,3,5,6-tetrafluorophenoxy)phenyl)-1H-pyrazolo[3,4-d]pyrimidin-1-yl)propyl)acrylamide Step A:

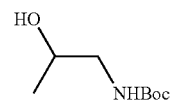

tert-butyl 2-hydroxypropylcarbamate

Procedure:

Boc$_2$O (29 g, 0.13 mol, 1.0 eq.) and triethylamine (37 mL, 0.27 mol, 2.0 eq.) were added to a solution of 1-aminopropan-2-ol (10 g, 0.13 mol, 1.0 eq.) in dichloromethane (200 mL). The reaction was stirred at 20° C. for 16 hours and washed with water (100 mL×2) and brine (100 mL). The organic phase was dried over anhydrous sodium sulfate, and concentrated to give the title compound (20 g, yield: 87%).

Step B:

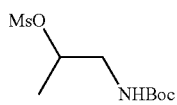

1-(tert-butoxycarbonyl)propan-2-yl methanesulfonate

Procedure:

Triethylamine (1.15 g, 11.4 mmol, 2.0 eq.) and methanesulfonyl chloride (0.98 g, 8.6 mmol, 1.5 eq.) were subsequently added to a solution of tert-butyl 2-hydroxypropylcarbamate (1.0 g, 5.7 mmol, 1.0 eq.) in dichloromethane (10 mL) at 0° C. The reaction was stirred at 20° C. for 3 hours, quenched with saturated NaHCO$_3$ (20 mL), and then extracted with dichloromethane (10 mL×2). The combined organic phases were dried over anhydrous sodium sulfate, and concentrated to give the title compound (0.8 g, yield: 69%).

Step C:

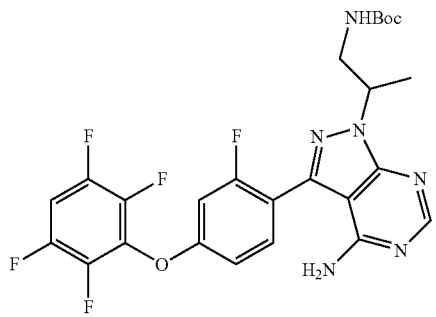 [SMILES: CC(CNC(=O)OC(C)(C)C)n1nc(-c2ccc(Oc3c(F)c(F)cc(F)c3F)cc2F)c2c(N)ncnc21]

tert-butyl 2-(4-amino-3-(2-fluoro-4-(2,3,5,6-tetra-fluorophenoxy)phenyl)-1H-pyrazolo[3,4-d]pyrimidin-1-yl)propylcarbamate Procedure:

Cesium carbonate (165 mg, 0.51 mmol, 2.0 eq.) and 3-(tert-butoxycarbonyl)butan-2-yl methanesulfonate (128 mg, 0.51 mmol, 2.0 eq.) were added to a solution of 3-(2-fluoro-4-(2,3,5,6-tetrafluorophenoxy)phenyl)-1H-pyrazolo[3,4-d]pyrimidin-4-amine (100 mg, 0.25 mmol, 1.0 eq.) in DMF (2 mL). The reaction was stirred at 85° C. for 3 hours, cooled to room temperature and filtered. The filtrate was concentrated to give the crude product, which was purified by silica gel column chcromotagraphy (eluent: petroleum ether:ethyl acetate=1:1) to give the title compound (30 mg, yield: 21%).

Step D:

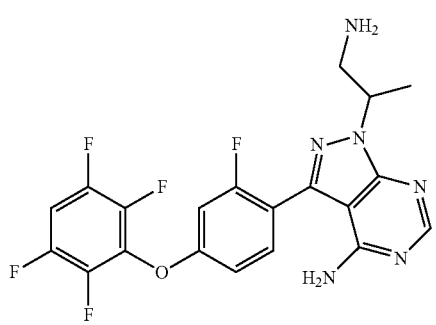 [SMILES: CC(CN)n1nc(-c2ccc(Oc3c(F)c(F)cc(F)c3F)cc2F)c2c(N)ncnc21]

1-(1-aminopropan-2-yl)-3-(2-fluoro-4-(2,3,5,6-tetra-fluorophenoxy)phenyl)-1H-pyrazolo[3,4-d]pyrimidin-4-amine Procedure:

4M HCl/EtOAc (5 mL) was added to a solution of tert-butyl 2-(4-amino-3-(2-fluoro-4-(2,3,5,6-tetrafluorophenoxy)phenyl)-1H-pyrazolo[3,4-d]pyrimidin-1-yl)propylcarbamate (30 mg, 0.054 mmol) in ethyl acetate (5 mL) at 0° C. The reaction mixture was stirred at room temperature for 1 h and concentrated to give the title compound hydrochloride (20 mg, yield: 77%).

Step E:

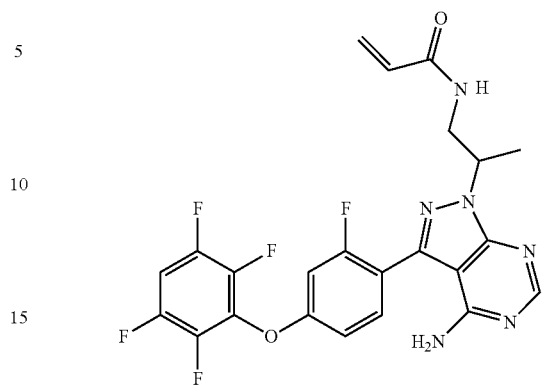

N-(2-(4-amino-3-(2-fluoro-4-(2,3,5,6-tetrafluorophenoxy)phenyl)-1H-pyrazolo[3,4-d]pyrimidin-1-yl)propyl)acrylamide Procedure:

Triethylamine (8.4 mg, 0.084 mmol, 2.0 eq.) and acrylic anhydride (6.3 mg, 0.05 mmol, 1.2 eq.) were subsequently added dropwise to a solution of 1-(1-aminopropan-2-yl)-3-(2-fluoro-4-(2,3,5,6-tetrafluorophenoxy)phenyl)-1H-pyrazolo[3,4-d]pyrimidin-4-amine (20 mg, 0.042 mmol, 1.0 eq.) in dichloromethane (2 mL) at 0° C. The reaction was stirred at 0° C. for 2 hour, and then quenched with water (5 mL). The aqueous phase was extracted with methylene chloride (5 mL×3). The combined organic phases were dried over anhydrous sodium sulfate, and concentrated to give the crude product, which was purified by HPLC (C18 reverse phase column, mobile phase: acetonitrile/water, gradient: 10%-100% (volume ratio)) to give the title compound (5.0 mg, yield: 24%).

LC/MS (Method: UFLC): RT=3.912 min; m/z=505.0 [M+H]$^+$; Total running time 7 min.

$^1$H NMR (400 MHz, CD$_3$OD) δ 8.34 (s, 1H), 7.74 (t, J=8.4 Hz, 1H), 7.55-7.48 (m, 1H), 7.13-7.06 (m, 2H), 6.10-6.08 (m, 2H), 5.60-5.57 (m, 1H), 5.27-5.24 (m, 1H), 3.82-3.73 (m, 2H), 1.66-1.64 (m, 3H).

Compound 85

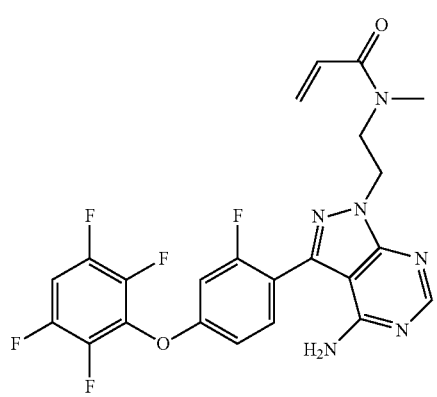 [SMILES: C=CC(=O)N(C)CCn1nc(-c2ccc(Oc3c(F)c(F)cc(F)c3F)cc2F)c2c(N)ncnc21]

261

N-(2-(4-amino-3-(2-fluoro-4-(2,3,5,6-tetrafluorophenoxy)phenyl)-1H-pyrazolo[3,4-d]pyrimidin-1-yl)ethyl)-N-methyl acrylamide Step A:

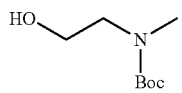

tert-butyl 2-hydroxyethyl(methyl)carbamate

Procedure:

Boc$_2$O (8.0 g, 36.6 mmol, 1.1 eq.) and triethylamine (6.75 g, 66.5 mmol, 2.0 eq.) were added to a solution of 2-(methylamino)ethanol (2.5 g, 33.3 mol, 1.0 eq.) in dichloromethane (50 mL). The reaction was stirred at 20° C. for 16 hours and washed with water (30 mL×2) and brine (30 mL). The organic phase was dried over anhydrous sodium sulfate, and concentrated to give the title compound (5.8 g, yield: 100%).

Step B:

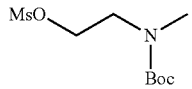

2-(tert-butoxycarbonyl)ethyl methanesulfonate

Procedure:

Triethylamine (2.31 g, 22.8 mmol, 2.0 eq.) and methanesulfonyl chloride (1.96 g, 17.7 mmol, 1.5 eq.) were subsequently added to a solution of tert-butyl 2-hydroxyethyl (methyl)carbamate (2.0 g, 11.4 mmol, 1.0 eq.) in dichloromethane (20 mL) at 0° C. The reaction was stirred at 20° C. for 3 hours, quenched with saturated NaHCO$_3$ (20 mL), and then extracted with dichloromethane (20 mL×2). The combined organic phases were dried over anhydrous sodium sulfate, and concentrated to give the title compound (2.8 g, yield: 100%).

Step C:

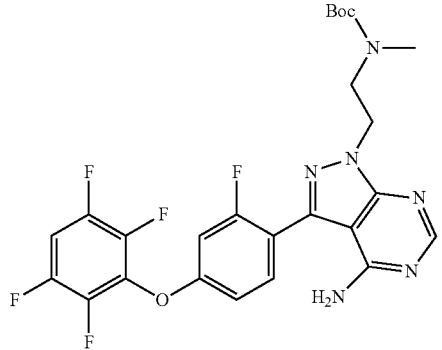 [SMILES: CN(CCn1nc(-c2ccc(Oc3c(F)c(F)cc(F)c3F)cc2F)c2c(N)ncnc21)C(=O)OC(C)(C)C]

262 tert-butyl 2-(4-amino-3-(2-fluoro-4-(2,3,5,6-tetrafluorophenoxy)phenyl)-1H-pyrazolo[3,4-d]pyrimidin-1-yl)ethyl(methyl)carbamate Procedure:

Cesium carbonate (116 mg, 0.36 mmol, 2.0 eq.) and 2-(tert-butoxycarbonyl)ethyl methanesulfonate (90 mg, 0.36 mmol, 2.0 eq.) were added to a solution of 3-(2-fluoro-4-(2,3,5,6-tetrafluorophenoxy)phenyl)-1H-pyrazolo[3,4-d]pyrimidin-4-amine (70 mg, 0.18 mmol, 1.0 eq.) in DMF (2 mL). The reaction was stirred at 85° C. for 3 hours, cooled to room temperature and filtered. The filtrate was concentrated to give the crude product, which was purified by thin layer chcromotaghraphy (developer:petroleum ether:ethyl acetate=1:1) to give the title compound (50 mg, yield: 52%).

Step D:

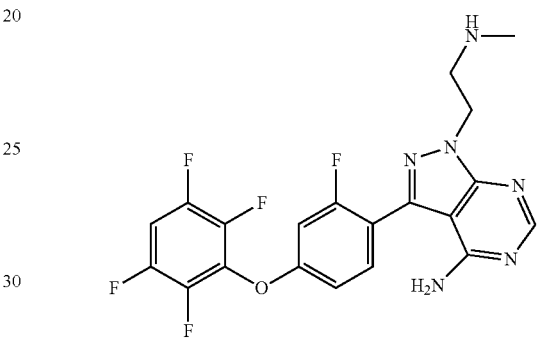

3-(2-fluoro-4-(2,3,5,6-tetrafluorophenoxy)phenyl)-1-(2-(methylamino)ethyl)-1H-pyrazolo[3,4-d]pyrimidin-4-amine Procedure:

4M HCl/EtOAc (5 mL) was added to a solution of tert-butyl 2-(4-amino-3-(2-fluoro-4-(2,3,5,6-tetrafluorophenoxy)phenyl)-1H-pyrazolo[3,4-d]pyrimidin-1-yl)ethyl (methyl)carbamate (50 mg, 0.092 mmol) in dichloromethane (5 mL) at 0° C. The reaction mixture was stirred at room temperature for 1 h and concentrated to give the title compound hydrochloride (44 mg, yield: 100%).

Step E:

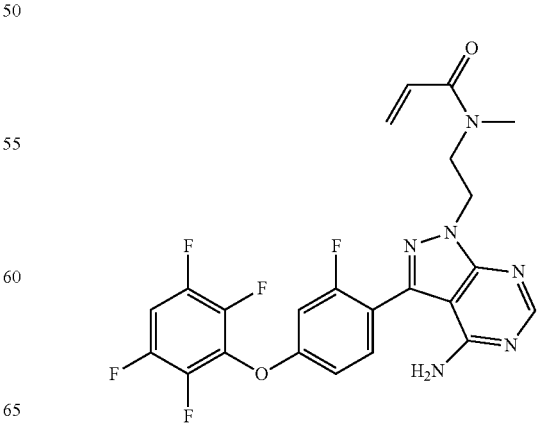

N-(2-(4-amino-3-(2-fluoro-4-(2,3,5,6-tetrafluorophenoxy)phenyl)-1H-pyrazolo[3,4-d]pyrimidin-1-yl)ethyl)-N-methyl acrylamide Procedure:

Triethylamine (28 mg, 0.28 mmol, 3.0 eq.) and acryloyl chloride (17 mg, 0.092 mmol, 1.0 eq.) were subsequently added dropwise to a solution of 3-(2-fluoro-4-(2,3,5,6-tetrafluorophenoxy)phenyl)-1-(2-(methylamino)ethyl)-1H-pyrazolo[3,4-d]pyrimidin-4-amine (50 mg, 0.092 mmol, 1.0 eq.) in dichloromethane (3 mL) at 0° C. The reaction was stirred at 0° C. for 2 hour, and then quenched with water (5 mL). The aqueous phase was extracted with methylene chloride (5 mL×3). The combined organic phases were dried over anhydrous sodium sulfate, and concentrated to give the crude product, which was purified by HPLC (C18 reverse phase column, mobile phase: acetonitrile/water/0.5% HCl, gradient: 10%-100% (volume ratio)) to give the title compound (7.7 mg, yield: 16%).

LC/MS (Method: UFLC): RT=3.872 min; m/z=505.0 [M+H]$^+$; Total running time 7 min.

Compound 86

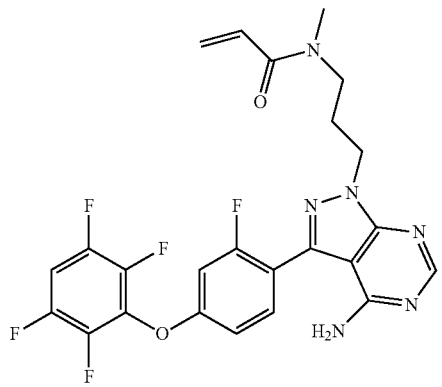 [SMILES: C=CC(=O)N(C)CCCn1nc(-c2ccc(Oc3c(F)c(F)cc(F)c3F)cc2F)c2c(N)ncnc21]

N-(3-(4-amino-3-(2-fluoro-4-(2,3,5,6-tetrafluorophenoxy)phenyl)-1H-pyrazolo[3,4-d]pyrimidin-1-yl)propyl)-N-methylacrylamide Step A:

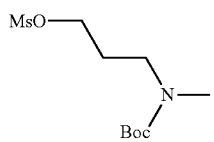

3-(tert-butoxycarbonyl)propyl methanesulfonate

Procedure:

Triethylamine (2.88 g, 28.5 mmol, 2.0 eq.) and methanesulfonyl chloride (1.64 g, 14.3 mmol, 1.0 eq.) were subsequently added to a solution of tert-butyl 3-hydroxypropyl (methyl)carbamate (1.8 g, 14.3 mmol, 1.0 eq.) in dichloromethane (10 mL) at 0° C. The reaction was stirred at 20° C. for 3 hours, quenched with saturated NaHCO$_3$ (20 mL), and then extracted with dichloromethane (20 mL×2). The combined organic phases were dried over anhydrous sodium sulfate, and concentrated to give the title compound (3.8 g, yield: 100%).

Step B:

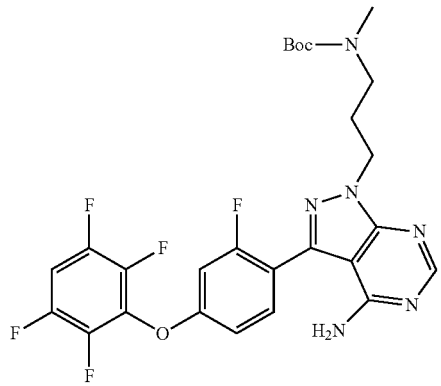 [SMILES: CN(CCCn1nc(-c2ccc(Oc3c(F)c(F)cc(F)c3F)cc2F)c2c(N)ncnc21)C(=O)OC(C)(C)C]

tert-butyl 3-(4-amino-3-(2-fluoro-4-(2,3,5,6-tetrafluorophenoxy)phenyl)-1H-pyrazolo[3,4-d]pyrimidin-1-yl)propyl(methyl)carbamate Procedure:

Cesium carbonate (331 mg, 1.02 mmol, 2.0 eq.) and 3-(tert-butoxycarbonyl)propyl methanesulfonate (272 mg, 1.02 mmol, 2.0 eq.) were added to a solution of 3-(2-fluoro-4-(2,3,5,6-tetrafluorophenoxy)phenyl)-1H-pyrazolo[3,4-d]pyrimidin-4-amine (200 mg, 0.51 mmol, 1.0 eq.) in DMF (2 mL). The reaction was stirred at 85° C. for 3 hours, cooled to room temperature and filtered. The filtrate was concentrated to give the crude product, which was purified by thin layer chcromotagraphy (developer:petroleum ether:ethyl acetate=1:1) to give the title compound (58 mg, yield: 20%).

Step C:

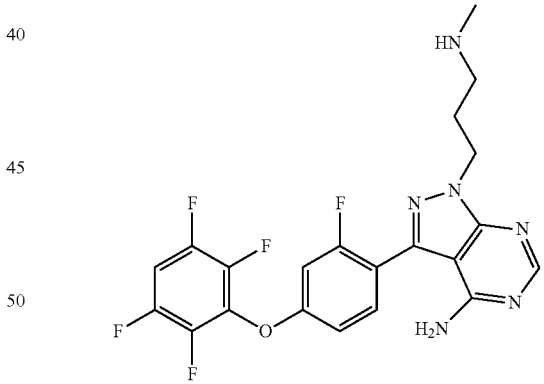

3-(2-fluoro-4-(2,3,5,6-tetrafluorophenoxy)phenyl)-1-(3-(methylamino)propyl)-1H-pyrazolo[3,4-d]pyrimidin-4-amine Procedure:

4M HCl/EtOAc (5 mL) was added to a solution of tert-butyl 3-(4-amino-3-(2-fluoro-4-(2,3,5,6-tetrafluorophenoxy)phenyl)-1H-pyrazolo[3,4-d]pyrimidin-1-yl)propyl (methyl)carbamate (50 mg, 0.089 mmol) in dichloromethane (5 mL) at 0° C. The reaction mixture was stirred at room temperature for 1 h and concentrated to give the title compound hydrochloride (45 mg, yield: 100%).

Step D:

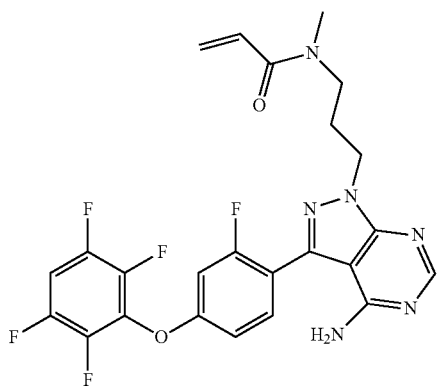 [SMILES: C=CC(=O)N(C)CCCn1nc(-c2ccc(Oc3c(F)c(F)cc(F)c3F)cc2F)c2c(N)ncnc21]

N-(3-(4-amino-3-(2-fluoro-4-(2,3,5,6-tetrafluorophenoxy)phenyl)-1H-pyrazolo[3,4-d]pyrimidin-1-yl)propyl)-N-methylacrylamide Procedure:

Triethylamine (27 mg, 0.27 mmol, 3.0 eq.) and acryloyl chloride (8 mg, 0.089 mmol, 1.0 eq.) were subsequently added dropwise to a solution of 3-(2-fluoro-4-(2,3,5,6-tetrafluorophenoxy)phenyl)-1-(3-(methylamino)propyl)-1H-pyrazolo[3,4-d]pyrimidin-4-amine (45 mg, 0.089 mmol, 1.0 eq.) in dichloromethane (3 mL) at 0° C. The reaction was stirred at 0° C. for 2 hours, and then quenched with water (5 mL). The aqueous phase was extracted with methylene chloride (5 mL×3). The combined organic phases were dried over anhydrous sodium sulfate, and concentrated to give the crude product, which was purified by HPLC (C18 reverse phase column, mobile phase: acetonitrile/water/0.5% HCl, gradient: 10%-100% (volume ratio)) to give the title compound hydrochloride (2.3 mg, yield: 5%).

LC/MS (Method: UFLC): RT=4.010 min; m/z=519.2 [M+H]$^+$; Total running time 7 min.

Compound 87

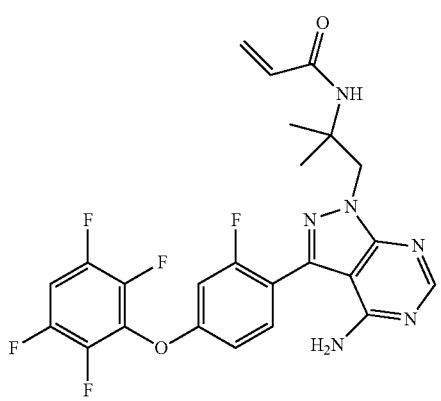 [SMILES: C=CC(=O)NC(C)(C)Cn1nc(-c2ccc(Oc3c(F)c(F)cc(F)c3F)cc2F)c2c(N)ncnc21]

N-(1-(4-amino-3-(2-fluoro-4-(2,3,5,6-tetrafluorophenoxy)phenyl)-1H-pyrazolo[3,4-d]pyrimidin-1-yl)-2-methylpropan-2-yl)acrylamide Step A:

2-(tert-butoxycarbonyl)-2-methylpropyl methanesulfonate

Procedure:

Triethylamine (1.60 g, 15.9 mmol, 3.0 eq.) and methanesulfonyl chloride (908 mg, 7.93 mmol, 1.5 eq.) were subsequently added to a solution of tert-butyl 1-hydroxy-2-methylpropan-2-ylcarbamate (1.0 g, 5.28 mmol, 1.0 eq.) in dichloromethane (10 mL) at 0° C. The reaction was stirred at 20° C. for 16 hours, quenched with saturated NaHCO$_3$ (20 mL), and then extracted with dichloromethane (20 mL×2). The combined organic phases were dried over anhydrous sodium sulfate, and concentrated to give the title compound (0.4 g, yield: 28%).

Step B:

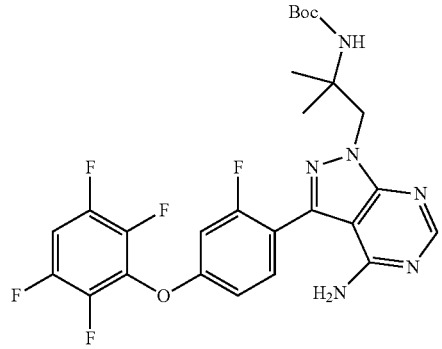 [SMILES: CC(C)(Cn1nc(-c2ccc(Oc3c(F)c(F)cc(F)c3F)cc2F)c2c(N)ncnc21)NC(=O)OC(C)(C)C]

tert-butyl 1-(4-amino-3-(2-fluoro-4-(2,3,5,6-tetrafluorophenoxy)phenyl)-1H-pyrazolo[3,4-d]pyrimidin-1-yl)-2-methylpropan-2-ylcarbamate Procedure:

Cesium carbonate (249 mg, 0.76 mmol, 2.0 eq.) and 2-(tert-butoxycarbonyl)-2-methylpropyl methanesulfonate (272 mg, 1.02 mmol, 2.0 eq.) were added to a solution of 3-(2-fluoro-4-(2,3,5,6-tetrafluorophenoxy)phenyl)-1H-pyrazolo[3,4-d]pyrimidin-4-amine (150 mg, 0.38 mmol, 1.0 eq.) in DMF (2 mL). The reaction was stirred at 85° C. for 3 hours, cooled to room temperature and filtered. The filtrate was concentrated to give the crude product, which was purified by HPLC (C18 reverse phase column, mobile phase: acetonitrile/water, gradient: 10%-100% (volume ratio)) to give the title compound (50 mg, yield: 23%).

Step C:

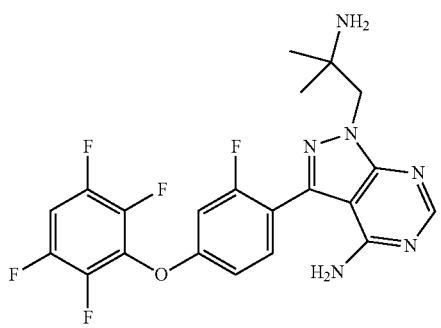 [SMILES: CC(C)(N)Cn1nc(-c2ccc(Oc3c(F)c(F)cc(F)c3F)cc2F)c2c(N)ncnc21]

1-(2-amino-2-methylpropyl)-3-(2-fluoro-4-(2, 3,5,6-tetrafluorophenoxy)phenyl)-1H-pyrazolo[3,4-d]pyrimidin-4-amine Procedure:
4M HCl/EtOAc (5 mL) was added to a solution of tert-butyl 1-(4-amino-3-(2-fluoro-4-(2,3,5,6-tetrafluorophenoxy)phenyl)-1H-pyrazolo[3,4-d]pyrimidin-1-yl)-2-methylpropan-2-ylcarbamate (20 mg, 0.035 mmol) in dichloromethane (5 mL) at 0° C. The reaction mixture was stirred at room temperature for 1 h and concentrated to give the title compound hydrochloride (18 mg, yield: 100%).

Step D:

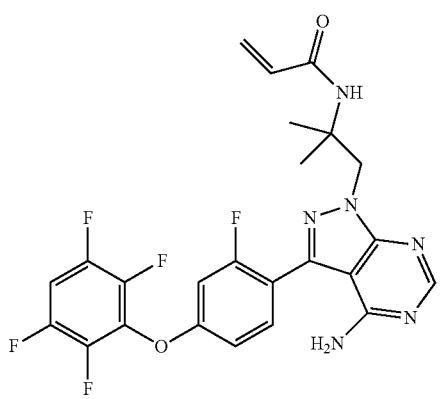 [SMILES: C=CC(=O)NC(C)(C)Cn1nc(-c2ccc(Oc3c(F)c(F)cc(F)c3F)cc2F)c2c(N)ncnc21]

N-(1-(4-amino-3-(2-fluoro-4-(2,3,5,6-tetrafluorophenoxy)phenyl)-1H-pyrazolo[3,4-d]pyrimidin-1-yl)-2-methylpropan-2-yl)acrylamide Procedure:
Triethylamine (12 mg, 0.12 mmol, 3.0 eq.) and acryloyl chloride (3.6 mg, 0.043 mmol, 1.0 eq.) were subsequently added dropwise to a solution of 1-(2-amino-2-methylpropyl)-3-(2-fluoro-4-(2,3,5,6-tetrafluorophenoxy)phenyl)-1H-pyrazolo[3,4-d]pyrimidin-4-amine (20 mg, 0.043 mmol, 1.0 eq.) in dichloromethane (3 mL) at 0° C. The reaction was stirred at 0° C. for 2 hours, and then quenched with water (5 mL). The aqueous phase was extracted with methylene chloride (5 mL×3). The combined organic phases were dried over anhydrous sodium sulfate, and concentrated to give the crude product, which was purified by HPLC (C18 reverse phase column, mobile phase: acetonitrile/water/0.5% HCl, gradient: 10%-100% (volume ratio)) to give the title compound hydrochloride (0.8 mg, yield: 3.6%).

LC/MS (Method: UFLC): RT=0.492 min; m/z=519.1 [M+H]$^+$; Total running time 1.5 min.

Compound 88

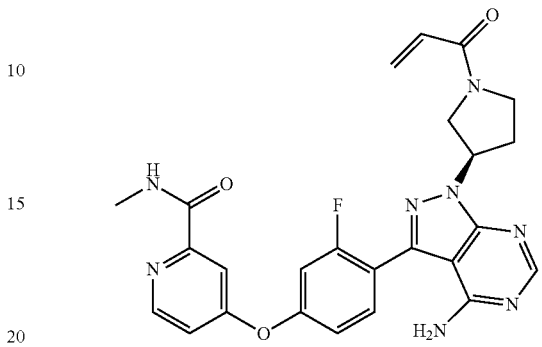

4-(4-(1-((R)-1-acryloylpyrrolidin-3-yl)-4-amino-1H-pyrazolo[3,4-d]pyrimidin-3-yl)-3-fluorophenoxy)-N-methylpicolinamide Step A:

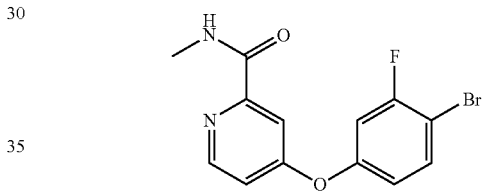

4-(4-bromo-3-fluorophenoxy)-N-methylpicolinamide

Procedure:
Potassium tert-butoxide (177 mg, 1.58 mmol, 1.0 eq.) was added to a solution of 4-bromo-3-fluorophenol (300 mg, 1.58 mmol, 1.0 eq.) in DMF (10 mL). The reaction was stirred at room temperature for 2 hours, followed by the addition of 4-chloro-N-methylpicolinamide (282 mg, 1.66 mmol, 1.05 eq.) and potassium carbonate (229 mg, 1.66 mmol, 1.05 eq.). The reaction solution was stirred at 80° C. for 14 hours under nitrogen atmosphere, cooled to room temperature and filtered. The filter cake was washed with ethyl acetate. The filtrate was concentrated to give the crude product by HPLC (C18 reverse phase column, mobile phase: acetonitrile/water, gradient: 10%-100% (volume ratio)) to give the title compound (95 mg, yield: 19%).

Step B:

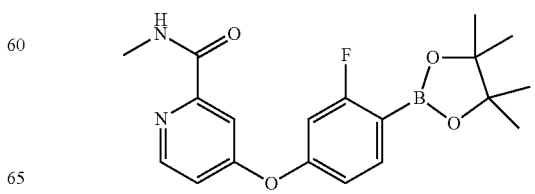

4-(3-fluoro-4-(4,4,5,5-tetramethyl-1,3,2-dioxaborolan-2-yl)phenoxy)-N-methylpicolinamide Procedure:

4-(4-bromo-3-fluorophenoxy)-N-methylpyridine amide (95 mg, 0.29 mmol, 1.0 eq.), bis(pinacolato)diboron (88 mg, 0.35 mmol, 1.2 eq.), potassium acetate (86 mg, 0.87 mmol, 3.0 eq.) and (1,1'-bis(diphenylphosphino)ferrocene)dichloropalladium (13 mg, 0.017 mmol, 0.06 eq.) were dissolved in 1,4-dioxane (10 mL), and stirred for 12 hours at 80° C. under nitrogen. The reaction mixture was filtered through celite. The filtrate was concentrated to give the crude product (100 mg, yield: 93%), which was used directly in the next step.

Step C:

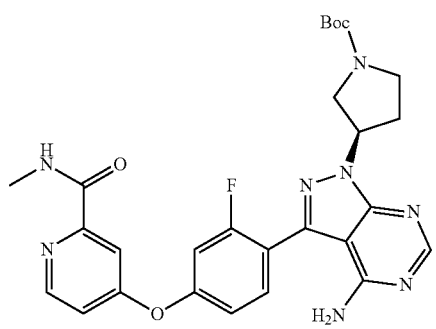 [SMILES: CNC(=O)c1cc(Oc2ccc(-c3nn([C@@H]4CCN(C(=O)OC(C)(C)C)C4)c4ncnc(N)c34)c(F)c2)ccn1]

(3R)-tert-butyl 3-(4-amino-3-(2-fluoro-4-(2-(methylcarbamoyl)pyridin-4-yloxy)phenyl)-1H-pyrazolo[3,4-d]pyrimidin-1-yl)pyrrolidine-1-carboxylate Procedure:

(R)-tert-butyl 3-(4-amino-3-iodo-1H-pyrazolo[3,4-d]pyrimidin-1-yl)pyrrolidine-1-carboxylate (52 mg, 0.12 mmol, 1.0 eq.), 4-(3-fluoro-4-(4,4,5,5-tetramethyl-1,3,2-dioxaborolan-2-yl)phenoxy)-N-methylpicolinamide (45 mg, 0.12 mmol, 1.0 eq.), potassium phosphate (51 mg, 0.24 mmol, 2.0 eq.) and Pd-118 (8 mg, 0.012 mmol, 0.1 eq.) were dissolved in 1,4-dioxane/water (4 mL, 3/1, v/v). The reaction was stirred at 80° C. for 40 minutes under nitrogen atmosphere with microwave irradiation. The reaction solution was diluted with water (10 mL) and extracted with ethyl acetate (10 mL×3). The combined organic phases were dried over anhydrous sodium sulfate and filtered. The filtrate was concentrated to give the crude produce, which was purified by silica gel column chromatography (eluent:ethyl acetate) to give the title compound (15 mg, yield: 24%).

Step D:

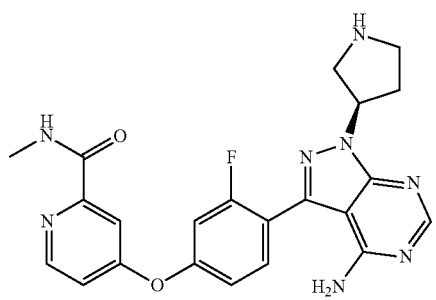 [SMILES: CNC(=O)c1cc(Oc2ccc(-c3nn([C@@H]4CCNC4)c4ncnc(N)c34)c(F)c2)ccn1]

4-(4-(4-amino-1-((R)-pyrrolidin-3-yl)-1H-pyrazolo[3,4-d]pyrimidin-3-yl)-3-fluorophenoxy)-N-methylpicolinamide Procedure:

4M HCl/EtOAc (5 mL) was added to a solution of (3R)-tert-butyl 3-(4-amino-3-(2-fluoro-4-(2-(methylcarbamoyl)pyridin-4-yloxy)phenyl)-1H-pyrazolo[3,4-d]pyrimidin-1-yl)pyrrolidine-1-carboxylate (15 mg, 0.028 mmol) in dichloromethane (5 mL) at 0° C. The reaction mixture was stirred at room temperature for 1 h and concentrated to give the title compound hydrochloride (10 mg, yield: 81%).

Step E:

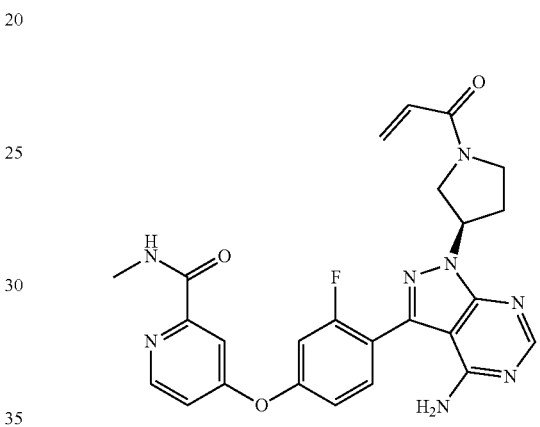

4-(4-(1-((R)-1-acryloylpyrrolidin-3-yl)-4-amino-1H-pyrazolo[3,4-d]pyrimidin-3-yl)-3-fluorophenoxy)-N-methylpicolinamide Procedure:

NaOH aqueous (2N, 0.4 mL) and acryloyl chloride (1.9 mg, 0.021 mmol, 1.0 eq.) were subsequently added dropwise to a solution of 4-(4-(4-amino-1-((R)-pyrrolidin-3-yl)-1H-pyrazolo[3,4-d]pyrimidin-3-yl)-3-fluorophenoxy)-N-methylpicolinamide (10 mg, 0.021 mmol, 1.0 eq.) in tetrahydrofuran (1 mL) at 0° C. The reaction was stirred at 0° C. for 2 hours, and then quenched with water (5 mL). The aqueous phase was extracted with methylene chloride (5 mL×3). The combined organic phases were dried over anhydrous sodium sulfate, and concentrated to give the crude product, which was purified by HPLC (C18 reverse phase column, mobile phase: acetonitrile/water/0.5% HCl, gradient: 10%-100% (volume ratio)) to give the title compound hydrochloride (6 mg, yield: 60%).

LC/MS (Method: UFLC): RT=2.445 min; m/z=489.1 [M+H]$^+$; Total running time 7 min.

Compound 89

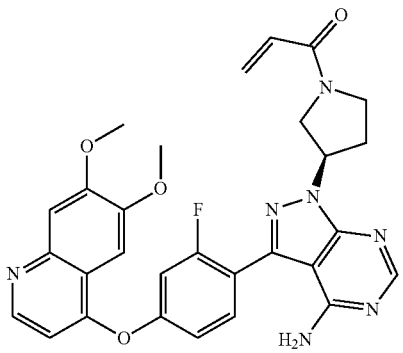 [SMILES: C=CC(=O)N1CC[C@@H](n2nc(-c3ccc(Oc4ccnc5cc(OC)c(OC)cc45)cc3F)c3c(N)ncnc32)C1]

1-((R)-3-(4-amino-3-(4-(6,7-dimethoxyquinolin-4-yloxy)-2-fluorophenyl)-1H-pyrazolo[3,4-d]pyrimidin-1-yl)pyrrolidin-1-yl)prop-2-en-1-one Step A:

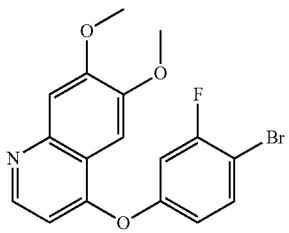 [SMILES: COc1cc2nccc(Oc3ccc(Br)c(F)c3)c2cc1OC]

4-(4-bromo-3-fluorophenoxy)-6,7-dimethoxyquinoline

Procedure:

A solution of potassium tert-butoxide in THF (1N, 1.24 mL, 1.24 mmol, 1.05 eq.) was added to a solution of 4-bromo-3-fluorophenol (225 mg, 1.18 mmol, 1.0 eq.) in DMF (2 mL). The reaction was stirred at 0° C. for 2 hours, followed by the addition of 4-chloro-6,7-dimethoxy quinoline (264 mg, 1.18 mmol, 1.0 eq.) and potassium carbonate (81 mg, 0.59 mmol, 0.5 eq.). The reaction solution was stirred at 80° C. for 14 hours under nitrogen atmosphere, cooled to room temperature and filtered. The filter cake was washed with ethyl acetate. The filtrate was concentrated to give the crude product by HPLC (C18 reverse phase column, mobile phase: acetonitrile/water, gradient: 10%-100% (volume ratio)) to give the title compound (100 mg, yield: 24%).

Step B:

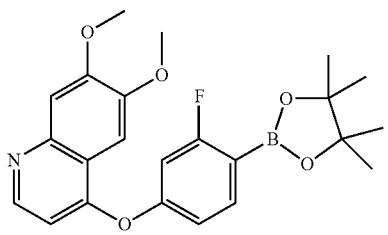 [SMILES: COc1cc2nccc(Oc3ccc(B4OC(C)(C)C(C)(C)O4)c(F)c3)c2cc1OC]

4-(3-fluoro-4-(4,4,5,5-tetramethyl-1,3,2-dioxaborolan-2-yl)phenoxy)-6,7-dimethoxyquinoline Procedure:

4-(4-bromo-3-fluorophenoxy)-6,7-dimethoxyquinoline (100 mg, 0.26 mmol, 1.0 eq.), bis(pinacolato)diboron (101 mg, 0.39 mmol, 1.5 eq.), potassium acetate (78 mg, 0.79 mmol, 3.0 eq.) and (1,1'-bis(diphenylphosphino)ferrocene) dichloropalladium (25 mg, 0.026 mmol, 0.1 eq.) were dissolved in 1,4-dioxane (2 mL), and stirred at 85° C. for 12 hours under nitrogen. The reaction mixture was filtered through celite. The filtrate was concentrated to give the crude product (110 mg, yield: 100%), which was used directly in the next step.

Step C:

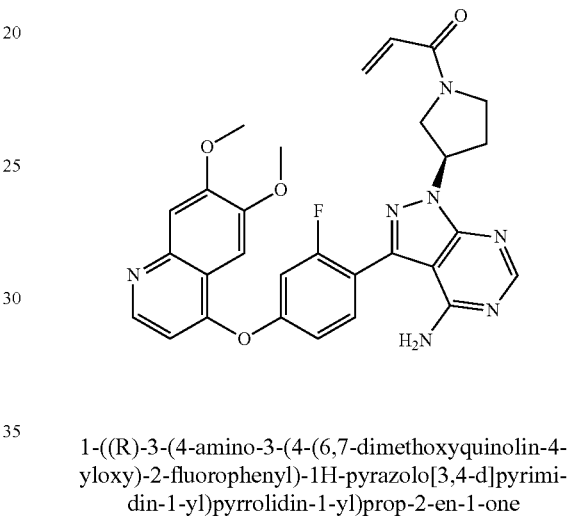

1-((R)-3-(4-amino-3-(4-(6,7-dimethoxyquinolin-4-yloxy)-2-fluorophenyl)-1H-pyrazolo[3,4-d]pyrimidin-1-yl)pyrrolidin-1-yl)prop-2-en-1-one Procedure:

(R)-1-(3-(4-amino-3-iodo-1H-pyrazolo[3,4-d]pyrimidin-1-yl)pyrrolidin-1-yl)prop-2-en-1-one (100 mg, 0.26 mmol, 1.0 eq.), 4-(3-fluoro-4-(4,4,5,5-tetramethyl-1,3,2-dioxaborolan-2-yl)phenoxy)-6,7-dimethoxyquinoline (145 mg, 0.39 mmol, 1.5 eq), sodium carbonate (83 mg, 0.78 mmol, 3.0 eq) and Pd(PPh$_3$)$_4$ (30 mg, 0.026 mmol, 0.1 eq.) were dissolved in 1,4-dioxane/water (10 mL, 1/1, v/v). The reaction mixture was stirred at 85° C. for 30 minutes under nitrogen atmosphere with microwave irradiation. The reaction solution was diluted with water (10 mL) and extracted with ethyl acetate (10 mL×3). The combined organic phases were dried over anhydrous sodium sulfate and filtered. The filtrate was concentrated to give the crude produce, which was purified by HPLC reverse phase column (mobile phase in C18: acetonitrile/water/0.5% HCl, gradient: 10%-100% (volume ratio)) to give the title compound hydrochloride (20 mg, yield: 12%).

LC/MS (Method: UFLC): RT=2.717 min; m/z=556.1 [M+H]$^+$; Total running time 7 min.

$^1$H NMR (400 MHz, CD$_3$OD) δ 8.79 (br, 1H), 8.51 (s, 1H), 7.92-7.86 (m, 2H), 7.57-7.47 (m, 3H), 7.29 (br, 1H), 6.74-6.60 (m, 1H), 6.34-6.29 (m, 1H), 5.82-5.76 (m, 2H), 4.27-4.23 (m, 0.5H), 4.15-4.10 (m, 8H), 3.97-3.82 (m, 1.5H), 2.67-2.59 (m, 2H).

Compound 90

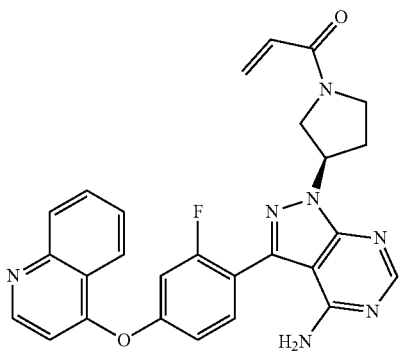 [SMILES: C=CC(=O)N1CC[C@@H](n2nc(-c3ccc(Oc4ccnc5ccccc45)cc3F)c3c(N)ncnc32)C1]

1-((R)-3-(4-amino-3-(2-fluoro-4-(quinolin-4-yloxy)phenyl)-1H-pyrazolo[3,4-d]pyrimidin-1-yl)pyrrolidin-1-yl)prop-2-en-1-one Step A:

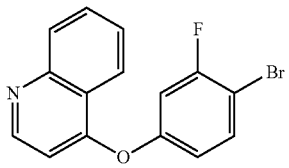 [SMILES: Fc1cc(Oc2ccnc3ccccc23)ccc1Br]

4-(4-bromo-3-fluorophenoxy)quinoline

Procedure:

4-chloro-quinoline (440 mg, 2.7 mmol, 1.0 eq.) was added to a solution of 4-bromo-3-fluorophenol (2.04 g, 10.8 mmol, 4.0 eq.) in chlorobenzene (5 mL). The reaction was stirred at 100° C. for 12 hours and then sodium hydroxide solution (1 N, 10 mL) was added. The resulting mixture was extracted with ethyl acetate (10 mL×3). The combined organic phase with anhydrous sodium sulfate and filtered. The filtrate was concentrated to give the crude product (800 mg, yield: 93%), which was used directly in the next step.

Step B:

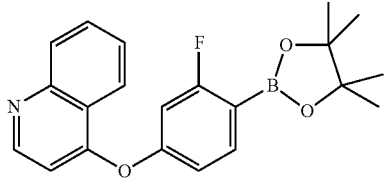 [SMILES: CC1(C)OB(c2ccc(Oc3ccnc4ccccc34)cc2F)OC1(C)C]

4-(3-fluoro-4-(4,4,5,5-tetramethyl-1,3,2-dioxaborolan-2-yl)phenoxy)quinoline

Procedure:

4-(4-bromo-3-fluorophenoxy)quinoline (400 mg, 1.26 mmol, 1.0 eq.), bis(pinacolato)diboron (480 mg, 1.89 mmol, 1.5 eq.), potassium acetate (370 mg, 3.78 mmol, 3.0 eq.) and (1,1'-bis(diphenylphosphino)ferrocene)dichloropalladium (117 mg, 0.126 mmol, 0.1 eq.) were dissolved in 1,4-dioxane (4 mL), and stirred at 85° C. for 12 hours under nitrogen. The reaction mixture was filtered through celite. The filtrate was concentrated to give the crude product (450 mg, yield: 98%), which was used directly in the next step.

Step C:

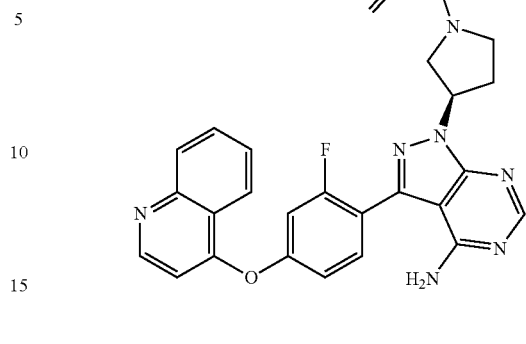

1-((R)-3-(4-amino-3-(2-fluoro-4-(quinolin-4-yloxy)phenyl)-1H-pyrazolo[3,4-d]pyrimidin-1-yl)pyrrolidin-1-yl)prop-2-en-1-one Procedure:

(R)-1-(3-(4-amino-3-iodo-1H-pyrazolo[3,4-d]pyrimidin-1-yl)pyrrolidin-1-yl)prop-2-en-1-one (100 mg, 0.26 mmol, 1.0 eq.), 4-(3-fluoro-4-(4,4,5,5-tetramethyl-1,3,2-dioxaborolan-2-yl)phenoxy)quinoline (142 mg, 0.39 mmol, 1.5 eq), sodium carbonate (83 mg, 0.78 mmol, 3.0 eq) and Pd(PPh$_3$)$_4$ (30 mg, 0.026 mmol, 0.1 eq.) were dissolved in 1,4-dioxane/water (10 mL, 1/1, v/v). The reaction mixture was stirred at 85° C. for 40 minutes under nitrogen atmosphere with microwave irradiation. The reaction solution was diluted with water (10 mL) and extracted with ethyl acetate (10 mL×3). The combined organic phases were dried over anhydrous sodium sulfate and filtered. The filtrate was concentrated to give the crude produce, which was purified by HPLC reverse phase column (mobile phase in C18: acetonitrile/water/0.5% HCl, gradient: 10%-100% (volume ratio)) to give the title compound hydrochloride (15 mg, yield: 10%).

LC/MS (Method: UFLC): RT=2.586 min; m/z=496.1 [M+H]$^+$; Total running time 7 min.

$^1$H NMR (400 MHz, CD$_3$OD) δ 9.08 (d, J=6.8 Hz, 1H), 8.72 (d, J=8.4 Hz, 1H), 8.49 (s, 1H), 8.26-8.20 (m, 2H), 8.06 (br, 1H), 7.91 (d, J=6.8 Hz, 1H), 7.56-7.44 (m, 3H), 6.71-6.57 (m, 1H), 6.31-6.27 (m, 1H), 5.80-5.74 (m, 2H), 4.27-3.92 (m, 4H), 2.70-2.55 (m, 2H).

Compound 91

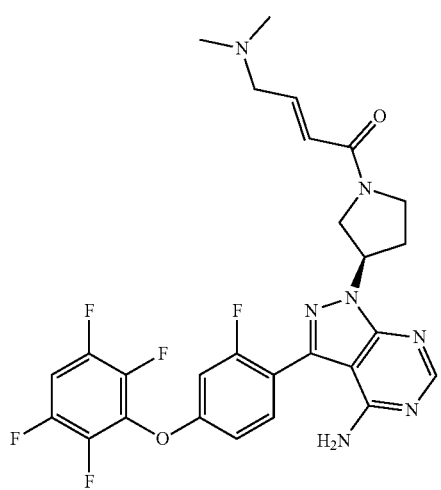 [SMILES: CN(C)C/C=C/C(=O)N1CC[C@@H](n2nc(-c3ccc(Oc4c(F)c(F)cc(F)c4F)cc3F)c3c(N)ncnc32)C1]

(E)-1-((R)-3-(4-amino-3-(2-fluoro-4-(2,3,5,6-tetra-fluorophenoxy)phenyl)-1H-pyrazolo[3,4-d]pyrimidin-1-yl)pyrrolidin-1-yl)-4-(dimethylamino)but-2-en-1-one Procedure:

(E)-4-(dimethylamino)but-2-enoic acid hydrochloride (23 mg, 0.14 mmol, 1.1 eq.), DIPEA (50 mg, 0.39 mmol, 3.0 eq.) and HATU (54 mg, 0.14 mmol, 1.1 eq.) were added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (60 mg, 0.13 mmol, 1.0 eq.) in dichloromethane (3 mL). The reaction was stirred at room temperature for 12 hours, and concentrated to give the crude product, which was purified by HPLC (C18 reverse phase column, mobile phase: acetonitrile/water/0.5% HCl, gradient: 10%-100% (volume ratio)) to give the title compound hydrochloride (29 mg, yield: 40%).

LC/MS (Method: UFLC): RT=3.625 min; m/z=574.1 [M+H]$^+$; Total running time 7 min.

$^1$H NMR (400 MHz, DMSO-$d_6$) δ 11.24 (br, 1H), 8.57 (s, 1H), 8.02-7.95 (m, 1H), 8.62 (t, J=8.4 Hz, 1H), 7.33 (dd, J=2.0, 10.8 Hz, 1H), 7.33 (dd, J=2.0, 8.4 Hz, 1H), 6.76-6.68 (m, 2H), 5.65-5.56 (m, 1H), 4.22-4.16 (m, 0.5H), 4.04-3.87 (m, 4.5H), 3.69-3.58 (m, 1H), 2.71-2.68 (m, 6H), 2.54-2.37 (m, 2H).

Compound 92

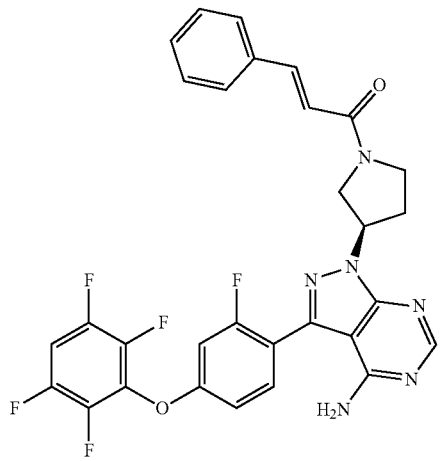 [SMILES: Nc1ncnc2c1c(-c1ccc(Oc3c(F)c(F)cc(F)c3F)cc1F)nn2[C@@H]1CCN(C(=O)/C=C/c2ccccc2)C1]

(E)-1-((R)-3-(4-amino-3-(2-fluoro-4-(2,3,5,6-tetra-fluorophenoxy)phenyl)-1H-pyrazolo[3,4-d]pyrimidin-1-yl)pyrrolidin-1-yl)-3-phenylprop-2-en-1-one Procedure:

Cinnamoyl chloride (19.7 mg, 0.12 mmol, 1.1 eq.) and triethylamine (22 mg, 0.22 mmol, 2.0 eq.) were added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.11 mmol, 1.0 eq.) in dichloromethane (3 mL). The reaction was stirred at room temperature for 2 hours, quenched with water (5 mL) and extracted with methylene chloride (5 mL×3). The combined organic phase with anhydrous sodium sulfate and filtered. The filtrate was concentrated to give the crude product, which was purified by HPLC (C18 reverse phase column, mobile phase: acetonitrile/water/0.5% HCl, gradient 10%-100% (volume ratio)) to give the title compound hydrochloride (16 mg, yield: 25%).

LC/MS (Method: UFLC): RT=4.371 min; m/z=593.1 [M+H]$^+$; Total running time 7 min.

$^1$H NMR (400 MHz, CD$_3$OD) δ 8.46 (s, 1H), 7.68-7.60 (m, 4H), 7.55-7.37 (m, 4H), 7.09-6.92 (m, 3H), 5.81-5.71 (m, 1H), 4.33-4.31 (m, 0.8H), 4.19-3.82 (m, 3.2H), 2.73-2.56 (m, 2H).

Compound 93

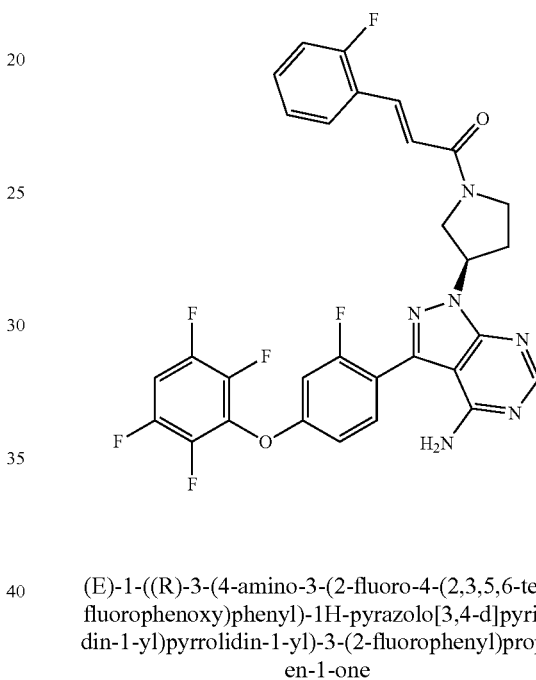

(E)-1-((R)-3-(4-amino-3-(2-fluoro-4-(2,3,5,6-tetra-fluorophenoxy)phenyl)-1H-pyrazolo[3,4-d]pyrimidin-1-yl)pyrrolidin-1-yl)-3-(2-fluorophenyl)prop-2-en-1-one Procedure:

(E)-3-(2-fluorophenyl)acrylic acid (24 mg, 0.14 mmol, 1.1 eq.), DIPEA (50 mg, 0.39 mmol, 3.0 eq.) and HATU (54 mg, 0.14 mmol, 1.1 eq.) were added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (60 mg, 0.13 mmol, 1.0 eq.) in dichloromethane (3 mL). The reaction was stirred at room temperature for 12 hours, and concentrated to give the crude product, which was purified by HPLC (C18 reverse phase column, mobile phase: acetonitrile/water/0.5% HCl, gradient: 10%-100% (volume ratio)) to give the title compound hydrochloride (25 mg, yield: 31%).

LC/MS (Method: UFLC): RT=5.220 min; m/z=611.1 [M+H]$^+$; Total running time 7 min.

$^1$H NMR (400 MHz, DMSO-$d_6$) δ 8.04 (s, 1H), 7.95-7.87 (m, 2H), 7.60-7.55 (m, 2H), 7.48-7.42 (m, 1H), 7.28-7.23 (m, 3H), 7.12-7.06 (m, 2H), 5.64-5.50 (m, 1H), 4.23-4.20 (m, 0.5H), 4.05-3.75 (m, 3.5H), 2.56-2.39 (m, 2H).

Compound 94

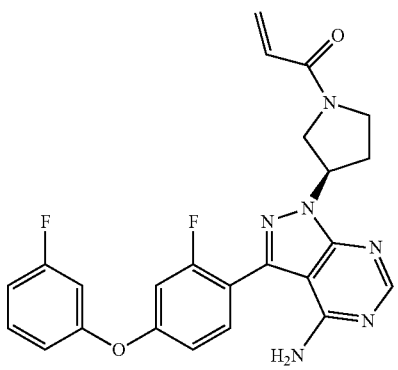 [SMILES: C=CC(=O)N1CC[C@@H](n2nc(-c3ccc(Oc4cccc(F)c4)cc3F)c3c(N)ncnc32)C1]

1-((R)-3-(4-amino-3-(2-fluoro-4-(3-fluorophenoxy)phenyl)-1H-pyrazolo[3,4-d]pyrimidin-1-yl)pyrrolidin-1-yl)prop-2-en-1-one Step A:

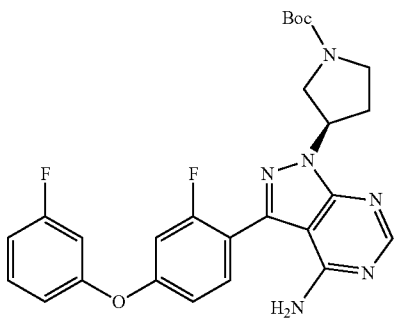 [SMILES: CC(C)(C)OC(=O)N1CC[C@@H](n2nc(-c3ccc(Oc4cccc(F)c4)cc3F)c3c(N)ncnc32)C1]

(3R)-tert-butyl 3-(4-amino-3-(2-fluoro-4-(3-fluorophenoxy)phenyl)-1H-pyrazolo[3,4-d]pyrimidin-1-yl)pyrrolidine-1-carboxylate Procedure:

(R)-tert-butyl 3-(4-amino-3-iodo-1H-pyrazolo[3,4-d]pyrimidin-1-yl)pyrrolidine-1-carboxylate (6.5 g, 15.0 mmol, 1.0 eq.), 2-(2-fluoro-4-(3-fluorophenoxy)phenyl)-4,4,5,5-tetramethyl-1,3,2-dioxaborolane (6.5 g, 19.6 mmol, 1.3 eq.), potassium phosphate (6.4 g, 30.1 mmol, 2.0 eq.) and Pd-118 (0.25 g, 0.39 mmol, 0.01 eq.) was dissolved in 1,4-dioxane/water (160 mL, 1/1, v/v). The reaction solution was stirred at 85° C. for 12 hours under nitrogen atmosphere. After cooling to room temperature, the reaction mixture was diluted with water (50 mL), and then extracted with ethyl acetate (100 mL×3) and. The combined organic phases were dried over anhydrous sodium sulfate, and concentrated to give the crude product, which was purified by silica gel column chromatography (eluent:ethyl acetate) to give the title compound (4.2 g, yield: 55%).

Step B:

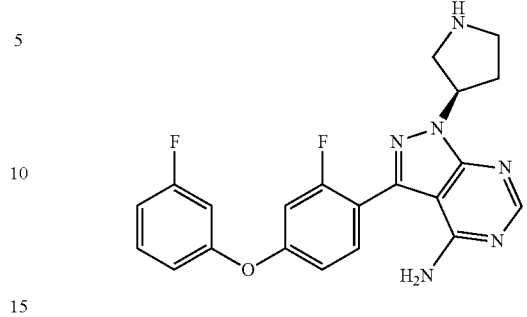

3-(2-fluoro-4-(3-fluorophenoxy)phenyl)-1-((R)-pyrrolidin-3-yl)-1H-pyrazolo[3,4-d]pyrimidin-4-amine Procedure:

4M HCl/EtOAc (10 mL) was added to a solution of (3R)-tert-butyl 3-(4-amino-3-(2-fluoro-4-(3-fluorophenoxy)phenyl)-1H-pyrazolo[3,4-d]pyrimidin-1-yl)pyrrolidine-1-carboxylate (4.2 g, 8.27 mmol) in dichloromethane (15 mL) at 0° C. The reaction mixture was stirred at room temperature for 1 hour and concentrated to give the title compound hydrochloride (3.7 g, yield: 92%).

Step C:

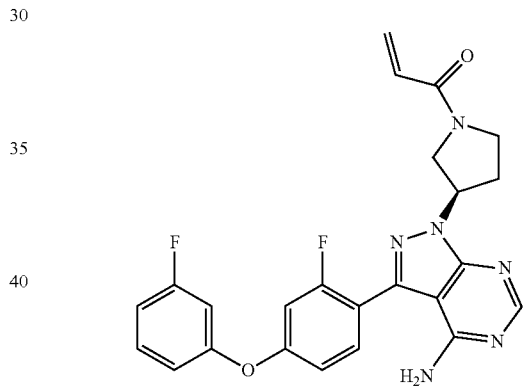

1-((R)-3-(4-amino-3-(2-fluoro-4-(3-fluorophenoxy)phenyl)-1H-pyrazolo[3,4-d]pyrimidin-1-yl)pyrrolidin-1-yl)prop-2-en-1-one Procedure:

NaOH aqueous (10%, 15.3 mL) and acryloyl chloride (0.67 g, 7.44 mmol, 0.9 eq.) were subsequently added dropwise to a solution of 3-(2-fluoro-4-(3-fluorophenoxy)phenyl)-1-((R)-pyrrolidin-3-yl)-1H-pyrazolo[3,4-d]pyrimidin-4-amine (3.7 g, 8.27 mmol, 1.0 eq.) in tetrahydrofuran (20 mL) at 0° C. The reaction was stirred at room temperature for 2 hour, and then quenched with saturated NaHCO$_3$ (20 mL). The aqueous phase was extracted with methylene chloride (30 mL×3). The combined organic phases were dried over anhydrous sodium sulfate, and concentrated to give the crude product, which was purified by silica gel column chromatography (eluent:petroleum ether:ethyl acetate=1:0~1:1) to give the title compound (2.5 g, yield: 65%).

LC/MS (Method: UFLC): RT=3.178 min; m/z=463.0 [M+H]$^+$; Total running time 7 min.

¹H NMR (400 MHz, CDCl₃) δ 8.36 (s, 1H), 7.53-7.49 (m, 1H), 7.40-7.35 (m, 1H), 6.95-6.81 (m, 4H), 6.41-6.39 (m, 2H), 5.69-5.55 (m, 3H), 4.14-3.98 (m, 3H), 3.78-3.72 (m, 1H), 2.71-2.54 (m, 2H).

Compound 95

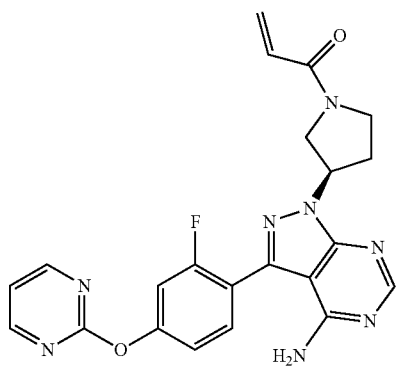 [SMILES: C=CC(=O)N1CC[C@@H](n2nc(-c3ccc(Oc4ncccn4)cc3F)c3c(N)ncnc32)C1]

1-((R)-3-(4-amino-3-(2-fluoro-4-(pyrimidin-2-yloxy)phenyl)-1H-pyrazolo[3,4-d]pyrimidin-1-yl)pyrrolidin-1-yl)prop-2-en-1-one Step A:

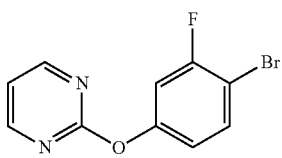 [SMILES: Fc1cc(Oc2ncccn2)ccc1Br]

2-(4-bromo-3-fluorophenoxy)pyrimidine

Procedure:

2-chloropyrimidine (1.98 g, 17.3 mmol, 1.1 eq.) and potassium carbonate (2.6 g, 18.8 mmol, 1.2 eq) were added to a solution of 4-bromo-3-fluorophenol (3.0 g, 15.7 mmol, 1.0 eq.) in acetone (30 mL) and dimethyl sulfoxide (10 mL) was added. The reaction was stirred at 110° C. for 16 hours. After cooled to room temperature, water (100 mL) was added, and then extracted with ethyl acetate (100 mL×3). The combined organic phases were dried over anhydrous sodium sulfate, and the filtrate was concentrated to spin dry, the crude product was purified by silica gel column chromatography (petroleum ether:ethyl acetate=5:1) to give the title compound (930 mg, yield: 22%).

Step B:

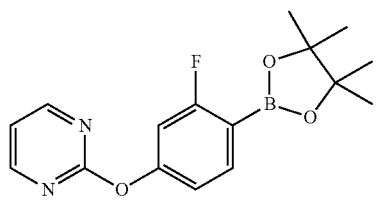 [SMILES: CC1(C)OB(c2ccc(Oc3ncccn3)cc2F)OC1(C)C]

2-(3-fluoro-4-(4,4,5,5-tetramethyl-1,3,2-dioxaborolan-2-yl)phenoxy)pyrimidine

Procedure:

4-(4-bromo-3-fluorophenoxy)-6,7-dimethoxyquinoline (300 mg, 1.11 mmol, 1.0 eq.), bis(pinacolato)diboron (425 mg, 1.67 mmol, 1.5 eq.), potassium acetate (328 mg, 3.34 mmol, 3.0 eq.) and (1,1'-bis(diphenylphosphino)ferrocene)dichloropalladium (89 mg, 0.11 mmol, 0.1 eq.) were dissolved in 1,4-dioxane (3 mL). The resulting mixture was stirred at 85° C. for 12 hours under nitrogen. The reaction mixture was filtered through celite. The filtrate was concentrated to give the crude product (207 mg, yield: 59%), which was used directly in the next step.

Step C:

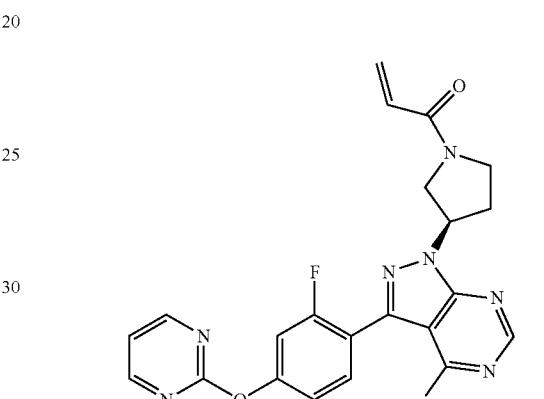

1-((R)-3-(4-amino-3-(2-fluoro-4-(pyrimidin-2-yloxy)phenyl)-1H-pyrazolo[3,4-d]pyrimidin-1-yl)pyrrolidin-1-yl)prop-2-en-1-one Procedure:

(R)-1-(3-(4-amino-3-iodo-1H-pyrazolo[3,4-d]pyrimidin-1-yl)pyrrolidin-1-yl)prop-2-en-1-one (80 mg, 0.21 mmol, 1.0 eq.), 2-(3-fluoro-4-(4,4,5,5-tetramethyl-1,3,2-dioxaborolan-2-yl)phenoxy)pyrimidine (132 mg, 0.42 mmol, 2.0 eq.), sodium carbonate (66 mg, 0.63 mmol, 3.0 eq.) and Pd(PPh₃)₄ (24 mg, 0.021 mmol, 0.1 eq.) were dissolved in 1,4-dioxane/water (2.4 mL, 5/1, v/v). The reaction mixture was stirred at 85° C. for 30 minutes under nitrogen atmosphere with microwave irradiation. The reaction solution was diluted with water (10 mL) and extracted with ethyl acetate (10 mL×3). The combined organic phases were dried over anhydrous sodium sulfate and filtered. The filtrate was concentrated to give the crude produce, which was purified by HPLC reverse phase column (mobile phase in C18: acetonitrile/water/0.5% HCl, gradient: 10%-100% (volume ratio)) to give the title compound hydrochloride (3.5 mg, yield: 3.7%).

LC/MS (Method: UFLC): RT=3.115 min; m/z=447.0 [M+H]⁺; Total running time 7 min.

Compound 96

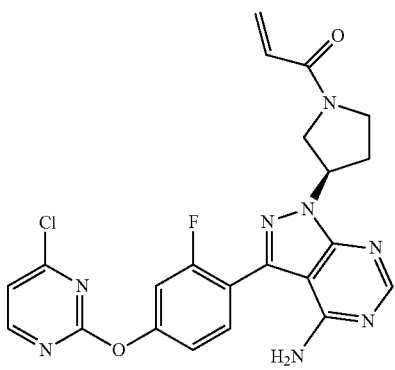 [SMILES: C=CC(=O)N1CC[C@@H](n2nc(-c3ccc(Oc4nccc(Cl)n4)cc3F)c3c(N)ncnc32)C1]

1-((R)-3-(4-amino-3-(4-(4-chloropyrimidin-2-yloxy)-2-fluorophenyl)-1H-pyrazolo[3,4-d]pyrimidin-1-yl)pyrrolidin-1-yl)prop-2-en-1-one Step A:

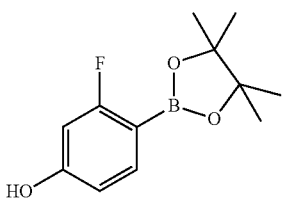 [SMILES: CC1(C)OB(c2ccc(O)cc2F)OC1(C)C]

3-fluoro-4-(4,4,5,5-tetramethyl-1,3,2-dioxaborolan-2-yl)phenol

Procedure:

4-bromo-3-fluorophenol (3.0 g, 15.7 mmol, 1.0 eq.), bis(pinacolato)diboron (5.98 g, 23.6 mmol, 1.5 eq.), potassium acetate (4.62 g, 47.1 mmol, 3.0 eq.), Pd$_2$(dba)$_3$ (1.44 g, 1.57 mmol, 0.1 eq.) and x-phos (749 mg, 1.57 mmol, 0.1 eq.) were dissolved in 1,4-dioxane (30 mL), and stirred at 85° C. for 12 hours under nitrogen. The reaction mixture was filtered through celite. The filtrate was concentrated to give the crude product (3.1 g, yield: 83%), which was used directly in the next step.

Step B:

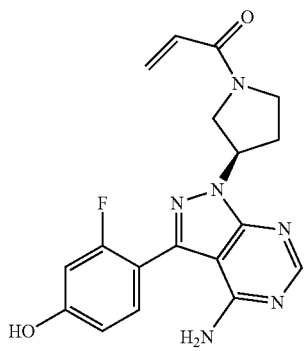 [SMILES: C=CC(=O)N1CC[C@@H](n2nc(-c3ccc(O)cc3F)c3c(N)ncnc32)C1]

1-((R)-3-(4-amino-3-(2-fluoro-4-hydroxyphenyl)-1H-pyrazolo[3,4-d]pyrimidin-1-yl)pyrrolidin-1-yl)prop-2-en-1-one Procedure:

(R)-1-(3-(4-amino-3-iodo-1H-pyrazolo[3,4-d]pyrimidin-1-yl)pyrrolidin-1-yl)prop-2-en-1-one (500 mg, 1.3 mmol, 1.0 eq.), 3-fluoro-4-(4,4,5,5-tetramethyl-1,3,2-dioxaborolan-2-yl)phenol (621 mg, 2.6 mmol, 2.0 eq.), sodium carbonate (415 mg, 3.9 mmol, 3.0 eq.) and Pd(PPh$_3$)$_4$ (150 mg, 0.13 mmol, 0.1 eq.) were dissolved in 1,4-dioxane/water (6 mL, 5/1, v/v). The reaction mixture was stirred at 85° C. for 30 minutes under nitrogen atmosphere with microwave irradiation. The reaction solution was diluted with water (10 mL) and extracted with ethyl acetate (10 mL×3). The combined organic phases were dried over anhydrous sodium sulfate and filtered. The filtrate was concentrated to give the crude produce, which was purified by silica gel column chromatography (petroleum ether:ethyl acetate=1:1) to give the title compound (12 mg, yield: 2.5%).

Step C:

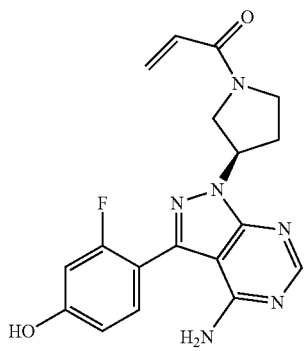 [SMILES: C=CC(=O)N1CC[C@@H](n2nc(-c3ccc(O)cc3F)c3c(N)ncnc32)C1]

1-((R)-3-(4-amino-3-(4-(4-chloropyrimidin-2-yloxy)-2-fluorophenyl)-1H-pyrazolo[3,4-d]pyrimidin-1-yl)pyrrolidin-1-yl)prop-2-en-1-one Procedure:

1-((R)-3-(4-amino-3-(2-fluoro-4-hydroxyphenyl)-1H-pyrazolo[3,4-d]pyrimidin-1-yl)pyrrolidin-1-yl)prop-2-en-1-one (12 mg, 0.033 mmol, 1.0 eq.) in tetrahydrofuran (2 mL) was added NaH (1.3 mg, 0.033 mmol, 1.0 eq.). The reaction was stirred at 0° C. for 30 minutes followed by the addition of 4-chloro-2-(methylsulfonyl)pyrimidine (6.3 mg, 0.033 mmol, 1.0 eq.). The reaction was stirred overnight at room temperature, diluted with water (10 mL), and extracted with ethyl acetate (10 mL×3). The combined organic phases were dried over anhydrous sodium sulfate and filtered. The filtrate was concentrated to give the crude produce, which was purified by HPLC reverse phase column (mobile phase in C18: acetonitrile/water/0.5% HCl, gradient: 10%-100% (volume ratio)) to give the title compound hydrochloride (4.1 mg, yield: 26%).

LC/MS (Method: UFLC): RT=3.554 min; m/z=481.0 [M+H]$^+$; Total running time 7 min.

Compound 97

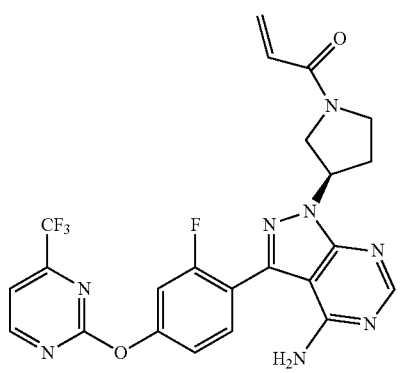 [SMILES: C=CC(=O)N1CC[C@@H](n2nc(-c3ccc(Oc4nccc(C(F)(F)F)n4)cc3F)c3c(N)ncnc32)C1]

1-((R)-3-(4-amino-3-(2-fluoro-4-(4-(trifluoromethyl)pyrimidin-2-yloxy)phenyl)-1H-pyrazolo[3,4-d]pyrimidin-1-yl)pyrrolidin-1-yl)prop-2-en-1-one Step A:

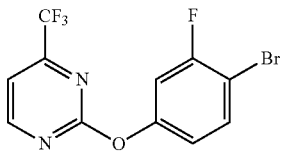 [SMILES: Fc1cc(Oc2nccc(C(F)(F)F)n2)ccc1Br]

2-(4-bromo-3-fluorophenoxy)-4-(trifluoromethyl)pyrimidine

Procedure:

2-chloro-4-(trifluoromethyl)pyrimidine (4.2 g, 23.0 mmol, 1.1 eq.) and potassium carbonate (3.5 g, 25.1 mmol, 1.2 eq) were added to a solution of 4-bromo-3-fluorophenol (4.0 g, 20.9 mmol, 1.0 eq.) in butanone (15 mL) and dimethyl sulfoxide (5 mL). The reaction was stirred at 100° C. for 12 hours. After cooled to room temperature, water (20 mL) was added, and then extracted with ethyl acetate (20 mL×3). The combined organic phases were dried over anhydrous sodium sulfate, and the filtrate was concentrated to spin dry, the crude product was isolated by HPLC (C18 reverse phase column in a mobile phase: acetonitrile/water, gradient: 10% to 100% (volume ratio)) to give the title compound (500 mg, yield: 7%).

Step B:

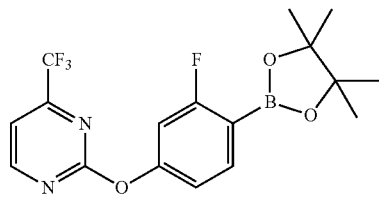 [SMILES: CC1(C)OB(c2ccc(Oc3nccc(C(F)(F)F)n3)cc2F)OC1(C)C]

2-(3-fluoro-4-(4,4,5,5-tetramethyl-1,3,2-dioxaborolan-2-yl)phenoxy)-4-(trifluoromethyl)pyrimidine Procedure:

2-(4-bromo-3-fluorophenoxy)-4-(trifluoromethyl)pyrimidine (300 mg, 0.89 mmol, 1.0 eq.), bis(pinacolato)diboron (452 mg, 1.78 mmol, 2.0 eq.), potassium acetate (272 mg, 2.78 mmol, 3.0 eq.) and (1,1'-bis(diphenylphosphino)ferrocene)dichloropalladium (40 mg, 0.05 mmol, 0.06 eq.) were dissolved in 1,4-dioxane (2 mL), and stirred at 85° C. for 12 hours under nitrogen. The reaction mixture was filtered through celite. The filtrate was concentrated to give the crude product (340 mg, yield: 100%), which was used directly in the next step.

Step C:

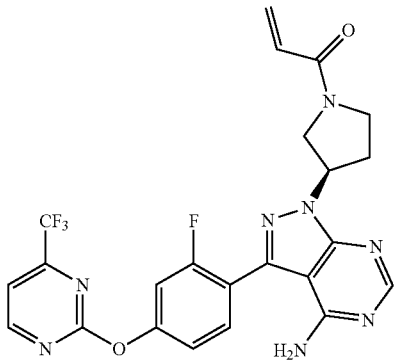 [SMILES: C=CC(=O)N1CC[C@@H](n2nc(-c3ccc(Oc4nccc(C(F)(F)F)n4)cc3F)c3c(N)ncnc32)C1]

1-((R)-3-(4-amino-3-(2-fluoro-4-(4-(trifluoromethyl)pyrimidin-2-yloxy)phenyl)-1H-pyrazolo[3,4-d]pyrimidin-1-yl)pyrrolidin-1-yl)prop-2-en-1-one Procedure:

(R)-1-(3-(4-amino-3-iodo-1H-pyrazolo[3,4-d]pyrimidin-1-yl)pyrrolidin-1-yl)prop-2-en-1-one (80 mg, 0.21 mmol, 1.0 eq.), 2-(3-fluoro-4-(4,4,5,5-tetramethyl-1,3,2-dioxaborolan-2-yl)phenoxy)-4-(trifluoromethyl)pyrimidine (160 mg, 0.42 mmol, 2.0 eq.), potassium carbonate (86 mg, 0.63 mmol, 3.0 eq.) and Pd(PPh$_3$)$_4$ (24 mg, 0.021 mmol, 0.1 eq.) were dissolved in 1,4-dioxane/water (10 mL, 1/1, v/v). The reaction mixture was stirred at 85° C. for 40 minutes under nitrogen atmosphere with microwave irradiation. The reaction solution was diluted with water (10 mL) and extracted with ethyl acetate (10 mL×3). The combined organic phases were dried over anhydrous sodium sulfate and filtered. The filtrate was concentrated to give the crude produce, which was purified by HPLC (C18 reverse phase column, mobile phase: acetonitrile/water/0.5% HCl, gradient: 10%-100% (volume ratio)) to give the title compound hydrochloride (14 mg, yield: 6%).

LC/MS (Method: UFLC): RT=2.800 min; m/z=515.0 [M+H]$^+$; Total running time 7 min.

285

Compound 98

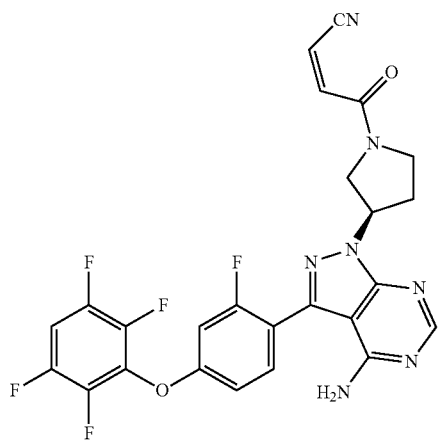 [SMILES: N#C/C=C\C(=O)N1CC[C@@H](n2nc(-c3ccc(Oc4c(F)c(F)cc(F)c4F)cc3F)c3c(N)ncnc32)C1]

(Z)-4-((R)-3-(4-amino-3-(2-fluoro-4-(2,3,5,6-tetra-fluorophenoxy)phenyl)-1H-pyrazolo[3,4-d]pyrimidin-1-yl)pyrrolidin-1-yl)-4-oxobut-2-enenitrile Procedure:

3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.108 mmol, 1.0 eq.) in DMF (3 mL) was added potassium (Z)-3-cyanoacrylate (29 mg, 0.216 mmol, 2.0 eq.), PyBrop (60 mg, 0.130 mmol, 1.2 eq.), N, N-diisopropylethylamine (42 mg, 0.324 mmol, 3.0 eq.). The reaction was stirred at 0° C. for 5 hours, and concentrated to give the crude product, which was purified by HPLC (C18 reverse phase column, mobile phase: acetonitrile/water/0.7% NH₄HCO₃, gradient: 10%-100% (by volume ratio)) to give the title compound (14 mg, yield: 24%).

LC/MS (Method: UFLC): RT=2.545 min; m/z=542.0 [M+H]⁺; Total running time 7 min.

¹H NMR (400 MHz, CD₃OD) δ 8.24 (s, 1H), 7.61-7.58 (m, 1H), 7.48-7.43 (m, 1H), 7.19-7.01 (m, 3H), 6.08-6.01 (m, 1H), 5.62-5.56 (m, 1H), 4.16-4.14 (m, 1H), 4.05-3.98 (m, 1.5H), 3.88-3.83 (m, 1H), 3.75-3.70 (m, 0.5H), 2.61-2.51 (m, 2H).

Compounds 99 and 100

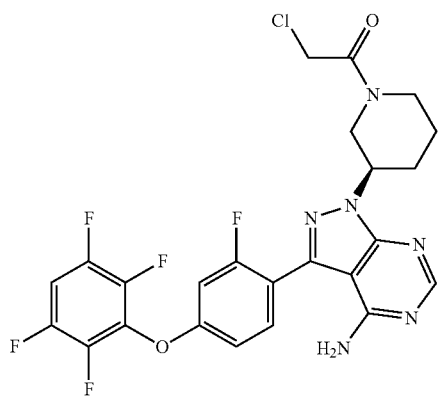 [SMILES: Nc1ncnc2c1c(-c1ccc(Oc3c(F)c(F)cc(F)c3F)cc1F)nn2[C@@H]1CCCN(C(=O)CCl)C1]

286

1-((R)-3-(4-amino-3-(2-fluoro-4-(2,3,5,6-tetrafluoro-phenoxy)phenyl)-1H-pyrazolo[3,4-d]pyrimidin-1-yl)piperidin-1-yl)-2-chloroethanone

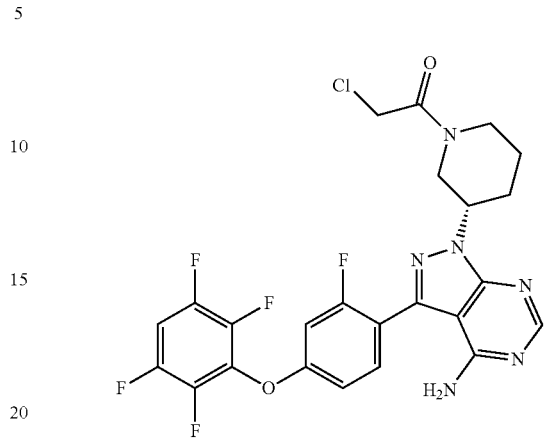

1-((S)-3-(4-amino-3-(2-fluoro-4-(2,3,5,6-tetrafluoro-phenoxy)phenyl)-1H-pyrazolo[3,4-d]pyrimidin-1-yl)piperidin-1-yl)-2-chloroethanone Step A:

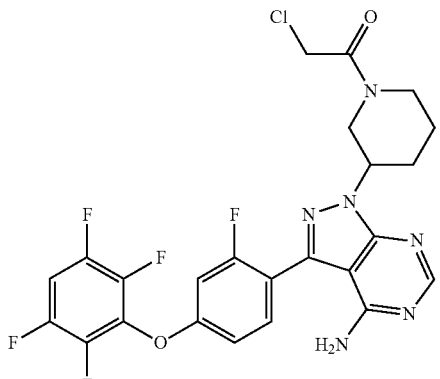

1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-chloroethanone Procedure:

Triethylamine (2 mL) and a solution of chloroacetyl chloride (21 mg, 0.19 mmol, 0.9 eq.) in dichloromethane (1 mL) were added dropwise to a solution of 3-(2-fluoro-4-(2,3,5,6-tetrafluorophenoxy)phenyl)-1-(piperidin-3-yl)-1H-pyrazolo[3,4-d]pyrimidin-4-amine (100 mg, 0.21 mmol, 1.0 eq.) in dichloromethane (10 mL) at 0° C. The reaction was stirred at room temperature for 2 hours, quenched with saturated NaHCO₃ (20 mL), and extracted with methylene chloride (30 mL×3). The combined organic layers were and concentrated to give the crude product, which was purified by HPLC (C18 reverse phase column, mobile phase: acetonitrile/water/7‰ NH₄HCO₃, gradient: 10%-100% (by volume ratio)) to give the title compound (80 mg, yield: 69%).

Step B:

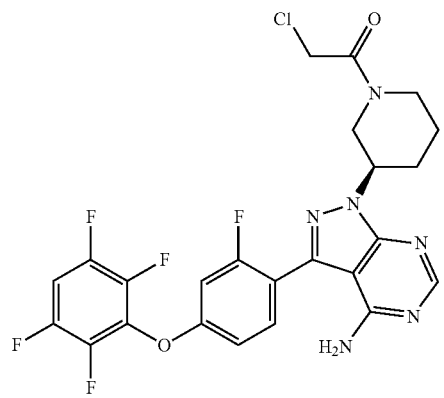 [SMILES: Nc1ncnc2c1c(-c1ccc(Oc3c(F)c(F)cc(F)c3F)cc1F)nn2[C@@H]1CCCN(C(=O)CCl)C1]

1-((R)-3-(4-amino-3-(2-fluoro-4-(2,3,5,6-tetrafluoro-phenoxy)phenyl)-1H-pyrazolo[3,4-d]pyrimidin-1-yl)piperidin-1-yl)-2-chloroethanone

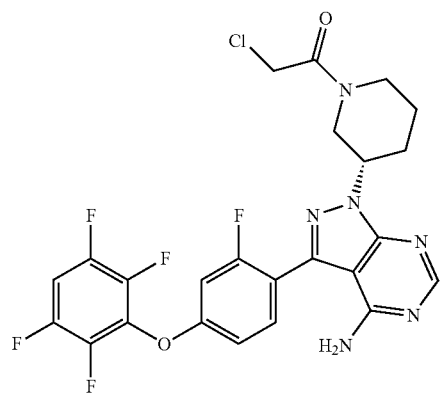 [SMILES: Nc1ncnc2c1c(-c1ccc(Oc3c(F)c(F)cc(F)c3F)cc1F)nn2[C@H]1CCCN(C(=O)CCl)C1]

1-((S)-3-(4-amino-3-(2-fluoro-4-(2,3,5,6-tetrafluoro-phenoxy)phenyl)-1H-pyrazolo[3,4-d]pyrimidin-1-yl)piperidin-1-yl)-2-chloroethanone Procedure:

1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2-chloroethanone was separated by supercritical fluid chromatogram to give Compound 99 (20 mg, yield: 25%) and Compound 100 (35 mg, yield: 44%).

Compound 99:

LC/MS (Method: UFLC): RT=3.566 min; m/z=552.9 [M+H]$^+$; Total running time 7 min.

Compound 100:

LC/MS (Method: UFLC): RT=3.572 min; m/z=552.9 [M+H]$^+$; Total running time 7 min.

Compounds 101 and 102

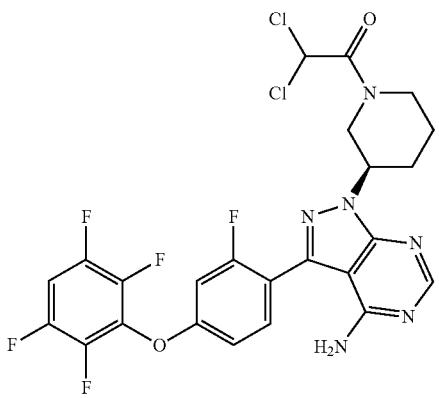 [SMILES: Nc1ncnc2c1c(-c1ccc(Oc3c(F)c(F)cc(F)c3F)cc1F)nn2[C@@H]1CCCN(C(=O)C(Cl)Cl)C1]

1-((R)-3-(4-amino-3-(2-fluoro-4-(2,3,5,6-tetrafluoro-phenoxy)phenyl)-1H-pyrazolo[3,4-d]pyrimidin-1-yl)piperidin-1-yl)-2,2-dichloroethanone

1-((S)-3-(4-amino-3-(2-fluoro-4-(2,3,5,6-tetrafluoro-phenoxy)phenyl)-1H-pyrazolo[3,4-d]pyrimidin-1-yl)piperidin-1-yl)-2,2-dichloroethanone Step A:

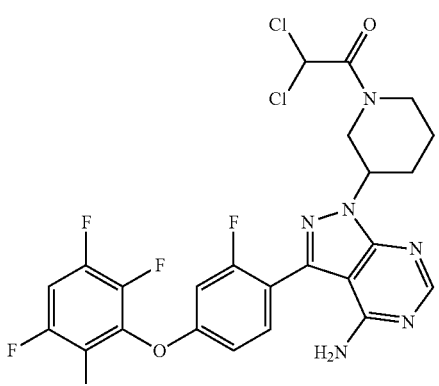

289

1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2,2-dichloroethanone Procedure:

Triethylamine (2 mL) and a solution of 2,2-dichloroacetyl chloride (28 mg, 0.19 mmol, 0.9 eq.) in dichloromethane (1 mL) were added dropwise to a solution of 3-(2-fluoro-4-(2,3,5,6-tetrafluorophenoxy)phenyl)-1-(piperidin-3-yl)-1H-pyrazolo[3,4-d]pyrimidin-4-amine (100 mg, 0.21 mmol, 1.0 eq.) in dichloromethane (10 mL) at 0° C. The reaction was stirred at room temperature for 2 hours, quenched with saturated NaHCO$_3$ (20 mL), and extracted with methylene chloride (30 mL×3). The combined organic layers were and concentrated to give the crude product, which was purified by HPLC (C18 reverse phase column, mobile phase: acetonitrile/water/7‰ NH$_4$HCO$_3$, gradient: 10%-100% (by volume ratio)) to give the title compound (80 mg, yield: 65%).

Step B:

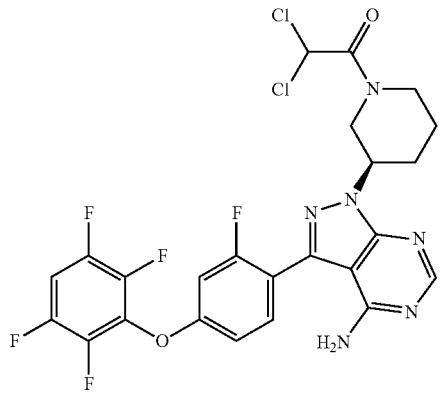 [SMILES: Nc1ncnc2c1c(-c1ccc(Oc3c(F)c(F)cc(F)c3F)cc1F)nn2[C@@H]1CCCN(C(=O)C(Cl)Cl)C1]

1-((R)-3-(4-amino-3-(2-fluoro-4-(2,3,5,6-tetrafluorophenoxy)phenyl)-1H-pyrazolo[3,4-d]pyrimidin-1-yl)piperidin-1-yl)-2,2-dichloroethanone

290

1-((S)-3-(4-amino-3-(2-fluoro-4-(2,3,5,6-tetrafluorophenoxy)phenyl)-1H-pyrazolo[3,4-d]pyrimidin-1-yl)piperidin-1-yl)-2,2-dichloroethanone Procedure:
1-(3-(4-amino-3-(2-fluoro-4-(2,3,5,6-tetrafluorophenoxy)phenyl)-1H-pyrazolo[3,4-d]pyrimidin-1-yl)piperidin-1-yl)-2,2-dichloroethanone was separated by supercritical fluid chromatogram to give Compound 101 (18 mg, yield: 23%) and Compound 102 (30 mg, yield: 38%).

Compound 101:
LC/MS (Method: UFLC): RT=3.788 min; m/z=586.9 [M+H]$^+$; Total running time 7 min.

Compound 102:
LC/MS (Method: UFLC): RT=3.793 min; m/z=586.9 [M+H]$^+$; Total running time 7 min.

Compound 103

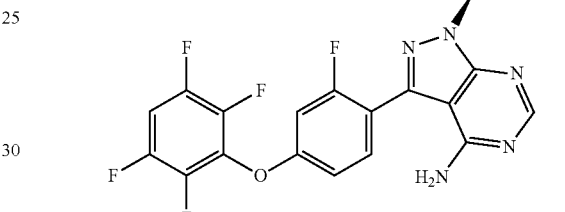

1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2,2-dichloroethanone Procedure:
DIPEA (42 mg, 0.324 mmol, 3.0 eq.) and a solution of 2,2-dichloroacetyl chloride (34 mg, 0.162 mmol, 1.5 eq.) were added dropwise to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.108 mmol, 1.0 eq.) in dichloromethane (10 mL) at 0° C. The reaction was stirred 0° C. for 5 hours, and concentrated to give the crude product, which was purified by HPLC (C18 reverse phase column, mobile phase: acetonitrile/water/0.5% HCl, gradient: 10%-100% (by volume ratio)) to give the title compound (26 mg, yield: 40%).

LC/MS (Method: UFLC): RT=4.760 min; m/z=572.9 [M+H]$^+$; Total running time 7 min.

Compound 104

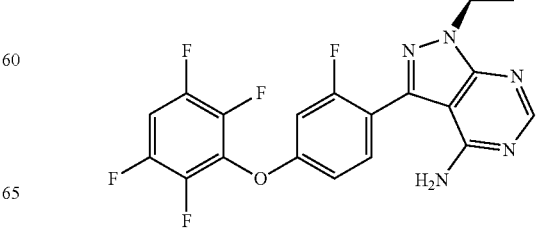

(E)-1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)but-2-en-1-one Procedure:

Triethylamine (30 mg, 0.3 mmol, 3.0 eq.) and (E)-but-2-enoyl chloride (10 mg, 0.1 mmol, 1.0 eq.) were added dropwise to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.1 mmol, 1.0 eq.) in dichloromethane (3 mL) at 0° C. The reaction was stirred at room temperature overnight, and concentrated to give the crude product, which was purified by HPLC (C18 reverse phase column, mobile phase: acetonitrile/water/0.5% HCl, gradient: 10%-100% (by volume ratio)) to give the title compound (19 mg, yield: 36%).

LC/MS (Method: UFLC): RT=3.854 min; m/z=553.0 [M+Na]$^+$; Total running time 7 min.

Compound 105

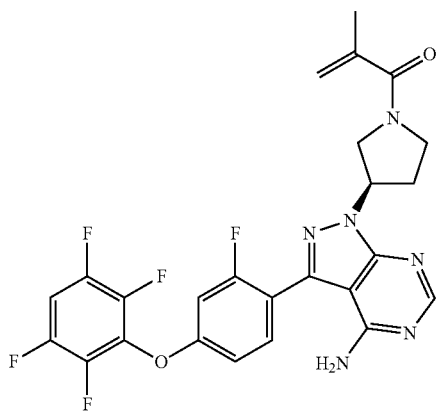 [SMILES: C=C(C)C(=O)N1CC[C@@H](n2nc(-c3ccc(Oc4c(F)c(F)cc(F)c4F)cc3F)c3c(N)ncnc32)C1]

1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2-methylprop-2-en-1-one Procedure:

2-methacrylic acid (11 mg, 0.134 mmol, 1.2 eq.), HATU (53 mg, 0.140 mmol, 1.3 eq.) and N, N-diisopropylethylamine (42 mg, 0.324 mmol, 1.0 eq.) were subsequently added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.108 mmol, 1.0 eq.) in dichloromethane (10 mL) at 0° C. The reaction was stirred at room temperature for 5 hours, diluted with water (10 mL), and then extracted with dichloromethane (10 mL×3). The combined organic phases were dried over anhydrous sodium sulfate, and concentrated to spin dry, the crude product was isolated by HPLC reverse phase column (mobile phase in C18: acetonitrile/water/0.5% HCl, gradient: 10%-100% (volume ratio)) to give the title compound hydrochloride (18 mg, yield: 32%).

LC/MS (Method: UFLC): RT=4.557 min; m/z=532.1 [M+H]$^+$; Total running time 7 min.

$^1$H NMR (400 MHz, CD$_3$OD) δ 8.44-8.43 (m, 1H), 7.71-7.65 (m, 1H), 7.53-7.47 (m, 1H), 7.13-7.06 (m, 2H), 5.76-5.65 (m, 1H), 5.36-5.32 (m, 1H), 5.24-5.21 (m, 1H), 4.21-3.99 (m, 2.5H), 3.88-3.80 (m, 1H), 3.70-3.65 (m, 0.5H), 2.59-2.52 (m, 2H), 1.94-1.89 (m, 3H).

Compound 106

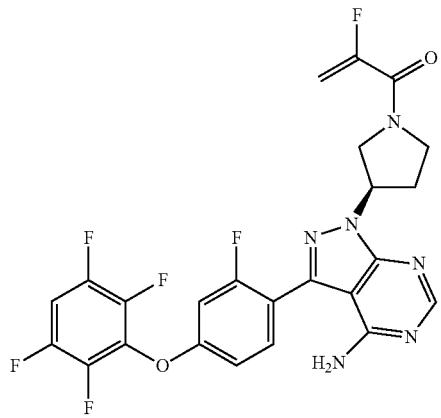 [SMILES: C=C(F)C(=O)N1CC[C@@H](n2nc(-c3ccc(Oc4c(F)c(F)cc(F)c4F)cc3F)c3c(N)ncnc32)C1]

1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2-fluoroprop-2-en-1-one Procedure:

2-fluoroacrylic acid (11 mg, 0.134 mmol, 1.2 eq.), HATU (53 mg, 0.140 mmol, 1.3 eq.) and N, N-diisopropylethylamine (42 mg, 0.324 mmol, 1.0 eq.) were subsequently added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.108 mmol, 1.0 eq.) in dichloromethane (10 mL) at 0° C. The reaction was stirred at room temperature for 5 hours, diluted with water (10 mL), and then extracted with dichloromethane (10 mL×3). The combined organic phases were dried over anhydrous sodium sulfate, and concentrated to spin dry, the crude product was isolated by HPLC reverse phase column (mobile phase in C18: acetonitrile/water/0.5% HCl, gradient: 10%-100% (volume ratio)) to give the title compound hydrochloride (10 mg, yield: 18%).

LC/MS (Method: UFLC): RT=4.624 min; m/z=535.0 [M+H]$^+$; Total running time 7 min.

$^1$H NMR (400 MHz, CD$_3$OD) δ 8.43-8.42 (m, 1H), 7.77-7.66 (m, 1H), 7.55-7.47 (m, 1H), 7.12-7.06 (m, 2H), 5.71-5.68 (m, 1H), 5.54-5.52 (m, 0.5H), 5.42-5.41 (m, 0.5H), 5.31-5.26 (m, 1H), 4.28-4.26 (m, 1H), 4.13-4.08 (m, 1.5H), 3.95-3.76 (m, 1.5H), 2.76-2.52 (m, 2H).

Compounds 107 and 108

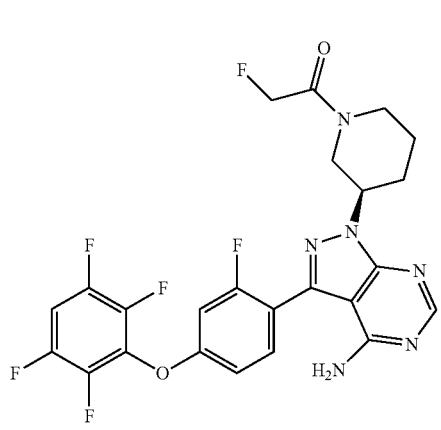 [SMILES: Nc1ncnc2c1c(-c1ccc(Oc3c(F)c(F)cc(F)c3F)cc1F)nn2[C@@H]1CCCN(C(=O)CF)C1]

1-((R)-3-(4-amino-3-(2-fluoro-4-(2,3,5,6-tetrafluoro-phenoxy)phenyl)-1H-pyrazolo[3,4-d]pyrimidin-1-yl)piperidin-1-yl)-2-fluoroethanone Step B:

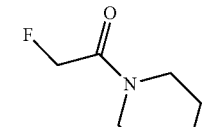

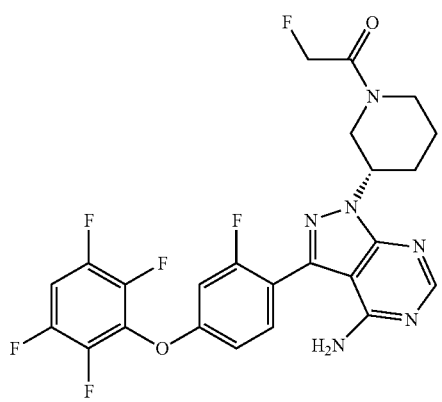

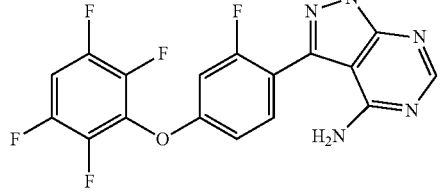

1-((S)-3-(4-amino-3-(2-fluoro-4-(2,3,5,6-tetrafluoro-phenoxy)phenyl)-1H-pyrazolo[3,4-d]pyrimidin-1-yl)piperidin-1-yl)-2-fluoroethanone 1-((R)-3-(4-amino-3-(2-fluoro-4-(2,3,5,6-tetrafluoro-phenoxy)phenyl)-1H-pyrazolo[3,4-d]pyrimidin-1-yl)piperidin-1-yl)-2-fluoroethanone Step A:

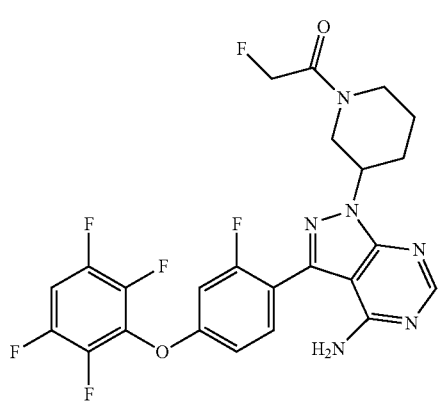 [SMILES: Nc1ncnc2c1c(-c1ccc(Oc3c(F)c(F)cc(F)c3F)cc1F)nn2C1CCCN(C(=O)CF)C1]

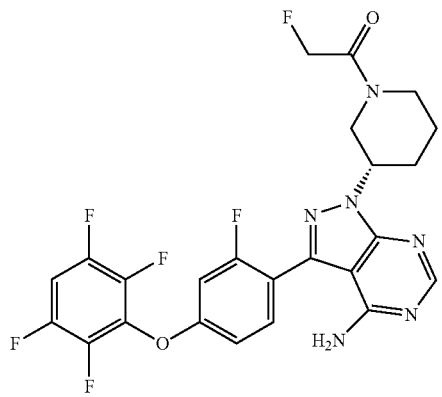

1-(3-(4-amino-3-(2-fluoro-4-(2,3,5,6-tetrafluorophe-noxy)phenyl)-1H-pyrazolo[3,4-d]pyrimidin-1-yl)piperidin-1-yl)-2-fluoroethanone Procedure:

Triethylamine (2 mL) and 2-fluoroacetyl chloride (18 mg, 0.19 mmol, 0.9 eq.) were added dropwise to a solution of 3-(2-fluoro-4-(2,3,5,6-tetrafluorophenoxy)phenyl)-1-((R)-piperidin-3-yl)-1H-pyrazolo[3,4-d]pyrimidin-4-amine (100 mg, 0.21 mmol, 1.0 eq.) in dichloromethane (10 mL) at 0° C. The reaction was stirred at room temperature overnight, and then quenched with saturated NaHCO$_3$ (20 mL). The aqueous phase was extracted with methylene chloride (30 mL×3). The combined organic phases were dried over anhydrous sodium sulfate and filtered. The filtrate was concentrated to give the crude product, which was purified by HPLC (C18 reverse phase column, mobile phase: acetonitrile/water/0.7% NH$_4$HCO$_3$, gradient: 10%-100% (by volume ratio)) to give the title compound (30 mg, yield: 29%).

1-((S)-3-(4-amino-3-(2-fluoro-4-(2,3,5,6-tetrafluoro-phenoxy)phenyl)-1H-pyrazolo[3,4-d]pyrimidin-1-yl)piperidin-1-yl)-2-fluoroethanone Procedure:

1-(3-(4-amino-3-(2-fluoro-4-(2,3,5,6-tetrafluorophe-noxy)phenyl)-1H-pyrazolo[3,4-d]pyrimidin-1-yl)piperidin-1-yl)-2-fluoroethanone was separated by supercritical fluid chromatogram to give Compound 107 (13 mg, yield: 43%) and Compound 108 (14 mg, yield: 47%).

Compound 107:

LC/MS (Method: UFLC): RT=3.362 min; m/z=537.1 [M+H]$^+$; Total running time 7 min.

Compound 108:

LC/MS (Method: UFLC): RT=3.359 min; m/z=537.1 [M+H]$^+$; Total running time 7 min.

Compound 109

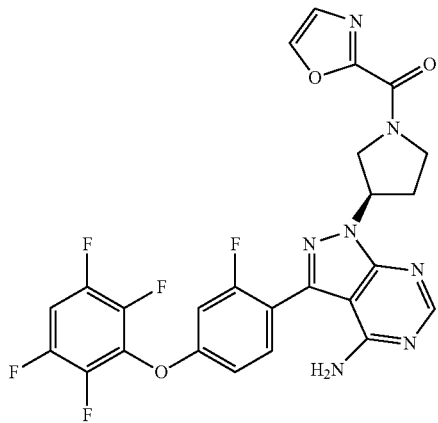 [SMILES: Nc1ncnc2c1c(-c1ccc(Oc3c(F)c(F)cc(F)c3F)cc1F)nn2[C@@H]1CCN(C(=O)c2ncco2)C1]

((R)-3-(4-amino-3-(2-fluoro-4-(2,3,5,6-tetrafluoro-phenoxy)phenyl)-1H-pyrazolo[3,4-d]pyrimidin-1-yl)pyrrolidin-1-yl)(oxazol-2-yl)methanone Procedure:

Oxazole-2-carboxylic acid (16 mg, 0.143 mmol, 1.1 eq.), HATU (54 mg, 0.143 mmol, 1.1 eq.) and N,N-diisopropylethylamine (50 mg, 0.389 mmol, 3.0 eq.) were subsequently added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (60 mg, 0.130 mmol, 1.0 eq.) in dichloromethane (3 mL) at 0° C. The reaction was stirred at room temperature for 5 hours, diluted with water (10 mL), and then extracted with dichloromethane (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.5% HCl, gradient: 10%-100% (volume ratio)) to give the title compound hydrochloride (24 mg, yield: 33%).

LC/MS (Method: UFLC): RT=4.417 min; m/z=558.1 [M+H]$^+$; Total running time 7 min.

Compound 110

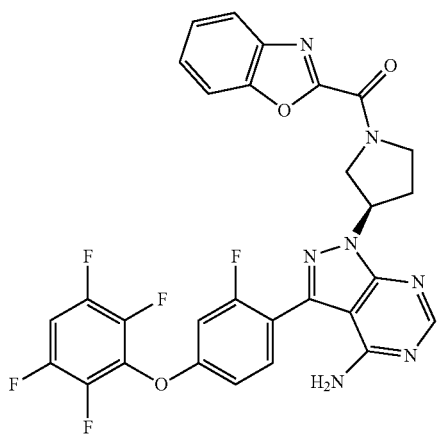 [SMILES: Nc1ncnc2c1c(-c1ccc(Oc3c(F)c(F)cc(F)c3F)cc1F)nn2[C@@H]1CCN(C(=O)c2nc3ccccc3o2)C1]

((R)-3-(4-amino-3-(2-fluoro-4-(2,3,5,6-tetrafluoro-phenoxy)phenyl)-1H-pyrazolo[3,4-d]pyrimidin-1-yl)pyrrolidin-1-yl)(benzo[d]oxazol-2-yl)methanone Procedure:

Benzo[d]oxazole-2-carboxylic acid (26 mg, 0.163 mmol, 1.5 eq.), HATU (45 mg, 0.119 mmol, 1.1 eq.) and N,N-diisopropylethylamine (42 mg, 0.324 mmol, 3.0 eq.) were subsequently added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.108 mmol, 1.0 eq.) in N,N-dimethylformamide (3 mL) at 0° C. The reaction was stirred at room temperature for 5 hours, diluted with water (10 mL), and then extracted with dichloromethane (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.5% HCl, gradient: 10%-100% (volume ratio)) to give the title compound hydrochloride (8.7 mg, yield: 13%).

LC/MS (Method: UFLC): RT=5.007 min; m/z=608.1 [M+H]$^+$; Total running time 7 min.

Compound 111

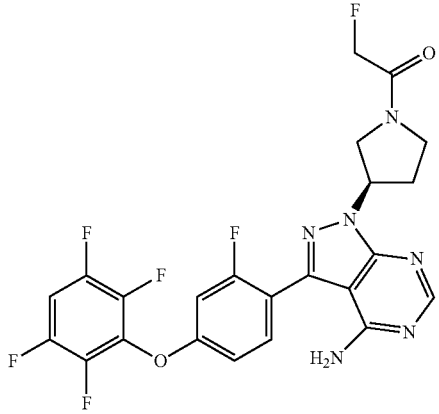 [SMILES: Nc1ncnc2c1c(-c1ccc(Oc3c(F)c(F)cc(F)c3F)cc1F)nn2[C@@H]1CCN(C(=O)CF)C1]

1-((R)-3-(4-amino-3-(2-fluoro-4-(2,3,5,6-tetrafluoro-phenoxy)phenyl)-1H-pyrazolo[3,4-d]pyrimidin-1-yl)pyrrolidin-1-yl)-2-fluoroethanone Procedure:

Triethylamine (60 mg, 0.6 mmol, 3.0 eq.) and 2-fluoroacetyl chloride (18 mg, 0.2 mmol, 1.0 eq.) were added dropwise to a solution of 3-(2-fluoro-4-(2,3,5,6-tetrafluoro-phenoxy)phenyl)-1-((R)-pyrrolidin-3-yl)-1H-pyrazolo[3,4-d]pyrimidin-4-amine hydrochloride (100 mg, 0.20 mmol, 1.0 eq.) in dichloromethane (3 mL) at 0° C. The reaction was stirred at room temperature for 16 hours, diluted with water (10 mL), and then extracted with dichloromethane (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.5% HCl, gradient: 10%-100% (volume ratio)) to give the title compound hydrochloride (9.5 mg, yield: 9%).

LC/MS (Method: UFLC): RT=3.516 min; m/z=523.3 [M+H]$^+$; Total running time 7 min.

Compound 112

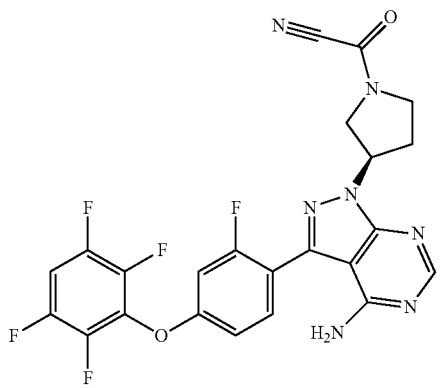 [SMILES: N#CC(=O)N1CC[C@@H](n2nc(-c3ccc(Oc4c(F)c(F)cc(F)c4F)cc3F)c3c(N)ncnc32)C1]

2-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2-oxoacetonitrile Step A:

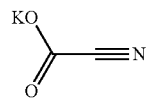

potassium cyanoformate

Procedure:

Potassium hydroxide (267 mg, 0.157 mmol, 1.0 eq.) was added to a solution of ethyl cyanoformate (300 mg, 0.157 mmol, 1.0 eq.) in tetrahydrofuran/water (10 mL/10 mL) at 0° C. The reaction was stirred at room temperature for 12 hours, and concentrated to give the title compound (570 mg, yield: 100%).

Step B:

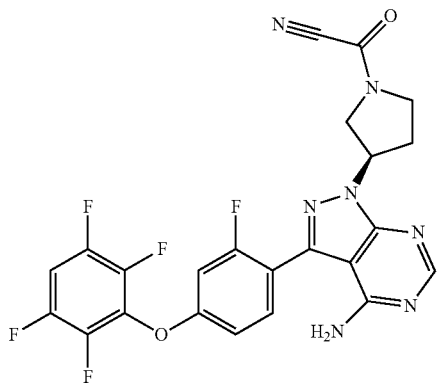 [SMILES: N#CC(=O)N1CC[C@@H](n2nc(-c3ccc(Oc4c(F)c(F)cc(F)c4F)cc3F)c3c(N)ncnc32)C1]

2-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2-oxoacetonitrile Procedure:

Triethylamine (39 mg, 0.39 mmol, 3.0 eq.), PyBrop (132 mg, 0.26 mmol, 2.0 eq.) and potassium cyanoformate (28 mg, 0.26 mmol, 2.0 eq.) were added dropwise to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (60 mg, 0.13 mmol, 1.0 eq.) in N,N-dimethylformamide (3 mL) at 0° C. The reaction was stirred at room temperature for 12 hours, quenched with saturated NaHCO$_3$ (10 mL), and then extracted with dichloromethane (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.7% NH$_4$HCO$_3$, gradient: 10%-100% (volume ratio)) to give the title compound (10 mg, yield: 15%).

LC/MS (Method: UFLC): RT=2.258 min; m/z=515.5 [M+H]$^+$; Total running time 7 min.

Compound 113

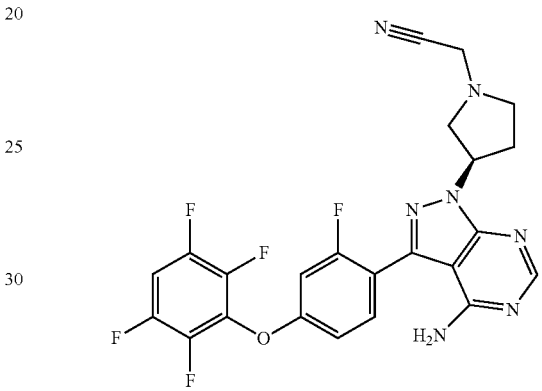

2-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)acetonitrile Procedure:

2-iodo acetonitrile (36 mg, 0.216 mmol, 2.0 eq.) and potassium carbonate (74 mg, 0.54 mmol, 5.0 eq.) was added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.108 mmol, 1.0 eq.) in DMF (0.5 mL). The reaction was stirred at room temperature for 5 hours, quenched with saturated NaHCO$_3$ (10 mL), and then extracted with dichloromethane (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.7% NH$_4$HCO$_3$, gradient: 10%-100% (volume ratio)) to give the title compound (12 mg, yield: 22%).

LC/MS (Method: UFLC): RT=4.350 min; m/z=502.0 [M+H]$^+$; Total running time 7 min.

$^1$H NMR (400 MHz, CDCl$_3$) δ 8.37 (s, 1H), 7.60 (t, J=8.4 Hz, 1H), 7.09-7.02 (m, 1H), 6.94-6.88 (m, 2H), 5.63-5.56 (m, 1H), 3.74 (s, 2H), 3.30-3.25 (m, 1H), 3.19-3.12 (m, 2H), 2.97-2.90 (m, 1H), 2.56-2.52 (m, 2H).

Compound 114

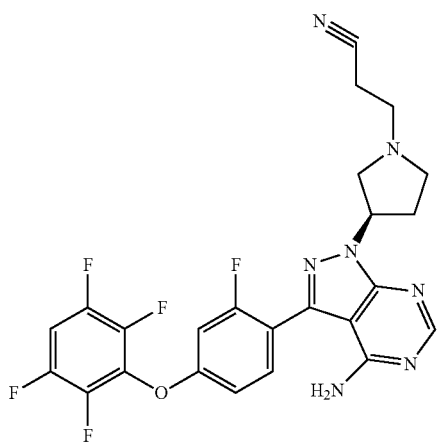 [SMILES: N#CCCN1CC[C@@H](n2nc(-c3ccc(Oc4c(F)c(F)cc(F)c4F)cc3F)c3c(N)ncnc32)C1]

3-((R)-3-(4-amino-3-(2-fluoro-4-(2,3,5,6-tetrafluoro-phenoxy)phenyl)-1H-pyrazolo[3,4-d]pyrimidin-1-yl)pyrrolidin-1-yl)propanenitrile Procedure:

3-bromo-propionitrile (28 mg, 0.216 mmol, 2.0 eq.) and potassium carbonate (74 mg, 0.54 mmol, 5.0 eq.) were added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.108 mmol, 1.0 eq.) in DMF (0.5 mL). The reaction was stirred at 80° C. for 12 hours, diluted with saturated water (10 mL), and then extracted with dichloromethane (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.7% NH$_4$HCO$_3$, gradient: 10%-100% (volume ratio)) to give the title compound (6 mg, yield: 11%).

LC/MS (Method: UFLC): RT=3.671 min; m/z=516.0 [M+H]$^+$; Total running time 7 min.

$^1$H NMR (400 MHz, CDCl$_3$) δ 8.36 (s, 1H), 7.59 (t, J=8.4 Hz, 1H), 7.10-7.04 (m, 1H), 6.94-6.88 (m, 2H), 5.65-5.52 (m, 1H), 3.35-3.31 (m, 1H), 3.05-2.91 (m, 5H), 2.58-2.44 (m, 4H).

Compound 115

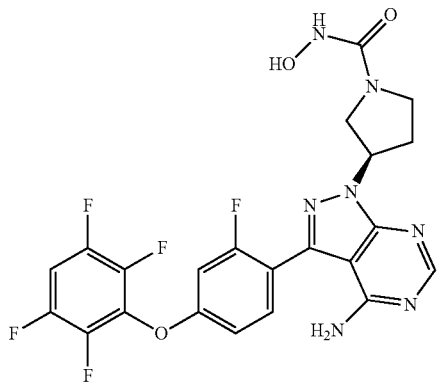 [SMILES: Nc1ncnc2c1c(-c1ccc(Oc3c(F)c(F)cc(F)c3F)cc1F)nn2[C@@H]1CCN(C(=O)NO)C1]

(3R)-3-(4-amino-3-(2-fluoro-4-(2,3,5,6-tetrafluoro-phenoxy)phenyl)-1H-pyrazolo[3,4-d]pyrimidin-1-yl)-N-hydroxypyrrolidine-1-carboxamide Step A:

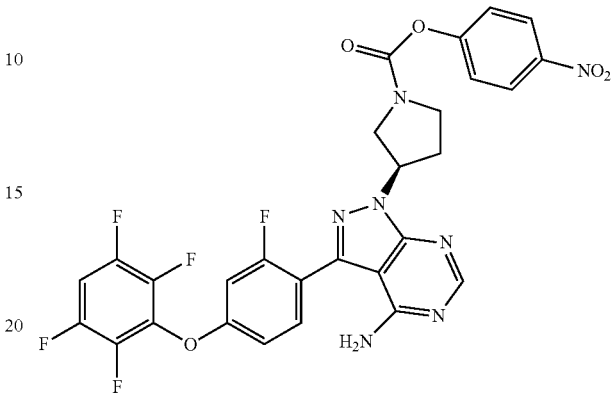

(3R)-4-nitrophenyl 3-(4-amino-3-(2-fluoro-4-(2,3,5,6-tetrafluorophenoxy)phenyl)-1H-pyrazolo[3,4-d]pyrimidin-1-yl)pyrrolidine-1-carboxylate Procedure:

Triethylamine (2 mL) and 4-nitrophenyl carbonochloridate (52 mg, 0.23 mmol, 1.1 eq.) were added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (100 mg, 0.21 mmol, 1.0 eq.) in dichloromethane (9 mL). The reaction was stirred at room temperature for 12 hours, quenched with saturated NaHCO$_3$ (10 mL), and then extracted with dichloromethane (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.7% NH$_4$HCO$_3$, gradient: 10%-100% (volume ratio)) to give the title compound (80 mg, yield: 69%).

Step B:

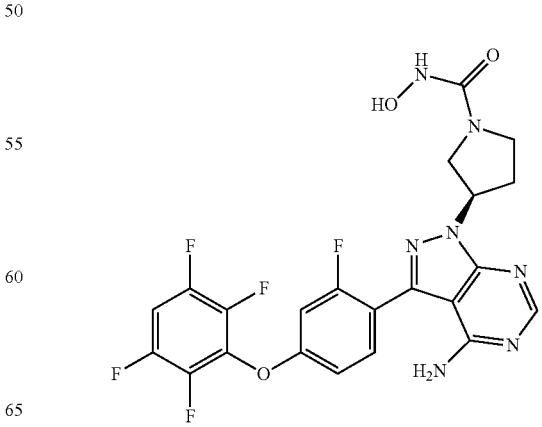

(3R)-3-(4-amino-3-(2-fluoro-4-(2,3,5,6-tetrafluorophenoxy)phenyl)-1H-pyrazolo[3,4-d]pyrimidin-1-yl)-N-hydroxypyrrolidine-1-carboxamide Procedure:

Hydroxylamine aqueous (50%, 0.5 mL, 0.254 mmol, 2 eq.) was added to a solution of (3R)-4-nitrophenyl 3-(4-amino-3-(2-fluoro-4-(2,3,5,6-tetrafluorophenoxy)phenyl)-1H-pyrazolo[3,4-d]pyrimidin-1-yl)pyrrolidine-1-carboxylate (80 mg, 0.13 mmol, 1.0 eq.) in DMF (3 mL). The reaction was stirred at 120° C. for 30 minutes, quenched with saturated NaHCO₃ (10 mL), and then extracted with dichloromethane (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.7% NH₄HCO₃, gradient: 10%-100% (volume ratio)) to give the title compound (5 mg, yield: 9%).

LC/MS (Method: UFLC): RT=2.803 min; m/z=522.1 [M+H]⁺; Total running time 7 min.

Compound 116

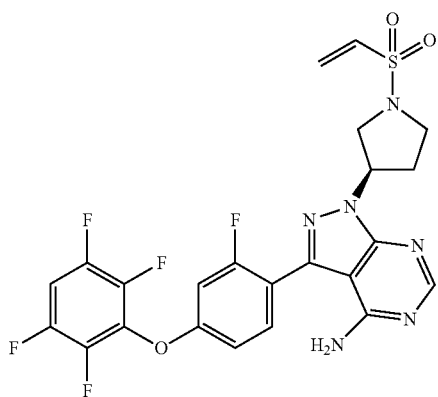 [SMILES: C=CS(=O)(=O)N1CC[C@@H](n2nc(-c3ccc(Oc4c(F)c(F)cc(F)c4F)cc3F)c3c(N)ncnc32)C1]

3-(2-fluoro-4-(2,3,5,6-tetrafluorophenoxy)phenyl)-1-((R)-1-(vinylsulfonyl)pyrrolidin-3-yl)-1H-pyrazolo[3,4-d]pyrimidin-4-amine Procedure:

N, N-diisopropylethylamine (31 mg, 0.238 mmol, 2.2 eq.), DMAP (1.32 mg, 0.011 mmol, 0.1 eq.) and 2-chloroethyl sulfonyl chloride (21 mg, 0.130 mmol, 1.2 eq.) were added to solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.108 mmol, 1.0 eq.) in methylene chloride (5 mL) at 0° C. The reaction was stirred at 20° C. for 12 hours, and concentrated to give the crude product, which was purified by HPLC (C18 reverse phase column, mobile phase: acetonitrile/water/0.5% HCl, gradient: 10%-100% (volume ratio)) to give the title compound (6 mg, yield: 11%).

LC/MS (Method: UFLC): RT=3.543 min; m/z=552.9[M+H]⁺; Total running time 7 min.

Compound 117

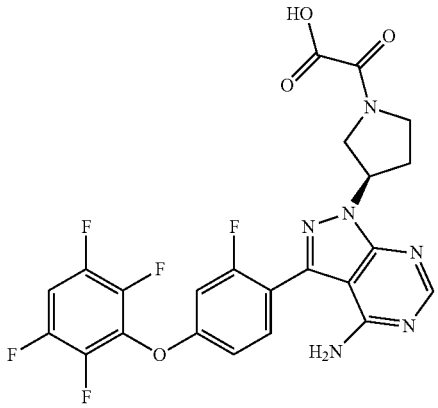 [SMILES: Nc1ncnc2c1c(-c1ccc(Oc3c(F)c(F)cc(F)c3F)cc1F)nn2[C@@H]1CCN(C(=O)C(=O)O)C1]

2-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)-2-oxoacetic acid Procedure:

N, N-diisopropylethylamine (41 mg, 0.33 mmol, 3.0 eq.) and ethyl cyanoformate (13 mg, 0.13 mmol, 1.2 eq.) was added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.11 mmol, 1.0 eq.) in toluene (3 mL). The reaction was stirred at room temperature for 12 hours, diluted with saturated NaHCO₃ (10 mL), and then extracted with dichloromethane (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.7% NH₄HCO₃, gradient: 10%-100% (volume ratio)) to give the title compound (5 mg, yield: 9%).

LC/MS (Method: UFLC): RT=1.884 min; m/z=535.1 [M+H]⁺; Total running time 3 min.

Compound 118

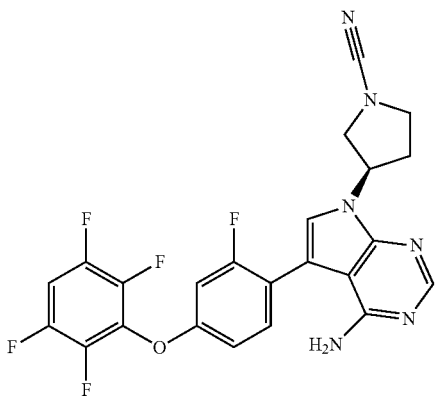 [SMILES: N#CN1CC[C@@H](n2cc(-c3ccc(Oc4c(F)c(F)cc(F)c4F)cc3F)c3c(N)ncnc32)C1]

(3R)-3-(4-amino-3-(2-fluoro-4-(2,3,5,6-tetrafluorophenoxy)phenyl)-1H-pyrrolo[2,3-d]pyrimidin-1-yl)pyrrolidine-1-carbonitrile Procedure:

Bromine cyanide (23 mg, 0.216 mmol, 2.0 eq.) and sodium bicarbonate (27 mg, 0.324 mmol, 3.0 eq.) were added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.108 mmol, 1.0 eq.) in acetonitrile (2 mL). The reaction was stirred at 20° C. for 12 hours, diluted with water (10 mL), and then extracted with dichloromethane (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.7% NH$_4$HCO$_3$, gradient: 10%-100% (volume ratio)) to give the title compound (26 mg, yield: 49%).

LC/MS (Method: UFLC): RT=3.338 min; m/z=488.1 [M+H]$^+$; Total running time 7 min.

$^1$H NMR (400 MHz, CD$_3$OD) δ 8.25 (s, 1H), 7.68 (t, J=8.4 Hz, 1H), 7.52-7.45 (m, 1H), 7.10-7.02 (m, 2H), 5.57-5.52 (m, 1H), 4.01-3.96 (m, 1H), 3.86-3.80 (m, 2H), 3.69-3.65 (m, 1H), 2.52-2.46 (m, 2H).

Compound 119

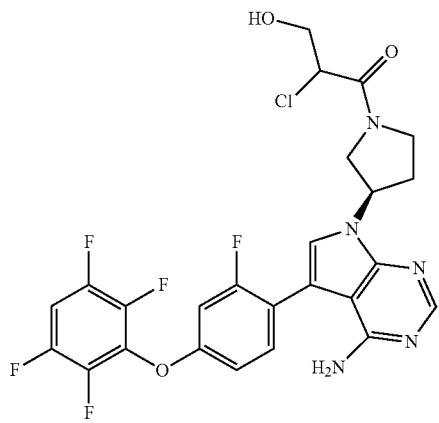 [SMILES: Nc1ncnc2c1c(-c1ccc(Oc3c(F)c(F)cc(F)c3F)cc1F)cn2[C@@H]1CCN(C(=O)C(Cl)CO)C1]

1-((R)-3-(4-amino-3-(2-fluoro-4-(2,3,5,6-tetrafluorophenoxy)phenyl)-1H-pyrrolo[2,3-d]pyrimidin-1-yl)pyrrolidin-1-yl)-2-chloro-3-hydroxypropan-1-one Step A:

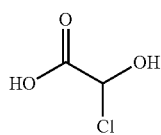

2-chloro-2-hydroxyacetic acid

Procedure:

Silver nitrate (620 mg, 3.669 mmol, 1.04 eq.) was added to a solution of sodium carbonate (530 mg, 6.386 mmol, 1.42 eq.) in water (3 mL). The resulting suspension was added dropwise to a solution of 2,2-dichloroacetic acid (500 mg, 3.521 mmol, 1.0 eq.) in water (3 mL). The reaction solution was refluxed for 2 hours and filtered. The filtrate was refluxed for 2 hours and filtered. The filtrate was concentrated to give the title compound (326 mg, yield: 84%).

Step B:

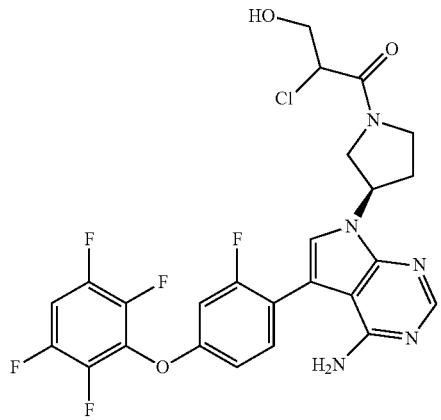 [SMILES: Nc1ncnc2c1c(-c1ccc(Oc3c(F)c(F)cc(F)c3F)cc1F)cn2[C@@H]1CCN(C(=O)C(Cl)CO)C1]

1-((R)-3-(4-amino-3-(2-fluoro-4-(2,3,5,6-tetrafluorophenoxy)phenyl)-1H-pyrrolo[2,3-d]pyrimidin-1-yl)pyrrolidin-1-yl)-2-chloro-3-hydroxypropan-1-one Procedure:

2-chloro-2-hydroxyacetic acid (15 mg, 0.163 mmol, 1.5 eq.), HATU (45 mg, 0.119 mmol, 1.1 eq.) and N, N-diisopropylethylamine (42 mg, 0.324 mmol, 3.0 eq.) were subsequently added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (50 mg, 0.108 mmol, 1.0 eq.) in dichloromethane (3 mL) at 0° C. The reaction was stirred at room temperature for 12 hours, quenched with saturated NaHCO$_3$ (10 mL), and then extracted with dichloromethane (10 mL×3). The combined organic phases were dried over anhydrous sodium sulfate and filtered. The filtrate was concentrated to give the crude product, which was purified by HPLC (C18 reverse phase column, mobile phase: acetonitrile/water/0.5% HCl, gradient: 10%-100% (volume ratio)) to give the title compound hydrochloride (3.4 mg, yield: 6%).

LC/MS (Method: UFLC): RT=4.221 min; m/z=569.0 [M+H]$^+$; Total running time 7 min.

Compound 120

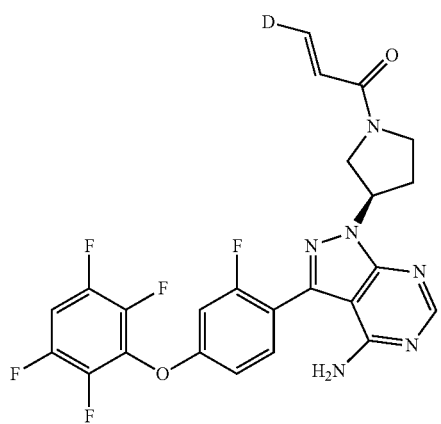 [SMILES: [2H]/C=C/C(=O)N1CC[C@@H](n2nc(-c3ccc(Oc4c(F)c(F)cc(F)c4F)cc3F)c3c(N)ncnc32)C1]

(E)-1-((R)-3-(4-amino-3-(2-fluoro-4-(2,3,5,6-tetra-fluorophenoxy)phenyl)-1H-pyrrolo[2,3-d]pyrimidin-1-yl)pyrrolidin-1-yl)-3-deuterium-prop-2-en-1-one Step A:

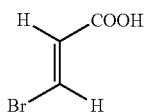

(E)-3-bromoacrylic acid

Procedure:
A mixture of propiolic acid (1 g, 14.28 mmol, 1.0 eq.) and HBr (40% aqueous solution, 1.7 mL, 0.88 eq.) was stirred overnight at 140° C. After the removal of solvent under reduced pressure, the obtained crude product was crystallized from water (4 mL) three times to give the title compound (0.76 g, yield: 35%).
¹H NMR (400 MHz, CDCl₃) δ 7.76 (d, J=14 Hz, 1H), 6.55 (d, J=14 Hz, 1H).

Step B:

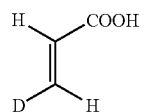

(E)-3-deuterium acrylate

Procedure:
Na—Hg (6 g, 49.67 mmol, 2.5 eq.) was added to a solution of (E)-3-bromoacrylic acid (3 g, 19.87 mmol, 1.0 eq.) in D₂O (30 mL) at 0~5° C. The reaction was stirred at room temperature for 36 hours. The aqueous phase was adjusted pH=5 with 1M hydrochloric acid, and then extracted with diethyl ether (20 mL×5). The combined organic phases were dried over anhydrous sodium sulfate and filtered. The filtrate was concentrated to give the title compound (0.52 g, yield: 36%).
¹H NMR (400 MHz, CDCl₃) δ 7.76 (d, J=17.2 Hz, 1H), 6.55 (d, J=17.2 Hz, 1H).

Step C:

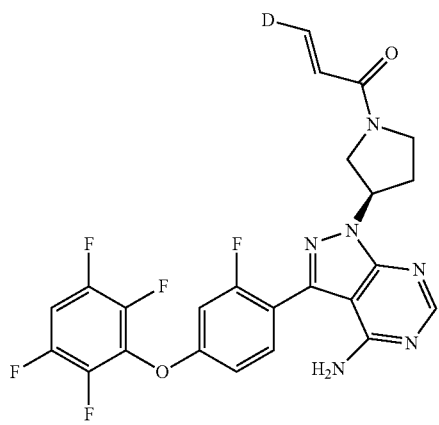 [SMILES: [2H]/C=C/C(=O)N1CC[C@@H](n2nc(-c3ccc(Oc4c(F)c(F)cc(F)c4F)cc3F)c3c(N)ncnc32)C1]

(E)-1-((R)-3-(4-amino-3-(2-fluoro-4-(2,3,5,6-tetra-fluorophenoxy)phenyl)-1H-pyrrolo[2,3-d]pyrimidin-1-yl)pyrrolidin-1-yl)-3-deuterium-prop-2-en-1-one Procedure:
(E)-3-deuterium acrylate (76 mg, 1.08 mmol, 1.0 eq.), HATU (530 mg, 1.40 mmol, 1.3 eq.) and N,N-diisopropylethylamine (419 mg, 3.24 mmol, 3.0 eq.) were subsequently added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (500 mg, 1.08 mmol, 1.0 eq.) in dichloromethane (3 mL) at 0° C. The reaction was stirred at room temperature for 12 hours and concentrated to give the crude product, which was purified by HPLC (C18 reverse phase column, mobile phase: acetonitrile/water/0.5% HCl, gradient: 36%-37% (volume ratio)) to give the title compound hydrochloride (76 mg, yield: 13%).
LC/MS (Method: UFLC): RT=2.765 min; m/z=518.1 [M+H]⁺; Total running time 7 min.
¹H NMR (400 MHz, CD₃OD) δ 8.41 (s, 1H), 7.66 (t, J=8.4 Hz, 1H), 7.51-7.44 (m, 1H), 7.09-7.01 (m, 2H), 6.66-6.56 (m, 1H), 6.28-6.23 (m, 1H), 5.75-5.66 (m, 1H), 4.19-4.16 (m, 1H), 4.06-4.02 (m, 1.5H), 3.89-3.85 (m, 1H), 3.78-3.72 (m, 0.5H), 2.63-2.49 (m, 2H).

Compound 121

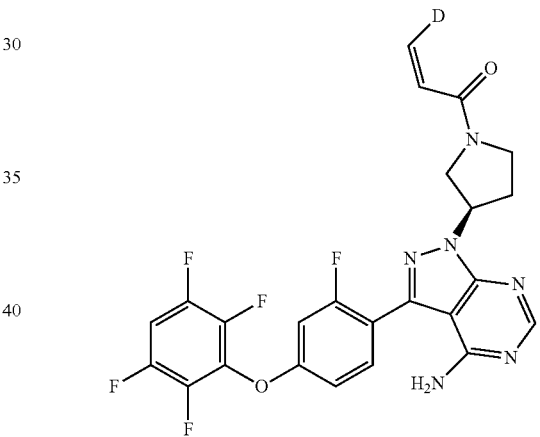

(Z)-1-((R)-3-(4-amino-3-(2-fluoro-4-(2,3,5,6-tetra-fluorophenoxy)phenyl)-1H-pyrrolo[2,3-d]pyrimidin-1-yl)pyrrolidin-1-yl)-3-deuterium-prop-2-en-1-one Step A:

(Z)-3-bromoacrylic acid

Procedure:
A mixture of propiolic acid (1 g, 14.28 mmol, 1.0 eq.) and HBr (40% aqueous solution, 1.7 mL, 0.88 eq.) was stirred overnight at 55° C. After the removal of solvent under reduced pressure, the obtained crude product was crystallized from water (4 mL) three times to give the title compound (0.3 g, yield: 14%).

¹H NMR (400 MHz, CDCl₃) δ 7.16 (d, J=8.4 Hz, 1H), 6.67 (d, J=8.4 Hz, 1H).

Step B:

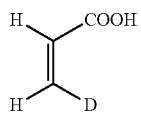

(Z)-3-deuterium acrylate

Procedure:

Na—Hg (6 g, 49.67 mmol, 2.5 eq.) was added to a solution of (Z)-3-bromoacrylic acid (3 g, 19.87 mmol, 1.0 eq.) in D₂O (30 mL) at 0~5° C. The reaction was stirred at room temperature for 36 hours. The aqueous phase was adjusted pH=5 with 1M hydrochloric acid, and then extracted with diethyl ether (20 mL×5). The combined organic phases were dried over anhydrous sodium sulfate and filtered. The filtrate was concentrated to give the title compound (0.34 g, yield: 23%).

¹H NMR (400 MHz, CDCl₃) δ 6.14 (d, J=10.4 Hz, 1H), 5.96 (d, J=10.4 Hz, 1H).

Step C:

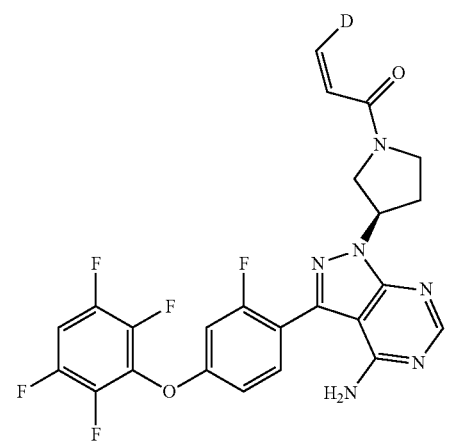 [SMILES: [2H]/C=C\C(=O)N1CC[C@@H](n2nc(-c3ccc(Oc4c(F)c(F)cc(F)c4F)cc3F)c3c(N)ncnc32)C1]

(Z)-1-((R)-3-(4-amino-3-(2-fluoro-4-(2,3,5,6-tetra-fluorophenoxy)phenyl)-1H-pyrrolo[2,3-d]pyrimidin-1-yl)pyrrolidin-1-yl)-3-deuterium-prop-2-en-1-one Procedure:

(Z)-3-deuterium acrylate (151 mg, 2.16 mmol, 1.0 eq.), HATU (1.06 g, 2.80 mmol, 1.3 eq.) and N,N-diisopropyl-ethylamine (838 mg, 6.48 mmol, 3.0 eq.) were subsequently added to a solution of 3-(2-fluoro-4-(2,3,5,6-tetrafluorophe-noxy)phenyl)-1-((R)-pyrrolidin-3-yl)-1H-pyrazolo[3,4-d]pyrimidin-4-amine (1.0 g, 2.16 mmol, 1.0 eq.) in dichloromethane (3 mL) at 0° C. The reaction was stirred at room temperature for 12 hours and concentrated to give the crude product, which was purified by HPLC (C18 reverse phase column, mobile phase: acetonitrile/water/0.5% HCl, gradient: 36%-37% (volume ratio)) to give the title compound hydrochloride (228 mg, yield: 20%).

LC/MS (Method: UFLC): RT=2.775 min; m/z=518.1 [M+H]⁺; Total running time 7 min.

¹H NMR (400 MHz, CD₃OD) δ 8.45 (s, 1H), 7.70 (t, J=8.4 Hz, 1H), 7.52-7.46 (m, 1H), 7.13-7.05 (m, 2H), 6.71-6.61 (m, 1H), 5.80-5.73 (m, 2H), 4.23-4.20 (m, 1H), 4.09-4.04 (m, 1.5H), 3.93-3.90 (m, 1H), 3.80-3.75 (m, 0.5H), 2.67-2.56 (m, 2H).

Compound 123

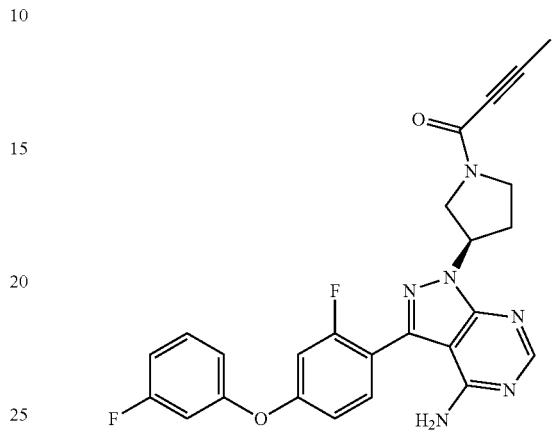

1-((R)-3-(4-amino-3-(2-fluoro-4-(3-fluorophenoxy) phenyl)-1H-pyrazolo[3,4-d]pyrimidin-1-yl)pyrroli-din-1-yl)but-2-yn-1-one A mixture of 3-[2-fluoro-4-(3-fluorophenoxy)phenyl]-1-[(3R)-pyrrolidin-3-yl]pyrazolo[3,4-d]pyrimidin-4-amine (200.00 mg, 489.72 umol, 1.00 eq.), but-2-ynoic acid (41.17 mg, 489.72 umol, 1.00 eq.), HATU (93.10 mg, 244.86 umol, 0.50 eq.) and DIPEA (75.95 mg, 587.66 umol, 102.64 uL, 1.20 eq.) in DCM (5.00 mL) was stirred at 15-18° C. for 2 hrs. TLC showed starting material consumed. The mixture was evaporated to dryness. The residue was purified by prep-HPLC (column: Boston Green ODS 150*30 5 u; mobile phase: acetonitrile/water/0.05% HCl, gradient: 22%-52% (volume ratio), time: 12 min) to give the title compound as hydrochloride salt (82.00 mg, yield: 32.77%).

LC/MS (Method: UFLC): RT=3.057 min; m/z=475.0 [M+H]⁺; Total running time 7.000 min.

¹H NMR (400 MHz, CDCl₃) δ 9.92 (s, 1H), 8.34 (d, J=8.8 Hz, 1H), 7.56 (br, 1H), 7.41-7.36 (m, 1H), 7.00-6.86 (m, 5H), 6.58 (br, 1H), 5.62-5.58 (m, 1H), 4.22-3.74 (m, 4H), 2.65-2.50 (m, 2H), 2.02-1.96 (m, 3H).

In Vitro Assay

Inhibition Assay of BTK Kinase Activity:

The enzyme reaction mixture of BTK wild type standard HTRF assay contained 1 nM BTK wild type, 1 M biotin-TK1 peptide, and 30 M ATP in a buffer. The enzyme reaction were carried out at room temperature for 60 minutes. 5 μl of 0.2 M EDTA were added to quench the reaction and then the inhibitors (5 μl) were added at final concentrations of 2 nM antibody and 62.5 nM XL665. The plates were incubated at room temperature for 60 minutes and then read in the Envision plate reader. The readouts were transformed into inhibition rate % by the equation of (Min Ratio)/(Max-Min) *100%. Hence the IC₅₀ data of test compounds were generated by using four parameters curve fitting.

Inhibition Assay of Tumor Cell Activity:

Tumor cells (TMD-8, DoHH2 and WSU-DLCL2) were transferred and attached to 96-well plates. After one night, blank buffer and selected concentrations (0.01 nM-100 μM) of the test compound solution were added. After 48 hours incubation, CellTiter-Go was added to lyse the cells. Recording luminescent signal and calculate the percent inhibition of cell viability. The two tables below show the inhibition on TMD-8 cell viability by single compound or triple combination with the latter demonstrating synergistic effect and synthetic lethality against tumor cells. Data from the experiments are presented in Tables 3 and 4 below.

TABLE 3

Single agent against TMD-8 cell viability

| Compound | Compound Name (Mechanism) | Inh % | 100 μM | 10 μM | 1 μM | 0.1 μM | 0.01 μM |
|---|---|---|---|---|---|---|---|
| 45 | 45 (BTK) | AVG | 99.69 | 74.93 | 61.66 | 59.59 | 46.07 |
|    |           | SD  | 0.10  | 0.64  | 3.97  | 1.49  | 1.60  |
| 45 | 45 (BTK) | AVG |       |       | 55.05 | 52.40 | 51.66 |
|    |           | SD  |       |       | 3.47  | 2.17  | 1.21  |
| 120 | 120 (BTK) | AVG | 99.38 | 62.52 | 60.21 | 52.99 | 32.29 |
|     |            | SD  | 0.09  | 1.58  | 3.62  | 3.53  | 5.50  |
| 121 | 121 (BTK) | AVG | 99.32 | 62.89 | 58.57 | 58.68 | 33.85 |
|     |            | SD  | 0.13  | 2.18  | 0.90  | 2.20  | 3.05  |

TABLE 4

Triple combination (compound 45/pomalidomide or 45a/everolimus or 45b) against TMD-8 cell viability

| Comp.@Conc. | Inh % | 45 @1 uM | 45 @0.1 uM | 45 @0.01 uM |
|---|---|---|---|---|
| 45a @0.1 uM + 45b @0.1 uM | AVG | 76.42 | 80.77 | 83.22 |
|                            | SD  | 4.50  | 1.38  | 0.37  |

In Vivo Assay

A pharmacokinetic study in male SD rats: Male SD rats for pharmacokinetic study within 24 hours were divided into two groups: intravenous administration and oral administration. Each group has three animals. For group of intravenous administration, blood samples were collected at pre-dose, 0.0833, 0.167, 0.5, 1, 2, 4, 8, 24 h post-dose; for group of oral administration, blood samples were collected at pre-dose, 0.167, 0.5, 1, 2, 4, 8, 24 h post-dose. After blood collection, HPLC-MS/MS was applied to determine plasma concentrations of the compound. The calculated pharmacokinetic parameters of intravenous group include mean plasma clearance (CLp), mean apparent volume of distribution at stead state (Vdss), 0-24 h area under the curve (AUC), 0-24 h mean residence time (MRT), the half-life (T½); The calculated pharmacokinetic parameters of oral group include mean peak concentration (Cmax), 0-24 h area under the curve (AUC), 0-24 h mean residence time (MRT); mean relative bioavailability for the study.

A pharmacokinetic study in Beagle dogs: Beagle dogs for pharmacokinetic study within 24 hours were divided into two groups: intravenous administration (1 mg per kilogram) and oral administration (3 mg per kilogram). Each group has three animals. For group of intravenous administration, blood samples were collected at pre-dose, 0.033, 0.083, 0.25, 0.5, 1, 3, 6, 9, 24 h post-dose; for group of oral administration, blood samples were collected at pre-dose, 0.083, 0.25, 0.5, 1, 3, 6, 9, 24 h post-dose. After blood collection, HPLC-MS/MS was applied to determine plasma concentrations of the compound. The calculated pharmacokinetic parameters of intravenous group include mean plasma clearance (CLp), mean apparent volume of distribution at stead state (Vdss), 0-24 h area under the curve (AUC), 0-24 h mean residence time (MRT), the half-life (T½); The calculated pharmacokinetic parameters of oral group include mean peak concentration (Cmax), 0-24 h area under the curve (AUC), 0-24 h mean residence time (MRT); mean relative bioavailability for the study.

Data from the experiments are presented in the tables below.

TABLE 5

PK Parameters for Compound 45 in rats

| | Group | | | |
|---|---|---|---|---|
| | 1 | | 2 | |
| | Dose Route | | | |
| | IV | | PO | |
| | Dose level | | | |
| | 2 mg/kg | | 10 mg/kg | |
| | Mean | SD | Mean | SD |
| $C_0$ or $C_{max}$ (ng/mL) | 1390 | 247 | 641 | 191 |
| $T_{max}$ (hr) | — | — | 1.33 | 0.753 |
| $T_{1/2}$ (hr) | 0.787 | 0.0895 | 1.71 | 0.489 |
| Vdss (L/kg) | 1.61 | 0.339 | — | — |
| CL (mL/min/kg) | 20.2 | 5.60 | — | — |
| $AUC_{0-last}$ (hr · ng/mL) | 1740 | 421 | 3230 | 1120 |
| $AUC_{0-inf}$ (hr · ng/mL) | 1740 | 420 | 3260 | 1140 |
| Bioavailability (%)[a] | — | — | 37.1 | — |

TABLE 6

PK Parameters for Compound 45 in dogs

| | Group | | | |
|---|---|---|---|---|
| | 1 | | 2 | |
| | Dose Route | | | |
| | IV | | PO | |
| | Dose level | | | |
| | 2 mg/kg | | 5 mg/kg | |
| | Mean | SD | Mean | SD |
| $C_0$ or $C_{max}$ (ng/mL) | 663 | 79.5 | 189 | 53.3 |
| $T_{max}$ (hr) | — | — | 1.17 | 0.408 |
| $T_{1/2}$ (hr) | 2.27 | 0.873 | 2.92 | 1.22 |
| Vdss (L/kg) | 4.24 | 0.370 | — | — |
| CL (mL/min/kg) | 34.6 | 5.58 | — | — |
| $AUC_{0-last}$ (hr · ng/mL) | 977 | 181 | 650 | 247 |
| $AUC_{0-inf}$ (hr · ng/mL) | 987 | 183 | 574 | 123 |
| Bioavailability (%)[a] | — | — | 26.2 | — |

TABLE 7

TK data for Compound 45 in rats

| Dose (mg/kg) | Study Day | Sex | Cmax (ng/mL) | Tmax (h) | $AUC_{0-24\,h}$ (h * ng/mL) |
|---|---|---|---|---|---|
| 40 | 1 | Male | 2160 | 2.0 | 13700 |
|    |   | Female | 2660 | 1.0 | 17300 |
|    | 28 | Male | 2090 | 2.0 | 15400 |
|    |    | Female | 2970 | 1.0 | 17300 |
| 100 | 1 | Male | 2740 | 2.0 | 21700 |
|     |   | Female | 3700 | 4.0 | 28900 |
|     | 28 | Male | 3990 | 2.0 | 30300 |
|     |    | Female | 3830 | 1.0 | 29600 |

TABLE 7-continued

TK data for Compound 45 in rats

| Dose (mg/kg) | Study Day | Sex | Cmax (ng/mL) | Tmax (h) | AUC$_{0\text{-}24\,h}$ (h * ng/mL) |
|---|---|---|---|---|---|
| 200 | 1 | Male | 4220 | 2.0 | 37600 |
|  |  | Female | 4680 | 4.0 | 65200 |
|  | 28 | Male | 4540 | 2.0 | 45100 |
|  |  | Female | 5490 | 8.0 | 60200 |

The TK data in rats show that the AUC of Compound 45 in rats is significantly higher than that of ibrutinib (U.S. FDA's NDA Application No. 205552Orig1s000_pharmacological review(s)).

TABLE 8

TK data for Compound 45 in dogs

| Dose (mg/kg/day) | Study Day | Sex | Cmax (ng/mL) | Tmax (h) | AUC$_{0\text{-}24\,h}$ (h * ng/mL) |
|---|---|---|---|---|---|
| 15 | 1 | Male | 746 ± 18.1 | 2.0 (1.0-2.0) | 3550 ± 562 |
|  |  | Female | 685 ± 212 | 1.0 (1.0-2.0) | 2930 ± 980 |
|  | 28 | Male | 576 ± 145 | 2.0 (2.0-2.0) | 3260 ± 732 |
|  |  | Female | 687 ± 123 | 2.0 (1.0-2.0) | 3730 ± 549 |
| 45 | 1 | Male | 1240 ± 381 | 2.0 (1.0-2.0) | 6480 ± 1670 |
|  |  | Female | 1220 ± 431 | 2.0 (2.0-2.0) | 6220 ± 3000 |
|  | 28 | Male | 1470 ± 538 | 2.0 (2.0-4.0) | 9170 ± 3810 |
|  |  | Female | 1060 ± 263 | 2.0 (2.0-4.0) | 8130 ± 1490 |
| 105 | 28 | Male | 2700 ± 769 | 2.0 (2.0-2.0) | 16400 ± 5410 |
|  |  | Female | 2420 ± 670 | 2.0 (2.0-4.0) | 17300 ± 2830 |
| 150 | 1 | Male | 2460 ± 858 | 4.0 (1.0-8.0) | 22900 ± 13900 |
|  |  | Female | 1850 ± 605 | 2.0 (1.0-4.0) | 11200 ± 5990 |

The above TK data in dogs show that the AUC of Compound 45 in dogs is significantly higher than that of ibrutinib (U.S. FDA's NDA Application No. 205552Orig1s000_pharmacological review(s)).

TMD-8 is a sensitive human diffuse large B-cell lymphoma cell line, and DoHH2 is a more difficult to treat human follicular lymphoma cell line, while WSU-DLCL2 is a multi-drug resistant (MDR) human non-Hodgkin's lymphoma cell line. Drug combination therapies provided better efficacies in all three tumor models than single targeted agent alone.

Compounds (Compounds 45 and others) alone and its combinations were evaluated against tumor growth in xenograft models in female CB-17 SCID mice. The TMD-8, DoHH2, WSU-DLCL2 tumor cells were maintained in vitro as a suspension culture in RPMI-1640 medium supplemented with 10% heat inactivated fetal calf serum at 37° C. in an atmosphere of 5% $CO_2$ in air. The tumor cells were routinely subcultured twice weekly. The cells growing in an exponential growth phase were harvested and counted for tumor inoculation. Each mouse was inoculated subcutaneously at the right flank with the tumor cells (10×10$^6$) in 0.2 ml of PBS with Matrigel (1:1) for tumor development. The treatments were started after the average tumor size reached approximately 100-200 mm$^3$. Each group consisted of 6-10 tumor-bearing mice. The testing article (vehicle, compound or combination) was orally administered to the mice according to the predetermined doses for 14-days or 21-days. Animal body weight and tumor volume were measured every 2- or 3-days throughout the treatment.

FIG. 1 shows that significant TMD-8 tumor growth suppressions were dose-depended with Compound 33 or 45.

Figure 2:
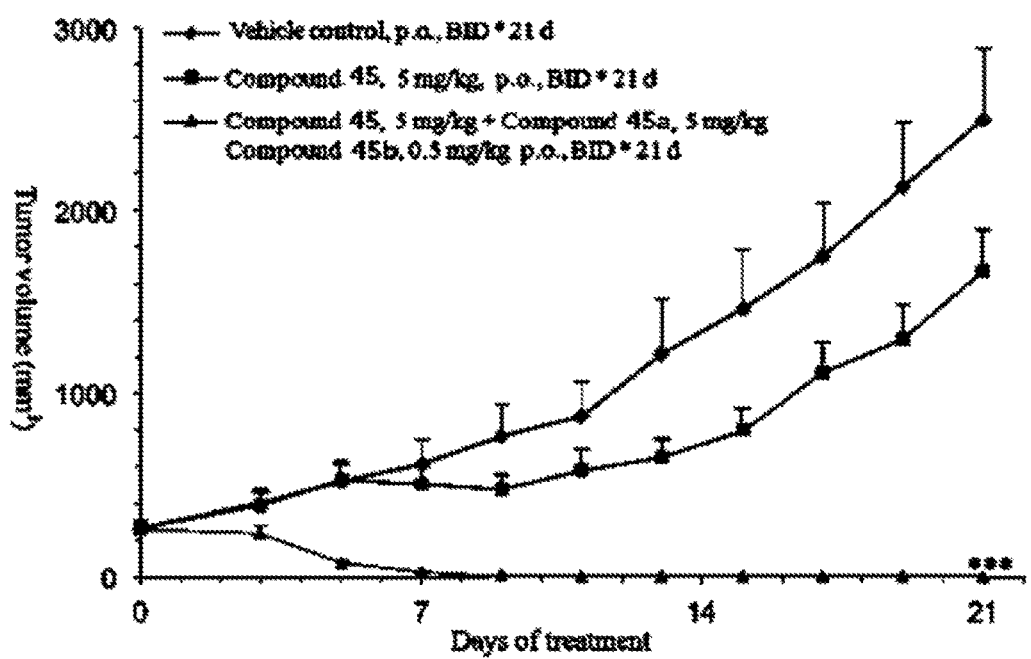
FIG. 2 is a graph showing the antitumor effect of multiple doses of Compounds 45, 45a, and 45b on tumor volume in a TMD-8 lymphoma xenograft SCID mouse model.

FIG. 2 shows that completed tumor regression was observed after 9 days of treatment of low dose combination of three drugs against TMD-8. No tumor rebound was seen 12 days after drug treatment was stopped and switched to vehicle control.

TABLE 9

Summary of Data from FIGS. 1 and 2

| Corresponding FIG. | Dose | Compound (mg/kg) | Antitumor effect (%) |
|---|---|---|---|
| FIG. 1 | Oral, BID, 14 days | Vehicle control | — |
|  |  | 33 (10 mg/kg) | 56 |
|  |  | 33 (30 mg/kg) | 77 |
|  |  | 45 (10 mg/kg) | 64 |
|  |  | 45 (30 mg/kg) | 82 |
|  |  | 45 (90 mg/kg) | 93 |
| FIG. 2 | Oral, BID, 21 days | Vehicle control | — |
|  |  | 45 (5 mg/kg) | 33 |
|  |  | 45 (5 mg/kg) Pomalidomide or 45a (5 mg/kg) Everolimus or 45b (0.5 mg/kg) | 100 (Tumor disappeared completely at day 9 and didn't rebound.) |

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art.

Throughout this specification and embodiments, the word "comprise," or variations such as "comprises" or "comprising" will be understood to imply the inclusion of a stated integer or group of integers but not the exclusion of any other integer or group of integers. The materials, methods, and examples are illustrative only and not intended to be limiting.

Various techniques and mechanisms of the present invention will sometimes be described in singular form for clarity. However, it should be noted that some embodiments include multiple iterations of a technique or multiple instantiations of a mechanism unless noted otherwise.

As used herein, the singular terms "a," "an," and "the" include plural referents unless the context clearly dictates otherwise. Thus, for example, reference to a compound can include multiple compounds unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

What is claimed is:

1. A method for treating an autoimmune disease or cancer, comprising administering to a subject in need thereof a therapeutically effective amount of a compound represented by Formula (I), or an enantiomer, diastereomer, prodrug, or pharmaceutically acceptable salt thereof:

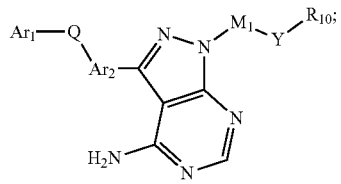
(I)

wherein $Ar_1$ and $Ar_2$ are represented by Formulae (III) and (IV), respectively:

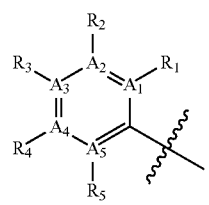
(III)

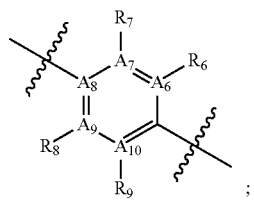
(IV)

or are pyrimidine, or quinolone, wherein:

each of $A_1$, $A_2$, $A_3$, $A_4$, $A_5$, $A_6$, $A_7$, $A_8$, $A_9$ and $A_{10}$, independently, is C, each of $R_1$, $R_2$, $R_3$, $R_4$, $R_5$, $R_6$, $R_7$, $R_8$, and $R_9$, independently, is selected from H, $NO_2$, $CF_3$, Cl, or F provided that at least two of $R_1$, $R_2$, $R_3$, $R_4$, $R_5$, $R_6$, $R_7$, $R_8$, and $R_9$ are F such that the compound is polyfluorinated, and $Ar_1$ is tetrafluorophenyl, fluorophenyl, pyrimidine, or quinolone, Q is O, $M_1$ is piperidinyl or pyrrolidinyl, Y is S, $NR_a$, or —C(=O)—, wherein $R_a$ is acyl, alkyl, alkenyl or alkynyl, and $R_{10}$ is $C_2$-$C_6$ alkenyl or $C_2$-$C_6$ alkynyl, optionally substituted with deuterium, wherein the autoimmune disease is selected from the group consisting of rheumatoid arthritis, psoriasis, multiple sclerosis, ulcerative colitis, Crohn's disease, or systemic lupus erythematosus, and wherein the cancer is a lymphoma or a myeloma.

2. The method of claim 1, wherein $Ar_1$ is represented by the following formula:

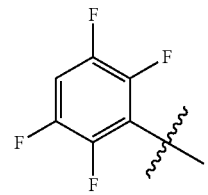

3. The method of claim 1, wherein $Ar_2$ is represented by a formula selected from the group consisting of

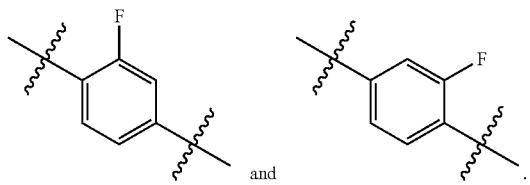

4. The method of claim 1, wherein the compound is represented by Formula (IX), or an enantiomer, diastereomer or pharmaceutically acceptable salt thereof:

(IX)

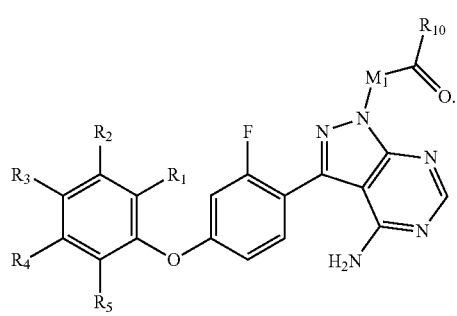

5. The method of claim 4, wherein $R_1$, $R_2$, $R_4$ and $R_5$ are F, and $R_3$ is H.

6. The method of claim 4, wherein $R_2$ is F, and $R_1$, $R_3$, $R_4$ and $R_5$ are H.

7. The method of claim 1, wherein $M_1$ is piperidinyl, and $R_{10}$ is vinyl, optionally substituted with deuterium.

8. The method of claim 2, wherein $M_1$ is piperidinyl, and $R_{10}$ is vinyl, optionally substituted with deuterium.

9. The method of claim 3, wherein $M_1$ is piperidinyl, and $R_{10}$ is vinyl, optionally substituted with deuterium.

10. The method of claim 4, wherein $M_1$ is piperidinyl, and $R_{10}$ is vinyl, optionally substituted with deuterium.

11. The method of claim 1, wherein $M_1$ is pyrrolidinyl, and $R_{10}$ is vinyl, optionally substituted with deuterium.

12. The method of claim 2, wherein $M_1$ is pyrrolidinyl, and $R_{10}$ is vinyl, optionally substituted with deuterium.

13. The method of claim 3, wherein $M_1$ is pyrrolidinyl, and $R_{10}$ is vinyl, optionally substituted with deuterium.

14. The method of claim 4, wherein $M_1$ is pyrrolidinyl, and $R_{10}$ is vinyl, optionally substituted with deuterium.

15. The method of claim 1, wherein $R_{10}$ is unsubstituted vinyl or deuterium-substituted vinyl.

16. The method of claim 1, wherein the compound is selected from the group consisting of:

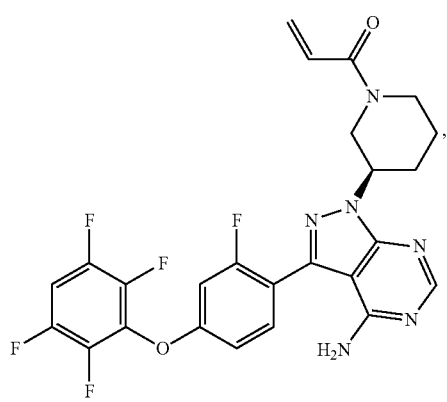

-continued

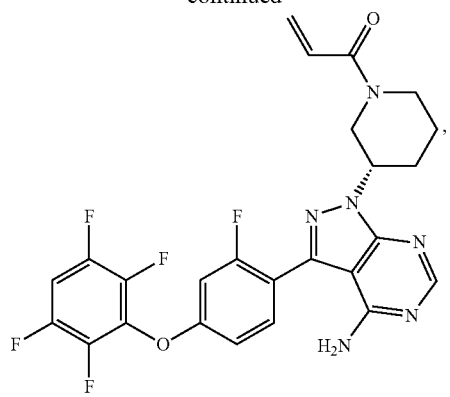

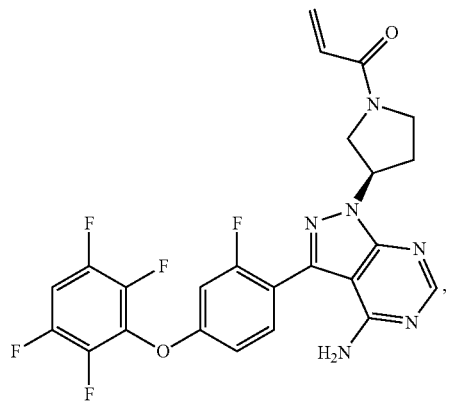

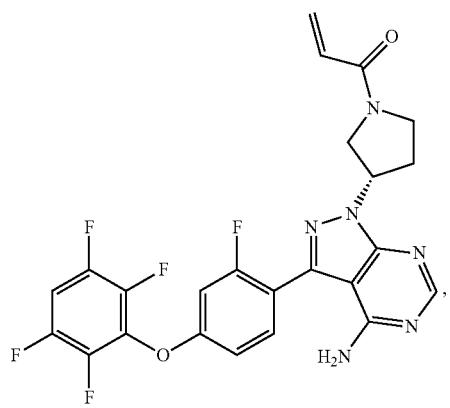

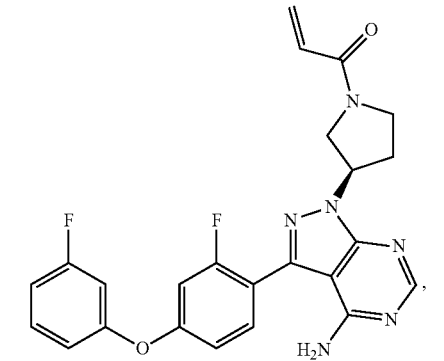

317

-continued

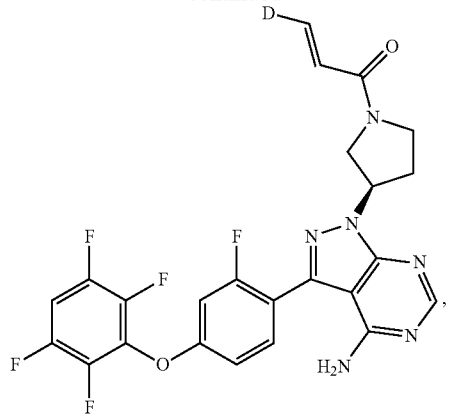

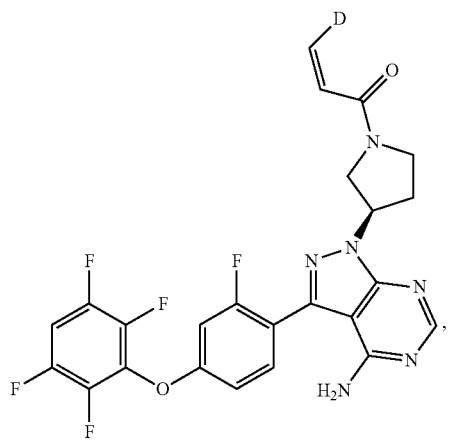

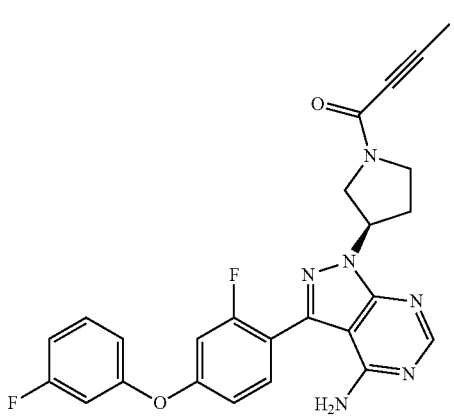 [SMILES: CC#CC(=O)N1CC[C@@H](n2nc(-c3ccc(Oc4cccc(F)c4)cc3F)c3c(N)ncnc32)C1]

and enantiomers, diastereomers, and pharmaceutically acceptable salts thereof.

17. The method of claim 1, wherein the compound is represented by the following formula:

318

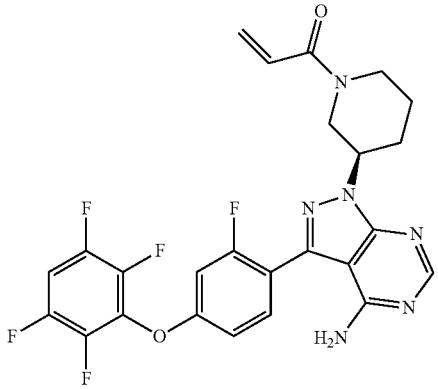 [SMILES: C=CC(=O)N1CCC[C@@H](n2nc(-c3ccc(Oc4c(F)c(F)cc(F)c4F)cc3F)c3c(N)ncnc32)C1]

or an enantiomer, diastereomer, or pharmaceutically acceptable salt thereof.

18. The method of claim 1, wherein the compound is represented by the following formula:

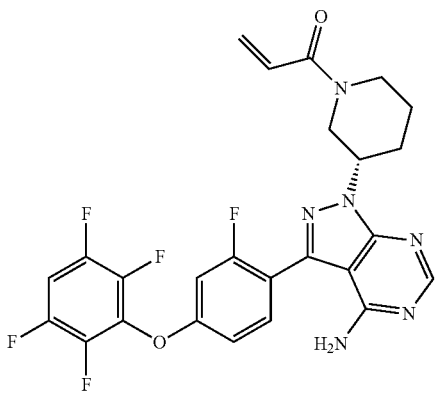 [SMILES: C=CC(=O)N1CCC[C@H](n2nc(-c3ccc(Oc4c(F)c(F)cc(F)c4F)cc3F)c3c(N)ncnc32)C1]

or an enantiomer, diastereomer, or pharmaceutically acceptable salt thereof.

19. The method of claim 1, wherein the compound is represented by the following formula:

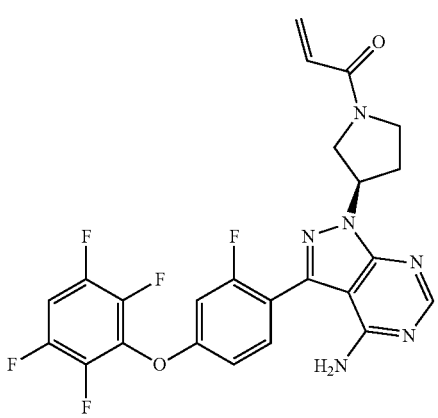 [SMILES: C=CC(=O)N1CC[C@@H](n2nc(-c3ccc(Oc4c(F)c(F)cc(F)c4F)cc3F)c3c(N)ncnc32)C1]

or an enantiomer, diastereomer, pharmaceutically acceptable salt thereof.

20. The method of claim 1, wherein the compound is represented by the following formula:

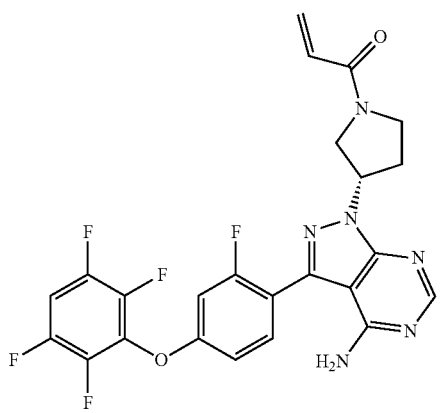 [SMILES: C=CC(=O)N1CC[C@H](n2nc(-c3ccc(Oc4c(F)c(F)cc(F)c4F)cc3F)c3c(N)ncnc32)C1]

or an enantiomer, diastereomer, or pharmaceutically acceptable salt thereof.

21. The method of claim 1, wherein the compound is represented by the following formula:

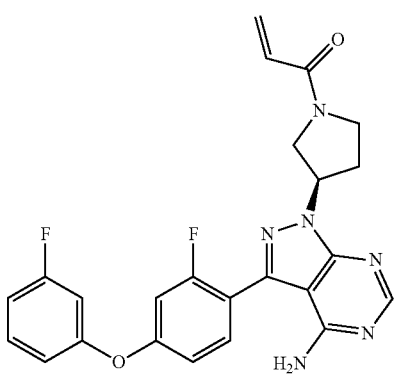 [SMILES: C=CC(=O)N1CC[C@@H](n2nc(-c3ccc(Oc4cccc(F)c4)cc3F)c3c(N)ncnc32)C1]

or an enantiomer, diastereomer, or pharmaceutically acceptable salt thereof.

22. The method of claim 1, wherein the compound is represented by the following formula:

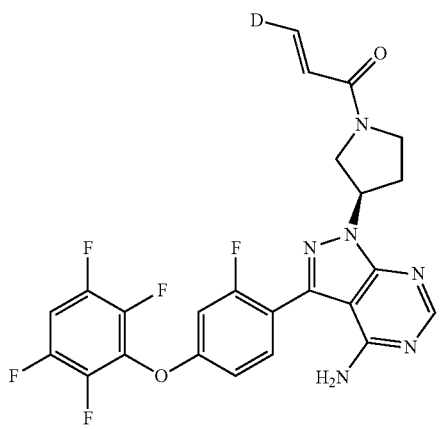 [SMILES: [2H]/C=C/C(=O)N1CC[C@@H](n2nc(-c3ccc(Oc4c(F)c(F)cc(F)c4F)cc3F)c3c(N)ncnc32)C1]

or an enantiomer, diastereomer, pharmaceutically acceptable salt thereof.

23. The method of claim 1, wherein the compound is represented by the following formula:

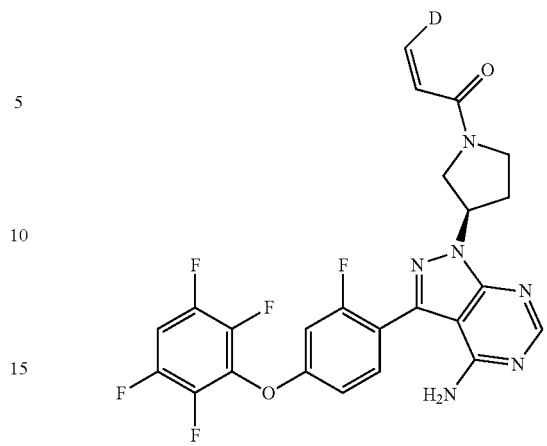

or an enantiomer, diastereomer, pharmaceutically acceptable salt thereof.

24. The method of claim 1, wherein the compound is represented by the following formula:

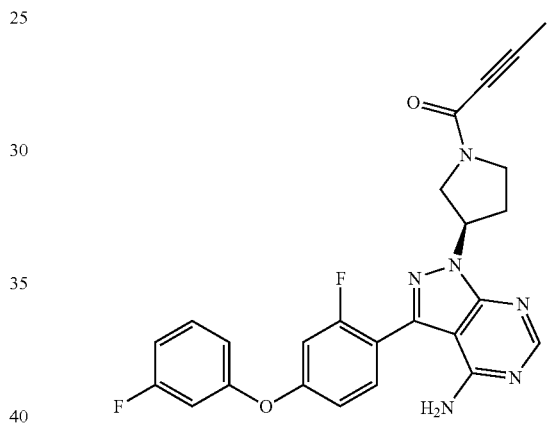

or an enantiomer, diastereomer, pharmaceutically acceptable salt thereof.

25. The method of claim 1, wherein the compound, enantiomer, diastereomer, or pharmaceutically acceptable salt inhibits Bruton's tyrosine kinase (BTK) with an IC$_{50}$ of 0.5 µM or less.

26. The method of claim 1, wherein the compound, enantiomer, diastereomer, or pharmaceutically acceptable salt inhibits BTK with an IC$_{50}$ of 0.05 µM or less.

27. The method of claim 1, wherein the method is for treating a lymphoma or myeloma selected from the group consisting of small lymphocytic lymphoma (SLL), prolymphocytic leukemia (PLL), acute lymphocytic leukemia (ALL), chronic lymphocytic leukemia (CLL), Richter's syndrome, diffuse large B-cell lymphoma (DLBCL), Waldenström Macroglobulinemia (WM), follicular lymphoma (FL), mantle cell lymphoma (MCL), Hodgkin lymphoma, non-Hodgkin lymphoma, and multiple myeloma (MM).

28. The method of claim 1, wherein the method is for treating rheumatoid arthritis.

29. The method of claim 1, wherein the method is for treating multiple sclerosis.

30. The method of claim 1, wherein the method is for treating systemic lupus erythematosus.

* * * * *